(12) United States Patent
Daniely et al.

(10) Patent No.: US 9,931,303 B1
(45) Date of Patent: *Apr. 3, 2018

(54) ABUSE DETERRENT FORMULATIONS OF AMPHETAMINE

(71) Applicant: Alcobra Ltd., Tel Aviv (IL)

(72) Inventors: Yaron Daniely, Tel Aviv (IL); David Baker, Tel Aviv (IL); Hanna Ron, Tel Aviv (IL); David Siner, Tel Aviv (IL)

(73) Assignee: Alcobra Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/591,677

(22) Filed: May 10, 2017

Related U.S. Application Data

(60) Provisional application No. 62/455,227, filed on Feb. 6, 2017.

(51) Int. Cl.
*A61K 31/137* (2006.01)
*A61K 9/48* (2006.01)

(52) U.S. Cl.
CPC .......... *A61K 9/4866* (2013.01); *A61K 31/137* (2013.01)

(58) Field of Classification Search
CPC ............................ A61K 9/4866; A61K 31/137
USPC ........................................................ 514/654
See application file for complete search history.

(56) References Cited

U.S. PATENT DOCUMENTS

2013/0287843 A1  10/2013  Young

*Primary Examiner* — Yevegeny Valenrod
(74) *Attorney, Agent, or Firm* — Cooley LLP; Ivor Elrifi; Cynthia Kozakiewicz

(57) ABSTRACT

The present invention relates generally to abuse-deterrent formulations containing dextroamphetamine sulfate.

20 Claims, 81 Drawing Sheets

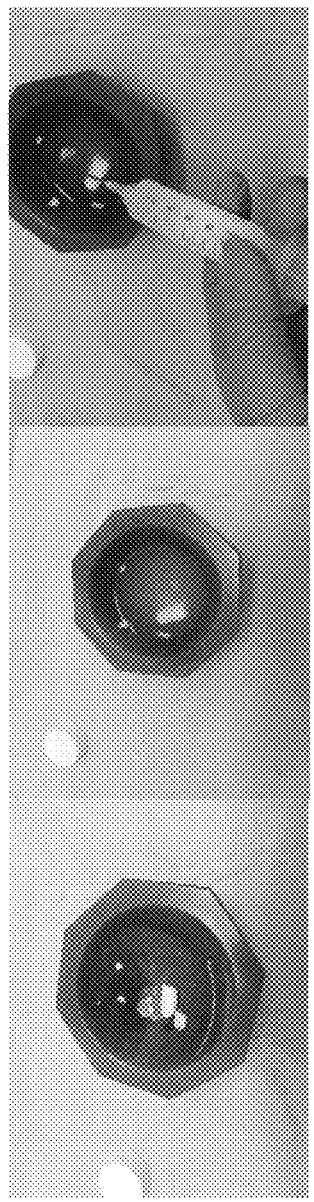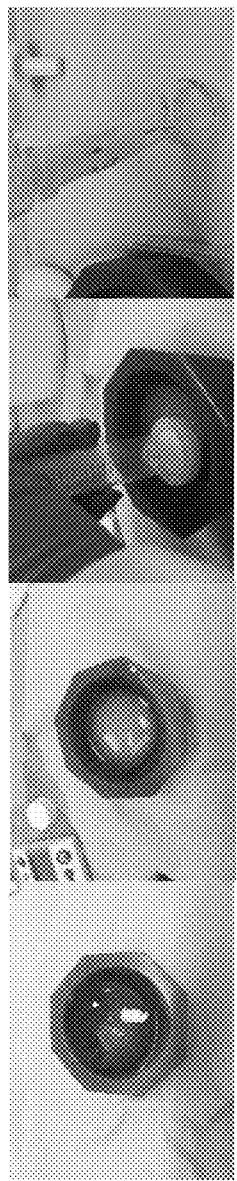

Fig. 31A
Fig. 31B
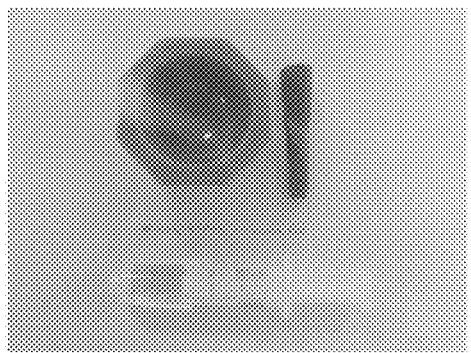
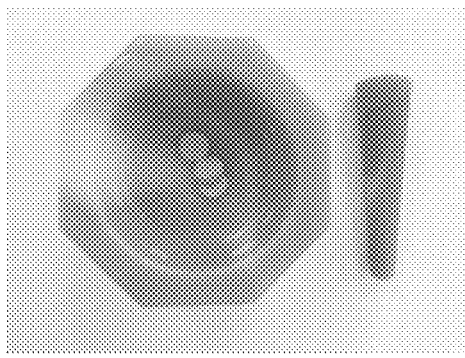
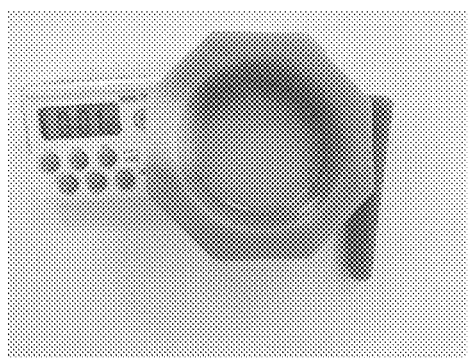
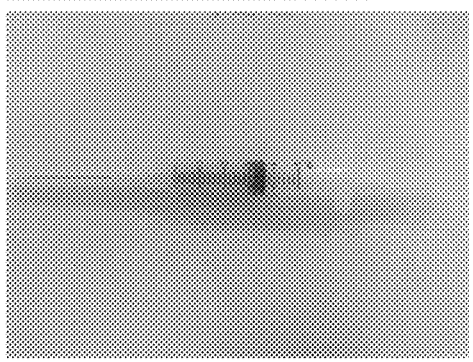
Fig. 31C
Fig. 31D

Fig. 34A  Fig. 34B  Fig. 34C
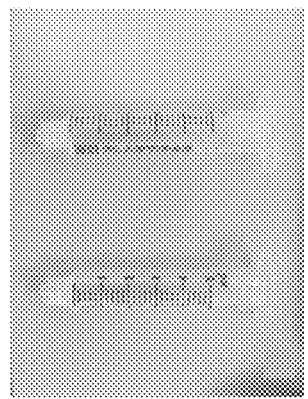 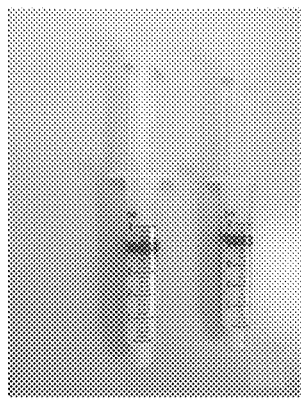 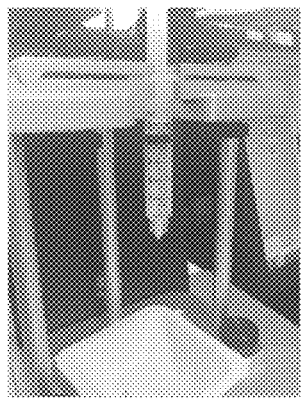
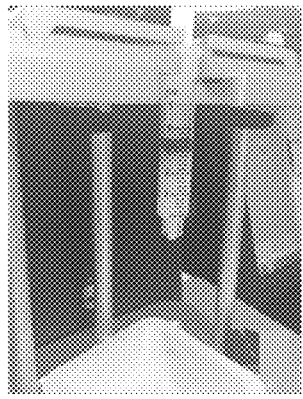 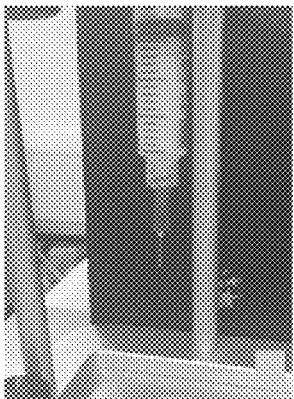 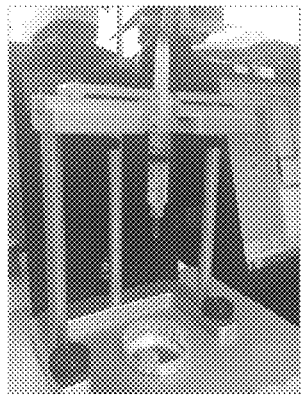
Fig. 34D  Fig. 34E  Fig. 34F

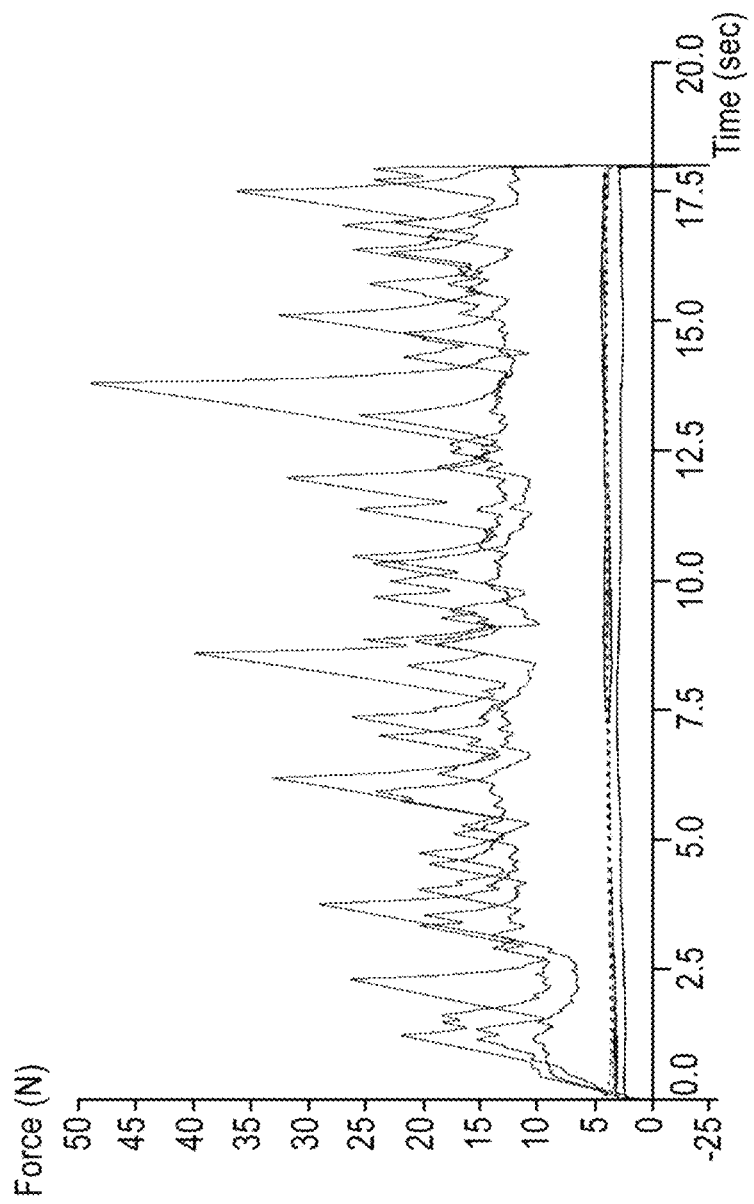

ABUSE DETERRENT FORMULATIONS OF AMPHETAMINE

RELATED APPLICATIONS

This application claims priority to, and benefit of, the U.S. Provisional Application No. 62/455,227 filed Feb. 6, 2017, the contents of which is incorporated herein by reference in its entirety.

FIELD OF THE INVENTION

The present invention relates generally to abuse deterrent oral formulations.

BACKGROUND OF THE INVENTION

The design and development of an abuse deterrent formulation involves the balance of limiting the potential for manipulation and abuse while maintaining acceptable dissolution rates and bioavailability. At the same time, the formulation must have processing characteristics that enables commercial manufacturing of dosage units. Because of these challenges, there is a need for a suitable abuse deterrent formulation.

SUMMARY OF THE INVENTION

The application provides an abuse-deterrent formulation having a medicament; and at least two excipients. The medicament, is typically a controlled substance. The controlled substance may target the central nervous system and/or may be used to treat psychiatric disorders. A preferred medicament is an amphetamine such as dextroamphetamine, or a pharmaceutically acceptable salt thereof.

In specific embodiments, the medicament has a formula

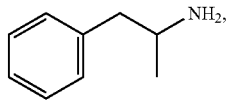

or a pharmaceutically acceptable salt thereof. In further specific embodiments, the medicament is the S enantiomer, or a pharmaceutically acceptable salt thereof.

Excipients include for example, PEG ester, poloxamer, water-soluble anionic polysaccharide, and carboxymethylcellulose.

Preferably, the abuse deterrent formulation is in the form of a capsule.

The abuse-deterrent formulation is characterized as having at least one of the properties (a) having a dissolution profile wherein at least 80% of the medicament is released in solution within 45 minutes; (b) the peak force to expel the abuse-deterrent formulation through a 26 gauge needle is about an order of magnitude greater than the peak force to inject a non-abuse deterrent formulation through a 26 gauge needle; (c) the area under the force vs. time curve to expel the abuse-deterrent formulation through a 26 gauge needle is about 4 times greater than the area under the force vs. time curve to expel a non-abuse-deterrent formulation through a 26 gauge needle, wherein the non-abuse deterrent formulation is a filtered sample; (d) the viscosity of the abuse-deterrent formulation is about three orders of magnitude greater than an non-abuse-deterrent formulation, wherein the non-abuse-deterrent formulation is an unfiltered sample; (e) a mixture of the abuse-deterrent formulation and water is not syringeable; (f) less than 5 wt % of the abuse-deterrent formulation passes through a 1 mm sieve after grinding for about 5 minutes; and (g) less than 10% of the medicament is extracted with 10 mL of water from a unit dose of the abuse-deterrent formulation.

In some embodiments, the abuse-deterrent formulation is characterized as having at least three or more of the properties (a)-(g). In some embodiments, the abuse-deterrent formulation is characterized as having at least four or more of the properties (a)-(g). In some embodiments, the abuse-deterrent formulation is characterized as having at least five or more of the properties (a)-(g). In some embodiments, the abuse-deterrent formulation is characterized as having at least six or more of the properties (a)-(g)

The abuse deterrent formulation is orally bioavailable and can have a dissolution profile similar to the profile of a non-abuse deterrent formulation. In some embodiments, the abuse-abuse deterrent formulation has a dissolution profile wherein release of the medicament in solution is complete within 45 minutes.

In some embodiments, the abuse-abuse deterrent formulation has a dissolution profile wherein at least about 93% of the medicament is released in solution within 45 minutes. In some embodiments, the abuse-abuse deterrent formulation has a dissolution profile wherein at least about 80% of the medicament is released in solution within 20 minutes. In some embodiments, the abuse-abuse deterrent formulation has a dissolution profile wherein at least about 80% of the medicament is released in solution within 10 minutes. In particular embodiments, the application discloses a dextroamphetamine-containing formulation having a dissolution profile wherein at least about 80% of the medicament is released in solution within 45 minutes.

The abuse deterrent formulation is resistant to chemical extraction or injection. For example, the formulation is resistant to chemical extraction or injection wherein an abuser extracts the active ingredient of a dosage unit, sometimes in a heated solvent, then swallows or injects the resulting mixture. For instance, combining the formulation with a solvent results in a mixture that blocks a syringe or is otherwise uninjectable. In some embodiments, the formulation forms a viscous gel with a solvent making it difficult to draw up in a syringe or expel from a syringe. In other embodiments, the amount of filtrate obtained from the attempted extraction is very little, providing the abuser with an insufficient amount of the desired active ingredient.

In some embodiments, a mixture of the abuse-deterrent formulation and water is not syringeable. In some embodiments, combining a unit dose of the abuse-deterrent formulation and water forms a gel.

In other embodiments, less than 20% of volume can be syringed from a mixture of the abuse-deterrent formulation and water. In a further specific embodiment, less than 10% of volume can be syringed from a mixture of the abuse-deterrent formulation and water. In another embodiment, less than 10% of the medicament is extracted with 10 mL from a unit dose of the abuse-deterrent formulation. In specific embodiments, the temperature of the water is about 90° C. In other embodiments, the temperature of the water is ambient temperature.

The physical properties of the abuse deterrent formulation deters abusers from grinding or cutting the formulation and then snorting the ground material. Upon grinding or a similar physical manipulation, the formulation may become sticky or have a waxy character that prevents forming an inhalable powder or snortable, even in the presence of a flow enhancer such as talc or sodium chloride.

In some embodiments, less than 5 wt % of the abuse-deterrent formulation passes through a 1 mm sieve after grinding for about 5 minutes. In specific embodiments, a flow enhancer is combined with the abuse-deterrent formulation during grinding.

In some embodiments, the abuse-deterrent formulation comprises a medicament, PEG ester, poloxamer, and water-soluble anionic polysaccharide. In specific embodiments, the PEG ester is polyoxyl stearate; the poloxamer is poloxamer 124; and the water-soluble anionic polysaccharide is gellan gum. In some embodiments, the ratio of poloxamer:polysaccharide:PEG ester is about 40:30:30.

In some embodiments, the abuse-deterrent formulation comprises medicament, PEG ester, and water-soluble anionic polysaccharide. In specific embodiments, the PEG ester is polyoxyl stearate; and the water-soluble anionic polysaccharide is gellan gum. In further specific embodiments, the ratio of PEG ester:water-soluble anionic polysaccharide is about 70:30.

In yet another embodiment, the abuse-deterrent formulation comprises medicament, PEG ester, and carboxymethylcellulose. In specific embodiments, the PEG ester is polyoxyl stearate. In further specific embodiments, the ratio of PEG ester and carboxymethylcellulose is about 70:30.

Specifically, the invention provides, an abuse-deterrent formulation, including a medicament, a poloxamer, a water-soluble anionic polysaccharide, and a PEG ester. The medicament is

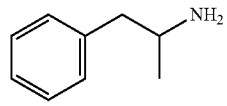

or a pharmaceutically acceptable salt thereof.

Alternatively, is the S enantiomer of amphetamine, or a pharmaceutically acceptable salt thereof.

Preferably, the medicament is dextroamphetamine, or a pharmaceutically acceptable salt thereof.

The pharmaceutically acceptable salt is for example, a sulfate salt. The unit dose of the medicament in the formulation is from about 10 mg to about 50 mg. Preferably, the abuse deterrent formulation is in the form of a capsule. The capsule is for example gelatin, The poloxamer is poloxamer 124. The water-soluble anionic polysaccharide is gellan gum.

The PEG ester is polyoxyl stearate. The ratio of poloxamer:water-soluble anionic polysaccharide:PEG ester is about 40:30:30.

The abuse-deterrent formulation included 33-43 wt % of poloxamer; 24-32 wt % of water-soluble anionic polysaccharide; and 24-32 wt % of PEG ester. The ratio of poloxamer 124:gellan gum:polyoxyl stearate is about 40:30:30.

The poloxamer is Kollisolv P124, the water-soluble anionic polysaccharide is Kelcogel CGHA, and the PEG ester is Gelucire 48/16.

A preferred formulation includes

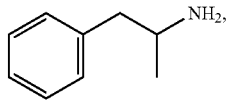

or the S enantiomer (dextroamphetamine), or a pharmaceutically acceptable salt as thereof as the medicament, poloxamer 124, gellan gum, and polyoxyl stearate where the ratio of poloxamer 124:gellan gum:polyoxyl stearate is about 40:30:30. In some embodiments, the poloxamer 124 is Kollisolv P124, the gellan gum is Kelcogel CGHA, and the polyoxyl stearate is Gelucire 48/16.

In some embodiments, at least 80% of the medicament is released in solution within 45 minutes.

In some aspects when the abuse-deterrent formulation and water is combined a gel is formed.

In other aspects, at least 80% of the medicament is released in solution within 45 minutes.

In a further aspect, the peak force to expel the abuse-deterrent formulation through a 26 gauge needle is at least 8 times greater than a peak force to inject a non-abuse deterrent formulation through a 26 gauge needle.

The area under a force vs. time curve to expel the abuse-deterrent formulation through a 26 gauge needle is at least 3 times greater than the area under a force vs. time curve to expel a non-abuse-deterrent formulation through a 26 gauge needle, wherein the non-abuse deterrent formulation is a filtered sample.

In yet another aspect the viscosity of the abuse-deterrent formulation is at least about 2 orders of magnitude greater than a non-abuse-deterrent formulation.

In a further aspect, a mixture of the abuse-deterrent formulation and water is not syringeable.

In another aspect, less than 5 wt % of the abuse-deterrent formulation passes through a 1 mm sieve after grinding for about 5 minutes.

In some aspects, less than 10% of the medicament is extracted with 10 mL of water from a unit dose of the abuse-deterrent formulation.

Also included in the invention are methods of treating attention-deficit/hyperactivity disorder (ADHD) in a subject by administering an abuse deterrent formulation of the invention, where the medicament is an amphetamine such as dextroamphetamine.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 21A-D shows images of syringing prototype 2 in ambient water with an 18 G needle (FIG. 21A) and a 0.2 μm nylon filter (FIG. 21B), cotton wool (FIG. 21C), and a cigarette filter (FIG. 21D).

FIG. 31A-D shows images on manipulating the LD, 10 mL of potable water was added to 3 full tablets (FIG. 31A) and (FIG. 31B). These were ground together to form a powder in liquid which could be loaded into a syringe (FIG. 31D).

(FIG. 32A) the equivalent of six 10 mg ADAIR capsules was aliquoted into a mortar and pestle (FIG. 32B) 20 mL of potable water was added (FIG. 32C) the material was ground until homogenous, and (FIG. 32D) a viscous, gel-like material was produced.

(FIG. 33A) and (FIG. 33B) 20 mL of water was added to a mortar and pestle, (FIG. 33C) these were ground together until homogenous, and (FIG. 33D) a viscous product was obtained.

FIG. 34A-F shows images illustrating set up for the texture analyzer syringability method development. The plungers were removed from 5 mL syringes and these were back-filled with the material under test (FIG. 34A). Air bubbles were then removed to achieve a homogenous fill of >3 mL (FIG. 34B). The filled syringe was loaded into the texture analyzer syringe testing rig (FIG. 34C). The plunger was set to 3 mL (FIG. 34D). The needle was attached (FIG. 34E and FIG. 34F). The test was carried out, moving the forces required to move the syringe plunger from the 3 mL to the 2 mL mark (9 mm), expelling material from the needle (where appropriate).

FIG. 53 is a graph showing texture analysis profiles of water (blue), filtered manipulated LD (red) and manipulated ADAIR (green) for depressing the plunger of Leur-Lok 5 mL syringe by 9 mm, whilst expelling the material under test through a 26 G needle.

DETAILED DESCRIPTION OF THE INVENTION

Figure 1:
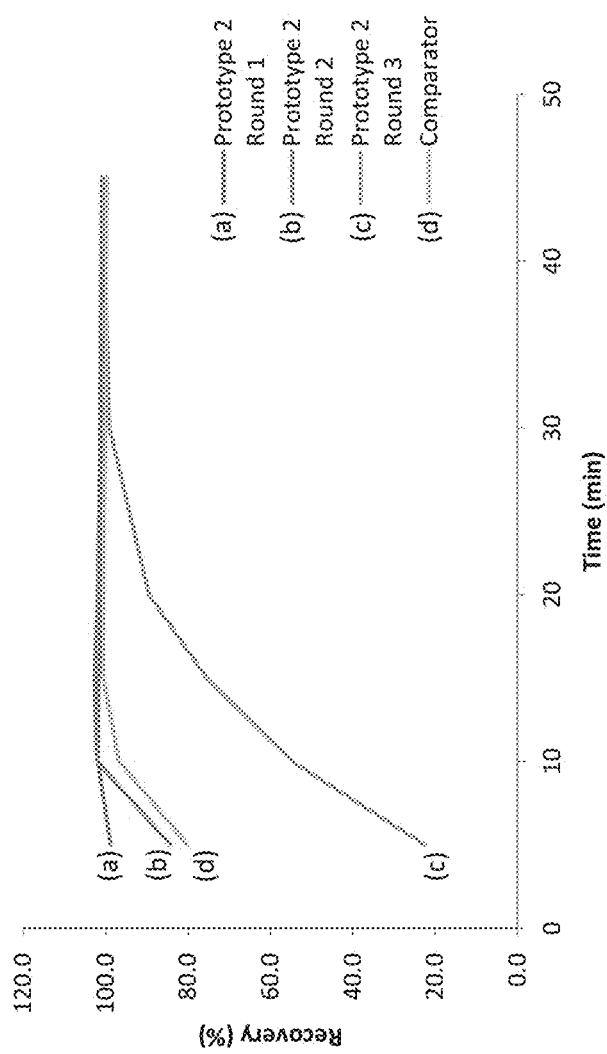
FIG. 1 shows dissolution profiles for Prototype 2.

The invention provides an abuse-deterrent formulation that is an immediate release formulation and has various barriers to abuse. In particular, the formulation deters abuse by preventing insufflation of a drug by crushing, cutting or grinding. The formulation also deters abuse by injection through barriers against syringeability. At the same time, the formulation is compatible with commercial manufacturing processes for making unit dosages.

The abuse deterrent formulation contains a medicament, which is typically a controlled substance. The controlled substance may target the central nervous system and/or may be used to treat psychiatric disorders such as ADHD. Preferred controlled substance include amphetamines such as dextroamphetamine. Also included in the invention or methods of treating ADHD in a subject by administering the an abuse deterrent formulation containing amphetamines such as dextroamphetamine. The subject is a pediatric subject. Alternatively, the subject is an adult.

In specific embodiments, the medicament has a formula

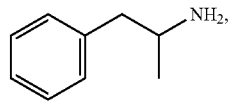

or a pharmaceutically acceptable salt thereof. In further specific embodiments, the medicament is the S enantiomer, or a pharmaceutically acceptable salt thereof.

The unit dosed of the medicament, e.g., amphetamine or dextroamphetamin is between about 10-50 mg. For example, the unit dose is 5 mg, 10 mg, 15 mg, 20 mg, 25 mg, 30 mg, 35 mg, 40 mg, 45 mg, or 50 mg.

The formulation contains one or more excipients. The excipients are selected to prevent abuse of the medicament.

Suitable abuse deterrent excipients may display one or more of the following properties. high melting point excipients resistant to heating and that prevent injecting; taste modifiers which prevent covert administration, snorting and dose dumping; water insolubles that are resistant to extraction and that prevent drink adulteration; waxy excipients that prevent snorting; viscosity modifiers resistant to dissolution and that prevent injecting and dose dumping; low density excipients that prevent drink adulteration; and dyes that disclose abuse of the pharmaceutical medicament.

Exemplary excipients include for example thermosoftening pharmaceutical bases including waxes, poloxamers, macrogol glycerides, PEGs, glycerol monooleates or monostearates, PEG esters such as polyoxyl stearate, hydrogenated or partially hydrogenated glycerides and hard fats such as beeswax, poloxamer 188 poloxamer 124, Gelucires™ polyethylene 6000, glycerol monostearate, hydrogenated palm kernel oil, hydrogenated cottonseed oil, Softisan™ 138, Gelucire 40/01™, hexadecan-1-ol; Thixotropes such as fumed silica and pulverised attapulgite and viscosity modifiers such as hydroxyl propyl methyl cellulose or Gellan Gum™ to increase viscosity or the standard pharmaceutical or food grade oils such as fractionated coconut oil, soybean oil etc to decrease viscosity.

Preferably, the abuse deterrent excipients include a poloxamer, a water-soluble anionic polysaccharide and a PEG ester. Preferably, the poloxamer is poloxamer 124 such as Kollisolv. Preferably, the water soluble anionic polysaccharide is gellan gum such as Kecogel CGHA. Preferably, the PEG ester is polyoxyl stearate such as Gelucire 48/16.

The abuse deterrent formulation may be in a capsule form, such as a hard shell liquid filled capsule. For example, the capsule comprises gelatin. Alternatively, the capsule comprises hydroxypropyl methylcellulose (HPMC), pullalan or other hard shell material.

The formulations of the invention are resistant to chemical extraction or injection, wherein an abuser extracts the active ingredient of a dosage unit, sometimes in a heated solvent, then swallows or injects the resulting mixture. For instance, combining the formulation with a solvent results in a mixture that blocks a syringe or is otherwise uninjectable. In other aspects, the formulations forms a viscous gel with a solvent making it difficult to draw up in a syringe or expel from a syringe. Alternatively, the amount of filtrate obtained from the attempted extraction is very little, providing the abuser with an insufficient amount of the desired active ingredient.

In some embodiments, a mixture of the abuse-deterrent formulation and water is not syringeable. In some embodiments, combining a unit dose of the abuse-deterrent formulation and water forms a gel.

An important aspect of the invention is that the medicament of the abuse deterrent formulation performs normally when taken as intended. For example, the abuse deterrent formulation is orally bioavailable and has a dissolution profile similar to the profile of a non-abuse deterrent formulation of the same medicament. In some embodiments, the abuse-abuse deterrent formulation has a dissolution profile wherein release of the medicament in solution is complete within 45 minutes.

Additionally, the abuse deterrent formulation is resistant to chemical extraction or injection, wherein an abuser extracts the active ingredient of a dosage unit, sometimes in a heated solvent, then swallows or injects the resulting mixture. For instance, combining the formulation with a solvent results in a mixture that blocks a syringe or is otherwise uninjectable. In some embodiments, the formulation forms a viscous gel with a solvent making it difficult to draw up in a syringe or expel from a syringe. In other embodiments, the amount of filtrate obtained from the attempted extraction is very little, providing the abuser with an insufficient amount of the desired active ingredient.

The physical properties of the abuse deterrent formulation deters abusers from grinding or cutting the formulation and then snorting the ground material. Upon grinding or a similar physical manipulation, the formulation may become sticky or have a waxy character that prevents forming an inhalable powder or snortable, even in the presence of a flow enhancer such as talc or sodium chloride.

Accordingly, the invention provides an abuse-deterrent formulation having a medicament; and at least two excipients selected from PEG ester, poloxamer, water-soluble anionic polysaccharide, and carboxymethylcellulose. In some aspects, the abuse-deterrent formulation is characterized as having at least one of the properties selected from the group consisting of (a) having a dissolution profile wherein at least 80% of the medicament is released in solution within 45 minutes; (b) the peak force to expel the abuse-deterrent formulation through a 26 gauge needle is about an order of magnitude greater than the peak force to inject a non-abuse deterrent formulation through a 26 gauge needle; (c) the area under the force vs. time curve to expel the abuse-deterrent formulation through a 26 gauge needle is about 4 times greater than the area under the force vs. time curve to expel a non-abuse-deterrent formulation through a 26 gauge needle, wherein the non-abuse deterrent formulation is a filtered sample; (d) the viscosity of the abuse-deterrent formulation is about three orders of magnitude greater than an non-abuse-deterrent formulation, wherein the non-abuse-deterrent formulation is an unfiltered sample; (e) a mixture of the abuse-deterrent formulation and water is not syringeable; (f) less than 5 wt % of the abuse-deterrent formulation passes through a 1 mm sieve after grinding for about 5 minutes; and (g) less than 10% of the medicament is extracted with 10 mL of water from a unit dose of the abuse-deterrent formulation.

Milling

Milling or grinding involves the physical break down of a dosage unit and can be accomplished by a variety of methods. Grinding can be accomplished by force on a dosage unit by a solid surface. for instance, the use of a coffee grinder, a mortar and pestle, or a spoon and a bowl may be involved. In some embodiments, the abuse-deterrent formulation becomes a paste when ground.

In some embodiments, the disclosed abuse-deterrent formulation resists the formation of an inhalable powder even when ground with a flow enhancer. Non-limiting examples of a flow enhancer, include talc and sodium chloride. In some embodiments, the abuse-deterrent formulation becomes a paste when ground with a flow enhancer.

In some embodiments, less than 5 wt %, 4 wt %, 3 wt %, 2 wt %, 1 wt %, or 0.5 wt % of the abuse-deterrent formulation passes through a 1 mm sieve after grinding for about 5 minutes.

In some embodiments, less than 5 wt %, 4 wt %, 3 wt %, 2 wt %, 1 wt %, or 0.5 wt % of the abuse-deterrent formulation passes through a 0.5 mm sieve after grinding for about 5 minutes.

In some embodiments, more than 95 wt %, 96 wt %, 97 wt %, 98 wt %, or 99 wt % of the abuse deterrent formulation is retained on a 1 mm sieve after grinding for about 5 minutes. In some embodiments, more than 95 wt %, 96 wt %, 97 wt %, 98 wt %, or 99 wt % of the abuse deterrent formulation is retained on a 0.5 mm sieve after grinding for about 5 minutes.

Extraction/Syringability

In some embodiments, the combination of the abuse-deterrent formulation and a solvent results in a difficult to filter mixture. In some embodiments, combination of the abuse-deterrent formulation and a solvent is not syringable because it forms a viscous gel.

In some embodiments, the formulation is combined with about 10 mL of solvent, and less than 50%, less than 40%, less than 30%, less than 20%, or less than 10% of the resulting solution is drawn up into a syringe.

In some embodiments a unit dose of the formulation is extracted with about 10 mL of solvent and less than 50%, less than 40%, less than 30%, less than 20%, or less than 10% of the medicament is recovered. In some of the foregoing embodiments, one or more unit doses of the abuse-deterrent formulation is extracted with 10 mL of solvent.

In particular embodiments, the solvent is water, or 40% ethanol solution. Water may be ambient temperature, boiling, or may have a temperature of 90-95° C.

In some of the foregoing embodiments, the solution is filtered while being drawn into the syringe. Examples of filters include a 0.2 micron filter, a 5.0 micron wheel filter, a wad of cotton, a cigarette filter tip, a cotton swab, a tampon, a fabric material, or any common material available in a household capable of being used as a filter.

The syringe may be attached to a 26, 23, or 18 gauge needle. A 26 gauge needle is the preferred size for abusers since it is easy to insert and remove, is more comfortable to use, and results in less damage to the skin and blood vessels. Larger bore needles may not be as comfortable to use, and may damage the skin and blood vessels especially after repeated usage. In specific embodiments, the abuse-deterrent formulation is expelled through a 26 gauge needle.

In specific embodiments, less than 10% of dextroamphetamine is recovered from extraction of a unit dose of the abuse deterrent formulation with 10 mL of ambient temperature water. In specific embodiments, extraction of a unit dose of the abuse deterrent formulation with 10 mL of heated water is not filterable. In specific embodiments, less than 15%, less than 10% or less than 5% of dextroamphetamine is extracted from a unit dose of the abuse deterrent formulation with 10 mL of water. In specific embodiments, less than 15%, less than 10% or less than 5% of dextroamphetamine is extracted and filtered from a unit dose of the abuse deterrent formulation with 10 mL of water.

In specific embodiments, less than 5%, or less than 2.5% of dextroamphetamine is extracted from a unit dose of the abuse deterrent formulation with 5 mL of water using a 26 gauge needle. In specific embodiments, less than 20% or less than 15% of dextroamphetamine is extracted from a unit dose of the abuse deterrent formulation with 5 mL of water using a 23 gauge needle. In specific embodiments, less than 30% or less than 25% of dextroamphetamine is extracted from a unit dose of the abuse deterrent formulation with 5 mL of water using a 20 gauge needle. In specific embodiments, less than 50% of dextroamphetamine is extracted from a unit dose of the abuse deterrent formulation with 5 mL of water using an 18 gauge needle.

In specific embodiments, less than 5% of dextroamphetamine is extracted from a unit dose of the abuse deterrent formulation with 5 mL of 90-95° C. water using a 26 or 23 gauge needle. In specific embodiments, less than 20% of dextroamphetamine is extracted from a unit dose of the abuse deterrent formulation with 5 mL of 90-95° C. water using a 20 or 18 gauge needle.

In specific embodiments less than 25% of dextroamphetamine is extracted and filtered from a unit dose of the abuse deterrent formulation with 5 mL of 0.2% sodium bicarbonate solution. In specific embodiments, a unit dose of the abuse-deterrent formulation comprising dextroamphetamine forms an unfilterable gel with 2 mL of 0.2% sodium bicarbonate solution. In specific embodiments, a unit dose of the abuse-deterrent formulation comprising dextroamphetamine forms an unfilterable gel with 5 mL of 0.2% sodium bicarbonate solution.

Application of Heat

In some instances, abusers of a controlled substance heat the substance and inject the resulting liquid. Injection of the melted abuse deterrent formulation disclosed in this application is unsuccessful because the drug product solidifies when removed from a heat source and drawn into the needle.

In some embodiments, the abuse deterrent formulation has a melting temperature above 60° C. In some embodiments, the abuse deterrent formulation has a melting temperature of about 70° C.

Dissolution

Descriptions of investigating the dissolution profile of abuse-deterrent formulations and comparators, and dissolution profile data may be found in the Examples.

In some embodiments, the abuse-abuse deterrent formulation has a dissolution profile wherein at least about 93% of the medicament is released in solution within 45 minutes. In some embodiments, the abuse-abuse deterrent formulation has a dissolution profile wherein at least about 80% of the medicament is released in solution within 20 minutes. In some embodiments, the abuse-abuse deterrent formulation has a dissolution profile wherein at least about 80% of the medicament is released in solution within 10 minutes. In particular embodiments, the invention provides a dextroamphetamine-containing formulation having a dissolution profile wherein at least about 80% of the medicament is released in solution within 45 minutes.

Viscosity

Viscosity measurements may be used to characterize the abuse-deterrent formulation and provides valuable comparative data to non-abuse-deterrent formulations. Such descriptions of methodology and data relating to manipulated formulations are provided in the Examples. A higher viscosity of a manipulated formulations indicates increased difficulty in injecting, making it more difficult for an abuser to use the formulation. In some embodiments, the viscosity of the abuse-deterrent formulation is about three orders of magnitude greater than a non-abuse deterrent formulation. In some embodiments, the viscosity of the abuse-deterrent formulation is about two orders of magnitude greater than a non-abuse deterrent formulation. In some of the foregoing embodiments, the viscosity of the non-abuse deterrent formulation is measured from an unfiltered sample.

In some embodiments, the viscosity of the abuse-deterrent formulation is greater than 6000 cP. In some embodiments, the viscosity of the abuse-deterrent formulation is greater than 5000 cP. In some embodiments, the viscosity of the abuse-deterrent formulation is greater than 4000 cP. In some embodiments, the viscosity of the abuse-deterrent formulation is greater than 3000 cP.

Injectability

The peak force and the area under the force vs. time curve to expel abuse-deterrent formulations may be used to characterize the formulation and provide valuable comparative data to a non-abuse-deterrent formulation. Descriptions of methodology to compare the required forces to expel abuse-deterrent formulations and comparators are described in Example 4. The data demonstrates that a greater force is required to expel manipulated abuse-deterrent formulation through a 26 gauge needle than that for the manipulated filtered comparator through the same needle size. This supports a more abuse-deterrent formulation with respect to syringeability than a comparable non-abuse deterrent formulation.

In some embodiments, the average peak force to expel the abuse deterrent formulation through a 26 gauge needle is about 10 times, 9 times, 8 times, 7 times, 6 times, 5 times, or 4 times greater than the average peak force to inject a non-abuse deterrent formulation through a 26 gauge needle. In some embodiments, the average peak force to expel the abuse deterrent formulation through a 26 gauge needle is greater than 40 N, 35 N, 30 N, 25 N, or 20 N.

In some embodiments, the average area under the force vs. time curve to expel the abuse-deterrent formulation through a 26 gauge needle is 4 times, 3, times, or 2 times greater than the average area under the force vs. time curve to expel a non-abuse-deterrent formulation through a 26 gauge needle. In some embodiments, the average area under the force vs. time curve is greater than 250 Ns, 200 Ns, 150 Ns, or 100 Ns.

Specific Formulations

In some embodiments, the abuse-deterrent formulation comprises at least two excipients selected from Kollisolv P124, Kolliphor EL, Kolliphor RH40, Tween 20, Gelucire 48/16, Gelucire 44/14, Super refined Corn Oil, Aerosil 200, Luxura, Xantural 75, Kelcogel CGHA, CMC 7H3SF, Methocel A4CP, Gelatin Type B 220 Bloom, and PEG6000.

In some embodiments, the abuse-deterrent formulation comprises a medicament, PEG ester, poloxamer, and water-soluble anionic polysaccharide. In specific embodiments, the PEG ester is polyoxyl stearate; the poloxamer is poloxamer 124; and the water-soluble anionic polysaccharide is gellan gum. In some embodiments, the ratio of poloxamer:polysaccharide:PEG ester is about 40:30:30.

In some embodiments, the abuse-deterrent formulation comprises medicament, PEG ester, and water-soluble anionic polysaccharide. In specific embodiments, the PEG ester is polyoxyl stearate; and the water-soluble anionic polysaccharide is gellan gum. In further specific embodiments, the ratio of PEG ester:water-soluble anionic polysaccharide is about 70:30.

In yet another embodiment, the abuse-deterrent formulation comprises medicament, PEG ester, and carboxymethylcellulose. In specific embodiments, the PEG ester is polyoxyl stearate. In further specific embodiments, the ratio of PEG ester and carboxymethylcellulose is about 70:30.

In some embodiments, the abuse-deterrent formulation comprises a medicament, Kollisolv P124, Kelcogel CGHA, and Gelucire 48/16. In further specific embodiments, the ratio of Kollisolv P124, Kelcogel CGHA, and Gelucire 48/16 is about 40:30:30.

In some embodiments, the abuse-deterrent formulation comprises a medicament, Gelucire 48/16 and Kelcogel CGHA. In further specific embodiments, the ratio of Gelucire 48/16 and Kelcogel CGHA is about 70:30.

In some embodiments, the abuse-deterrent formulation comprises a medicament, Kolliphor EL and CMC 7H3SF. In further specific embodiments, the ratio of Kolliphor EL and CMC 7H3SF is about 70:30.

In any of the foregoing embodiments, the medicament is a controlled substance. The controlled substance may target the central nervous system and/or may be used to treat psychiatric disorders. Preferably, the controlled substance is an amphetamine, or a pharmaceutically acceptable salt thereof. More preferably, the medicament is dextroamphetamine, or a pharmaceutically acceptable salt thereof.

The use of the term "about" includes and describes the value or parameter per se. For example, "about x" includes and describes "x" per se. In some embodiments, the term "about" when used in association with a measurement, or used to modify a value, a unit, a constant, or a range of values, refers to variations of +/−5%, or +/−10%.

"Amphetamine" as used herein has the formula:

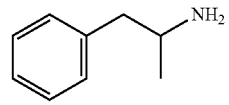

"Dextroamphetamine" as used herein is the S enantiomer of amphetamine and has the formula:

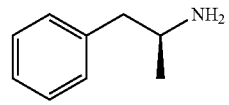

In some embodiments, the abuse-deterrent formulation comprises one or more medicaments selected from the group consisting of dextroamphetamine saccharate, amphetamine aspartate, dextroamphetamine sulfate, and amphetamine sulfate. In some embodiments, the abuse-deterrent formulation comprises two medicaments selected from the group consisting of dextroamphetamine saccharate, amphetamine aspartate, dextroamphetamine sulfate, and amphetamine sulfate. In some embodiments, the medicament is dextroamphetamine sulfate.

In preferred embodiments the abuse-deterrent formulation, includes a medicament, a poloxamer, a water-soluble anionic polysaccharide, and a PEG ester. The medicament is

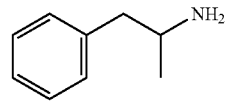

or a pharmaceutically acceptable salt thereof.

Alternatively, is the S enantiomer of amphetamine, or a pharmaceutically acceptable salt thereof such as dextroamphetamine. The unit dose of the medicament in the formulation is from about about 10 mg to about 50 mg, The abuse deterrent formulation is in the form of a capsule. The capsule is for example gelatin. The poloxamer is poloxamer 124. The water-soluble anionic polysaccharide is gellan gum. The PEG ester is polyoxyl stearate. The ratio of poloxamer: water-soluble anionic polysaccharide:PEG ester is about 40:30:30. The abuse-deterrent formulation included 33-43 wt % of poloxamer; 24-32 wt % of water-soluble anionic polysaccharide; and 24-32 wt % of PEG ester. The ratio of poloxamer 124:gellan gum:polyoxyl stearate is about 40:30:30. The poloxamer is Kollisolv P124, the water-soluble anionic polysaccharide is Kelcogel CGHA, and the PEG ester is Gelucire 48/16.

A further preferred formulation includes

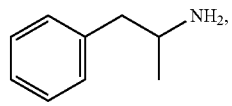

or the S enantiomer (dextroamphetamine), or a pharmaceutically acceptable salt as thereof as the medicament, poloxamer 124, gellan gum, and polyoxyl stearate where the ratio of poloxamer 124:gellan gum:polyoxyl stearate is about 40:30:30. In some embodiments, the poloxamer 124 is Kollisolv P124, the gellan gum is Kelcogel CGHA, and the polyoxyl stearate is Gelucire 48/16.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

EXAMPLES

The following examples are provided to further aid in understanding the embodiments disclosed in the application, and presuppose an understanding of conventional methods well known to those persons having ordinary skill in the art to which the examples pertain. The particular materials and conditions described hereunder are intended to exemplify particular aspects of embodiments disclosed herein and should not be construed to limit the reasonable scope thereof.

Example 1: Prototypes 1-10

The examples herein describe ten immediate release abuse deterrent formulations of dextroamphetamine sulfate.

Materials & Equipment

Excipients and Drug Substance

The excipient and manufacturer's name used in these studies are detailed in Table 1.

TABLE 1

Batch details for excipients and drug substance used in preformulation work.

| Material | Manufacturer |
|---|---|
| Kollisolv P124 | BASF |
| Kolliphor EL | BASF |

TABLE 1-continued

Batch details for excipients and drug substance used in preformulation work.

| Material | Manufacturer |
|---|---|
| Kolliphor RH40 | BASF |
| Tween 20 | Croda |
| Gelucire 48/16 | Gattefosse |
| Gelucire 44/14 | Gattefosse |
| Super refined corn oil | Croda |
| Aerosil 200 | Evonik |
| Luxura | Arthur Branwell and Co. |
| Xantural 75 | Kelco |
| Kelcogel CGHA | Kelco |
| Methocel A4C P | Colorcon |
| CMC 7H3SF | ASHLAND |
| PEG6000 | Renex |
| Dextroamphetamine Sulfate | Cambrex |

Capsule Shells

The capsule shells used for the capsule shell compatibility are detailed in Table 2.

TABLE 2

Batch details for the capsules used in capsule shell compatibility work.

| Material | Manufacturer |
|---|---|
| Conisnap size 0 white gelatin capsules | Capsugel |
| VCaps Plus size 0 white HPMC shells | Capsugel |

Banding Materials

The raw material and manufacturer's name used in these studies are detailed in Table 3.

TABLE 3

Batch details for components of banding solutions.

| Material | Manufacturer |
|---|---|
| Sterile water for irrigation | Fresenius Kabi Ltd. |
| Gelatin 220 Bloom | Gelita |
| EtOH 99% | VWR |
| Pharmacoat 603 | Shin-Etsu |

Methods

Preparation of Bulk Mixes

Prototype formulations were prepared on a 30 g scale with 5.455% w/w API (for a target dose of 30 mg per capsule). Excipient ratios are outlined in Table 4. Kolliphor RH40 was heated in an oven at 50° C. prior to dispensing. Prototypes 1, 2, 6, 7, 9 and 10 were mixed and filled at room temperature. Prototypes 3, 4 and 5 were heated to between 45-55° C. to melt the PEG and Gelucire before mixing and filling. Prototype 8 was mixed and filled at 75-85° C. Excipients were blended together by vortex mixing prior to dispensing the API. Following the API dispense, all prototypes were briefly vortex mixed again to wet the API. The prototype bulk mixes were then high shear mixed for 1 minute using a Silverson mixer.

TABLE 4

Ratio of excipients in the ten prototype formulations.

| Prototype # | Excipients |
|---|---|
| 1 | Kollisolv P124:Luxura (60:40) |
| 2 | Kollisolv P124:Kelcogel CGHA (70:30) |
| 3 | Gelucire 48/16:Kelcogel CGHA (70:30) |
| 4 | Kolliphor RH40:Kelcogel CGHA (60:40) |
| 5 | Gelucire 48/16:CMC7H3SF (60:40) |
| 6 | Kolliphor EL:Xantural 75 (60:40) |
| 7 | Kolliphor EL:CMC 7H35F (60:40) |
| 8 | Gelucire 48/16:PEG6000:Xantural 75 (20:40:40) |
| 9 | Tween 20:Aerosil 200:Kelcogel (58:2:40) |
| 10 | Corn oil:Kolliphor EL:Methocel A4CP (40:30:30) |

Prototypes 9 and 10 were adjusted with the addition of Tween 20 or corn oil, respectively, to improve handlability and filling. This resulted in sub-potent capsules.

Capsule Filling and Banding

Bulk mixes were degassed in a vacuum chamber prior to filling. Thermosoftening prototypes were degassed after heating in a fan oven. The bulk mixes were filled by syringe into gelatin and HPMC capsules at a target weight of 550 mg (±7.5%). Thermosoftening materials were kept warm using a water bath for the duration of filling. Filled capsules were banded using the appropriate banding solution (gelatin or HPMC) and left to dry on trays overnight.

Capsule Shell Compatibility Study

Following band drying, the capsules were spread onto witness paper and subjected to a vacuum challenge for 20 min at −22.5 "Hg. Any capsules found to be leaking were removed from the batch and the remainder was examined for signs of embrittlement or cracking. After providing capsules to Analytical Development, the remaining capsules from each batch were placed in amber glass jars, sealed with paraffin film and incubated in a stability cabinet at 40° C./75% RH for two weeks. After this time the capsules were equilibrated to room temperature and then examined for signs of embrittlement.

Dissolution

Preliminary dissolution tests were carried out on Prototypes 1-10 on USP Apparatus III (Table 5). Prototypes 1 and 4 were tested in triplicate. The remainder were analyzed in duplicate or singly. 2 mL samples were injected into the system without further sample preparation. The HPLC conditions for dissolution analysis involve an Agilent Eclipse XDB-C18 4.6 mm×250 mm (5 μm) column, a flow rate of 1.5 mL/min, a column temperature of 40° C., an injection volume of 100 μL, UV detection at 210 nm, room temperature autosampling, and a mobile phase of 1.1 g sodium 1-heptanesulfonate in 575:25:400 Water:Acetic Acid:Methanol at pH3.3.

TABLE 5

Dissolution method using USP apparatus III.

| | |
|---|---|
| Media: | 0.01 M Hydrochloric Acid |
| Media Volume: | 250 mL |
| Time points: | 5, 10, 15, 20, 30 and 45 minutes |
| Sample Volume: | 2 mL, injected without further sample prep |
| Dip rate: | 30 dpm |
| Mesh Screen Size: | 840 μm |
| Filtration: | 35 μm probe filters |

Viscosity

Viscosity assessments were carried out on a Brookfield DV-III Ultra Programmable Rheometer operating with Rheocalc v3.3 Build 49.0 (Brookfield Labs, 1999) and spindle CP-52. The instrument was calibrated at 25° C. with 5000 cP viscosity standard (RRM5907, batch 110514, Brookfield, expiry 10 May 2016). A suitable ramp of rotations per minute (rpm) was established prior to each measurement. Due to analytical issues related to very high viscosity, samples were analyzed at 50° C., apart from 1003/057/08 which was analyzed at 80° C.

Results and Discussion

Preparation of Bulk Mixes

The theoretical quantities, actual dispensed quantities, actual excipient ratios and subsequent capsule doses are detailed in Table 6 to Table 15 below. Following preparation, bulk mixes were each high shear mixed for 1 minute. Temperatures before and after high shear were recorded and detailed in Table 16. At the bulk mix preparation stage, Prototypes 9 and 10 were found to be too viscous to be high shear mixed effectively and so additional aliquots of Tween 20 and corn oil, respectively, were added until a processable mix was obtained. Note that the quantity of API was not adjusted at this point (22.3 and 22.9 mg per cap, respectively). Prototype 4 was also found to have very high viscosity at this point however it could still be mixed without issue and filled by syringe, and therefore the mix was not adjusted.

TABLE 6

Prototype 1 theoretical and actual components.
Kollisolv P124:Luxura 60:40

| | % (w/w) Theoretical | Quantity (g) Theoretical | Actual dispensed weight (g) | Balance ID | Actual ratio excipients (% w/w) | Potency of (% w/w) | Dose per cap (mg) |
|---|---|---|---|---|---|---|---|
| API | 5.4550 | 1.6365 | 1.6362 | EI/171 | | 5.5 | 30.0 |
| Kollisolv 124 | 56.7270 | 17.0181 | 17.0672 | EI/043 | 60.2 | | |
| Luxura | 37.8180 | 11.3454 | 11.2914 | EI/043 | 39.8 | | |
| Total | 100.0000 | 30.0000 | | | 100.0 | | |

TABLE 7

Prototype 2 theoretical and actual components.
Kollisolv P124:Kelcogel CGHA 70:30

|  | % (w/w) Theoretical | Quantity (g) Theoretical | Actual dispensed weight (g) | Balance ID | Actual ratio of excipients (% w/w) | Potency (% w/w) | Dose per cap (mg) |
|---|---|---|---|---|---|---|---|
| API | 5.4550 | 1.6365 | 1.6311 | EI/171 |  | 5.4 | 29.9 |
| Kollisolv P124 | 66.1815 | 19.85445 | 19.8186 | EI/043 | 69.9 |  |  |
| Kelcogel CGHA | 28.3635 | 8.50905 | 8.5305 | EI/043 | 30.1 |  |  |
| Total | 100.0000 | 30.0000 |  |  | 100.0 |  |  |

TABLE 8

Prototype 3 theoretical and actual components.
Gelucire 48/16:Kelcogel CGHA 70:30

|  | % (w/w) Theoretical | Quantity (g) Theoretical | Actual dispensed weight (g) | Balance ID | Actual ratio of excipients (% w/w) | Potency (% w/w) | Dose per cap (mg) |
|---|---|---|---|---|---|---|---|
| API | 5.4550 | 1.6365 | 1.6324 | EI/171 |  | 5.4 | 29.9 |
| Gelucire 48/16 | 66.1815 | 19.85445 | 19.8835 | EI/043 | 70.1 |  |  |
| Kelcogel CGHA | 28.3635 | 8.50905 | 8.4982 | EI/043 | 29.9 |  |  |
| Total | 100.0000 | 30.0000 |  |  | 100.0 |  |  |

TABLE 9

Prototype 4 theoretical and actual components.
Kolliphor RH40:Kelcogel CGHA 60:40

|  | % (w/w) Theoretical | Quantity (g) Theoretical | Actual dispensed weight (g) | Balance ID | Actual ratio of excipients (% w/w) | Potency (% w/w) | Dose per cap (mg) |
|---|---|---|---|---|---|---|---|
| API | 5.4550 | 1.6365 | 1.6335 | EI/171 |  | 5.4 | 29.9 |
| Kolliphor RH40 | 56.7270 | 17.0181 | 17.0153 | EI/043 | 59.9 |  |  |
| Kelcogel CGHA | 37.8180 | 11.3454 | 11.3702 | EI/043 | 40.1 |  |  |
| Total | 100.0000 | 30.0000 |  |  | 100.0 |  |  |

TABLE 10

Prototype 5 theoretical and actual components.
Gelucire 48/16:CMC 7H3SF 60:40

|  | % (w/w) Theoretical | Quantity (g) Theoretical | Actual dispensed weight (g) | Balance ID | Actual ratio of excipients (% w/w) | Potency (% w/w) | Dose per cap (mg) |
|---|---|---|---|---|---|---|---|
| API | 5.4550 | 1.6365 | 1.6288 | EI/171 |  | 5.4 | 29.8 |
| Gelucire 48/16 | 56.7270 | 17.0181 | 17.0637 | EI/043 | 60.0 |  |  |
| CMC 7H3SF | 37.8180 | 11.3454 | 11.3576 | EI/043 | 40.0 |  |  |
| Total | 100.0000 | 30.0000 |  |  | 100.0 |  |  |

TABLE 11

Prototype 6 theoretical and actual components.
Kolliphor EL:Xantural 75 60:40

| | % (w/w) Theoretical | Quantity (g) Theoretical | Actual dispensed weight (g) | Balance ID | Actual ratio of excipients (% w/w) | Potency (% w/w) | Dose per cap (mg) |
|---|---|---|---|---|---|---|---|
| API | 5.4550 | 1.6365 | 1.6291 | EI/171 | | 5.4 | 29.9 |
| Koliphor EL | 56.7270 | 17.0181 | 17.0294 | EI/043 | 60.0 | | |
| Xantural 75 | 37.8180 | 11.3454 | 11.3454 | EI/043 | 40.0 | | |
| Total | 100.0000 | 30.0000 | | | 100.0 | | |

TABLE 12

Prototype 7 theoretical and actual components.
Kolliphor EL:CMC 7H3SF 60:40

| | % (w/w) Theoretical | Quantity (g) Theoretical | Actual dispensed weight (g) | Balance ID | Actual ratio of excipients (% w/w) | Potency (% w/w) | Dose per cap (mg) |
|---|---|---|---|---|---|---|---|
| API | 5.4550 | 1.6365 | 1.6346 | EI/171 | | 5.4 | 29.9 |
| Kolliphor EL | 56.7270 | 17.0181 | 17.0465 | EI/043 | 60.0 | | |
| CMC 7H3SF | 37.8180 | 11.3454 | 11.3517 | EI/043 | 40.0 | | |
| Total | 100.0000 | 30.0000 | | | 100.0 | | |

TABLE 13

Prototype 8 theoretical and actual components.
Gelucire 48/16:PEG6000:Xantural 75 (20:40:40)

| | % (w/w) | Bulk mix quantity theoretical (g) | Actual dispensed weight (g) | Balance ID | ratio of excipients (%w/w) | Potency (% w/w) | Dose per cap (mg) |
|---|---|---|---|---|---|---|---|
| API | 5.4550 | 1.6365 | 1.6412 | EI/171 | | 5.5 | 30.0 |
| Gelucire 48/16 | 18.9090 | 5.6727 | 5.6639 | EI/043 | 19.9 | | |
| PEG 6000 | 37.8180 | 11.3454 | 11.3910 | EI/043 | 40.1 | | |
| Xantural 75 | 37.8180 | 11.3454 | 11.3505 | EI/043 | 40.0 | | |
| Total | 100.0000 | 30.0000 | | | 100.0 | | |

TABLE 14

Prototype 9 theoretical and actual components*.
Tween 20:Aerosil:Kelcogel (58:2:40)

| | % (w/w) Theoretical | Quantity (g) Theoretical | Actual dispensed weight (g) | Balance ID | Actual ratio of excipients (% w/w) | Potency (% w/w) | Dose per cap (mg) |
|---|---|---|---|---|---|---|---|
| API | 5.4550 | 1.6365 | 1.6382 | EI/171 | | 4.1 | 21.7 |
| Tween 20 | 54.8361 | 16.4508 | 27.9073 | EI/043 | 70.1 | | |
| Aerosil | 1.8909 | 0.5673 | 0.5684 | EI/043 | 1.4 | | |
| Kelcogel | 37.8180 | 11.3454 | 11.3493 | EI/043 | 28.5 | | |
| Total | 100.0000 | 30.0000 | | | 100.0 | | |

Note:
Additional carrier added due to processing issues. Note API potency of 4.1% and subsequent nominal lowered dose of 21.7 mg*

TABLE 15

Prototype 10 theoretical and actual components*.
Corn oil:Kolliphor EL:Methocel A4CP (40:30:30)

|  | % (w/w) Theoretical | Quantity (g) Theoretical | Actual dispensed weight (g) | Balance ID | Actual ratio of excipients (% w/w) | Potency (% w/w) | Dose per cap (mg) |
|---|---|---|---|---|---|---|---|
| API | 5.4550 | 1.6365 | 1.6353 | EI/171 |  | 4.2 | 22.9 |
| Corn oil | 37.8180 | 11.3454 | 20.6441 | EI/043 | 54.8 |  |  |
| Kolliphor EL | 28.3635 | 8.5091 | 8.5250 | EI/043 | 22.6 |  |  |
| Methocel A4CP | 28.3635 | 8.5091 | 8.5052 | EI/043 | 22.6 |  |  |
| Total | 100.0000 | 30.0000 |  |  | 100.0 |  |  |

Note:
Additional carrier added due to processing issues. Note API potency of 4.2% and subsequent nominal lowered dose of 22.9 mg*

TABLE 16

High shear temperatures.

| Prototype # | Batch number | Temperature prior to high shear (° C.) | Temperature following high shear (° C.) |
|---|---|---|---|
| 1 | 1003/057/01 | 21.5 | 31.1 |
| 2 | 1003/057/02 | 21.5 | 26.4 |
| 3 | 1003/057/03 | 49.7 | 43.1 |
| 4 | 1003/057/04 | 54.6 | 52.9 |
| 5 | 1003/057/05 | 45.3 | 42.0 |
| 6 | 1003/057/06 | 21.4 | 32.3 |
| 7 | 1003/057/07 | 21.5 | 31.7 |
| 8 | 1003/057/08 | 81.6 | 79.6 |
| 9 | 1003/057/09 | 28.8 | 30.0 |
| 10 | 1003/057/10 | 22.0 | 30.2 |

Capsule Filling and Banding

The highly viscous nature of ADFs (and the presence of surfactants) can result in challenges during degassing, particularly on bench scale equipment where stirring, heating and degassing cannot be performed in parallel. On scale up this problem is less significant in jacketed mixing vessels, which can be stirred with an applied vacuum and regulated temperature. Formulations 1, 4 and 7 were particularly challenging due to high viscosity. It is recommended that large mixing vessels (relative to the scale of the bulk mix) are used moving forward, so as to allow ample headspace for bubbles to expand and burst freely during degassing.

The formulations were filled into size 0 gelatin and HPMC capsules by hand using syringes to a target weight of 550 mg (±7.5%). It was challenging, but possible, to fill all of the formulations with this technique. Prototypes 1 and 7 proved to be more challenging and it was expected that these may not fill well on the semi-automatic Hibar capsule filling machine without modification. Prototype 4 is thermosoftening however, and although this was challenging to fill by hand, this may be easier to handle in a heated hopper.

Following filling, capsules were banded with or gelatin banding solution using a bench scale semi-automatic Qualiseal banding machine, and left to cure in ambient laboratory conditions overnight.

Dissolution

Prototypes 1-10 were subjected to the dissolution apparatus and then analyzed by HPLC at the 45 minute mark. Table 18 summarizes the initial dissolution results at 45 minutes.

Although prototype 1 samples appeared visually dissolved within 45 minutes, challenges occurred during HPLC analysis of these samples (column blockages after a few injections). A simple sample treatment of centrifuging the HPLC sample vials followed by re-injection at a higher needle height was investigated but again, the HPLC column became blocked quickly and the complete data set could not be acquired. Further HPLC method development would be required if this prototype is taken forward.

For prototype 2, 99.5% release was achieved after 45 min.

Despite residue remaining in the cylinders for prototype 3, 100.4% release was measured at 45 min.

A significant amount of foaming was observed for prototype 4, which overspilled from the dissolution apparatus and therefore quantitative data was not reported. Again, further method development would be required for these capsules if the prototype is chosen for progression, and the addition of an anti-foaming agent would be required.

For prototype 5, a significant amount of residue remained at the end of the dissolution test, and low release (31.3% and 25.9%) was measured after 45 min.

Prototype 6 had low release at 45 min (59.0% and 65.5%) but some residue remained at the end of the test. It is anticipated that reducing the concentration of Xantural 75 in the formulation may reduce the persistence of the residue and improve release going forward.

Prototype 7 appeared not to have fully dissolved, with a gel-like residue remaining, but a release of 94.6% was measured at 45 min.

Poor dissolution of prototype 8 was measured after 45 min (20.3, 28.9) with a capsule-shaped plug remaining at the end of the test.

Finally, prototypes 9 and 10 were sub-potent due to the addition of further carrier excipients during compounding. When adjusting for this, release of 107.0% and 101.4% were measured for prototypes 9 an 10, respectively.

TABLE 18

Initial dissolution results for prototype formulations in gelatin shells.

| Prototype # | Release at 45 min (% Label Claim) | Observations |
|---|---|---|
| 1 | N/A | Visually fully dissolved within 45 minutes. |
| 2 | 99.5 | First breach noted at 2 minutes, at 3-4 minutes a dense suspension was noted to have formed throughout the moving cylinder. Small amounts of |

TABLE 18-continued

Initial dissolution results for prototype formulations in gelatin shells.

| Prototype # | Release at 45 min (% Label Claim) | Observations |
|---|---|---|
| | | capsule remained but visually, full dissolution had occurred by 45 minutes. |
| 3 | 100.4 | Capsule noted to be stuck to side of cylinder at 1 minute. Capsule breached at 2 minutes. At 10 minutes a large residue of capsule remained along with a fine suspension in the cylinder. Visually, at 45 minutes only a small residue of capsule remained. |
| 4 | N/A | First breach noted at 2 minutes, at 3-4 minutes a dense suspension was noted to have formed throughout the moving cylinder. Small amounts of capsule remained but visually, full dissolution had occurred by 7 minutes. Surfactant bubbling noted. |
| 5 | 31.3, 25.9 | A small amount of bubbling was observed during the test and a significant residue remained at 45 minutes. |
| 6 | 59.0, 65.5 | A small amount of bubbling was observed during the test and a gel-like residue remained at 45 minutes. |
| 7 | 94.6 | First breach noted at 2 minutes, at around 10 minutes, the capsule contents were noted to have flattened against the mesh. At 30 minutes the capsule contents appeared to be dissolved, but when the cylinder was examined at the end of the test a clear residue was noted. |
| 8 | 20.3, 28.9 | A capsule shaped residue remained at 45 minutes. |
| 9 | 107.0 | First breach noted at 2 minutes, at 3-4 minutes a dense suspension was noted to have formed throughout the moving cylinder. Small amounts of capsule remained but visually, full dissolution had occurred by 7 minutes. Surfactant bubbling noted. |
| 10 | 101.4 | First breach noted at 2 minutes, visually. Complete dissolution appeared to have occurred by 10 minutes. |

Viscosity

Preliminary viscosity measurements were attempted for all ten prototype formulations. Viscosity testing of formulations was carried out at 50° C. rather than 25° C. due to very viscous nature of samples. Prototype 8 was examined at 80° C. due to presence of PEG6000.

In general, the prototypes were found to display shear-thinning properties (reduced viscosity on increased applied shear), which is typical of ADFs. Prototype 1 displayed very high viscosity compared to the rest of the samples which were analyzed, and could only be examined over a very small range of low speeds (Table 19). Prototypes 2 and 3 displayed viscosities in a similar order of magnitude to each other, over a similar speed ramp (Table 20 and 21). Prototypes 8 and 9 had similar viscosities to 2 and 3 at the high end of the speed ramp (Table 23 and 24), but with a greater viscosity than 2 and 3 at low rpm, suggesting higher viscosity on standing, with a greater degree of thinning upon the application of shear. The viscosity of prototype 6 remained higher than 2, 3, 6 and 9 for the duration of the speed ramp (Table 22).

Prototypes 4 and 7 proved challenging to analyze, and a suitable method could not be established with the small volume of sample available. Prototype 4 was grainy, with low cohesive properties, meaning it lost its fluid characteristics easily upon attempts at analysis. Prototype 7 was very excessively viscous and it is anticipated that this would need to be addressed by modification of the excipient ratios in the next round of development. An insufficient amount of prototype 5 remained after capsule filling to carry out the viscosity assessment on this prototype. Finally, prototype 10 proved challenging to analyze. More extensive method development and a larger sample size would be required to obtain useful rheological data on prototype 10.

TABLE 19

Prototype 1 speed ramp rheology results.

| Step | Viscosity (cP) | Speed (rpm) | Torque (%) |
|---|---|---|---|
| 1 | 7352202.0 | 0.01 | 74.1 |
| 2 | 3671140.0 | 0.02 | 74.0 |
| 3 | 2437504.6 | 0.03 | 73.7 |
| 4 | 1818206.5 | 0.04 | 73.3 |
| 5 | 2381280.0 | 0.03 | 72.0 |
| 6 | 3507427.0 | 0.02 | 70.7 |
| 7 | 6925556.0 | 0.01 | 69.8 |

TABLE 20

Prototype 2 speed ramp rheology results.

| Step | Viscosity (cP) | Speed (rpm) | Torque (%) |
|---|---|---|---|
| 1 | 4709.64 | 7.50 | 35.6 |
| 2 | 3175.04 | 15.00 | 48.0 |
| 3 | 2742.88 | 22.50 | 62.2 |
| 4 | 2387.89 | 30.00 | 72.2 |
| 5 | 2632.64 | 22.50 | 59.7 |
| 6 | 2877.38 | 15.00 | 43.5 |
| 7 | 3651.30 | 7.50 | 27.6 |

TABLE 21

Prototype 3 speed ramp rheology results.

| Step | Viscosity (cP) | Speed (rpm) | Torque (%) |
|---|---|---|---|
| 1 | 6330.24 | 5.00 | 31.9 |
| 2 | 4613.73 | 10.00 | 46.5 |
| 3 | 4028.33 | 15.00 | 60.9 |
| 4 | 3715.79 | 20.00 | 74.9 |
| 5 | 3995.26 | 15.00 | 60.4 |
| 6 | 4613.73 | 10.00 | 46.5 |
| 7 | 6032.58 | 5.00 | 30.4 |

TABLE 22

Prototype 6 speed ramp rheology results.

| Step | Viscosity (cP) | Speed (rpm) | Torque (%) |
|---|---|---|---|
| 1 | 51594.40 | 0.50 | 26.0 |
| 2 | 37405.94 | 1.00 | 37.7 |
| 3 | 32808.75 | 1.50 | 49.6 |
| 4 | 29617.17 | 2.00 | 59.7 |
| 5 | 27543.47 | 2.50 | 69.4 |
| 6 | 26359.45 | 3.00 | 79.7 |
| 7 | 26511.58 | 2.50 | 66.8 |
| 8 | 27285.50 | 2.00 | 55.0 |
| 9 | 28575.36 | 1.50 | 43.2 |
| 10 | 31452.74 | 1.00 | 31.7 |
| 11 | 38497.36 | 0.50 | 19.4 |

TABLE 23

Prototype 8 speed ramp rheology results.

| Step | Viscosity (cP) | Speed (rpm) | Torque (%) |
|---|---|---|---|
| 1 | 10021.22 | 1.00 | 10.1 |
| 2 | 5671.65 | 7.33 | 41.9 |
| 3 | 4833.98 | 13.67 | 66.6 |
| 4 | 4365.68 | 20.00 | 88.0 |
| 5 | 4536.39 | 13.67 | 62.5 |
| 6 | 5048.98 | 7.33 | 37.3 |
| 7 | 7441.50 | 1.00 | 7.5 |

TABLE 24

Prototype 9 speed ramp rheology results.

| Step | Viscosity (cP) | Speed (rpm) | Torque (%) |
|---|---|---|---|
| 1 | 16272.08 | 1.00 | 16.4 |
| 2 | 6335.91 | 7.00 | 44.7 |
| 3 | 4327.52 | 13.00 | 56.7 |
| 4 | 3806.91 | 19.00 | 72.9 |
| 5 | 3278.23 | 25.00 | 82.6 |
| 6 | 3655.47 | 19.00 | 70.0 |
| 7 | 3900.11 | 13.00 | 51.1 |
| 8 | 5442.93 | 7.00 | 38.4 |
| 9 | 22126.06 | 1.00 | 22.3 |

TABLE 25

Prototype 10 speed ramp rheology results.

| Step | Viscosity (cP) | Speed (rpm) | Torque (%) |
|---|---|---|---|
| 1 | 5873.82 | 5.00 | 29.6 |
| 2 | 756.16 | 23.75 | 18.1 |
| 3 | 431.90 | 42.50 | 18.5 |
| 4 | 239.75 | 61.25 | 14.8 |
| 5 | 182.32 | 80.00 | 14.7 |
| 6 | 226.79 | 61.25 | 14.0 |
| 7 | 410.89 | 42.50 | 17.6 |
| 8 | 994.29 | 23.75 | 23.8 |
| 9 | 4722.87 | 5.00 | 23.8 |

Summary

Following collation and examination of the results above, prototype formulations 2, 3, 6, 7 and 10 was selected for progression to the next round of development. This decision was reached on review of the early dissolution results and also the ease of handling during mixing, degassing and filling.

Additionally, it was attempted to keep the scope of gelling agents as wide as possible within this reduced number of lead prototypes. For this reason, prototype 6 was included as it allowed the inclusion of the viscosity modifier Xantural 75 (which was not present in prototypes 2, 3, 7 or 10) in the next round of optimisation. Selecting Prototype 9, which had a more favourable dissolution profile at this stage, would have used Kelcogel which was already present in Prototype 3 and had been selected for progression. It was anticipated that there was scope for reducing the concentration of viscosity modifier in Prototype 6 in order to obtain the desired release profile, whilst still maintaining a high viscosity and abuse deterrent characteristics.

It is recommended that the ratios of excipients in prototype 7 be adjusted to lower the percentage of viscosity modifier (CMC 7H3SF) in the formulation. Although the release of this prototype was not as favourable as some of the others, the very high viscosity suggests that there is scope for reduce the concentration of CMC 7H3SF, which would also be expected to result in a more favourable dissolution profile.

Example 2: Prototypes 2, 3, 6, 7, and 10

This example demonstrates the optimization and testing of five lead prototypes 2, 3, 6, 7, and 10.

Prototypes 2, 3, 6, 7 and 10 were prepared on a larger scale (100 g, 50 g, and 30 g) to allow a better appreciation of how the formulation handles and fills. These prototype formulations have been subject to dissolution testing and extraction in 3 mL 40% EtOH (to simulate preparation in a small volume for injection) and an initial assessment of solvent extractability (related to abuse deterrent behaviour). The results of these assessments were then used to optimise the formulations by adjusting ratios of excipients and/or substituting excipients to achieve the desired dissolution and abuse deterrence profiles.

From the results of these tests, a lead round from each prototype was then subject to a short stage of abuse deterrence testing. Based on the results of these tests, along with observations of the formulations and their handle-ability/process-ability, Prototype 2 (round 3), Prototype 3 (round 1) and Prototype 7 (round 1) have demonstrated superior dissolution and ADF characteristics.

Prototypes, 6 and 10 were excluded from further development at this stage. Prototype 6 failed to achieve complete dissolution within 45 min in any round of development, and the lead (Round 3) was significantly syringe-able/extractable in ambient water. Improving dissolution in this formulation would likely result in loss of remaining ADF characteristics unless extensive reformulation was carried out. Despite promising dissolution, Prototype 10 proved challenging to handle. It was observed to separate upon standing and the most favourable (Round 3) was extensively syringe-able/extractable in hot and ambient water. Attempts to improve handle-ability by reducing content of viscosity modifier to would likely result in increased extraction potential.

Materials & Equipment
Raw Materials

The raw material (RRM) number, manufacturer's batch number, manufacturer and expiry date for the materials used in these studies are detailed in Table 28.

TABLE 26

Batch details for excipients and drug substance used during this study.

| Material | Function | Manufacturer |
|---|---|---|
| Kollisolv P124 | Carrier | BASF |
| Kolliphor EL | Carrier | BASF |
| Gelucire 48/16 | Carrier | Gattefosse |
| Super refined Corn Oil | Carrier | Croda |
| Xantural 75 | Viscosity modifier | Kelco |
| Kelcogel CGHA | Viscosity modifier | Kelco |
| CMC 7H3 SF | Viscosity modifier | ASHLAND |
| Methocel A4CP | Viscosity modifier | Dow |
| Gelatin Type B 220 Bloom | Banding solution component | Gelita |
| Sterile water for Irrigation | Banding solution component | Flowfusor |
| Absolute ethanol | Banding solution component | Fisher |
| Pharmacoat 603 | Banding solution component | Shin-Etsu |
| Size 0 Conisnap white/white (gelatin) | Capsule shell | Capsugel |

TABLE 26-continued

Batch details for excipients and drug substance used during this study.

| Material | Function | Manufacturer |
|---|---|---|
| Size 0 VCaps Plus white/white (HPMC) | Capsule shell | Capsugel |
| Ethanol absolute (Emprove) | Extraction solvent | Merck |
| MilliQ water | Extraction solvent | Filtered in-house on day of use |
| Dextroamphetamine Sulfate | API | Cambrex |

Methods

Preparation of Bulk Mixes

Three rounds of prototypes 2, 3, 6, 7 and 10 were prepared during the optimisation phase. See Table 27 for excipient ratios for each round of optimisation. The excipients were dispensed into labelled amber glass jars and high shear mixed until visually homogenous. The temperature before and after high shear mixing was recorded for each formulation, along with mixing time. The Gelucire 48/16 was dispensed as a solid at room temperature (pelletised) and allowed to melt in an oven at 60° C. before mixing. Once homogenous, the mixes were degassed in a vacuum chamber prior to filling into capsules.

TABLE 27

Excipient ratios used in rounds 1, 2 and 3 for the five prototypes.

| | Excipient | Round 1 | Round 2 | Round 3 |
|---|---|---|---|---|
| Prototype 2 | Kollisolv P124 | 70 | 65 | 40 |
| | Kelcogel CGHA | 30 | 35 | 30 |
| | Gelucire 48/16 | N/A | N/A | 30 |
| Prototype 3 | Gelucire 48/16 | 70 | 75 | 55 |
| | Kelcogel CGHA | 30 | 25 | 25 |
| | Miglyol 812N | N/A | N/A | 20 |
| Prototype 6 | Kolliphor EL | 60 | 50 | 50 |
| | Xantural 75 | 40 | 30 | 15 |
| | Miglyol 812N | N/A | 20 | 35 |
| Prototype 7 | Kolliphor EL | 70 | 50 | 40 |
| | CMC 7H3SF | 30 | 30 | 30 |
| | Miglyol 812N | N/A | 20 | 30 |
| Prototype 10 | Corn oil | 51 | 18 | 47.5 |
| | Kolliphor EL | 22 | N/A | N/A |
| | Kolliphor RH40 | N/A | 60 | 29 |
| | Methocel A4CP | 27 | 22 | 22 |
| | Aerosil 200 | N/A | N/A | 1.5 |

Capsule Filling and Banding

Bulk mixes were filled into capsule shells at a target fill weight of 550 mg (±7.5%) with a target dose of 30 mg dextroamphetamine sulfate. Round 1 formulations were prepared at 100 g scale and filled using the Hibar semi-automatic capsule filling machine. The round 1 formulations were filled half into gelatin and half into HPMC capsules.

Formulations from rounds two and three were filled exclusively into gelatin capsule shells. Round 2 formulations were prepared at 30 g scale and round 3 formulations at 50 g scale. Round 2 and 3 formulations were filled into capsules by hand, using a syringe body with no needle. Initially a third Round of prototype 2 was not carried out, however this was performed later following review of available data.

Multiple gelatin banding solutions and HPMC banding solutions were used during this study, prepared as per SOP-MAN-0513. These were used to apply a band to the cap/body join of the filled capsules using a benchtop Qualiseal banding machine and left to cure overnight. Following band drying, capsules were spread onto witness paper and subject to vacuum testing for 20 min at <−7.4 "Hg. Any capsules found to leak were removed from the batch. In all cases of leaking, this was a result of a flaw in the banding resulting from formulation contamination on the outside of the capsule body during hand-filling, and was not a function of the formulation itself.

Dissolution

Dissolution was carried out on all prototype formulations from each round, using USP Apparatus III dissolution bath (n=6). The dissolution conditions used are outlined in Table 28 and the analytical reagents used are outlined in Table 29. The mobile phase was prepared by dissolving 1.1 g of Sodium-1-heptanesulfonate in 575 mL of UHQ Water. 25 mL of dilute glacial acetic acid (prepared by diluting 14 mL acetic acid in 100 mL UHQ Water) and 400 mL of methanol were added and pH was adjusted to pH 3.3±0.1 using glacial acetic acid. The API working standard was prepared by dissolving 8 mg Dextroamphetamine Sulfate in 150 mL of dissolution media and sonicating for 10 min before making up to 250 mL.

TABLE 28

Dissolution conditions

| Parameter | Equipment/Setting |
|---|---|
| Dissolution apparatus | USP apparatus III (EI/415) |
| Filter type | 40/35 μm probe filter |
| Medium type | 0.01M HCl |
| Medium volume | 250 mL |
| Sample times | 5, 10, 15, 20, 30 and 45 minutes |
| Sample volume | 2 mL (filter not replaced) |
| Vessel temperature | 37° C. ± 0.5° C. |
| Dip rate | 30 dips per minute |
| Mesh screen size | 840 μm |

TABLE 29

Reagents used for dissolution

| Reagent | Grade |
|---|---|
| UHQ water | UHQ |
| Acetic acid glacial | ARG grade |
| Methanol | HPLC grade |
| Hydrochloric acid | ARG |
| Sodium-1-HeptaneSulfonate 1-Heptanesulphonic Acid Sodium Salt | HPLC grade |
| Dextroamphetamine Sulfate | USP |

Extraction

A brief extraction assessment was carried out on one capsule from each batch. The capsule was crushed using a mortar and pestle then ground with 2 mL 40% EtOH at room temperature for 5 minutes. The resultant material was transferred into a scintillation vial and a further 1 mL of solvent (total 3 mL) was used to rinse the mortar and pestle into the vial. This was shaken at room temperature for 120 minutes an ambient shaking table before being passed through a 0.45 μm syringe filter. Any filtrate produced was collected and passed to analytical development for quantification of API by HPLC.

For the sample preparation, 15 mL of diluent was added and shaken thoroughly by hand before filtering through a 0.45 μm syringe filter. 3 mL of the resulting filtrate was then made to volume into a 25 mL volumetric flask with diluent.

For the HPLC analysis, mobile phase A was prepared by dissolving 5 mL of Trifluoroacetic Acid in 900 mL of water before adjusting to pH of 2.2 (±0.1) with ammonium hydroxide. Acetonitrile (100 mL) was then added and mixed. The solution was allowed to equilibrate to room temperature before use. The HPLC conditions are detailed in Table 30 and the HPLC gradient method used is detailed in Table 31. Finally, the reagents used are detailed in Table 32.

TABLE 30

HPLC conditions used for extraction test

| Parameter | Equipment/Setting |
|---|---|
| Column | Phenomenex Prodigy C18 150 mm × 3.0 mm (5 μm) |
| Flow rate | 0.7 mL/min |
| Injection volume | 20 μL |
| Column temperature | 40° C. |
| UV detection | 257 nm |
| Mobile phase A | TFA: Water: Acetonitrile 90/0.5/10 v/v/v (pH2.2) |
| Mobile phase B | 100% Acetonitrile |
| Typical retention time | Approximately 6-7 min |
| Run time | 30 min |

TABLE 31

HPLC gradient for analysis of extraction samples.

| Time (min) | % A | % B |
|---|---|---|
| 0 | 100 | 0 |
| 15 | 65 | 35 |
| 20 | 0 | 100 |
| 22 | 0 | 100 |
| 23 | 100 | 0 |
| 30 | 100 | 0 |

TABLE 32

Reagents used for analysis of extraction samples

| Reagent | Grade |
|---|---|
| UHQ water | UHQ |
| Trifluoroacetic acid | LC/MS |
| Ammonium Hydroxide | ARG 35% |
| Acetonitrile | HPLC grade |
| Dextroamphetamine Sulfate | USP |

Short ADF Screen

The ADF screen included evaluating (1) the ability of the prototypes to be physically manipulated into a form suitable for insufflation, (2) the amount of API chemically extracted, (3) the syringable volume, and (4) the volume of dilution for syringability. The acceptance criteria for the testing are described in Table 33.

TABLE 33

Acceptance criteria for short ADF screen.

| Test | Description | Pass Criteria |
|---|---|---|
| Physical | The percentage passing through the sieve | ≤30% |
| Chemical Extraction | The quantity extracted | ≤30% |
| Syringeability | The quantity syringe-able/extracted | ≤30% |
| Syringeability | The volume of dilution for syringeability | >10 mL |

Syringeability. For syringeability testing, where the sample could not be drawn into the syringe using a cotton wool filter, a cigarette filter was used for the second preparation. If the cigarette filter was unsuccessful, no filter was used and an attempt was made to draw the sample into the syringe barrel in the absence of a filter or needle, before attaching a needle and attempting to expel the contents into a volumetric flask for analysis. Analysis by HPLC carried out as per the extraction method detailed above.

Physical manipulation. Samples were prepared for insufflation. Capsules were frozen in a domestic freezer and then ground in a domestic coffee grinder before attempting to pass the ground material through a sieve (106 μm) by gravity and weighing the material which passed through.

Capsule Shell Compatibility Assessment with Gelatin and HPMC Shells

Twenty capsules from each of the first round batches were packed into amber glass jars and sealed with parafilm. These jars were then placed in a stability cabinet (40° C./75% RH) for two weeks. Following the required storage period, the capsules were removed and examined visually for signs of gross incompatibility.

Results

Preparation of Bulk Mixes, Capsule Filling and Capsule Banding

Details of dispensed quantities for the first round of prototypes are outlined in Table 34 to Table 38. Following review of the dissolution and initial extraction data, these were adjusted for second and third rounds of preparation (see Table 39 to Table 43 for Round 2; see Table 44 to Table 48 for Round 3). The original planned ratio has been detailed in the first line of each table, with the actual excipient ratio included in the last column to account for any adjustments that had to be made during preparation for handle-ability. Temperatures of mixes before and after high shearing, where available, are recorded in Table 49.

Following banding and curing, all capsules were subject to a vacuum test to remove any leaking capsules. All leaking capsules were examined, and the leaks were found to be a result of poor band adherence, due to contamination of outside of capsule shell with formulation. This is common in technical scale manufactures, due to the level of manual handling required at this scale. All of the round 1 prototypes were subject to a physical examination and no signs of capsule embrittlement were present at t=0.

TABLE 34

Dispensed quantities for Prototype 2 Round 1
Kollisolv P124:Kelcogel CGHA 70:30 PROTOTYPE 2 ROUND 1

| | % (w/w) | Bulk mix quantity theoretical (g) | Actual dispensed weight (g) | Balance ID | Actual excipient ratio |
|---|---|---|---|---|---|
| API | 5.4550 | 5.4550 | 5.4409 | EI/171 | |
| Kollisolv P124 | 66.1815 | 66.1815 | 66.16 | EI/77 | 69.99 |
| Kelcogel CGHA | 28.3635 | 28.3635 | 28.37 | EI/77 | 30.01 |
| Total | 100.0000 | 100.0000 | | | |

TABLE 35

Dispensed quantities for Prototype 3 Round 1
Gelucire 48/16:Kelcogel CGHA 70:30 PROTOTYPE 3 ROUND 1

|  | % (w/w) | Bulk mix quantity theoretical (g) | Actual dispensed weight (g) | Balance ID | Actual excipient ratio |
|---|---|---|---|---|---|
| API | 5.4550 | 5.4550 | 5.4438 | EI/171 |  |
| Gelucire 48/16 | 28.3635 | 28.3635 | 66.14 | EI/77 | 70.00 |
| Kelcogel CGHA | 66.1815 | 66.1815 | 28.35 | EI/77 | 30.00 |
| Total | 100.0000 | 100.0000 |  |  |  |

TABLE 36

Dispensed quantities for Prototype 6 Round 1
Kolliphor EL:Xantural 75 60:40 PROTOTYPE 6 ROUND 1

|  | % (w/w) | Bulk mix quantity theoretical (g) | Actual dispensed weight (g) | Balance ID | Actual excipient ratio |
|---|---|---|---|---|---|
| API | 5.4550 | 5.4550 | 5.4412 | EI/171 |  |
| Koliphor EL | 56.7270 | 56.7270 | 56.74 | EI/77 | 60.02 |
| Xantural 75 | 37.8180 | 37.8180 | 37.8 | EI/77 | 39.98 |
| Total | 100.0000 | 100.0000 |  |  |  |

TABLE 37

Dispensed quantities for Prototype 7 Round 1
Kolliphor EL:CMC 7H3SF 70:30 PROTOYPE 7 ROUND 1

|  | % (w/w) | Bulk mix quantity theoretical (g) | Actual dispensed weight (g) | Balance ID | Actual excipient ratio |
|---|---|---|---|---|---|
| API | 5.4550 | 5.4550 | 5.4753 | EI/171 |  |
| Kolliphor EL | 66.1815 | 66.1815 | 66.14 | EI/77 | 70.00 |
| CMC 7H3SF | 28.3635 | 28.3635 | 28.35 | EI/77 | 30.00 |
| Total | 100.0000 | 100.0000 |  |  |  |

TABLE 38

Dispensed quantities for Prototype 10 Round 1
Corn oil:Kolliphor EL:Methocel A4CP (54:23:23) PROTOTYPE 10 ROUND 1

|  | % (w/w) | Bulk mix quantity theoretical (g) | Actual dispensed weight (g) | Balance ID | Actual excipient ratio |
|---|---|---|---|---|---|
| API | 5.4550 | 5.4550 | 5.4531 | EI/171 |  |
| Corn oil | 51.0543 | 51.0543 | 51.05 | EI/77 | 51.27 |
| Kolliphor EL | 21.7454 | 21.7454 | 21.73 | EI/77 | 21.82 |
| Methocel A4CP | 21.7454 | 21.7454 | 26.79 | EI/77 | 26.91 |
| Total | 100.0000 | 100.0000 |  |  |  |

TABLE 39

Dispensed quantities for Prototype 2 Round 2
Kollisolv P124:Kelcogel CGHA 60:40 PROTOTYPE 2 ROUND 2

|  | % (w/w) | Bulk mix quantity theoretical (g) | Actual dispensed weight (g) | Balance ID | Actual excipient ratio |
|---|---|---|---|---|---|
| API | 5.4550 | 1.6365 | 1.6317 | EI/171 |  |
| Kollisolv P124 | 56.7270 | 17.0181 | 21.0864 | EI/7 | 65.00 |
| Kelcogel CGHA | 37.8180 | 11.3454 | 11.3542 | EI/77 | 35.00 |
| Total | 100.0000 | 30.0000 |  |  |  |

Note
additional Kollisolv required for handle-ability.

TABLE 40

Dispensed quantities for Prototype 3 Round 2
Gelucire 48/16:Kelcogel CGHA 75:25 PROTOTYPE 3 ROUND 2

|  | % (w/w) | Bulk mix quantity theoretical (g) | Actual dispensed weight (g) | Balance ID | Actual excipient ratio |
|---|---|---|---|---|---|
| API | 5.4550 | 1.6365 | 1.63106 | EI/234 |  |
| Gelucire 48/16 | 70.9088 | 21.2726 | 21.2366 | EI/043 | 74.99 |
| Kelcogel CGHA | 23.6363 | 7.0909 | 7.081 | EI/043 | 25.01 |
| Total | 100.0000 | 30.0000 |  |  |  |

TABLE 41

Dispensed quantities for Prototype 6 Round 2
Kolliphor EL:Miglyol 812N:Xantural 75 50:20:30 PROTOTYPE 6 ROUND 2

|  | % (w/w) | Bulk mix quantity theoretical (g) | Actual dispensed weight (g) | Balance ID | Actual excipient ratio |
|---|---|---|---|---|---|
| API | 5.4550 | 1.6365 | 1.6337 | EI/171 |  |
| Koliphor EL | 47.2725 | 14.1818 | 14.1108 | EI/7 | 50.00 |
| Miglyol 812N | 18.9090 | 5.6727 | 5.6443 | EI/7 | 20.00 |
| Xantural 75 | 28.3635 | 8.5091 | 8.4665 | EI/7 | 30.00 |
| Total | 100.0000 | 30.0000 |  |  |  |

TABLE 42

Dispensed quantities for Prototype 7 Round 2
Kolliphor EL:Miglyol 812N:CMC 7H3SF 50:20:30 PROTOYPE 7 ROUND 2

|  | % (w/w) | Bulk mix quantity theoretical (g) | Actual dispensed weight (g) | Balance ID | Actual excipient ratio |
|---|---|---|---|---|---|
| API | 5.4550 | 1.6365 | 1.6324 | EI/171 |  |
| Kolliphor EL | 47.2725 | 14.1818 | 14.14 | EI/7 | 49.80 |

TABLE 42-continued

Dispensed quantities for Prototype 7 Round 2
Kolliphor EL:Migyol 812N:CMC 7H3SF 50:20:30
PROTOYPE 7 ROUND 2

|  | % (w/w) | Bulk mix quantity theoretical (g) | Actual dispensed weight (g) | Balance ID | Actual excipient ratio |
|---|---|---|---|---|---|
| Miglyol 812N | 18.9090 | 5.6727 | 5.7011 | EI/7 | 20.08 |
| CMC 7H3SF | 28.3635 | 8.5091 | 8.5516 | EI/7 | 30.12 |
| Total | 100.0000 | 30.0000 | | | |

TABLE 43

Dispensed quantities for Prototype 10 Round 2
Corn oil:Kolliphor RH40:Methocel A4CP (20:50:30)
PROTOTYPE 10 ROUND 2

|  | % (w/w) | Bulk mix quantity theoretical (g) | Actual dispensed weight (g) | Balance ID | Actual excipient ratio |
|---|---|---|---|---|---|
| API | 5.4550 | 1.6365 | 2.2216 | EI/171 | |
| Corn oil | 18.9090 | 5.6727 | 6.74 | EI/7 | 17.48 |
| Kolliphor RH40 | 47.2725 | 14.1818 | 23.29 | EI/7 | 60.42 |
| Methocel A4CP | 28.3635 | 8.5091 | 8.52 | EI/7 | 22.10 |
| Total | 100.0000 | 30.0000 | | | |

Note
additional Kolliphor RH40 and corn oil required for handleability.

TABLE 44

Dispensed quantities for Prototype 2 Round 3
Kollisolv P124:Kelcogel CGHA:Gelucire 48/16 40:30:30
PROTOTYPE 2 ROUND 3

|  | % (w/w) | Bulk mix quantity theoretical (g) | Actual dispensed weight (g) | Balance ID | Actual excipient ratio |
|---|---|---|---|---|---|
| API | 5.4550 | 1.0910 | 1.0906 | EI/171 | |
| Kollisolv P124 | 37.8180 | 7.5636 | 7.5769 | EI/043 | 40.05 |
| Kelcogel CGHA | 28.3635 | 5.6727 | 5.6722 | EI/043 | 29.98 |
| Gelucire 48/16 | 28.3635 | 5.6727 | 5.6716 | EI/043 | 29.98 |
| Total | 100.0000 | 14.3273 | | | |

Note
this was carried out after the other prototypes

TABLE 45

Dispensed quantities for Prototype 3 Round 3
Gelucire 48/16:Kelcogel CGHA:Miglyol 50:25:20
PROTOTYPE 3 ROUND 3

|  | % (w/w) | Bulk mix quantity theoretical (g) | Actual dispensed weight (g) | Balance ID | Actual excipient ratio |
|---|---|---|---|---|---|
| API | 5.4550 | 2.7275 | 2.7195 | EI/171 | |
| Gelucire 48/16 | 51.9998 | 25.9999 | 25.99 | EI/7 | 55.02 |
| Kelcogel CGHA | 23.6363 | 11.8181 | 11.8 | EI/7 | 24.98 |
| Miglyol 812N | 18.9090 | 9.4545 | 9.45 | EI/7 | 20.00 |
| Total | 100.0000 | 50.0000 | | | |

TABLE 46

Dispensed quantities for Prototype 6 Round 3
Kolliphor EL:Miglyol 812N:Xantural 75 50:35:15
PROTOTYPE 6 ROUND 3

|  | % (w/w) | Bulk mix quantity theoretical (g) | Actual dispensed weight (g) | Balance ID | Actual excipient ratio |
|---|---|---|---|---|---|
| API | 5.4550 | 2.7275 | 2.72 | EI/171 | |
| Koliphor EL | 47.2725 | 23.6363 | 23.63 | EI/7 | 50.02 |
| Miglyol 812N | 33.0908 | 16.5454 | 16.53 | EI/7 | 34.99 |
| Xantural 75 | 14.1818 | 7.0909 | 7.08 | EI/7 | 14.99 |
| Total | 100.0000 | 50.0001 | | | |

TABLE 47

Dispensed quantities for Prototype 7 Round 3
Kolliphor EL:Migyol 812N:CMC 7H3SF 40:30:30
PROTOYPE 7 ROUND 3

|  | % (w/w) | Bulk mix quantity theoretical (g) | Actual dispensed weight (g) | Balance ID | Actual excipient ratio |
|---|---|---|---|---|---|
| API | 5.4550 | 2.7275 | 2.724 | EI/171 | |
| Kolliphor EL | 37.8180 | 18.9090 | 18.89 | EI/7 | 39.99 |
| Miglyol 812N | 28.3635 | 14.1818 | 14.17 | EI/7 | 30.00 |
| CMC 7H3SF | 28.3635 | 14.1818 | 14.13 | EI/7 | 29.91 |
| Total | 100.0000 | 50.0000 | | | |

TABLE 48

Dispensed quantities for Prototype 10 Round 3
Corn oil:Kolliphor RH40:Methocel A4CP:Aerosil 30:40:28:2
PROTOTYPE 10 ROUND 3

|  | % (w/w) | Bulk mix quantity theoretical (g) | Actual dispensed weight (g) | Balance ID | Actual excipient ratio |
|---|---|---|---|---|---|
| API | 5.4550 | 2.7275 | 2.7158 | EI/171 | |
| Corn oil | 28.3635 | 14.1818 | 30.73 | EI/7 | 47.49 |
| Kolliphor RH40 | 37.8180 | 18.9090 | 18.91 | EI/7 | 29.22 |

TABLE 48-continued

Dispensed quantities for Prototype 10 Round 3
Corn oil:Kolliphor RH40:Methocel A4CP:Aerosil 30:40:28:2
PROTOTYPE 10 ROUND 3

|  | % (w/w) | Bulk mix quantity theoretical (g) | Actual dispensed weight (g) | Balance ID | Actual excipient ratio |
|---|---|---|---|---|---|
| Methocel A4CP | 26.4726 | 13.2363 | 14.12 | EI/7 | 21.82 |
| Aerosil 200 | 1.8909 | 0.9455 | 0.95 | EI/7 | 1.47 |
| Total | 100.0000 | 50.0000 |  |  |  |

Note
additional corn oil added for handle-ability. Nominal dose of this batch adjusted to 22.15 mg and results of analyzes corrected accordingly.

TABLE 49

Temperatures before and after high shear mixing,
and duration of high shear, where recorded.

|  |  | Temp prior to high shear (° C.) | Temp following high shear (° C.) | Duration of high shear (min) |
|---|---|---|---|---|
| Prototype 2 | Round 1 | 20.6 | 38.5 | 4 |
|  | Round 2 | 23.6 | 29.4 | 3 |
|  | Round 3 | 42.4 | 30.4 | not recorded |
| Prototype 3 | Round 1 | not recorded | not recorded | 4 |
|  | Round 2 | 55.5 | 46.4 | 1.5 |
|  | Round 3 | not recorded | not recorded | 2 |
| Prototype 6 | Round 1 | 21.8 | 34.6 | 7 |
|  | Round 2 | 21.7 | 40.1 | 3 |
|  | Round 3 | not recorded | not recorded | 2 |
| Prototype 7 | Round 1 | 21.6 | 42.6 | 3.5 |
|  | Round 2 | 23.7 | 36 | 3 |
|  | Round 3 | not recorded | not recorded | 2 |
| Prototype 10 | Round 1 | 21.6 | 31.7 | 5 |
|  | Round 2 | ~50 | 47.3 | 4 |
|  | Round 3 | 20.1 | 18.9 | 2 |

Capsule Shell Compatibility Assessment with Gelatin and HPMC Shells

Following storage for two weeks in glass jars at 40° C./75% RH, the gelatin and HPMC capsules from Round 1 were removed and examined for signs of gross incompatibility. One minor leak was observed in Prototype 6 (gelatin), however on examination this was found to be from a bubble in the gelatin band, rather than any incompatibility. All other capsules were viable and there were no signs of incompatibility in either gelatin or HPMC. This assessment was included at this stage as brittle capsules had been found at the early capsule shell compatibility study. At the time of that investigation, it was anticipated that this was a result of a gross humidity deviation in the development laboratory during band drying. Results of the latest study confirm that there are no signs of incompatibility between these formulations and either gelatin or HPMC shells.

Optimisation Testing Results and Discussion
Dissolution

Dissolution profiles were obtained using a USP Apparatus III dissolution bath and are shown in FIGS. 1 to 5. The equivalent dissolution profile for the comparator (Barr 10 mg IR tablet) has been included for information. In order to obtain an appropriate dose, three tablets were placed in a gelatin shell (unbanded) to represent one 30 mg dosage form.

For Prototype 2, all rounds achieved complete release within 45 min, with a more gradual release profile for the third round, following the addition of Gelucire 48/16, a thermosoftening excipient which produced a plug which eroded more slowly in the dissolution bath, shown in FIG. 1.

Figure 2:
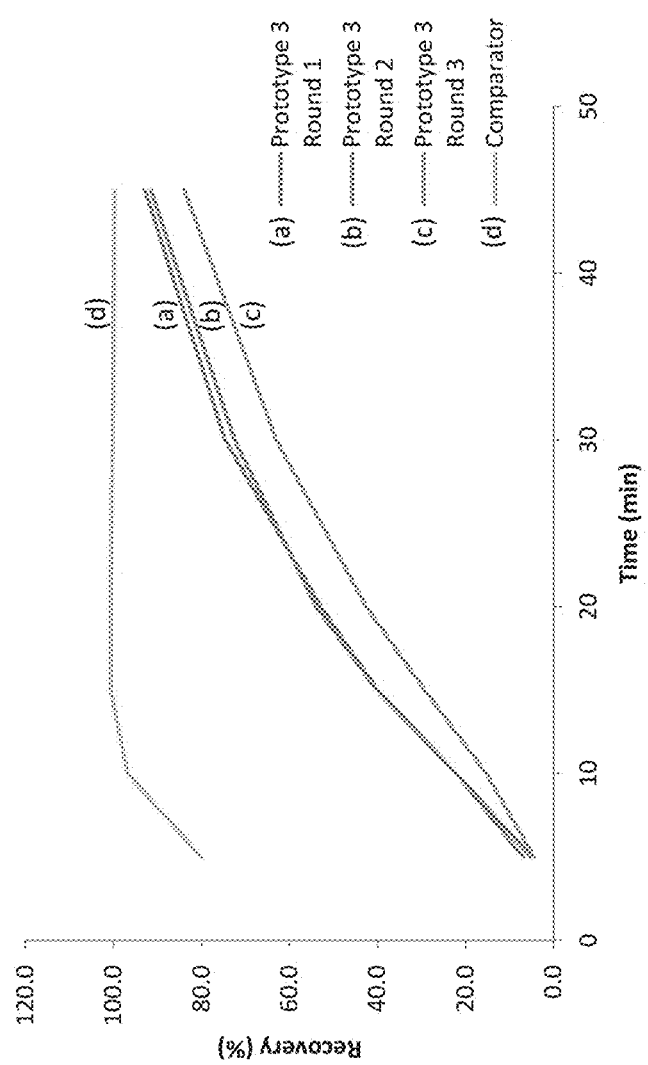
FIG. 2 shows dissolution profiles for Prototype 3.

For Prototype 3, there was not a significant difference between the dissolution profiles from the first to second rounds, following a slight reduction in Kelcogel content (92.9% release c.f 91.5%, FIG. 2). Substitution of a portion of the Gelucire 48/16 carrier excipient for Miglyol 812 resulted in a slight reduction in release (83.9%).

Figure 3:
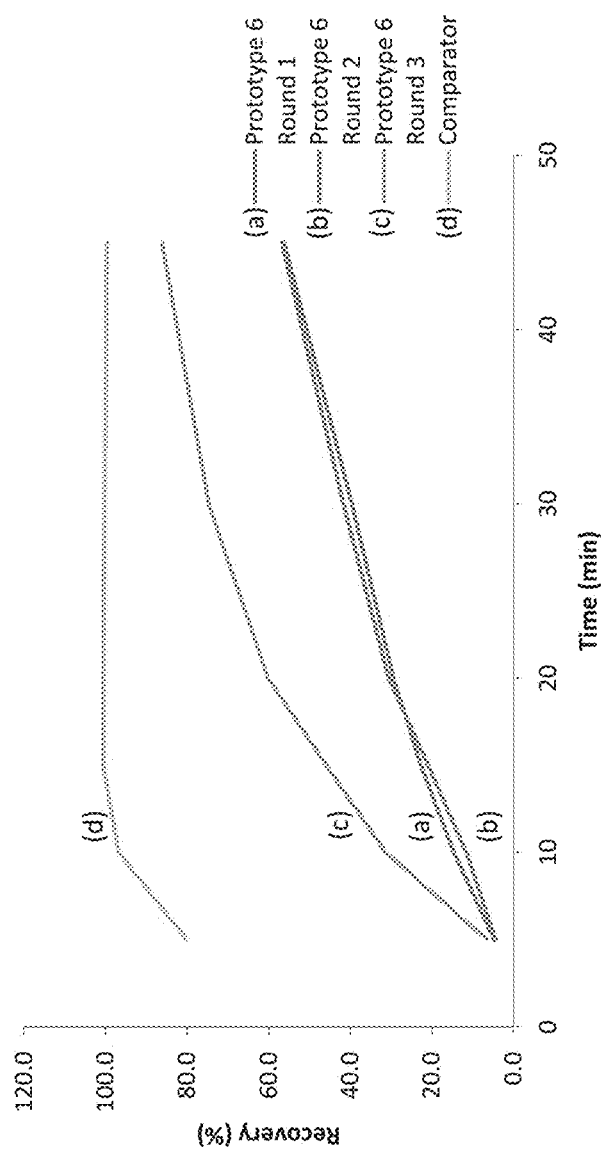
FIG. 3 shows dissolution profiles for Prototype 6.

For Prototype 6, the third round of dissolution was most favourable, with 86.2% release after 45 min, compared to 56.8% and 56.2% in the earlier rounds, see FIG. 3. More favourable dissolution was achieved by lowering the content of Xantural (xanthan gum) for Migylol 812N (a medium chain triglyceride), however dissolution at 45 min was still significantly less than the comparator, under these conditions, and further formulation optimisation would be required on this prototype.

Figure 4:
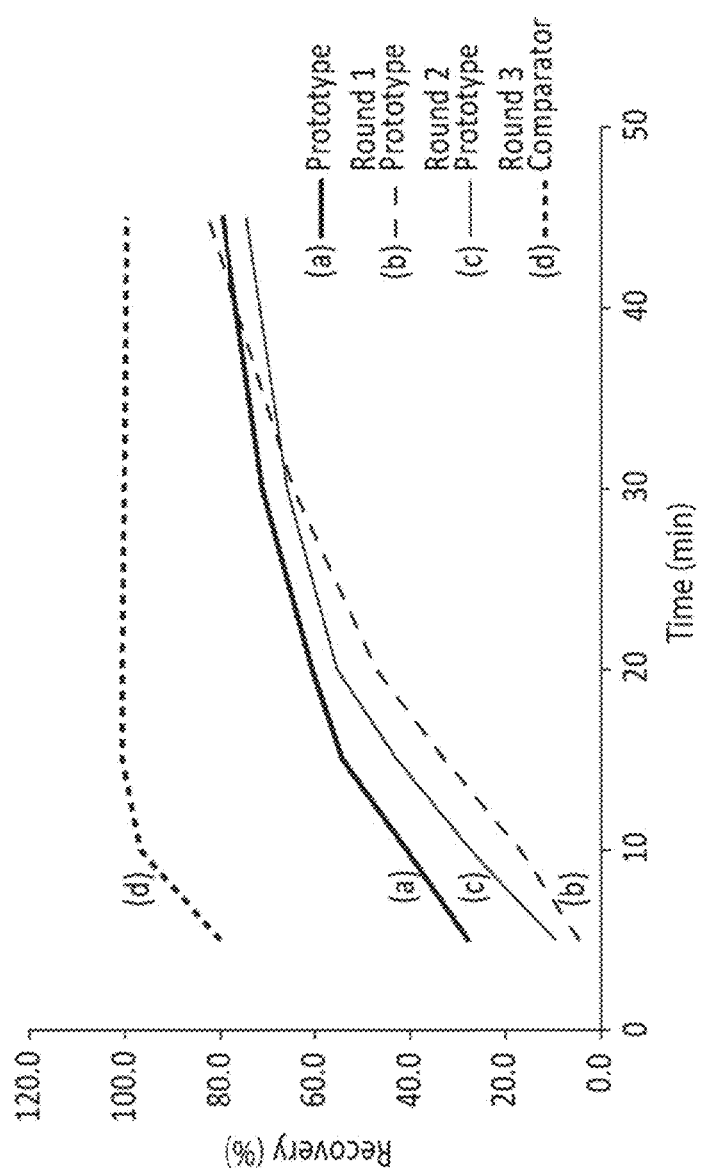
FIG. 4 shows dissolution profiles for Prototype 7.

For prototype 7, only 79.5% 82.6% and 74.4% release were achieved in 45 min for Rounds 1, 2 and 3, respectively, see FIG. 4.

Figure 5:
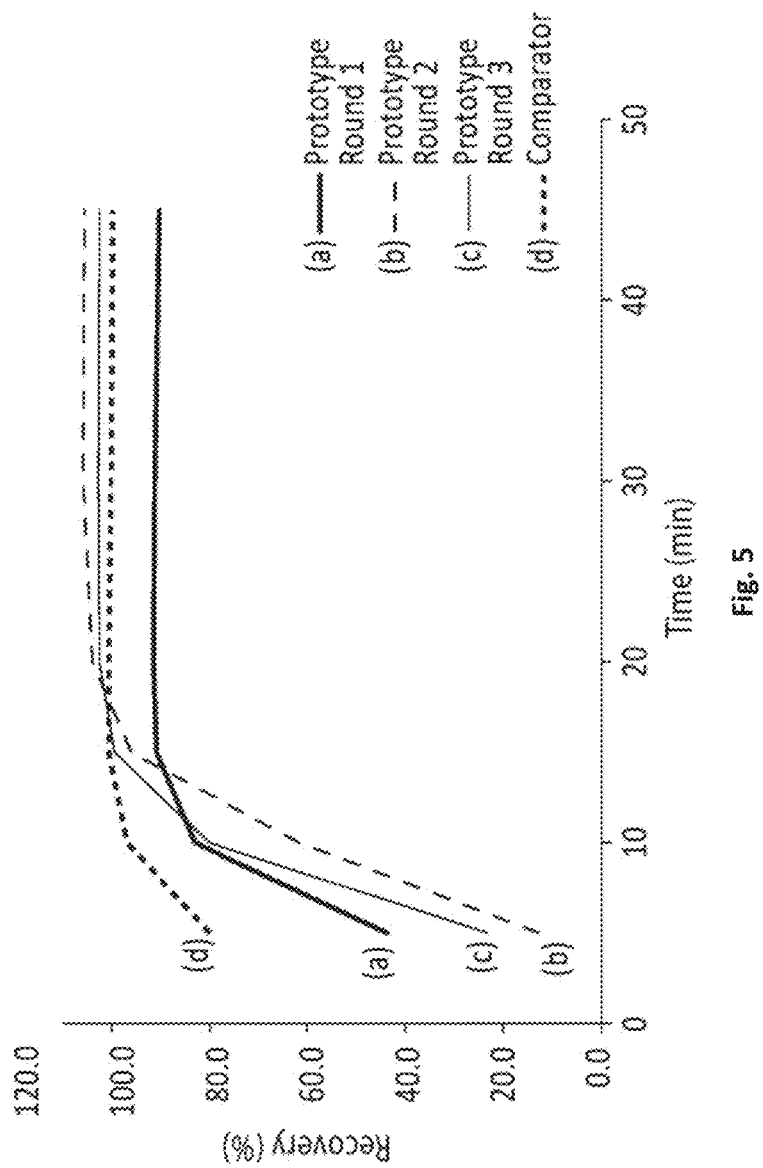
FIG. 5 shows dissolution profiles for Prototype 10.

Finally, an adjustment of Prototype 10 provided an improvement in dissolution from 90.4% in Round 1 to 105.5% in Round 2 and 102.5% in Round 3 (FIG. 5). In the second round this was achieved by reducing the content of corn oil from (a long chain triglyceride) and Methocel, and substituting Kolliphor EL for Kolliphor RH40 at a greater percentage (see Table 27 for details). In the third round, Aerosil 200 was added in an attempt to prevent sedimentation in the formulation but this resulted in handling issues and additional corn oil was added during processing. A suitable formulation viscosity was not achieved whilst maintaining a stable suspension for this prototype and further development would be required.

Extraction

In order to assess abuse deterrence potential, a small volume extraction was performed in 40% ethanol. Complete extraction was not obtained in 3 mL 40% EtOH for any of the prototypes. On manipulation, prototypes 6, 7 and 10 produced very viscous gels which were challenging to handle. Prototype 6 rapidly blocked the syringe filter and no filtrate was obtained in any round. A small amount of cloudy filtrate was obtained for Prototype 10 for rounds 1 and 2. In round 2, prototype 7 appeared to produce a small amount of filtrate, however a significant amount of API was not recovered. In round 3 only prototype 3 produced a filtrate.

Figure 6:
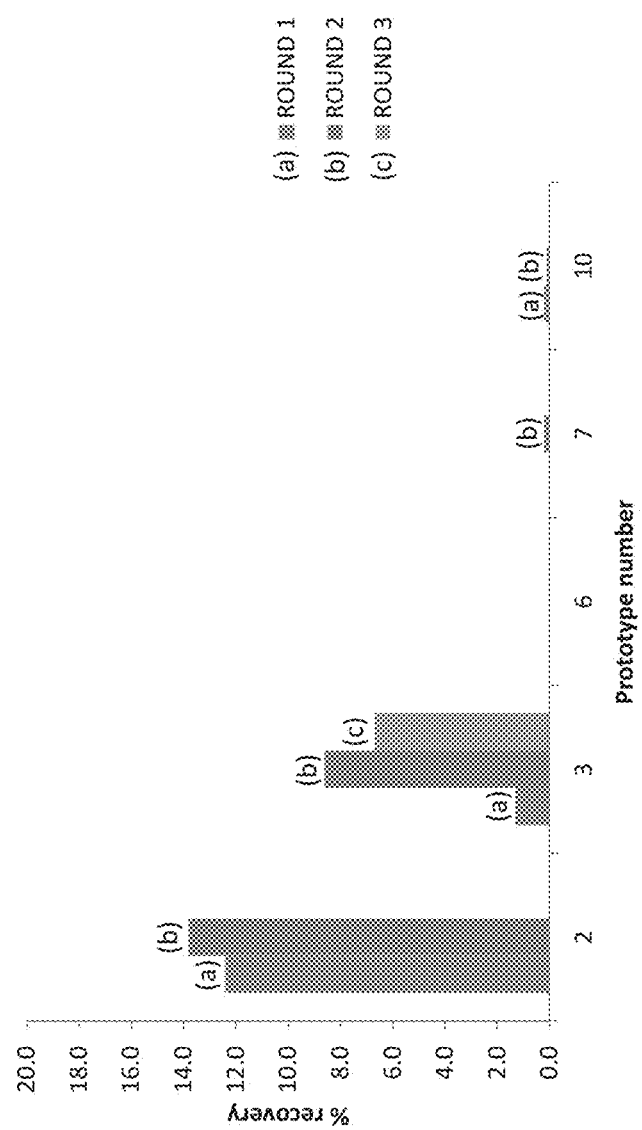
FIG. 6 shows extraction data for Prototypes 2, 3, 6, 7 and 10.

Table 50 summarizes the extraction data, which is also presented in the bar graph of FIG. 6. In general, prototypes 6, 7 and 10 demonstrated superior best performance in this test in all Rounds.

TABLE 50

Initial extraction data for Prototypes
2, 3, 6, 7 and 10 in gelatin shells (n = 1).

|  | % Recovered based on Label Content | | |
|---|---|---|---|
| Prototype | Round 1 | Round 2 | Round 3 |
| 2 | 12.4 | 13.8 | ND |
| 3 | 1.3 | 8.6 | 6.7 |
| 6 | ND | ND | ND |
| 7 | ND | 0.2 | ND |
| 10 | 0.2 | 0.1 | ND |

The extraction test was then repeated for Prototype 3 Round 1 and Prototype 7 Round 1 with a greater number of repeats (n=3), in order to assess the reliability of the original assessments prior to selection for full ADF screening. The extraction results of the repeated tests are summarized in Table 51. The repeat analyzes were consistent with the original n=1 data.

TABLE 51

Repeat extraction test on Prototype
3 and 7 Round 1 in gelatin shells (n = 3)

| | % Recovered based on Label Content | | | |
|---|---|---|---|---|
| Prototype | 1 | 2 | 3 | Average |
| Prototype 3 Round 1 | 0.6 | 2.3 | 7.0 | 3.3 |
| Prototype 7 Round 1 | ND | ND | ND | ND |

Short ADF Screen

A brief set of abuse deterrence tests were carried out on the lead formulation from each prototype to give an indication of potential ADF performance. The lead formulations tested at this stage were Prototype 2 Round 2, Prototype 3 Round 2, Prototype 6 Round 3, Prototype 7 round 3 and Prototype 10 Round 3. All prototypes passed the physical manipulation test (an indication of ease of preparation for insufflation), with less than 30% of mass passing through the sieve, suggesting an inherent resistance against preparation for insufflation with these formulations due to the liquid or semisolid nature.

A summary of the extractability/syringeability in 10 mL water is provided in Table 53. Following these results, it was decided to carry out the short ADF testing on Prototype 2 round 3, Prototype 3 round 1 and Prototype 7 Round 1, to determine if these rounds had more favourable ADF characteristics.

For the extractability/syringeability there was no measurable recovery from Prototype 2 Round 2 in ambient water (n=2), however 13.2 mg (44%) and 5.7 mg (19%) were recovered from the hot water preparations (Table 52). Moving to the third round prototype, this improved to 0.33 mg (1.1%), 0.25 mg (0.8%) and no recovery for cotton wool, cigarette filter and no filter, respectively in hot water (Table 53). The third round formulation also showed superior resistance in the 40% EtOH extraction test, c.f. rounds 1 and 2 (see section 3.3.2).

Figure 7:
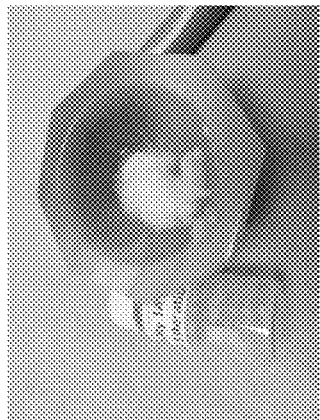
FIG. 7 shows an image of Prototype 3 (round 1) following the shaking period.
Figure 8:
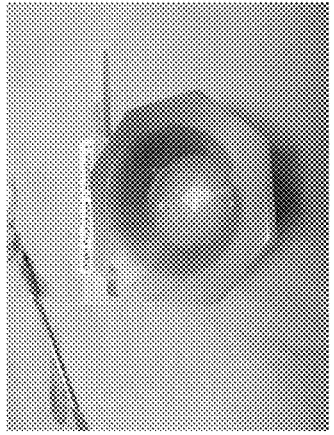
FIG. 8 shows an image of Prototype 7 (round 1) following shaking period in hot water.

For prototype 3 round 2, there was no recovery from one ambient water sample, and 1.2 mg recovery from the other. For the hot water samples, 3.7 mg and 5.8 mg were recovered (Table 52). Moving to the First Round for Prototype 3, there was no measurable recovery of API from any of the repeats in the syringeability/extraction testing (Table 53). FIG. 7 shows an image of the sample following the shaking period. This indicates favourable AD behaviour in Prototype 3 Round 1. The first round formulation also showed superior resistance in the 40% EtOH extraction test, c.f. rounds 1 and 2 (see section 3.3.2).

Results for Prototype 7 were inconsistent, with one hot water sample producing no measurable extraction, and the other hot water sample resulting in recovery of 13.8 mg. This may have been a result of inhomogeneity due to separation of the formulation. There was no measurable extraction in either of the cold water samples for this prototypes. Following this and review of dissolution data, it was decided to perform a short ADF of the first round prototype for Prototype 7. For this prototype, there was no recovery of API from ambient water preparations (n=3) and for hot water preparations, 0.5%, 0.5% and 0% of API was recovered for cotton filter, cigarette filter and no filter, respectively. This indicated good AD performance of Prototype 7 Round 1.

Prototype 10 Round 3 showed some extraction in both hot and cold water, and therefore the least AD potential in these tests.

Whilst there was no measurable extraction in the hot water preparations for Prototype 6, 15.1 mg API and 9.2 mg API were recovered in ambient water preparations making this less favourable as an AD formulation.

TABLE 52

Results of initial short ADF screening. Syringeability/extraction
carried out using 26 gauge needle and cotton wool filter.

| Sample | Physical test | Hot Water Prep 1 | Hot Water Prep 2 | Ambient water Prep 1 | Ambient water Prep 2 |
|---|---|---|---|---|---|
| Prototype 2 Round 2 | Pass | 6 mL syringed API = 13.2 mg | 2.5 mL syringed API = 5.7 mg | Not Syringeable | Not Syringeable |
| Prototype 3 Round 2 | Pass | 1 mL syringed API = 3.7 mg | 2 mL syringed API = 5.8 mg | Not Syringeable | 0.5 mL syringed API = 1.2 mg |
| Prototype 6 Round 3 | Pass | Not Syringeable | Not Syringeable | 8 mL syringed API = 15.1 mg | 6 mL syringed API = 9.2 mg |
| Prototype 7 Round 3 | Pass | 2 mL syringed API = 13.8 mg | Not Syringeable | Not Syringeable | Not Syringeable |
| Prototype 10 Round 3 | Pass | 6 mL syringed API = 7.6 mg | 2 mL syringed API = 1.6 mg | 5 mL syringed API = 7.2 mg | 6 mL syringed API = 15.0 mg |

TABLE 53

Further syringeability/extraction investigation results along with conditions under which sample was drawn into the syringe barrel

|  | Hot water | | | Ambient Water | | |
| --- | --- | --- | --- | --- | --- | --- |
|  | 1 | 2 | 3 | 1 | 2 | 3 |
| Prototype 2 Round 3 | 0.33 mg (1.1%) (cotton wool filter) | N/A (cotton wool filter) | 0.25 mg (0.8%) (cotton wool filter) | Not Syringeable (cotton wool filter) | Not Syringeable cigarette filter | Small amount drawn into syringe. No sample expelled through needle to volumetric for testing (without) needle or filter) |
| Prototype 3 Round 3 | Not Syringeable (cotton wool filter) | Not Syringeable (cigarette filter) | Small amount drawn into syringe insufficient expelled to volumetric for testing (without needle or filter) | Not Syringeable (cotton wool filter) | Not Syringeable cigarette filter | Not Syringeable (without) needle or filter) |
| Prototype 7 Round 1 | Not Syringeable (cotton wool filter) | Not Syringeable (cigarette filter) | Small amount drawn into syringe insufficient expelled to volumetric for testing (without needle or filter) | 0.14 mg (0.5%) drug syringed (cotton wool filter) | 0.14 mg (0.5%) drug syringed (cotton wool filter) | Drug syringed but no recovery by HPLC (without needle or filter) |

TABLE 54

Observations and comments from preparation of bulk mixes, capsule filling and subsequent testing.

| Prototype Number | | Summary of Results and Observations |
| --- | --- | --- |
| Prototype 2 | Round 1 | Mixed and degassed easily at room temperature. Formulation tailed on filling, alleviated with use of bottom function. Favourable dissolution but most extractable out of five prototypes in this round. Rapid dissolution. |
| | Round 2 | Kelcogel content was increased in this round to attempt to improve extractability. 60:40 formulation was too viscous to allow processing and so additional Kollisolv was added (65:35 resulted). Remained challenging to process due to viscosity. Some syringeability in hot water observed in short ADF screen. |
| | Round 3 | Gelucire 48/16 added. Handled well at elevated temperature (40-60° C.). No filtrate could be produced for 40% EtOH extraction. Minimal extraction/syringeability in hot water. No measureable extraction/syringeability in ambient water. Favourable dissolution. |
| Prototype 3 | Round 1 | Thermosoftening formulation. Filled with hopper and pump block at 55° C. Some tailing but possible to fill without bottom function. Slow dissolution. Promising syringeability/extractability performance in short ADF screen in all conditions |
| | Round 2 | Reduced quantity of Kelcogel, but this did not significantly change dissolution. Mixed, degassed and filled easily. More extractable than Round 1. |
| | Round 3 | Mixed, degassed and filled easily. Dissolution slower than Round 1 or 2. Improvement in extractability c.f Round 2 but less favourable than round 1. |
| Prototype 6 | Round 1 | Mixed easily. Degassing challenging due to proliferation of bubbles (result of surfactant content). Tailed badly even with bottom on. <60% dissolution achieved. No extraction achieved with 40% EtOH extraction. Reduce viscosity and improve dissolution by reducing Xantural content in next round and/or addition of miglyol. |
| | Round 2 | Miglyol added for improved process-ability. Mixed, degassed and filled easily. Dissolution remained poor. No extraction achieved with 40% EtOH extraction. |
| | Round 3 | Xantural content decreased and Miglyol content increased. Mixed, degassed and filled easily. No extraction achieved with 40% EtOH extraction. Improved dissolution on third round, but still only achieved ~80% release. Whilst this may be improved further with a further reduction in Xantural 75, this formulation was the most syringe-able in short ADF testing, with syringe-ablty/extractability in ambient water. Addition of a modifier which gels or swells in ambient water may improve this formulation. |
| 7 | Round 1 | Mixed easily. Degassing challenging due to proliferation of bubbles (result of surfactant content). Bottom function required to prevent tailing. Only ~80% dissolution achieved. No API recovery for 40% EtOH extraction (n = 3). Minimal recovery from ambient water syringeability/extraction, no detectable recovery from hot water preparations. |
| | Round 2 | Miglyol added in an attempt to improve dissolution. Mixed, degassed and filled easily. Minimal recovery from 40% EtOH extraction. No improvement in dissolution. |
| | Round 3 | Further miglyol added. Mixed, degassed and filled easily. Dissolution remains poor. Minimal recovery from 40% EtOH extraction. Some separation observed in formulation. Not syringe-able in hot water but inconsistent syringeability observed in ambient water, may have been due to splitting and inhomogeneity. |
| 10 | Round 1 | Mixed easily. Grainy texture obtained c.f. other formulations. Additional Methocel added prior to filling as mixture was separating upon standing. Filled without bottom function but formulation incorporated air easily and had to be manually fed towards pump in hopper. Separation may be likely. |
| | Round 2 | Switched to Kolliphor RH40 to prevent separation and improve handling. A placebo mix was prepared with corn oil :Kolliphor RH40:Methocel (30:40:30) however this was too viscous to allow for processing and so 20:50:30 was investigated. Substituted Kolliphor EL for Kolliphor RH40 for improved handling. 20:50:30 |

TABLE 54-continued

Observations and comments from preparation of bulk mixes, capsule filling and subsequent testing.

| Prototype Number | Summary of Results and Observations |
|---|---|
| | trialed but viscosity too high, likely due to concentration of methocel. Further RH40 and Miglyol added during bulk mix preparation. Dissolution improved. Additional API added to maintain dose. May be prone to separating. Dissolution improved c.f round 2. |
| Round 3 | Aerosil added to prevent separation. Very challenging to process at 30:40:28:2 so more corn oil was added to improve handleability. No significant change on dissolution profile but remained challenging to fill by syringe and most extractable in short ADF testing. Some extraction in all conditions. |

Example 3: Comparison of Prototype 2 and a Non-Abuse Deterrent Tablet

This example compares abuse-deterrent formulation Prototype 2 to reference product Barr's 10 mg Dextroamphetamine sulfate tablet and evaluates the relative susceptibility to manipulation or abuse. Barriers to crushing, extraction, and syringeability were evaluated. The tests were based on the methods and protocols described in Appendix A and B.

Physical Barriers to Abuse by Crushing, Cutting or Grinding

Prototype 2 contains the following components per capsule: 10 mg of dextroamphetamine sulfate; 70 mg of poloxamer 124; 52.5 mg of Gelucire 48/16; and 52.5 mg of Kelcogel GCHA for a total fill weight of 185 mg. A size 3 gelatin capsule was used.

Following grinding of prototype 2 capsule contents, it was observed that very little of the material passed through the top sieve (1 mm). There was no change in this result following the addition of flux enhancers such as talc and sodium chloride. As such, this demonstrated that prototype 2 was able to prevent abuse via insufflation, which is a known route of abuse of amphetamines. In comparison, the ground comparator tablet was collected on all the sieve layers. This shows that the comparator tablet has the potential to be abused by insufflation.

Prototype 2 capsules and the comparator tablets were subjected to further physical testing by grinding with 95% ethanol and evaporating the ethanol. Both the capsule and the tablet performed equally well in this test as the resultant mixture for both was non-powder like and therefore insufflation assessments could not be performed on either.

Barriers to Abuse Involving Chemical Extraction

Various solvents were used to assess the chemical extraction of prototype 2 and the comparator tablet. Phase 1 testing was performed using water, 8% acetic acid, 0.2% sodium bicarbonate, 95% ethanol and a carbonated soft drink. At ambient temperature using 10 mL solvent, greater than 90% of the API was detected in samples after 5 minutes for both prototype 2 and the comparator tablets. The only exception to this was the extraction into water, for which the samples could not be filtered for both formulations.

The effect of 10 mL of hot water was also assessed. For prototype 2, no samples were analyzed as they could not be filtered. However for the comparator tablets, full extraction was obtained after 5 minutes. This demonstrates that prototype 2 would not be subject to abuse if hot water was used as a means of extraction.

Further chemical extraction assessment was performed using ambient 10 mL 40% ethanol. For prototype 2, between 66-81% API was assayed in samples over the course of the experiment (180 min). However, full extraction was obtained for the comparator tablets after 5 minutes. These results show that the amount of the API extracted for prototype 2 is less than the amount extracted for the comparator tablet and has an extended extraction time.

Phase 1 Studies

Syringeability Barriers

Phase 1 syringeability assessments were performed using 26 gauge needles, which are commonly used by abusers. For prototype 2, the temperature of the water did not appear to effect the syringeability of the sample and for both ambient and hot water, the amount of API assayed was below 10%. For the comparator tablets, the temperature of the water resulted in a 20% difference in the API assayed as a greater amount was obtained following the use of ambient water (66%) compared with hot water (46%). This demonstrates that prototype 2 is much less susceptible to abuse via injection in comparison to the comparator tablets.

Phase 2 Studies

Syringeability in Different Gauge Needles after Preparation with Water

In Phase 2 investigations, the effect of different needle gauges was assessed as well as the effect of different filtration materials (0.2 μm filter, cotton wool and cigarette filter). Using ambient water and an 18 gauge needle, the assayed API results for the prototype 2 samples were much lower than the comparator tablets (17% API for needle alone samples for prototype 2 and 52% API for needle alone samples for the comparator tablets). In general, these were reduced by the introduction of a filter except for filtration through the cigarette filter for the comparator tablet samples.

For samples prepared in hot water, the amount of API present in the samples for the comparator tablets and prototype 2 were similar when an 18 gauge needle was used alone (52% for the comparator and 46% for the prototype 2). Filtration of the prototype 2 samples through cotton wool and cigarette filter reduced the amount of API present in the samples. Filtration of comparator tablet samples reduced the API present when a 0.2 μm filter and cotton wool was used but again the cigarette filter had no effect.

The recovery of API in both ambient and hot water was comparable for prototype 2 and comparator tablet samples when taken up through a 20 gauge needle. The prototype 2 samples were subjected to filtration through cotton wool only, which reduced the recovery of API. Filtration of the comparator samples through a 0.2 μm filter and cotton wool resulted in reductions in the recovery of API. However, as observed previously, no reductions in the recovery of API was observed following filtration of comparator tablet samples through cigarette filters.

The recovery of API in samples prepared with ambient water and taken up using a 23 gauge needle was greater in the comparator tablet samples compared with the prototype 2 samples. Filtration of samples was only performed using the comparator tablet samples. A reduction in the recovery of the API was observed for all filters used (0.2 μm filter, cotton wool and cigarette filter), with the greatest reduction when cotton wool was used. Samples prepared in hot water showed a similar overall trend to those prepared in ambient water. However for the filtration step of the comparator tablet samples, the greatest reduction in recovery was observed when a 0.2 µm filter was used.

It should be noted that the use of wider bore needles such as 18, 20 and 23 gauge needles is unlikely in an abuse situation as the needle is a much wider bore and 26 gauge needles would be used preferential as they are narrower for injection into the vein and more readily available in needle exchange programmes. In addition, the use of filters only reduces the amount of the amphetamine available for abuse as opposed to "cleaning up" the solution for injection. In all cases, the recovery of the API in prototype 2 was much less compared with the comparator demonstrating that abuse via injection would be more challenging and would result in low yields of the drug in compared with the comparator tablets.

Application of Heat-Melting Temperature

Heat was applied to a crushed prototype 2 capsule or comparator tablet and if the contents melted, the ability to syringe the mixture through various gauge needles was assessed. The comparator tablet was heated to 200° C. with no changes observed to the powder.

Following the application of heat, the content of prototype 2 melted and was tested in various gauge needles. It was noted that when the drug product was removed from the heat and taken up into the syringe, it solidified. An 18 gauge and 26 gauge needle was tested and in both cases, the melted prototype 2 formulation was drawn up but did not reach the syringe as it solidified.

Although it was possible to melt the prototype 2 formulation, it would be unlikely to be susceptible to abuse as it solidified when taken up in the needle and would therefore not be suitable for injecting.

Syringeability after Preparation in Water and Multi-Pass Filtering

Following the grinding of either prototype 2 capsules or comparator tablets and testing for syringeability and repeat filtering through a cigarette filter, no samples were deemed suitable for analysis from the prototype 2 samples. Comparator tablet samples were analyzed and 38% recovery was observed.

As previously observed, this demonstrates that prototype 2 is not suitable for abuse via syringing when passed through filters due to the losses of volume on each pass. In contrast, some API was available following the same procedure using the comparator tablets.

Syringeability in Different Gauge Needles after Preparation with Ambient and Hot Water The syringeability of prototype 2 and comparator tablet samples was compared following preparation in 5 mL ambient and hot water. For all gauge needles tested, the recovery of API in the comparator tablet samples was greater than in the prototype 2 samples.

The more commonly used 26 gauge needles demonstrated that prototype 2 would be much less susceptible to abuse via injection due to the low yields of drug and the difficulty in syringing the formulation. The comparator tablets showed higher yields of the drug and the data for the 26 gauge needle was comparable to the wider bore needles when used with prototype 2 in ambient water.

Extraction in Small Volumes of 0.2% Sodium Bicarbonate Solution

The extraction of the API following grinding of the prototype 2 capsule and comparator tablets was assessed using 5 mL and 2 mL of ambient and hot 0.2% sodium bicarbonate.

Using ambient 0.2% sodium bicarbonate, the recovery was higher in the comparator tablet samples compared with prototype 2 samples. For prototype 2 samples prepared using 2 mL of ambient 0.2% sodium bicarbonate, the sample was not suitable for analysis.

Extraction of samples into hot 0.2% sodium bicarbonate, resulted in full extraction for the comparator tablet samples. The prototype 2 samples were not suitable for analysis.

These results demonstrate the difficulty in extracting the drug for prototype 2 making this an unsuitable route for abuse. Whereas, the comparator tablet was readily extracted in both volumes of sodium bicarbonate regardless of temperature.

Ethanol Extraction Test

Prototype 2 and comparator tablet samples were ground with 10 mL 95% ethanol. The resultant mixture was heated to evaporate the ethanol and the resulting residue was examined. For both formulations, the samples were non-powder like and could not be subjected to physical testing to assess the potential for insufflation.

This demonstrates that prototype 2 could not be converted into a powder form. This would prevent abuse via insufflation.

Physical Barriers to Abuse by Crushing, Cutting or Grinding

A common type of misuse of oral pharmaceuticals is abuse by snorting: where an abuser inhales a powdered dosage unit (insufflation).

Phase I Studies

Establish Requirement for Thermal Pre-Treatment

The shell of a whole dose unit was removed and the capsule contents was placed into a coffee grinder and ground for five minutes. The resulting product was milled to greater than 1 mm. Therefore for all consequent analyzes, thermal pre-treatment was performed by freezing the capsules for 24 hours prior to use.

Milling with a Coffee Grinder

The shells of five whole dosage units (which had been frozen for 24 hours) were removed and the capsule contents transferred into a vial and weighed. The capsule contents were placed into a coffee grinder and ground for one minute (it should be noted that the comparator tablet could have been ground further, however in order to provide a suitable comparison, it was ground for the same amount of time as the prototype 2 capsules). The coffee grinder containing the capsule contents was weighed and then the contents transferred to a 1 mm sieve at the top of an array. The grinder was re-weighed to confirm the amount of capsule contents that had been transferred to the sieve array. The particle size distribution was determined using 1, 0.5, 0.25 and 0.106 mm pore size sieves.

The amount of API retained on each sieve was analyzed by HPLC, to determine if there is any API/excipient segregation during physical manipulation.

TABLE 55

Physical testing of Prototype 2 Formulation Sample 1

| Sieve level | Weight after (g) | Weight before (g) | Weight present (mg) | % of recovered weight |
|---|---|---|---|---|
| 1 mm | 218.27126 | 217.48313 | 788.13 | 99.12 |
| 0.5 mm | 208.12782 | 208.12711 | 0.71 | 0.09 |
| 0.25 mm | 201.92086 | 201.91843 | 2.43 | 0.31 |

TABLE 55-continued

Physical testing of Prototype 2 Formulation Sample 1

| Sieve level | Weight after (g) | Weight before (g) | Weight present (mg) | % of recovered weight |
|---|---|---|---|---|
| 0.106 mm | 197.23675 | 197.23555 | 1.20 | 0.15 |
| base | 128.63762 | 128.63500 | 2.62 | 0.33 |

TABLE 56

Physical testing of Prototype 2 Formulation Sample 2

| Sieve level | Weight after (g) | Weight before (g) | Weight present (mg) | % of recovered weight |
|---|---|---|---|---|
| 1 mm | 218.39539 | 217.56326 | 832.13 | 100 |
| 0.5 mm | 209.33688 | 209.33735 | −0.47 | n/a |
| 0.25 mm | 200.84730 | 200.85005 | −2.75 | n/a |
| 0.106 mm | 197.29304 | 197.29672 | −3.68 | n/a |
| base | 128.07354 | 128.07638 | −2.84 | n/a |

TABLE 57

Physical testing of Comparator Tablet Formulation Sample 1

| Sieve level | Weight after (g) | Weight before (g) | Weight present (mg) | % of recovered weight | HPLC Assay % API |
|---|---|---|---|---|---|
| 1 mm | 217.98044 | 217.48976 | 490.68 | 35.79 | 96.8 |
| 0.5 mm | 208.36158 | 208.13418 | 227.40 | 16.59 | 92.8 |
| 0.25 mm | 202.15150 | 201.92550 | 226.00 | 16.49 | 68.2 |
| 0.106 mm | 197.46574 | 197.24249 | 223.25 | 16.29 | 60.6 |
| base | 128.83609 | 128.63267 | 203.42 | 14.84 | 94.6 |

TABLE 58

Physical testing of Comparator Tablet Formulation Sample 2

| Sieve level | Weight after (g) | Weight before (g) | Weight present (mg) | % of recovered weight | HPLC Assay % API |
|---|---|---|---|---|---|
| 1 mm | 218.11425 | 217.55891 | 555.34 | 43.19 | 95.3 |
| 0.5 mm | 209.51810 | 209.33242 | 185.68 | 14.44 | 87.8 |
| 0.25 mm | 201.04832 | 200.84843 | 199.89 | 15.55 | 65.1 |
| 0.106 mm | 197.50918 | 197.29753 | 211.65 | 16.46 | 61.0 |
| base | 128.20872 | 128.07554 | 133.18 | 10.36 | 83.6 |

Figure 9A:
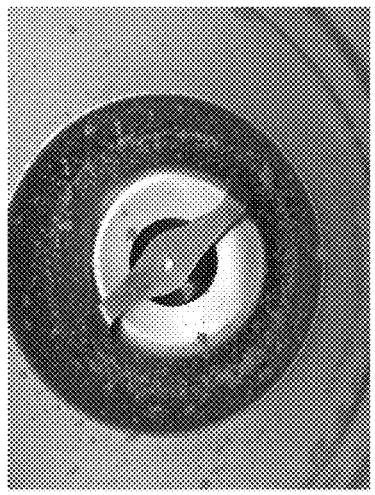
FIG. 9A-B shows images of prototype 2 after grinding (FIG. 9A), and shaking (FIG. 9B).
Figure 9B:
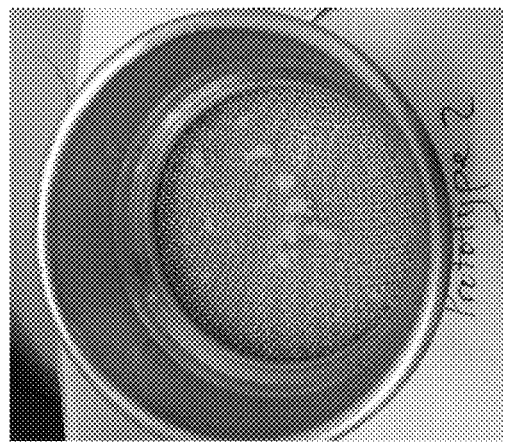
Figure 10A:
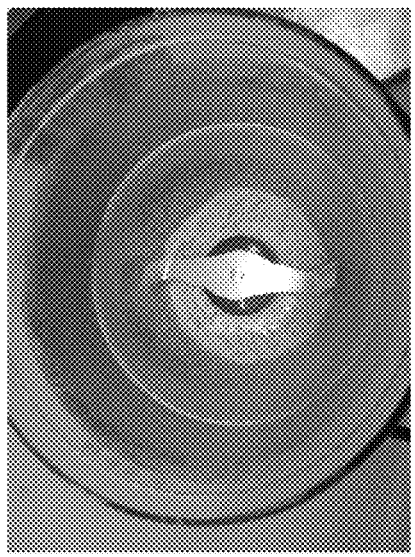
FIG. 10A-F shows images of the comparator after grinding (FIG. 10A), and the amount collected on 1 mm sieve (FIG. 10B), 500 μm sieve (FIG. 10C), 250 μm sieve. Note: picture labelled 1 mm in error (FIG. 10D), 106 μm sieve (FIG. 10E), and on base (FIG. 10F).
Figure 10B:
Figure 10C:
Figure 10E:
Figure 10F:
Figure 10D:
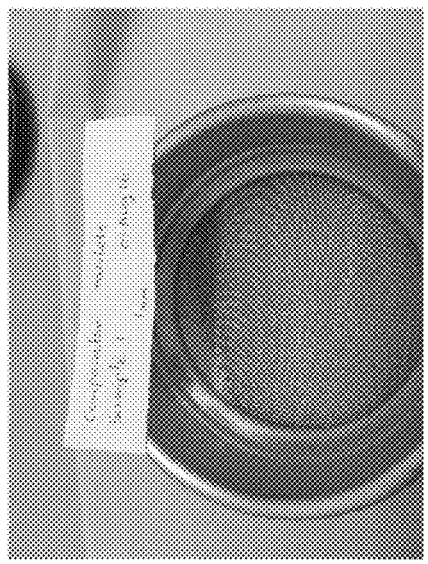

For prototype 2, the ground capsule contents had clumped together and remained on the 1 mm sieve (see FIG. 9B). Therefore no HPLC assay was performed.

For the comparator tablets, both samples showed the greatest amount material retained on the 1 mm layer sieve with similar amounts down to the 0.106 mm sieve and a decrease on the base (see FIG. 10). This may be due to the comparator tablets being ground for the same amount of time as the prototype 2 capsules, as a finer powder could have been achieved if the grinding time had been increased. However, it was deemed that the same grinding time should be used for both to provide a more comparable assessment.

Comparator powder from each layer was transferred to 50 ml volumetric flask and made up to volume with the diluent described in the protocol. An HPLC assay was performed on the solutions in the volumetric flasks after filtering through a 0.45 μm filter. A decrease in the amount of API present as the sieve size decreased until the base where a slight increase was observed.

Phase II Studies

Phase II studies were performed using all prototype formulations.

Grind with Flux (Flow Enhancers)

The shells of five whole dosage units (which had been frozen for 24 hours) were removed. The capsule contents were placed into a mortar and pestle and 0.2 g of a flow enhancer was added, then immediately ground for five minutes. The particle size distribution was determined using 1, 0.5, 0.25 and 0.106 mm pore size sieves, as per Phase I.

TABLE 59

Physical testing of Prototype 2 Formulation Sample 1 using Talc as a Flow Enhancer

| Sieve level | Weight after (g) | Weight before (g) | Weight present (mg) | % of recovered weight |
|---|---|---|---|---|
| 1 mm | 218.49497 | 217.49147 | 1003.50 | 99.29 |
| 0.5 mm | 208.12175 | 208.11952 | 2.23 | 0.22 |
| 0.25 mm | 201.91328 | 201.91279 | 0.49 | 0.05 |
| 0.106 mm | 197.24210 | 197.25852 | −16.42 | n/a |
| base | 128.63586 | 128.63140 | 4.46 | 0.44 |

TABLE 60

Physical testing of Prototype 2 Formulation Sample 2 using Talc as a Flow Enhancer

| Sieve level | Weight after (g) | Weight before (g) | Weight present (mg) | % of recovered weight |
|---|---|---|---|---|
| 1 mm | 218.62971 | 217.54824 | 1081.47 | 100 |
| 0.5 mm | 209.32293 | 209.32447 | −1.54 | n/a |
| 0.25 mm | 200.83707 | 200.83836 | −1.29 | n/a |
| 0.106 mm | 197.28371 | 197.28656 | −2.85 | n/a |
| base | 128.07159 | 128.07228 | −0.69 | n/a |

Figure 11B:
FIG. 11A-B shows images of Prototype 2 after grinding with Talc (FIG. 11A), and after shaking capsule contents remain on the 1 mm sieve (FIG. 11B).
Figure 11A:

For prototype 2, following grinding with talc, both samples became a sticky off white paste (see FIG. 11A). Following visual inspection and weighing of the sieves, the capsule contents was retained on the 1 mm sieve (see FIG. 11B). The data for the weights recovered for the 0.5 mm, 0.25 mm and base layers of the sieve array may be attributed to balance variability as no capsule contents was observed on these layers. As no capsule contents passed through the 1 mm sieve, no HPLC assay was performed.

TABLE 61

Physical testing of Prototype 2 Formulation Sample 1 using Sodium Chloride as a Flow Enhancer

| Sieve level | Weight after (g) | Weight before (g) | Weight present (mg) | % of recovered weight |
|---|---|---|---|---|
| 1 mm | 218.49926 | 217.47733 | 1021.93 | 99.55 |
| 0.5 mm | 208.12390 | 208.12197 | 1.93 | 0.19 |
| 0.25 mm | 201.91493 | 201.91461 | 0.32 | 0.03 |
| 0.106 mm | 197.23175 | 197.23029 | 1.46 | 0.14 |
| base | 128.63717 | 128.63624 | 0.93 | 0.09 |

TABLE 62

Physical testing of Prototype 2 Formulation Sample 2 using Sodium Chloride as a Flow Enhancer

| Sieve level | Weight after (g) | Weight before (g) | Weight present (mg) | % of recovered weight |
|---|---|---|---|---|
| 1 mm | 218.59888 | 217.55217 | 1046.7100 | 100 |
| 0.5 mm | 209.32548 | 209.32748 | −2.0000 | n/a |
| 0.25 mm | 200.83530 | 200.83860 | −3.3000 | n/a |
| 0.106 mm | 197.28289 | 197.28752 | −4.6300 | n/a |
| base | 128.07198 | 128.07338 | −1.4000 | n/a |

Figure 12B:
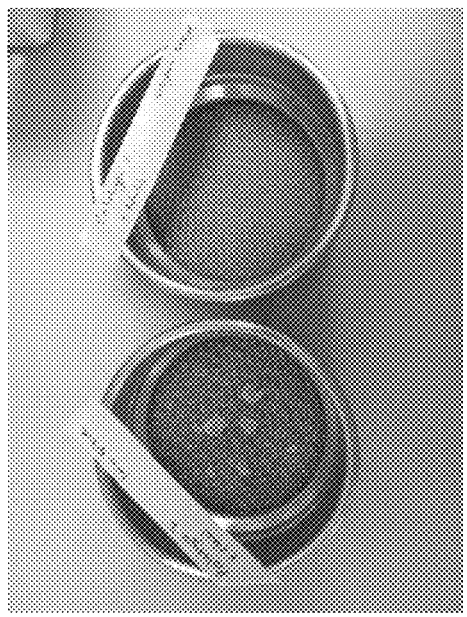
FIG. 12A-B shows images of Prototype 2 after grinding with Sodium Chloride (FIG. 12A), and after shaking (FIG. 12B), where capsule contents remain mainly on the 1 mm sieve.
Figure 12A:
Figure 13A:
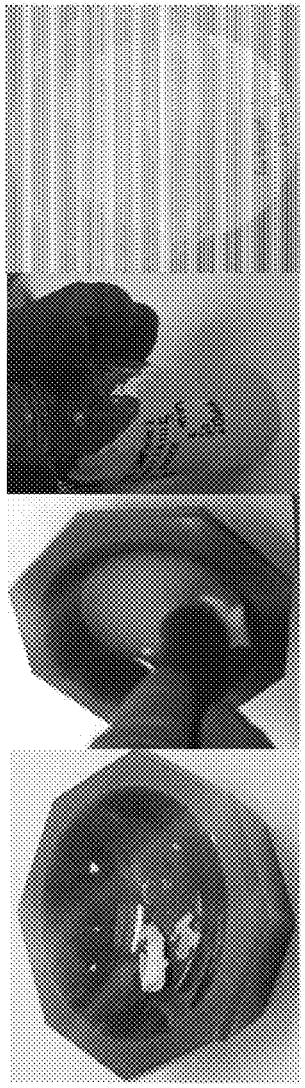
FIG. 13A-E shows images of Prototype 2 in ambient Water (FIG. 13A), ambient acetic acid (FIG. 13B), ambient 0.2% Sodium Bicarbonate (FIG. 13C), ambient Ethanol (95%) (FIG. 13D), and ambient carbonated soft drink (FIG. 13E).
Figure 13B:
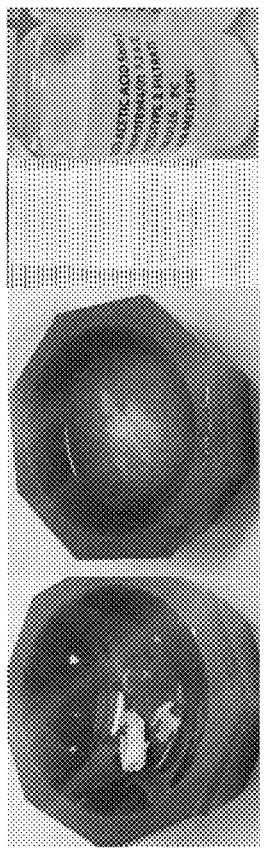
Figure 13C:
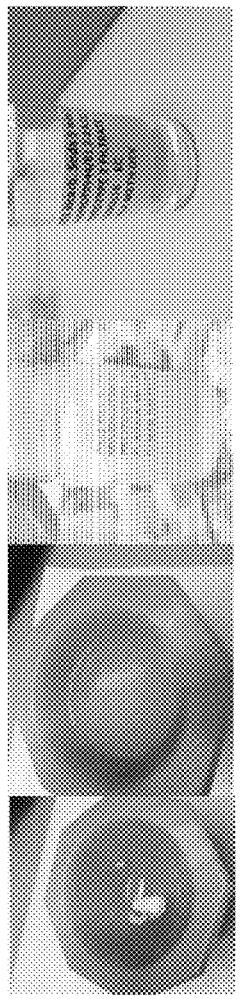
Figure 13D:
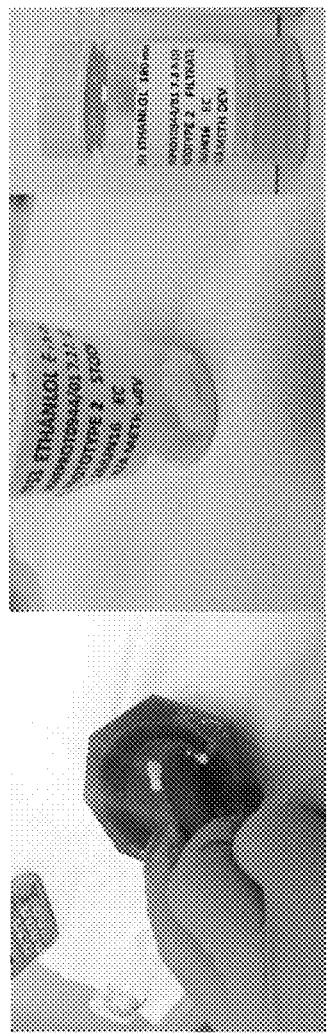
Figure 13E:
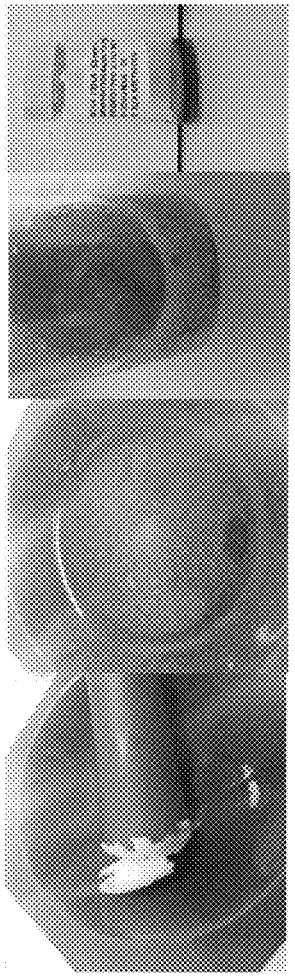
Figure 14A:
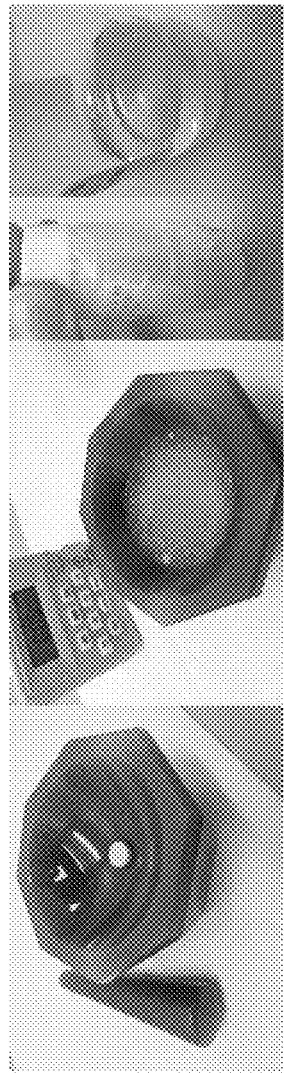
FIG. 14A-D shows images of the comparator in ambient water (FIG. 14A), ambient 0.2% sodium bicarbonate (FIG. 14B), ambient ethanol (95%)(FIG. 14C), and ambient carbonated soft drink (FIG. 14D).
Figure 14B:
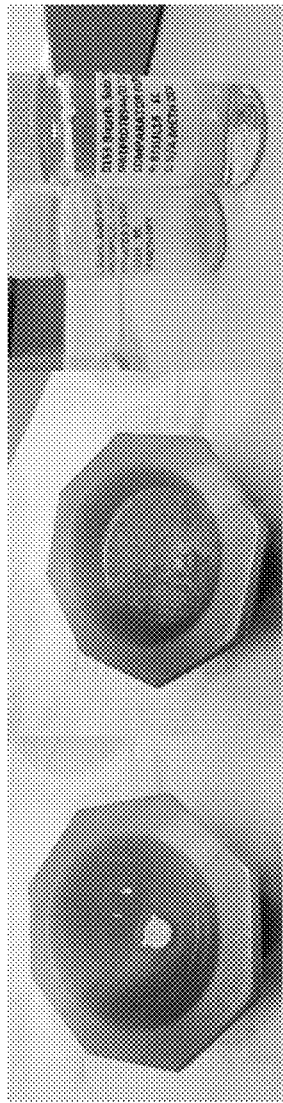
Figure 14C:
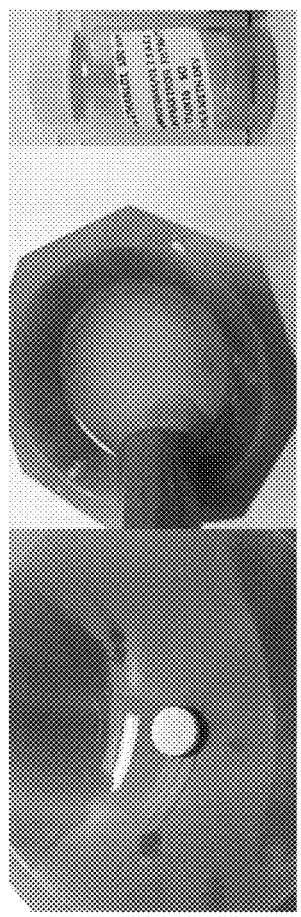
Figure 14D:
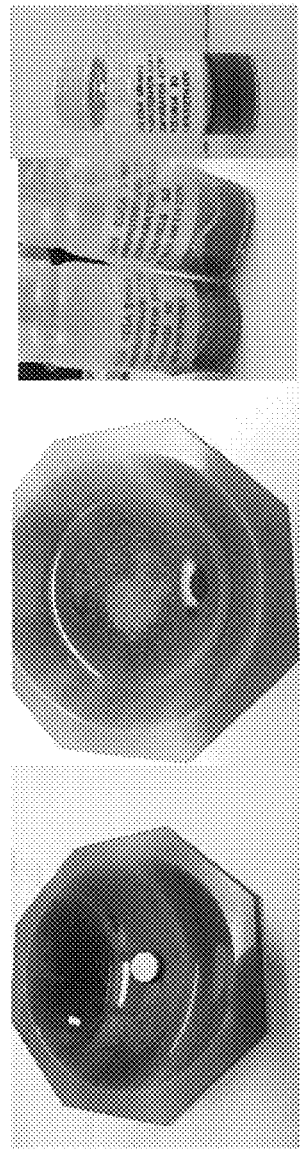

For prototype 2, following grinding with sodium chloride, both samples became a sticky off white paste (see FIG. 12A). Following visual inspection and weighing of the sieves, the capsule contents was retained on the 1 mm sieve (see FIG. 12B). The data for the weights recovered for the 0.5 mm, 0.25 mm and base layers of the sieve array may be attributed to balance variability as no capsule contents was observed on these layers. As no capsule contents passed through the 1 mm sieve, no HPLC assay was performed.

Barriers to Abuse Involving Chemical Extraction

Another common type of abuse is by injection or ingestion. The abuser reduces the unit to particles and extracts or melts the contents of a dosage unit in a heated solvent, then swallows or injects the liquid.

Phase I studies were performed using Tier 1 solvents and Phase II studies were performed using Tier 2 solvents:

Tier 1 solvents: Water, Acetic acid (8%), 0.2% Sodium bicarbonate, Ethanol (95%), Carbonated soft drink (cola, acidic pH).

Tier 2 solvents: Mineral (white) spirits, Ethanol (40%), Isopropyl alcohol, Methanol, Acetone, 0.1N HCl, 0.1N NaOH.

Phase I Studies

Extraction in Small Volumes of Ambient Tier 1 Solvents

A capsule was crushed to reduce the particle size of the dose and then ground with 10 mL of a Tier 1 solvent for five minutes or until homogeneous. The resulting suspension was transferred to a scintillation vial, the lid covered with Parafilm and shaken in a water bath at ambient temperature. Samples were removed at 5, 15, 60 and 180 minutes and filtered through a 0.45 μm filter into a flask and diluted to volume using the standard assay method diluent.

The filtered samples were analyzed by HPLC to quantify the API present.

FIGS. 13 and 14 show photographic observations of solvent extraction for Prototype 2 and comparator in Tier 1 solvents.

TABLE 63

Comparison of Solvent Extraction for Prototype 2 (Mean n = 3)

| | % Assay Average Amount | | | | |
|---|---|---|---|---|---|
| Sample | Water | Acetic Acid (8%) | 0.2% Sodium Bicarbonate | Ethanol (95%) | Carbonated soft drink |
| 5 mins | NOT | 97 | 93 | 113 | 105 |
| 15 mins | FIL- | 106 | 92 | 108 | 96 |
| 60 mins | TER- | 105 | 106 | 109 | 102 |
| 180 mins | ABLE | 104 | 95 | 109 | 98 |

TABLE 64

Comparison of Solvent Extraction for Comparator Tablet Formulation (Mean n = 3)

| | % Assay Average Amount | | | | |
|---|---|---|---|---|---|
| Sample | Water | Acetic Acid (8%) | 0.2% Sodium Bicarbonate | Ethanol (95%) | Carbonated soft drink |
| 5 mins | NOT | 100 | 102 | 102 | 99 |
| 15 mins | FIL- | 102 | 105 | 93 | 98 |
| 60 mins | TER- | 101 | 102 | 94 | 101 |
| 180 mins | ABLE | 101 | 103 | 104 | 103 |

Note -
% Assay calculation based on assumed 10 mg dose

Extraction in Small Volumes of Hot Water

Only hot water was analyzed for this part of the protocol due to the extraction performance of the other prototypes with acetic acid, 0.2% sodium bicarbonate, carbonated soft drink and Ethanol 95%, at ambient conditions.

Water was pre-heated to a proposed extraction temperature of 90° C. as outlined in protocol.

A capsule was crushed to reduce the particle size of the dose and then ground with 10 mL of hot water for five minutes until homogeneous. The resulting suspension was transferred to a scintillation vial, the lid covered with Parafilm and shaken in a water bath at 90° C. Samples were removed at 5, 15, 60 and 180 minutes and, where possible, filtered through a 0.45 μm filter into a flask and diluted to volume using the standard assay method diluent.

Figure 15B:
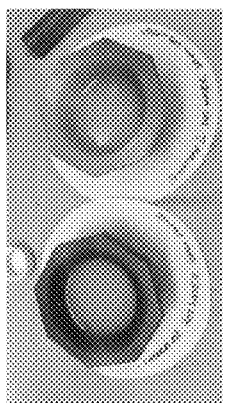
FIG. 15A-B shows images of the comparator and Prototype 2 after crushing (FIG. 15A), and homogenized in hot water (FIG. 15B).
Figure 15A:
Figure 16B:
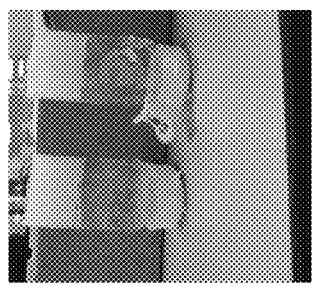
FIG. 16A-B shows images of the filtrate of the comparator (FIG. 16A) and Prototype 2 (FIG. 16B) in hot water and after shaking.
Figure 16A:
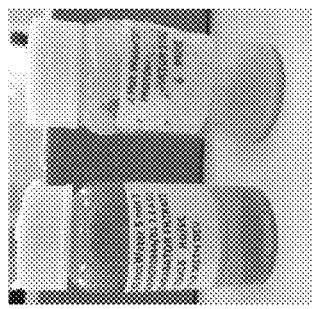

The filtered samples were analyzed by HPLC to quantify the API present. FIGS. 15 and 16 show photographic observations of solvent extraction for comparator and Prototype 2 in hot solvent.

TABLE 65

Comparison of Hot Solvent Extraction into Water (Mean n = 3)

| | % Assay Average Amount | |
|---|---|---|
| Sample | Prototype 2 | Comparator |
| 5 mins | NOT | 103 |
| 15 mins | FILTERABLE | 104 |
| 60 mins | | 103 |
| 180 mins | | 106 |

Phase II Studies

A capsule was crushed to reduce the particle size of the dose and then ground with 10 mL of 40% ethanol for five minutes until homogeneous. The resulting suspension was transferred to a scintillation vial, the lid covered with Parafilm and shaken in a water bath at ambient temperature. Samples were removed at 5, 15, 60 and 180 minutes and filtered through a 0.45 μm filter into a flask and diluted to volume using the standard assay method diluent.

Figure 17:
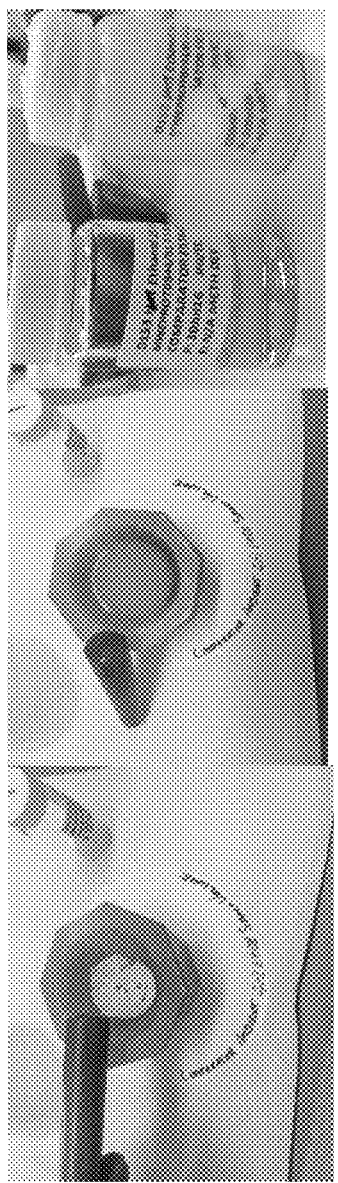
FIG. 17 shows images of crushed comparator, comparator in ambient Ethanol (40%), the filtrate and after shaking.

The filtered samples were analyzed by HPLC to quantify the API present. FIG. 17 shows photographic observations of solvent extraction for comparator and prototype 2 in ambient ethanol.

TABLE 66

Comparison of Solvent Extraction for Comparator
and Prototype 2 in 40% Ethanol (Mean n = 3)

| | % Assay Average Amount | |
|---|---|---|
| Sample | Prototype 2 | Comparator |
| 5 mins | 73 | 104 |
| 15 mins | 66 | 102 |
| 60 mins | 81 | 104 |
| 180 mins | 79 | 101 |

Syringeability Barriers
Phase I Studies

A capsule was crushed to reduce the particle size of the dose and then ground with 10 mL of water at ambient temperature for up to thirty minutes until homogeneous. The solution was drawn into a syringe via a 26-gauge needle and the approximate amount of liquid drawn recorded. In cases where 1 mL or greater was drawn up and was fluid enough to be expelled through the needle, the syringe contents was dispensed into suitably sized volumetric flasks and prepared for HPLC analysis using the standard assay method diluent.

Figure 18A:
FIG. 18A-B shows images of syringing the comparator (FIG. 18A) and prototype 2 (FIG. 18B) in ambient water with a 26 gauge needle.
Figure 18B:
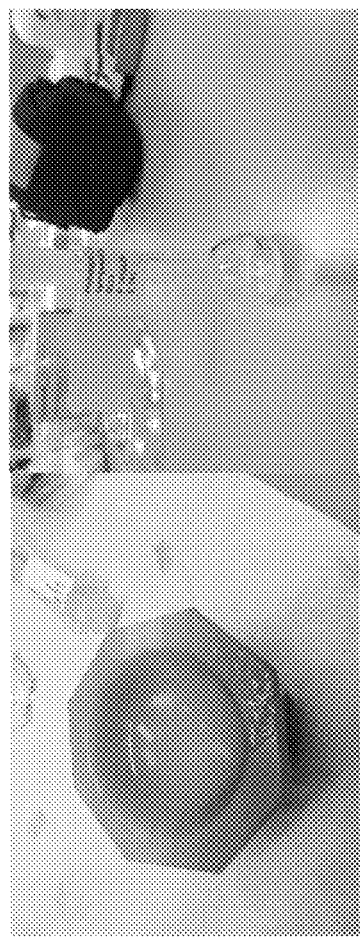
Figure 19A:
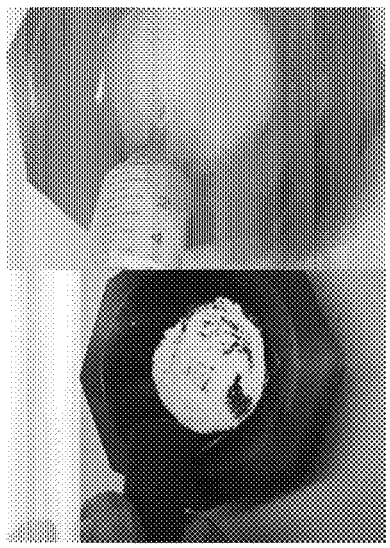
FIG. 19A-B shows images of syringing the comparator (FIG. 19A) and prototype 2 (FIG. 19B) in hot water with a 26 gauge needle.
Figure 19B:
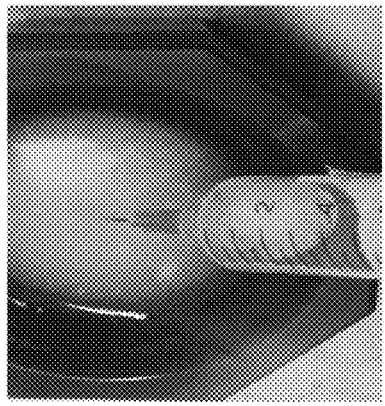
Figure 20A:
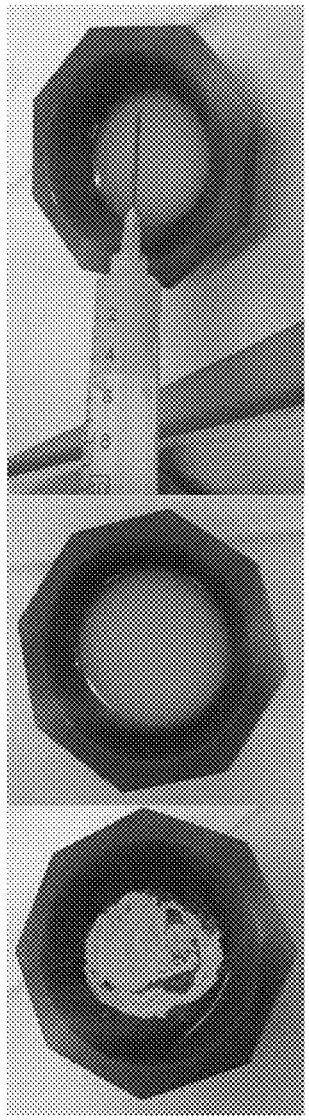
FIG. 20A-D shows images of syringing the comparator in ambient water with an 18 G needle (FIG. 20A) and a 0.2 μm nylon filter (FIG. 20B), cotton wool (FIG. 20C), and a cigarette filter (FIG. 20D).
Figure 20B:
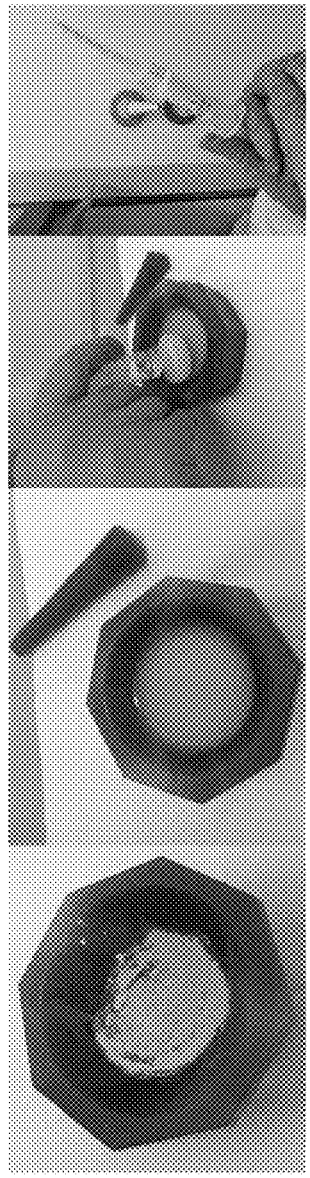
Figure 20C:
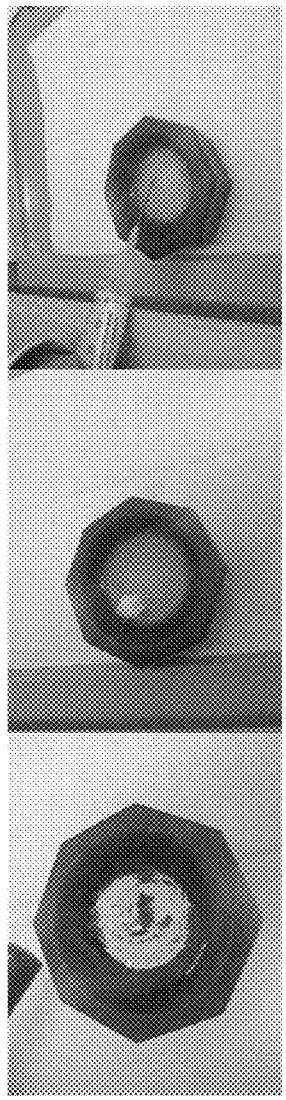
Figure 20D:
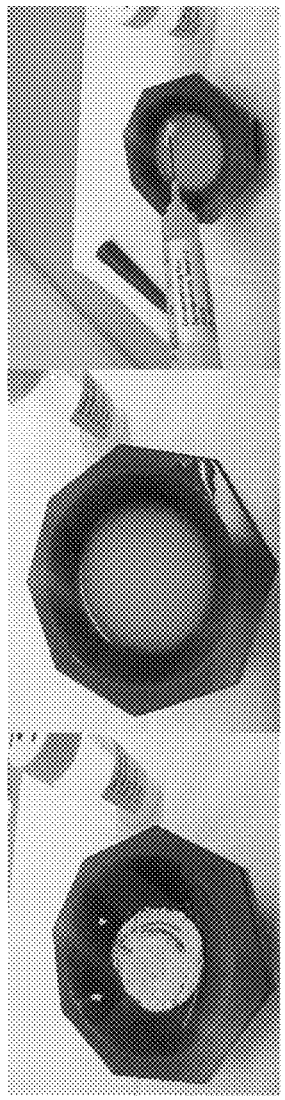

Samples that passed the test criteria at room temperature (<5% yield) were repeated using water heated to 90-95° C. FIGS. 18 and 19 show photographic observations of the syringability in ambient water and hot water, respectively, of comparator and Prototype 2 with a 26 gauge needle.

TABLE 67

Syringeability in Ambient Water with a 26 Gauge
Needle and Assay of Syringed Samples

| Formulation | Sample | Volume syringed/drawn (mL) | Assayed concentration % | Average Assayed Concentration % |
|---|---|---|---|---|
| Prototype 2 | 1 | 1.0 | 7.4 | 4 |
| | 2 | 1.0 | 5.2 | |
| | 3 | <0.5 ml | 4.9 | |
| Comparator | 1 | 6.0 | 61.6 | 66 |
| | 2 | 6.0 | 62.0 | |
| | 3 | 7.0 | 73.4 | |

TABLE 68

Syringeability in Hot Water with a 26 Gauge
Needle and Assay of Syringed Samples

| Formulation | Sample | Volume syringed/drawn (mL) | Assayed concentration % | Average Assayed Concentration % |
|---|---|---|---|---|
| Prototype 2 | 1 | 1.0 | 9.2 | 7 |
| | 2 | 1.0 | 7.2 | |
| | 3 | 1.0 | 5.1 | |
| Comparator | 1 | 4.5 | 46.8 | 46 |
| | 2 | 5.0 | 54.1 | |
| | 3 | 3.5 | 36.9 | |

Phase II Studies

Phase II studies were performed using all prototype formulations.

Syringeability in Different Gauge Needles after Preparation with Water

A capsule was crushed to reduce the particle size of the dose and then ground with 10 mL of water at ambient temperature for five minutes or until homogenous. The solution was drawn into a syringe via an 18-gauge needle and the approximate amount of liquid drawn recorded. In cases where 1 mL or greater was drawn up and was fluid enough to be expelled through the needle, the syringe contents was dispensed into suitably sized volumetric flasks and prepared for HPLC analysis using the standard assay method diluent.

The above process was repeated with attempts to draw the solution via a 0.2 μm filter, a wad of cotton wool and a cigarette filter tip. A fresh sample was prepared for each filter used.

The above experiment was repeated using a narrower gauge needle for samples that were syringeable with the 18-gauge needle and progressed via the 20 and 23-gauge needles as long as the recovered quantity of API was greater than 5% of the dose recovered.

Samples that passed the test criteria at room temperature (<5% yield) were repeated using water heated to 90-95° C.

Figure 21C:
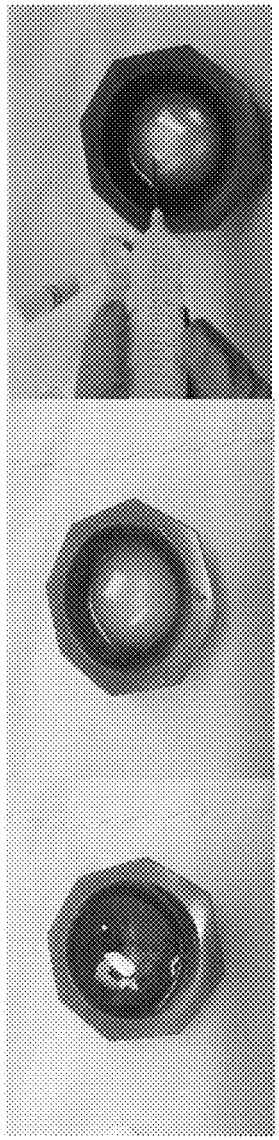
Figure 21D:
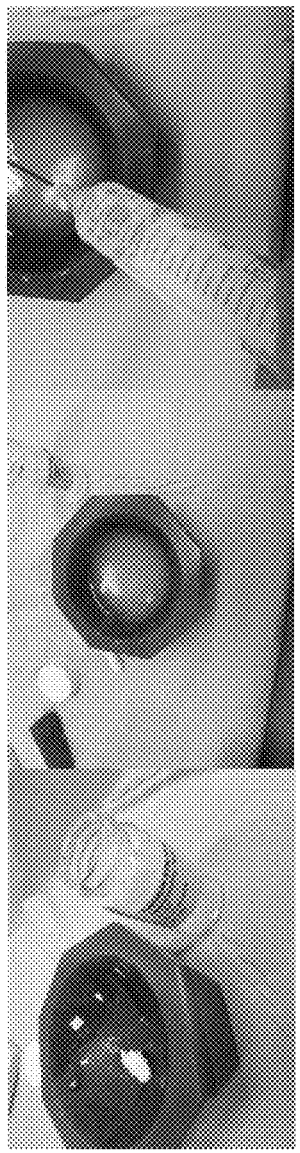
Figure 22A:
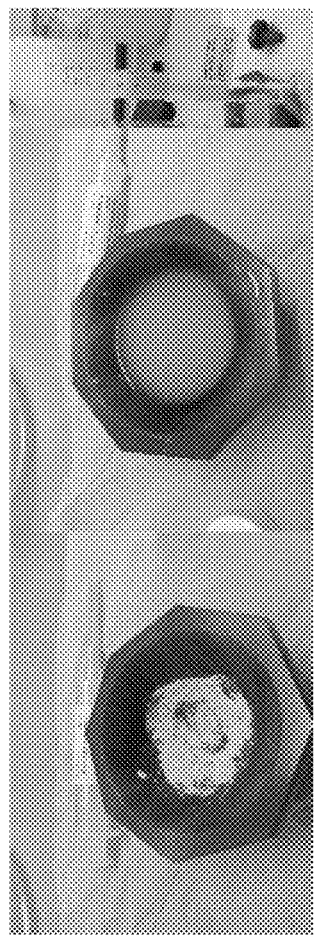
FIG. 22A-D shows images of syringing comparator in hot water with an 18 G needle (FIG. 22A) and a 0.2 μm nylon filter (FIG. 22B), cotton wool (FIG. 22C), and a cigarette filter (FIG. 22D).
Figure 22B:
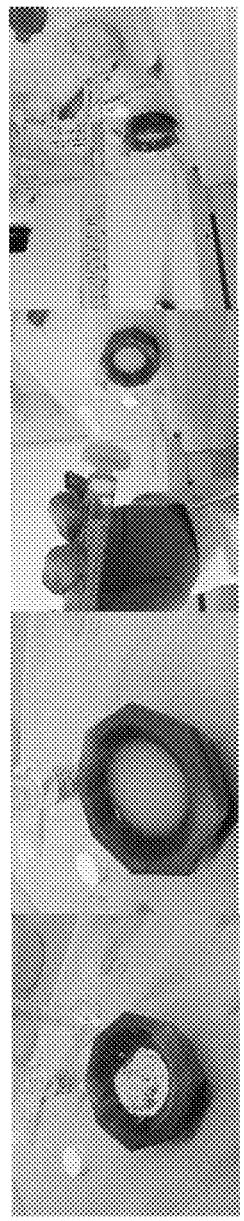
Figure 22C:
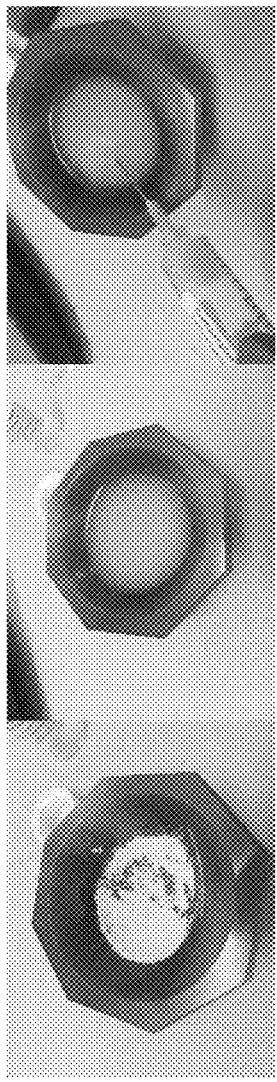
Figure 22D:
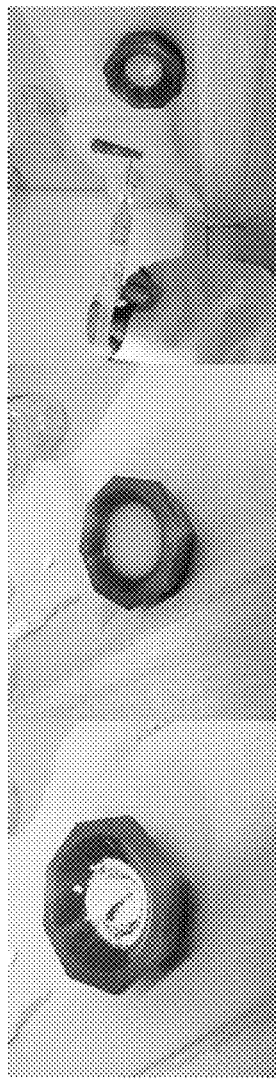
Figure 23A:
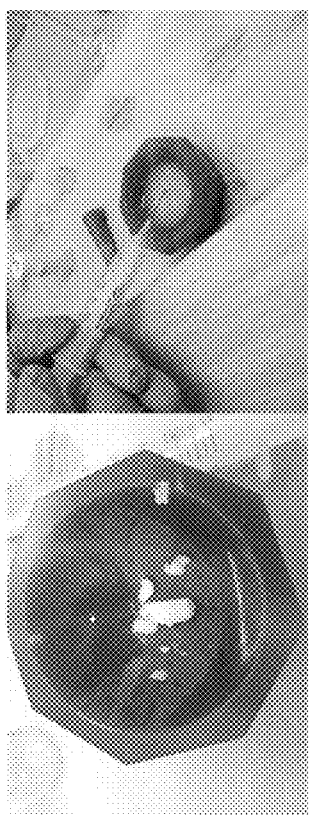
FIG. 23A-D shows images of syringing prototype 2 in hot water with an 18 G needle (FIG. 23A) and a 0.2 μm nylon filter (FIG. 23B), cotton wool (FIG. 23C), and a cigarette filter (FIG. 23D).
Figure 23B:
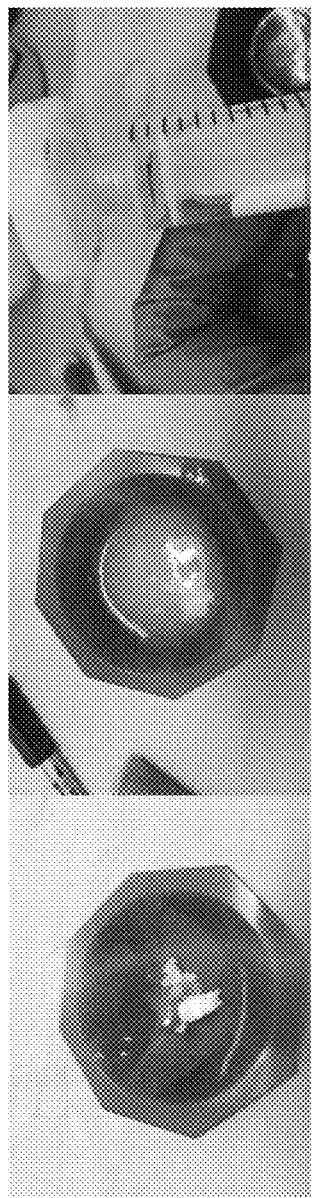
Figure 23C:
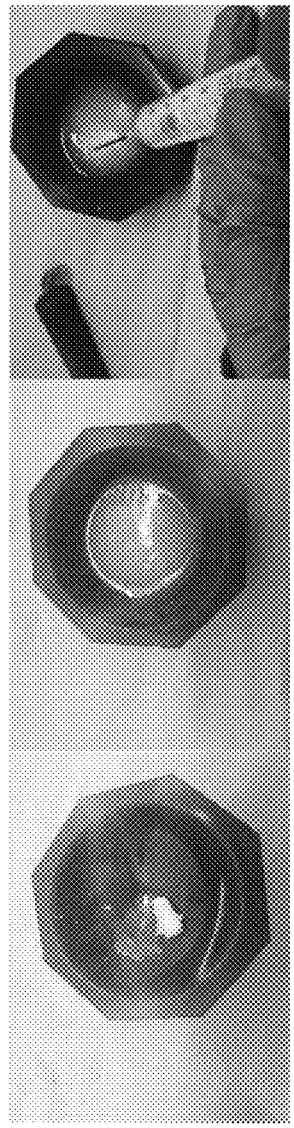
Figure 23D:
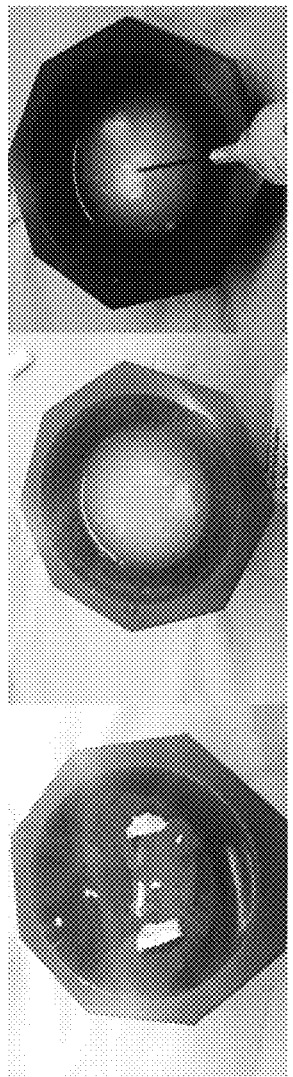
Figure 24A:
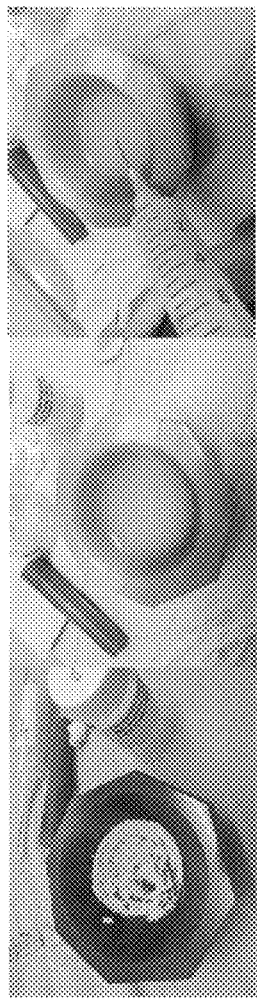
FIG. 24A-C shows images of syringing the comparator in ambient water with a 20 G needle (FIG. 24A) and a 0.2 μm nylon filter (FIG. 24B), and a cigarette filter (FIG. 24C).
Figure 24B:
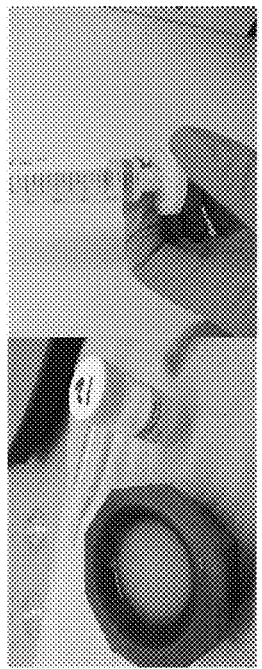
Figure 24C:
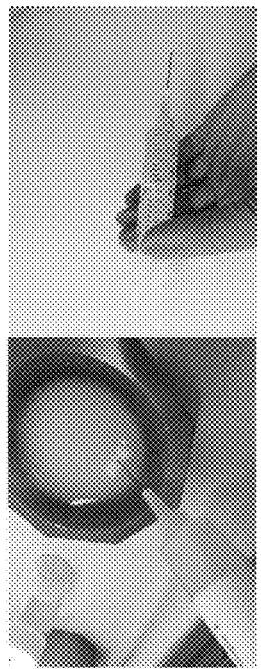
Figure 25A:
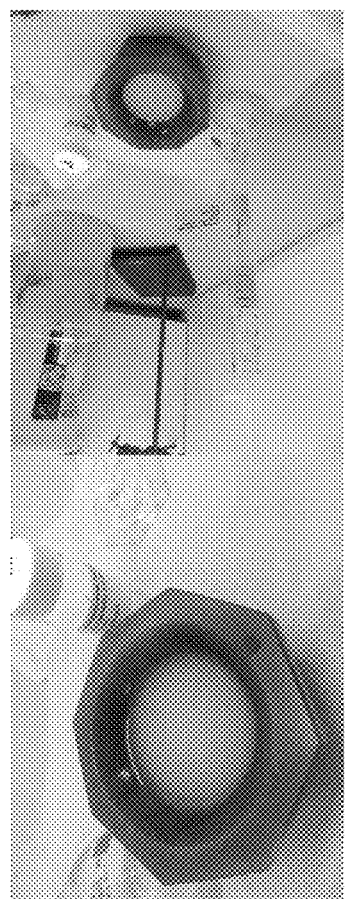
FIG. 25A-B shows images of syringing the comparator (FIG. 25A) and prototype 2 (FIG. 25B) in hot water with a 20 G needle.
Figure 25B:
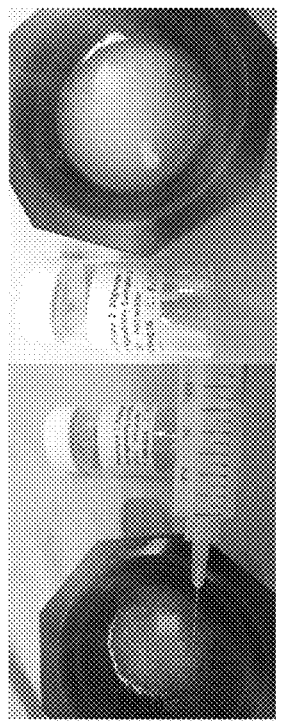
Figure 26A:
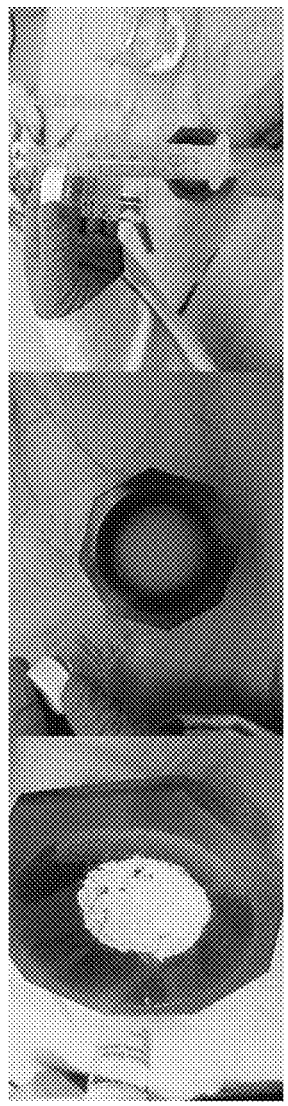
FIG. 26A-B shows images of syringing the comparator in ambient water with a 23 G needle (FIG. 26A) and a cigarette filter (FIG. 26B).
Figure 26B:
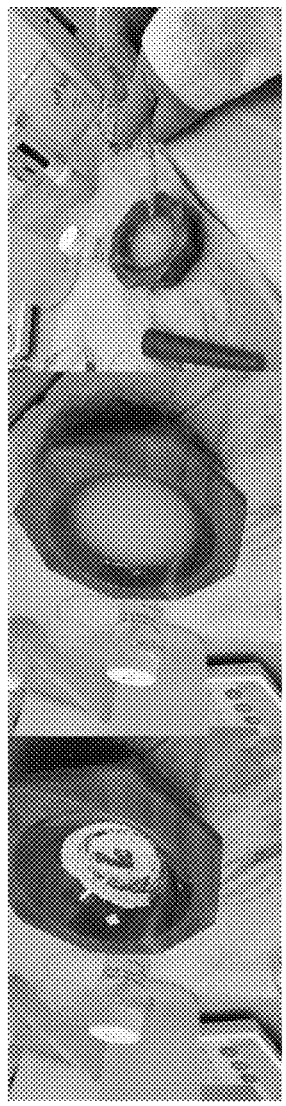
Figure 27B:
FIG. 27A-D shows images of syringing comparator in hot water with a 23 G needle (FIG. 27A) and a 0.2 μm nylon filter (FIG. 27B), cotton wool (FIG. 27C), and a cigarette filter (FIG. 27D).
Figure 27A:
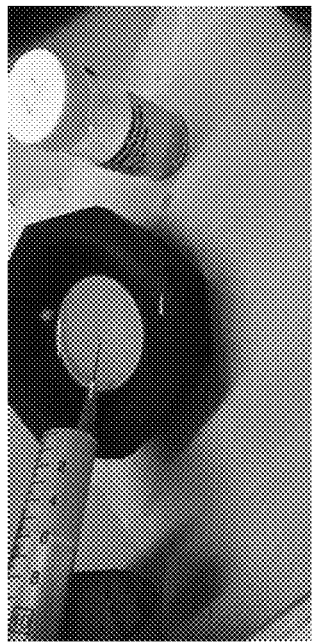
Figure 27D:
Figure 27C:
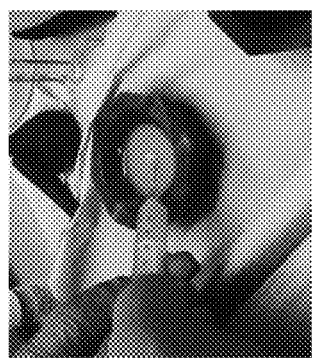
Figure 28B:
FIG. 28A-D shows images of syringing prototype 2 in ambient water with an 18 G needle (FIG. 28A), 20 G needle (FIG. 28B), 23 G needle (FIG. 28C), and a 26 G needle (FIG. 28D).
Figure 28A:
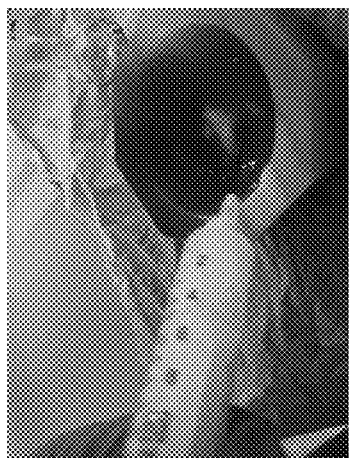
Figure 28D:
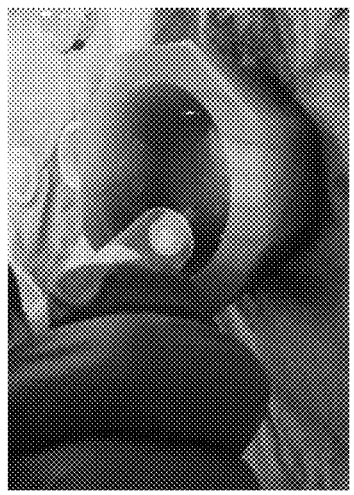
Figure 28C:
Figure 29A:
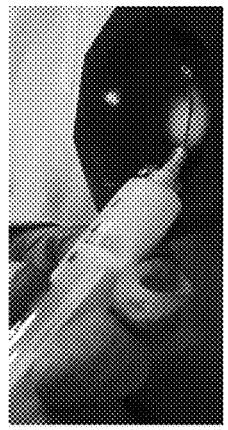
FIG. 29A-D shows images of syringing comparator in hot water with an 18 G needle (FIG. 29A), 20 G needle (FIG. 29B), 23 G needle (FIG. 29C), and a 26 G needle (FIG. 29D).
Figure 29B:
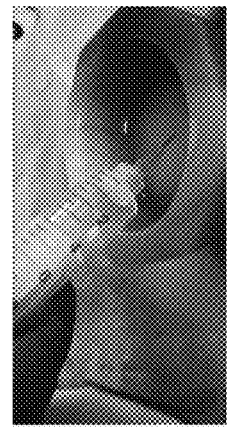
Figure 29C:
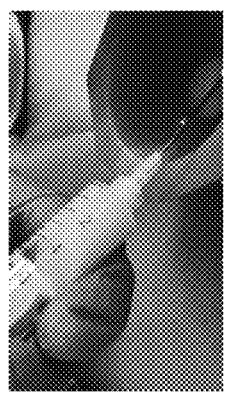
Figure 29D:
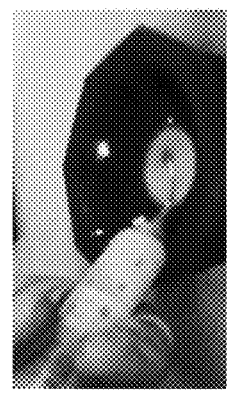
Figure 30B:
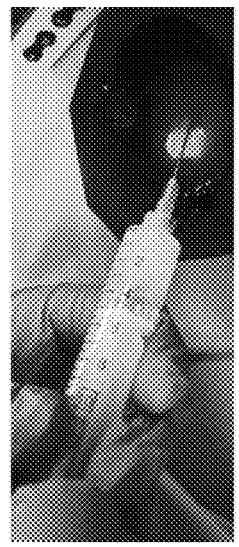
FIG. 30A-D shows images of syringing Prototype 2 in hot water with an 18 G needle (FIG. 30A), 20 G needle (FIG. 30B), 23 G needle (FIG. 30C), and a 26 G needle (FIG. 30D).
Figure 30D:
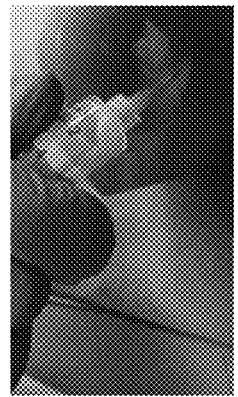
Figure 30A:
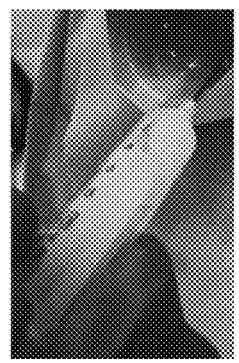
Figure 30C:
Figure 32A:
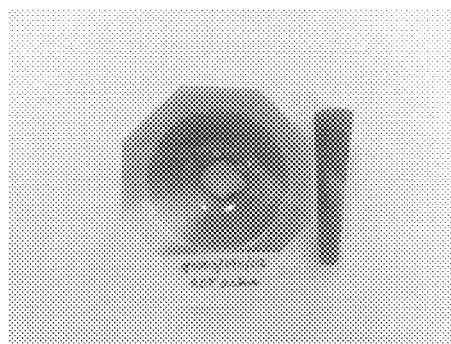
FIG. 32A-D shows images manipulating the ADAIR formulation.
Figure 32B:
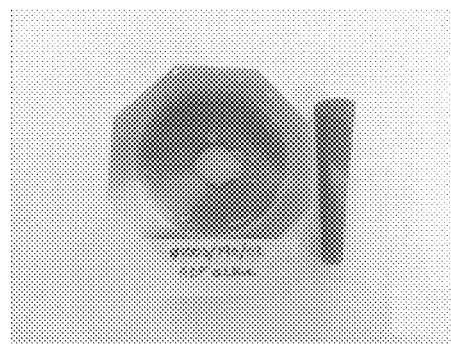
Figure 32C:
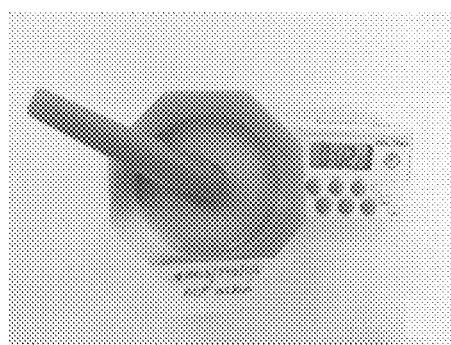
Figure 32D:
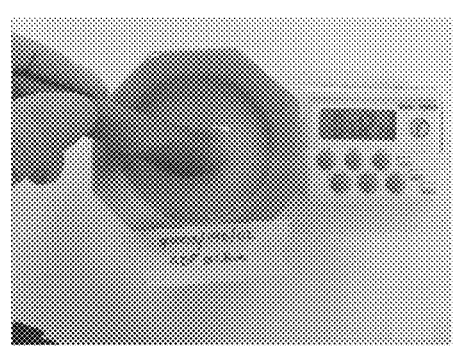
Figure 33A:
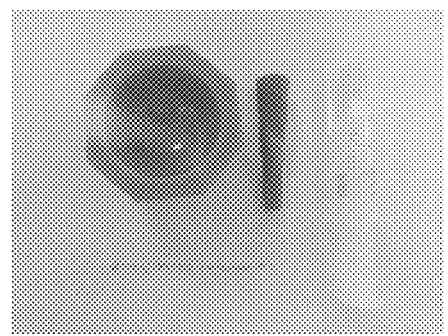
FIG. 33A-D shows images manipulating the placebo formulation.
Figure 33B:
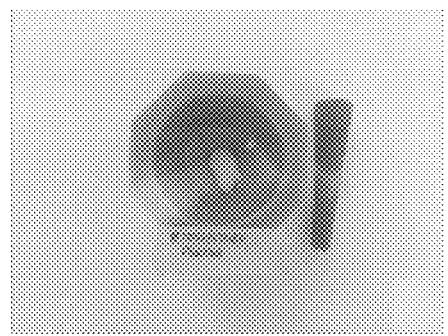
Figure 33C:
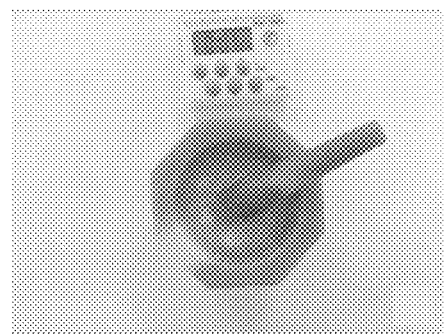
Figure 33D:
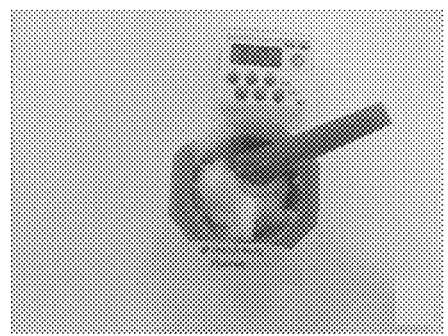
Figure 35:
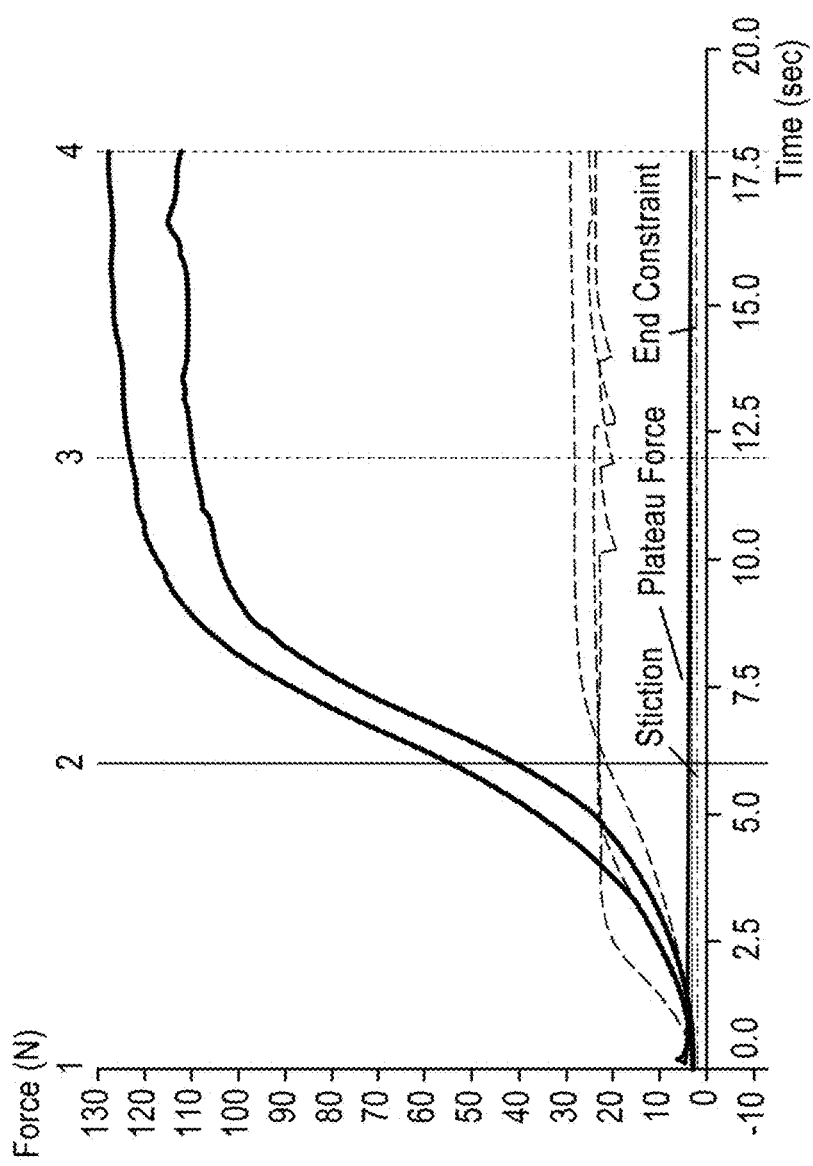
FIG. 35 is a graph showing texture analyser syringe profiles for the method development samples: manipulated ADF with 26 G needle (green), manipulated ADF with 18 G needle (dark blue), empty 5 mL syringe 18 G (black), water 5 mL syringe 26 G (light blue), water 5 mL syringe 18 G (red) and empty 5 mL syringe 26 G (pink). The maximum force between points 1 and 2 is the stiction. The maximum force between points 2 and 3 is the plateau force. The maximum force between point 3 and 4 is the end constraint.
Figure 36:
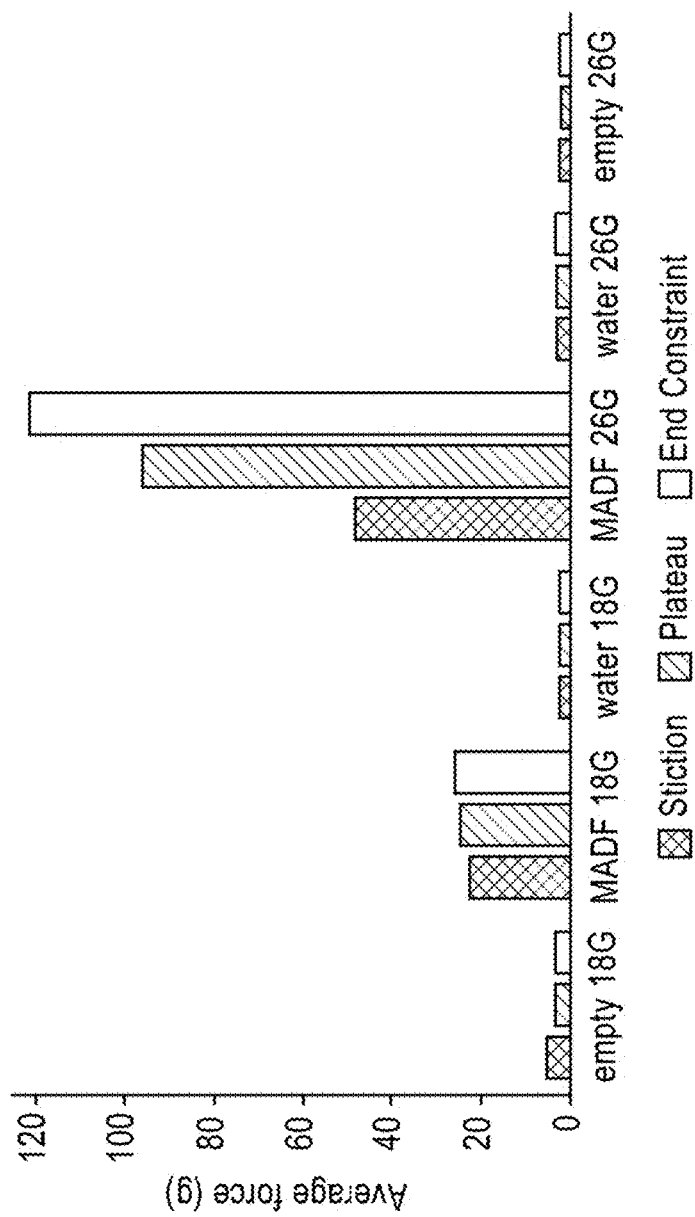
FIG. 36 is a bar chart showing the of average stiction force, plateau force and end constraint for empty syringes, manipulated placebo (MADF) and water obtained using the texture analyser for 18 G and 26 G needles.

FIGS. 20 and 21 show photographic observations of the syringeability of comparator and Prototype 2, respectively, in ambient water with an 18 gauge needle with and without a variety of filters. FIGS. 22 and 23 show photographic observations of the syringeability of comparator and Prototype 2, respectively, in hot water with an 18 gauge needle with and without a variety of filters. FIG. 24 shows photographic observations of the syringeability of comparator in ambient water with a 20 gauge needle with and without a filter. FIG. 25 shows photographic observations of the syringeability of comparator and Prototype 2 in hot water with a 20 gauge needle. FIG. 26 shows photographic observations of the syringeability of comparator in ambient water with a 23 gauge needle with and without a filter. FIG. 27 shows photographic observation of the syringeability of comparator in hot water with a 23 gauge needle with and without a filter.

TABLE 69

Syringeability in Ambient Water with an 18 Gauge
Needle and Assay of Syringed Samples

| | Comparator | | Prototype 2 | |
|---|---|---|---|---|
| Sample Name | Volume syringed/drawn (mL) | % Recovery | Volume syringed/drawn (mL) | % Recovery |
| 18 gauge Needle 1 | 5.0 | 57.1 | 1.0 | 9.0 |
| 18 gauge Needle 2 | 5.0 | 48.5 | 1.5 | 21.6 |
| 18 gauge Needle 3 | 5.0 | 50.8 | 5.0 | 21.2 |
| Mean | | 52 | | 17 |
| 0.2 μm filter 1 | 2.0 | 23.6 | <1.0* | 0.1 |
| 0.2 μm filter 2 | 2.0 | 25.5 | <1.01* | 1.2 |
| 0.2 μm filter 3 | 1.5 | 16.8 | <1.01* | 0.6 |
| Mean | | 22 | | 1 |
| Cotton wool 1 | 2.5 | 24.5 | 1.0 | 9.7 |
| Cotton wool 2 | 4.0 | 12.8 | <1.0* | 7.8 |
| Cotton wool 3 | 1.0 | 42.5 | 1.75 | 12.0 |
| Mean | | 27 | | 10 |
| Cig filter 1 | 5.0 | 53.6 | 5.0 | 4.6 |
| Cig filter 2 | 5.0 | 40.2 | 5.0 | 6.1 |
| Cig filter 3 | 5.0 | 52.7 | 1.0 | 5.0 |
| Mean | | 49 | | 5 |

*Samples <1 ml not required to be tested according to the protocol however they were analyzed at formulation development request for information only and have been reported here for information only.

TABLE 70

Syringeability in Hot Water with an 18 Gauge Needle and Assay of Syringed Samples

|  | Comparator | | Prototype 2 | |
| --- | --- | --- | --- | --- |
| Sample Name | Volume syringed/drawn (mL) | % Recovery | Volume syringed/drawn (mL) | % Recovery |
| 18 gauge Needle 1 | 5.0 | 56.7 | 4.0 | 43.8 |
| 18 gauge Needle 2 | 5.0 | 50.6 | 4.0 | 52.1 |
| 18 gauge Needle 3 | 5.0 | 48.3 | 4.0 | 41.4 |
| Mean | | 52 | | 46 |
| 0.2 μm filter 1 | 2.0 | 23.5 | <1.0* | 1.3 |
| 0.2 μm filter 2 | 2.5 | 25.4 | <1.0* | 1.6 |
| 0.2 μm filter 3 | 2.0 | 16.7 | <1.0* | 0.2 |
| Mean | | 22 | | 1 |
| Cotton wool 1 | <1.0* | 24.3 | 5.0 | 13.9 |
| Cotton wool 2 | 2.0 | 42.3 | 5.0 | 3.7 |
| Cotton wool 3 | <1.0* | 12.8 | 5.0 | 6.0 |
| Mean | | 26 | | 8 |
| Cig filter 1 | 4.0 | 53.3 | 5.0 | 11.7 |
| Cig filter 2 | 5.0 | 40.0 | 5.0 | 10.3 |
| Cig filter 3 | 5.0 | 52.3 | 5.0 | 12.9 |
| Mean | | 49 | | 12 |

*Samples <1 ml not required to be tested according to the protocol however they were analyzed at formulation development request for information only and have been reported here for information only.

TABLE 71

Syringeability in Ambient Water with a 20 Gauge Needle and Assay of Syringed Samples

|  | Comparator | | Prototype 2 | |
| --- | --- | --- | --- | --- |
| Sample Name | Volume syringed/drawn (mL) | % Recovery | Volume syringed/drawn (mL) | % Recovery |
| 20 gauge Needle 1 | 4.0 | 49.1 | 5.0 | 44.3 |
| 20 gauge Needle 2 | 5.0 | 49.3 | 5.0 | 49.9 |
| 20 gauge Needle 3 | 5.0 | 53.0 | 5.0 | 48.3 |
| Mean | | 50 | | 48 |
| 0.2 μm filter 1 | 1.0 | 12.3 | | |
| 0.2 μm filter 2 | 1.0 | 16.8 | | |
| 0.2 μm filter 3 | 2.0 | 24.1 | | |
| Mean | | 18 | | |
| Cotton wool 1 | 2.0 | 20.3 | 1.0 | 10.6 |
| Cotton wool 2 | 2.5 | 26.9 | 2.0 | 19.7 |
| Cotton wool 3 | 4.0 | 47.8 | 1.0 | 5.9 |
| Mean | | 32 | | 12 |
| Cig filter 1 | 5.0 | 51.4 | | |
| Cig filter 2 | 5.0 | 51.8 | | |
| Cig filter 3 | 5.0 | 54.7 | | |
| Mean | | 53 | | |

Note:
0.2 μm and cigarette filter samples for prototype 2 not progressed from 18 Gauge.

TABLE 72

Syringeability in Hot Water with a 20 Gauge Needle and Assay of Syringed Samples

|  | Comparator | | Prototype 2 | |
| --- | --- | --- | --- | --- |
| Sample Name | Volume syringed/drawn (mL) | % Recovery | Volume syringed/drawn (mL) | % Recovery |
| 20 gauge Needle 1 | 4.0 | 50.6 | 5.0 | 47.8 |
| 20 gauge Needle 2 | 5.0 | 52.1 | 5.0 | 52.8 |
| 20 gauge Needle 3 | 5.0 | 53.5 | 5.0 | 52.7 |
| Mean | | 52 | | 52 |
| 0.2 μm filter 1 | 1.0 | 10.5 | | |
| 0.2 μm filter 2 | 1.0 | 11.0 | | |
| 0.2 μm filter 3 | 1.0 | 11.9 | | |
| Mean | | 11 | | |
| Cotton wool 1 | <1.0* | 4.1 | <1.0* | 3.2 |
| Cotton wool 2 | <1.0* | 9.4 | 1.0 | 5.9 |
| Cotton wool 3 | 1.5 | 17.3 | <1.0* | 2.4 |
| Mean | | 10 | | 4 |
| Cig filter 1 | 5.0 | 42.6 | | |
| Cig filter 2 | 5.0 | 51.4 | | |
| Cig filter 3 | 5.0 | 51.6 | | |
| Mean | | 49 | | |

*Samples <1 ml not required to be tested according to the protocol however they were analyzed at formulation development request for information only and have been reported here for information only.
Note:
0.2 μm and cigarette filter samples for prototype 2 not progressed from 18 gauge.

TABLE 73

Syringeability in Ambient Water with a 23 Gauge Needle and Assay of Syringed Samples

|  | Comparator | | Prototype 2 | |
| --- | --- | --- | --- | --- |
| Sample Name | Volume syringed/drawn (mL) | % Recovery | Volume syringed/drawn (mL) | % Recovery |
| 23 gauge Needle 1 | 7.0 | 73.6 | 1.5 | 15.6 |
| 23 gauge Needle 2 | 4.0 | 43.1 | 4.0 | 37.4 |
| 23 gauge Needle 3 | 10.0 | 95.8 | 4.0 | 44.4 |
| Mean | | 71 | | 32 |
| 0.2 μm filter 1 | 1.5 | 19.3 | | |
| 0.2 μm filter 2 | 2.0 | 21.7 | | |
| 0.2 μm filter 3 | 2.0 | 20.1 | | |
| Mean | | 20 | | |
| Cotton wool 1 | <1.0* | 6.2 | | |
| Cotton wool 2 | <1.0* | 6.5 | | |
| Cotton wool 3 | <1.0* | 3.5 | | |
| Mean | | 5 | | |
| Cig filter 1 | 6.0 | 62.9 | | |
| Cig filter 2 | 5.0 | 53.6 | | |
| Cig filter 3 | 5.0 | 50.7 | | |
| Mean | | 56 | | |

*Samples <1 ml not required to be tested according to the protocol however they were analyzed at formulation development request for information only and have been reported here for information only.
Note:
0.2 μm and cigarette filter samples not progressed from 18 gauge and cotton wool from 20 gauge.

TABLE 74

Syringeability in Hot Water with a 23 Gauge Needle and Assay of Syringed Samples

|  | Comparator | | Prototype 2 | |
| --- | --- | --- | --- | --- |
| Sample Name | Volume syringed/drawn (mL) | % Recovery | Volume syringed/drawn (mL) | % Recovery |
| 23 gauge Needle 1 | 5 | 61.8 | 3.5 | 46.5 |
| 23 gauge Needle 2 | 5 | 64.8 | 4 | 40.4 |
| 23 gauge Needle 3 | 5 | 58.0 | 5 | 49.3 |
| Mean | | 62 | | 45 |
| 0.2 μm filter 1 | 1.5 | 23.4 | | |
| 0.2 μm filter 2 | 2.5 | 31.1 | | |
| 0.2 μm filter 3 | 1.5 | 17.7 | | |

TABLE 74-continued

Syringeability in Hot Water with a 23 Gauge
Needle and Assay of Syringed Samples

| Sample Name | Comparator | | Prototype 2 | |
|---|---|---|---|---|
| | Volume syringed/ drawn (mL) | % Recovery | Volume syringed/ drawn (mL) | % Recovery |
| Mean | | 24 | | |
| Cotton wool 1 | 5 | 54.8 | | |
| Cotton wool 2 | 2 | 22.7 | | |
| Cotton wool 3 | 4.5 | 50.7 | | |
| Mean | | 43 | | |
| Cig filter 1 | 5 | 60.9 | | |
| Cig filter 2 | 3.5 | 34.4 | | |
| Cig filter 3 | 5 | 57.4 | | |
| Mean | | 51 | | |

Note:
0.2 μm and cigarette filter samples not progressed from 18 gauge and cotton wool from 20 gauge.

Application of Heat-Melting Temperature

A capsule was crushed to reduce the particle size of the dose. The crushed capsule contents was placed in a watch glass and heated using a hot plate until melted. The temperature of melting were recorded. Any mixes that could be drawn by syringe via an 18, 20, 26 or 28-gauge needle were further investigated. The syringe was pre-weighed and then re-weighed after the mix had been drawn to measure the percentage entering the syringe.

TABLE 75

Prototype 2 Drug Product Weights Following
Melting and Drawing into an 18 Gauge Needle

| Sample Name | Weight of empty syringe (g) | Weight of syringe after test (g) | Amount of drug product (g) | Amount of drug product % |
|---|---|---|---|---|
| prototype 2-1 | 4.94598 | 4.95980 | 0.01382 | 7.5 |
| prototype 2-2 | 4.94609 | 4.97653 | 0.03044 | 16.5 |

TABLE 76

Prototype 2 Drug Product Weights Following Melting
and Expelling from an 18 Gauge Needle

| Sample Name | Weight of empty syringe (g) | Weight of syringe after test (g) | Amount of drug product (g) | Amount of drug product % |
|---|---|---|---|---|
| prototype 2-1 | 4.95833 | 4.98309 | 0.02476 | 13.4 |
| prototype 2-2 | 4.96619 | 4.98547 | 0.01928 | 10.4 |

TABLE 77

Prototype 2 Drug Product Weights Following
Melting and Drawing into a 26 Gauge Needle

| Sample Name | Weight of empty syringe (g) | Weight of syringe after test (g) | Amount of drug product (g) | Amount of drug product % |
|---|---|---|---|---|
| prototype 2-1 | 4.95962 | 4.95964 | 0.00002 | 0.0 |
| prototype 2-2 | 4.97193 | 4.97327 | 0.00134 | 0.7 |

Note -
Amount of drug product % calculated as follows:
(Amount of drug product/Fill Weight (185 mg)) * 100

The melting point for prototype 2 was 70° C. for both samples tested.

Following melting, the drug product for both samples of prototype 2 were drawn up into an 18 gauge needle. The drug product solidified when removed from the heat and drawn into the needle. None reached the syringe.

During the expel test for prototype 2, there was only a very small amount in the needle and none of it reached the syringe. For both preparations, the drug product solidified inside of the needle and nothing was expelled when pressure was applied.

Samples for prototype 2 were attempted to be drawn up into a 26 gauge needle however no drug product reached the needle or syringe.

For the comparator tablet, the powder was heated to 200° C. and did not melt into a sufficient fluid to be syringed.

Syringeability after Preparation in Water and Multi-Pass Filtering

A capsule was crushed to reduce the particle size of the dose and then ground with 10 mL of water at ambient temperature for up to thirty minutes until homogenous. The solution was drawn into a syringe via an 18-gauge needle. A cigarette filter was placed into the mortar and allowed to absorb any remaining liquid. The needle was placed into the cigarette filter to transfer any liquid taken up. In cases where 1 mL or greater was drawn up and was fluid enough to be expelled through the needle, the syringe contents was dispensed into suitably sized vessel. The filtering process was repeated a further two times or until the fluid was translucent. Where a translucent solution was produced, the solution was dispensed into a suitably sized volumetric flasks and prepared for HPLC analysis using the standard assay method diluent. Where a translucent solution was not produced, the sample was not analyzed.

TABLE 78

Syringeability after Preparation in Water
and Multi-pass Filtering

| Sample Name | % Recovery Comparator | % Recovery Prototype 2 |
|---|---|---|
| Sample 1 | 32.7 | Not analyzed |
| Sample 2 | 36.1 | Not analyzed |
| Sample 3 | 39.8 | Not analyzed |
| Mean | 36 | — |

For prototype 2, sample preparation 1 and 2: 5 ml was drawn into the syringe on the first filter and the resulting solution was opaque. 0.5 ml was drawn into the syringe on the second filter and the solution was opaque and therefore not assayed.

For prototype 2, sample preparation 3: 3 ml was drawn into the syringe on the first filter and the resulting solution was opaque. 1.5 ml was drawn into the syringe on the second filter and the solution was opaque and therefore not assayed.

For the comparator, sample preparation 1: 5 ml was drawn into the syringe on the first filter and the resulting solution was opaque. 4.5 ml was drawn into the syringe on the second filter and the solution was opaque. 4 ml was drawn into the syringe on the third filter and the solution was opaque. Due to the volume recovered, the sample was analyzed by HPLC.

For the comparator, sample preparation 2: 4 ml was drawn into the syringe on the first filter and the resulting solution was opaque. 3 ml was drawn into the syringe on the second filter and the solution was opaque. 3 ml was drawn into the syringe on the third filter and the solution was opaque. Due to the volume recovered, the sample was analyzed by HPLC.

For the comparator, sample preparation 3: 4 ml was drawn into the syringe on the first filter and the resulting solution was opaque. 3.5 ml was drawn into the syringe on the second filter and the solution was opaque. 3 ml was drawn into the syringe on the third filter and the solution was opaque. Due to the volume recovered, the sample was analyzed by HPLC.

Test of Syringeability (Prototype 2 and Comparator Only)

See Appendix B for a detailed description of the method used for the test of syringeability and chemical extraction.

A capsule was crushed to reduce the particle size of the dose and then ground with 5 mL of water at ambient temperature for up to thirty minutes until homogeneous. The mix was tested in order to ascertain if it could be sufficiently fluid to be drawn up into a Luer-lok syringe via a 26-gauge needle. The syringe plunger was drawn back to the 5 mL mark, maintaining a maximum pressure for 30 seconds or until the syringe has equilibrated pressure. If approximately 1 mL or greater was drawn into the syringe and was fluid enough to be expelled through the needle (for injection) then the syringe contents was dispensed into a suitably sized volumetric flask and prepared for HPLC analysis using the standard assay method diluent.

The above process was repeated using narrower gauge needles (18, 20 and 23 gauge) and water heated to 90-95° C.

TABLE 79

Syringeability in Ambient Water (5 mL)

| | Comparator | | Prototype 2 | |
|---|---|---|---|---|
| Sample Name | Volume syringed/ drawn (mL) | % Recovery | Volume spinged/ drawn (mL) | % Recovery |
| 18 gauge Needle 1 | 4.0 | 90.4 | 2.0 | 44.5 |
| 18 gauge Needle 2 | 4.5 | 88.3 | 2.5 | 50.9 |
| 18 gauge Needle 3 | 4.5 | 92.2 | 2.5 | 47.4 |
| Mean | | 90 | | 48 |
| 20 gauge Needle 1 | 1.5 | 48.6 | 1.0 | 18.1 |
| 20 gauge Needle 2 | 1.5 | 59.4 | 1.0 | 27.1 |
| 20 gauge Needle 3 | 1.5 | 66.9 | 1.0 | 26.7 |
| Mean | | 58 | | 24 |
| 23 gauge Needle 1 | 1.5 | 48.7 | 1.0 | 17.1 |
| 23 gauge Needle 2 | 1.5 | 39.0 | 1.0 | 1.2 |
| 23 gauge Needle 3 | 3.0 | 65.2 | <1.0* | 19.0 |
| Mean | | 51 | | 12 |
| 26 gauge Needle 1 | 2.0 | 37.0 | <1.0* | 0.5 |
| 26 gauge Needle 2 | 1.5 | 0** | <1.0* | 3.0 |
| 26 gauge Needle 3 | 1.0 | 21.6 | <1.0* | 1.1 |
| Mean | | 20 | | 2 |

*Samples <1 ml not required to be tested according to the protocol however they were analyzed at formulation development request for information only and have been reported here for information only.
**Note
1.5 mL drawn but could not be expelled.

Observations:

For the comparator tablet in ambient Water 18 Gauge Needle: All three preparations easy to syringe and easy to expel.

For the comparator tablet in ambient water 20 Gauge Needle: All three preparations easy to syringe and hard to expel.

For the comparator tablet in ambient water 23 Gauge Needle: All three preparations easy to syringe and hard to expel.

For the comparator tablet in ambient water 26 Gauge Needle, sample preparations 1 and 3 were hard to syringe and hard to expel. Sample preparation 2 did not expel.

FIG. 28 shows photographic observations of the syringeability of Prototype 2 in ambient water with varying gauged needles. FIGS. 29 and 30 show photographic observations of the syringeability of comparator and Prototype 2, respectively, in hot water with varying gauged needles.

TABLE 80

Syringeability in Hot Water (5 mL)

| | Comparator | | Prototype 2 | |
|---|---|---|---|---|
| Sample Name | Volume syringed/drawn (mL) | % Recovery | Volume syringed/drawn (mL) | % Recovery |
| 18 gauge Needle 1 | 4.0 | 81.9 | <1.0* | 2.9 |
| 18 gauge Needle 2 | 4.0 | 84.9 | <1.0* | 17.4 |
| 18 gauge Needle 3 | 4.0 | 91.0 | 1.5 | 24.2 |
| Mean | | 86 | | 15 |
| 20 gauge Needle 1 | 4.0 | 87.2 | 1.0 | 21.8 |
| 20 gauge Needle 2 | 4.0 | 87.5 | <1.0* | 5.5 |
| 20 gauge Needle 3 | 4.0 | 94.9 | 1.0 | 26.2 |
| Mean | | 90 | | 18 |
| 23 gauge Needle 1 | 4.0 | 86.1 | <1.0* | 0.5 |
| 23 gauge Needle 2 | 4.0** | 0 | <1.0* | 2.3 |
| 23 gauge Needle 3 | 4.0 | 93.6 | <1.0* | 5.8 |
| Mean | | 60 | | 3 |
| 26 gauge Needle 1 | 4.0 | 87.6 | <1.0* | 2.1 |
| 26 gauge Needle 2 | 3.0 | 64.5 | <1.0* | 4.3 |
| 26 gauge Needle 3 | 0.0 | 0 | <1.0* | 2.1 |
| Mean | | 50.7 | | 3 |

*Samples <1 ml not required to be tested according to the protocol however they were analyzed at formulation development request for information only and have been reported here for information only.
**Note 4 mL drawn but could not be expelled.

Abuse Involving Chemical Extraction (Prototype 2 and Comparator Only)

See Appendix B for a detailed description of the method used for the test of chemical extraction.

Extraction in Small Volumes of Ambient 0.2% Sodium Bicarbonate Solution (Each Sample in Triplicate)

A capsule was crushed to reduce the particle size of the dose and then ground with 5 mL of 0.2% Sodium Bicarbonate solution for five minutes until homogeneous. The resulting suspension was transferred to a scintillation vial, the lid covered with Parafilm and shaken in a water bath at ambient temperature. Samples were removed at 60 minutes and filtered through a 0.45 μm filter into a flask and diluted to volume using the standard assay method diluent.

The filtered samples were analyzed by HPLC to quantify the API present.

The experiment was repeated using 2 mL of ambient 0.2% Sodium Bicarbonate solution.

TABLE 81

Comparison of Ambient Solvent Extraction (Mean n = 3)

| | % Assay Average Amount | |
|---|---|---|
| Sample 60 Mins | 0.2% Sodium Bicarbonate 5 mL | 0.2% Sodium Bicarbonate 2 mL |
| Prototype 2 | 23 | N/A |
| Comparator | 103 | 96 |

For prototype 2, after grinding with 5 mL ambient 0.2% sodium bicarbonate, a thick opaque solution was obtained. After 60 mins shaking contents were thickened and difficult to filter approximately 1 ml of filtrate collected.

For prototype 2, after grinding with 2 mL ambient 0.2% sodium bicarbonate, a thick gel like semi solution mixture was obtained. After shaking unable to be filtered therefore no HPLC analysis was performed.

For comparator tablets, a salmon pink solution was obtained after grinding with 5 mL ambient 0.2% sodium bicarbonate which was easy to filter after 60 mins shaking.

For comparator tablets, the crushed sample absorbed the 2 mL ambient 0.2% sodium bicarbonate during grinding and shaking. After shaking, less than 1 mL of the filtered solution was collected.

Extraction in Small Volumes of Hot 0.2% Sodium Bicarbonate Solution (Each Sample in Triplicate).

A capsule was crushed to reduce the particle size of the dose and then ground with pre-heated 5 mL of 0.2% Sodium Bicarbonate solution for five minutes or until homogeneous. The resulting suspension was transferred to a scintillation vial, the lid covered with Parafilm and shaken in a water bath at ambient temperature. Samples were removed at 60 minutes and filtered through a 0.45 μm filter into a flask and diluted to volume using the standard assay method diluent.

Repeat the experiment using 2 mL of pre-heated 0.2% Sodium Bicarbonate solution

TABLE 82

Comparison of Hot Solvent Extraction (Mean n = 3)

| Sample 60 Mins | % Assay Average Amount | |
|---|---|---|
| | 0.2% Sodium Bicarbonate 5 ml | 0.2% Sodium Bicarbonate 2 ml |
| Prototype 2 | N/A | N/A |
| Comparator | 108 | 109 |

For prototype 2, after grinding with 5 mL hot 0.2% sodium bicarbonate, a viscous opaque soft solid solution was obtained. It could not be filtered and therefore no HPLC analysis was performed.

For prototype 2, after grinding with 2 mL hot 0.2% sodium bicarbonate, a-Semi solid solution was obtained which turned solid after shaking. The mixture could not be filtered and therefore no HPLC analysis was performed.

No observations were recorded following grinding of the comparator tablets with 5 mL hot 0.2% sodium bicarbonate.

For the comparator tablets, the 2 mL hot 0.2% sodium bicarbonate was absorbed during the grinding and shaking process, which resulted in less than 1 mL of filtrate being collected.

Ethanol Extraction Test (Prototype 2 and Comparator Only, Prepared in Triplicate)

See Appendix B for a detailed description of the method used for the test of chemical extraction.

A capsule was crushed to reduce the particle size of the dose and then ground with 10 mL of 95% ethanol solution for five minutes or until homogeneous. The resulting sample was filtered through a 0.45 μm nylon filter into a round bottom flask. The ethanol was evaporated by transferring the flask to a beaker containing water on a hot plate. The nature of the resultant mixture was recorded.

For prototype 2, the filtrate after evaporation was not syringeable therefore no HPLC analysis was performed.

For the comparator, the filtrate after evaporation was not syringeable therefore no HPLC analysis was performed.

For prototype 2 and the comparator, the residue left in each round bottom flask was agitated with a spatula and stuck to a spatula.

Based on the results above, it can be concluded that prototype 2 is more resistant to abuse when compared with the comparator tablet. This includes both by preventing the capsule contents to be physically ground for insufflation or by chemical extraction followed by drying to generate a powder residue. The risk of abuse via injection is also reduced, as the yields of drug recovered are much lower compared with the comparator. It was found that the resulting prototype 2 solution was more difficult to draw into a syringe and expel when compared with the comparator tablet.

Example 4: Comparison of Prototype 2, Placebo and a Non-Abuse Deterrent Tablet: Texture Analysis and Rheology listed drug (LD This example compares abuse-deterrent formulation Prototype 2 (ADAIR) to placebo and-Barr's 10 mg Immediate Release tablet) using a texture analyzer and a rheometer.

This example demonstrates that a greater force is required to expel manipulated ADAIR through a 26 G needle than that for the manipulated filtered LD through the same needle size. The data described supports that the abuse-deterrent formulation Prototype 2 and the placebo were more abuse deterrent, with respect to syringeability, than the LD.

The rheology of manipulated formulations of ADAIR, placebo and LD were characterised using a rheometer. Manipulated LD has been found to have a viscosity profile similar to water, wherase manipulated ADAIR and placebo were shown to have significantly higher viscosities, indicating that they would be more difficult to inject.

The placebo and ADAIR bulk formulations have been examined at various temperatures and a recommended filling temperature of 55±10° C. has been established, provided there are no stability issues at this temperature.

Introduction

Prototype 2 is an immediate release (IR) abuse deterrent formulation (ADF) of dextroamphetamine, now known as ADAIR (Abuse Deterrent Amphetamine Immediate Release), for clinical trial use. ADAIR is a 10 mg formulation of dextroamphetamine sulfate with a desired immediate release profile comparable to the selected non-AD listed drug (LD, Barr's 10 mg IR tablet containing dextroamphetamine sulfate).

ADAIR has been formulated using Kollisolv P124 (Poloxamer 124), Gelucire 48/16 (Polyoxyl stearate) and Kelcogel CGHA (gellan gum) and it is delivered as a 10 mg dose, in a size 3 banded gelatin capsule (previously called prototype 2). The bulk mix has been filled into capsules at 55° C.

A method capable of quantifying syringeability against a repeatable force of injection is described. A texture analyzer (TA), equipped with a syringe testing rig, was used to quantify the force required to eject the manipulated formulation from the syringe after developing a suitable method.

In parallel to the texture analyzer syringeability (TAS) testing, viscosity assessments were performed on the samples using a Brookfield DV-III Ultra Programmable Rheometer, in an attempt to correlate force of injection to rheological behaviour. The increased force required to expel manipulated ADAIR and its manipulated placebo through a 26 G needle, compared to filtered LD, has been attributed to greater viscosity.

Finally, the viscosity of the bulk ADAIR formulation, along with a suitable placebo, was measured at various temperatures between 25-65° C. in order to verify the suitability of 55° C. for filling and the determine the suitable range. For the placebo formulation, the API was replaced with Avicel PH101, and used as a surrogate for Dextroamphetamine Sulfate in scale-up trials. A filling temperature of 55±10° C. has been recommended for ADAIR and the placebo, provided that there are no concerns with thermal stability at this temperature.

Materials and Equipment

The Capsugel Edinburgh received raw material (RRM) number, manufacturer's batch number, manufacturer and expiry date for the materials used in these studies are detailed in Table 83.

TABLE 83

Batch details for excipients used during this study.

| Material | Function | Manufacturer |
|---|---|---|
| Dextroamphetamine Sulfate | API | Cambrex |
| Kollisolv P124 | Carrier | BASF |
| Gelucire 48/16 | Carrier | Gattefosse |
| Kelcogel CGHA | Viscosity modifier | Kelco |
| Avicel PH101 | Placebo | FMC Biopolymer |
| Avicel PC101 | Placebo (method development) | FMC Biopolymer |
| 10 mg Dextroamphetamine Sulfate tablets | Comparator | Teva |

The details of needles used in this work are shown in Table 84.

TABLE 84

Batch details for needles and syringes used during this study.
Material 18 gauge BD Microlance 3
26 gauge BD Microlance 3
BD 5 mL syringe Luer-lok ™

Equipment

Equipment used during these studies is detailed in Table 85.

TABLE 85

Formulation development equipment used in this work.
Equipment

Balances
Silverson high shear mixer
Fan oven
Temperature probe
Stainless steel spatulas
Vacuum desiccator
PVDF 25 mm 0.45 µm syringe filter
Texture Analyzer TA-XTPlus with Universal Syringe rig
Brookfield RVDV-III UCP programmable rheometer
Amber glass jars
Mortar and pestle
Stopwatch Method 3. Placebo Formulation Preparation To prepare the placebo bulk mix formulation for method development, materials were dispensed into a 60 mL amber jar (see Table for quantities) and heated in an oven to melt. The bulk material was high shear mixed for 1 minute, during which time the temperature reduced from 59.1 to 51.2° C. The bulk mix was then degassed in a vacuum chamber to remove air bubbles. Note that due to material availability Avicel PC101 was used for this work rather than PH101 which was used for subsequent technical manufactures. These are considered physiochemically equivalent, with PC the grade used for personal care, and PH the pharmaceutical grade material.

TABLE 86

Dispensed quantities for the placebo bulk mix preparation for method development.

| Material | Unit formulation (%) | Batch Quantity (g) | Lower limit (g) | Upper limit (g) | Actual (g) |
|---|---|---|---|---|---|
| Avicel PC101 | 5.4054 | 1.08108 | 1.0757 | 1.0865 | 1.0820 |
| Kollisolv P124 | 37.8378 | 7.56756 | 7.5297 | 7.6054 | 7.5424 |
| Gelucire 48/16 | 28.3784 | 5.67568 | 5.6473 | 5.7041 | 5.6876 |
| Kelcogel CGHA | 28.3784 | 5.67568 | 5.6473 | 5.7041 | 5.6843 |
| Total | 100 | 20 | | | 19.9963 |

To prepare the placebo bulk mix for analysis, materials were dispensed into a 60 mL jar (see Table 86) and placed in the oven prior to high shear mixing. The bulk material was high shear mixed for a total of 1 min, during which time the temperature dropped from 50° C. to 42° C.

TABLE 87

Dispensed quantities for the placebo bulk mix preparation for analysis.

| Material | Unit formulation (%) | Batch Quantity (g) | Lower limit (g) | Upper limit (g) | Actual (g) |
|---|---|---|---|---|---|
| Avicel PC101 | 5.4054 | 1.08108 | 1.0757 | 1.0865 | 1.0802 |
| Kollisolv P124 | 37.8378 | 7.56756 | 7.5297 | 7.6054 | 7.5928 |
| Gelucire 48/16 | 28.3784 | 5.67568 | 5.6473 | 5.7041 | 5.6821 |
| Kelcogel CGHA | 28.3784 | 5.67568 | 5.6473 | 5.7041 | 5.6699 |
| Total | 100 | 20 | | | 20.0250 |

ADAIR Formulation Preparation

To prepare the active ADAIR formulation, the Kollisolv P124, Gelucire 48/16 and Kelcogel CGHA were dispensed into a 60 mL amber jar (see Table 88) and placed in an oven (53° C.) to melt the Gelucire 48/16. The API was then dispensed into the jar, mixed with a spatula to wet the powder, and the bulk material returned to the oven for 10 minutes to increase the fluidity again prior to high shear mixing. High shear mixing was carried out for a total of 1 min, during which the temperature reduced from 43° C. to 36-37° C. It was noted that the material was beginning to harden at the end of the mixing time but a homogenous mix had been achieved prior to this.

TABLE 88

Dispensed quantities for the ADAIR bulk mix preparation for analysis.

| Material | Unit formulation (%) | Batch Quantity (g) | Lower limit (g) | Upper limit (g) | Actual (g) |
|---|---|---|---|---|---|
| Dextro-amphetamine sulfate | 5.4054 | 1.08108 | 1.0757 | 1.0865 | 1.0789 |
| Kollisolv P124 | 37.8378 | 7.56756 | 7.5297 | 7.6054 | 7.5706 |
| Gelucire 48/16 | 28.3784 | 5.67568 | 5.6473 | 5.7041 | 5.6774 |
| Kelcogel CGHA | 28.3784 | 5.67568 | 5.6473 | 5.7041 | 5.6552 |
| Total | 100 | 20 | | | 19.9821 |

Preparation of Manipulated Samples

To prepare samples of manipulated placebo and ADAIR formulations for syringeability and viscosity assessment, ~1.11 g (equivalent to fill material for 6 capsules) was ground in a mortar and pestle with 20 mL of room temperature potable water until homogenous. The manipulated material was stored in an amber glass jar prior to analysis. An attempt was made to filter a sample of manipulated active material through a PVDF 0.45 µm syringe filter, however only a few drops of filtrate were produced before the filter blocked.

To prepare samples of manipulated listed drug (LD), three full tablets were ground in 10 mL of room temperature potable water until homogenous.

Texture Analyzer Syringeability

The texture analyzer TAXTPlus was used with a Universal syringe rig and 30 kg load cell. The instrument was calibrated for height and weight prior to use, and programmed for a set start position of 3 mL, and a target distance of 9 mm. See 88 for method settings. 5 mL Leur-Lok' syringes were used to prevent expulsion of the needle from the syringe during the test, and samples were assessed (n=2 or 3, depending on available sample) using 18 gauge and 26 gauge needles.

During the method development phase, water and manipulated placebo formulation were analyzed, as well as empty syringes and empty syringes with needles attached, as controls (n=2 or 3). For the sample analysis, these were included in addition to the manipulated placebo, manipulated ADAIR and manipulated LD (n=2 or 3). Syringes were back-filled, except from free-flowing liquids (water and LD samples), where the syringes were loaded by drawing the material to be tested up through the tip, with no needle present.

TABLE 89

Texture Analyzer settings used to assess syringeability.

| Parameter | Setting |
| --- | --- |
| Test mode | Compression |
| Test speed | 0.50 mm/s |
| Post-test speed | 5.00 mm/s |
| Target mode | Distance |
| Distance | 9.000 mm |
| Distance unit | mm |
| Force unit | N |
| Time unit | s |

Viscosity

Viscosity was assessed using a Brookfield RVDV-III Ultra Cone and Plate rheometer, with geometries CP40 and CP52. Manipulated ADAIR, manipulated placebo and manipulated LD were analyzed at 25° C. Placebo and ADAIR bulk mixes were analyzed at 25, 35, 45, 55 and 65° C. to assess filling temperature. A suitable method was developed for each sample type, and shear stress was measured on application of an increasing and decreasing speed ramp, for each sample.

Results and Discussion 4.1 Preparation of ADAIR and Placebo Formulations

The ADIAR and placebo formulations were prepared without issue. Processing was aided by pre-heating stainless steel spatulas and high shear heads prior to use. At elevated temperatures the bulk formulation, although viscous, had sufficient process-ability to facilitate mixing and aliquoting at the bench scale.

3.2 Preparation of Manipulated Samples

Grinding the comparator tablets with a mortar and pestle resulted in a coarse powder/liquid mixture with a pink/brown hue. The tablets could be crushed quickly with the mortar and pestle to aid grinding with the solvent.

For the placebo and ADAIR, the formulations were heated to facilitate aliquoting into the mortar (FIG. 32-33) This was not heated prior to use and the material solidified quickly. The waxy consistency of the solid fill material made it slightly more challenging to process using a pestle. On grinding with water, a gel-like material was formed. The placebo formulation formed a gel with greater apparent viscosity. This was likely due to the presence of Avicel PH101 which had been added to replace the dextroamphetamine sulfate.

The quantities of materials used for the manipulations, along with the tests they were utilised for are documented in Table 90

TABLE 90

Table documenting the amount of material used for manipulation, the volume of water and grinding time used during the manipulation and what analysis the sample was used for.

| Batch number | Material under test | Quantity of unmanipulated material | Volume of water (mL) | Grinding time (s) | Used for |
| --- | --- | --- | --- | --- | --- |
| 1003/174/02 | Placebo | 1.1239 g | 20 | 60 | Method development |
| 1003/187/06 | LD | 3 tablets | 10 | 64 | Analysis 18 Gauge needle (unfiltered) |
| 1003/187/07 | LD | 3 tablets | 10 | 63 | Analysis 26 gauge needle (unfiltered) |
| 1003/190/01 | Placebo | 1.1167 g | 20 | 155 | Analysis 18 Gauge needle (unfiltered) |
| 1003/190/01 | ADAIR | 1.1087 g | 20 | 148 | Analysis 18 Gauge needle (unfiltered) |
| 1003/190/03 | Placebo | 1.1199 | 20 | 60 | Analysis 26 Gauge |
| 1003/190/04 | ADAIR | 1.1170 | 20 | 94 | Attempt to filter. Analysis 26 Gauge. |
| 1003/191/03 | LD | 3 tablets | 10 | 60 | Analysis 18 Gauge (filtered). |
| 1003/191/04 | LD | 3 tablets | 10 | 60 | Analysis 26 Gauge (filtered). |

3.3 Texture Analysis Development

A method was developed which was capable of measuring the forces associated with injecting empty syringes with 18 G needles, empty syringes with 26 G needles, water (with both 18 and 26 G needles) and a manipulated ADF placebo (with both 18 G and 26 G needles). Due to the viscous nature of the manipulated ADF, the syringe barrels were back-filled, rather than drawing liquid into the syringe from the tip. for an illustration of the set-up The texture analyzer software was used to calculate the stiction force, plateau force and end constraint. In order to carry this out the profile was divided into three time zones (1-2, 2-3 and 3-4 on 35 below). During this test, a button trigger is used and so the data is captured from the point where the test starts. There was an initial peak in force as the syringe plunger begins to move and the syringe contents start to move. This is called the stiction, and is the force required to overcome the static friction. This was taken as the maximum value during the first third of the analysis (1-2). As the test progressed and the plunger moved into the central area of the syringe barrel, a force plateau was reached. The plateau force was therefore taken as the maximum force between points 2 and 3 (FIG. 5) The final peak force was recorded as the end constraint. The average results are shown in FIG. 6.

Texture Analyzer Syringeability

In order to remove any contribution of any constraint as a result of the syringe barrel geometry during the analysis of the samples, the test was carried out moving the plunger from 3 mL position to 2 mL position, rather than moved to fully expel the material from the syringe. This meant that any influence from the geometry of the syringe was avoided, for clarity of results, and meant that the "end constraint" was no longer applicable.

Figure 37:
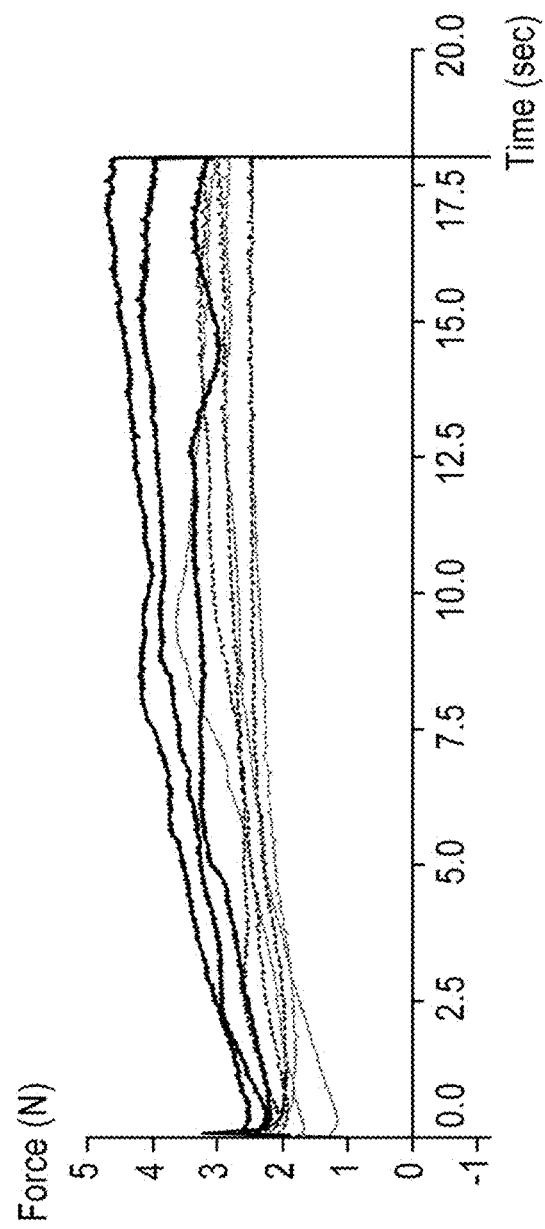
FIG. 37 is a graph showing texture analysis profiles for the empty syringe 18 G needle (red), empty syringe 26 G needle (blue) and empty syringe, no needle (black), n=3.
Figure 38:
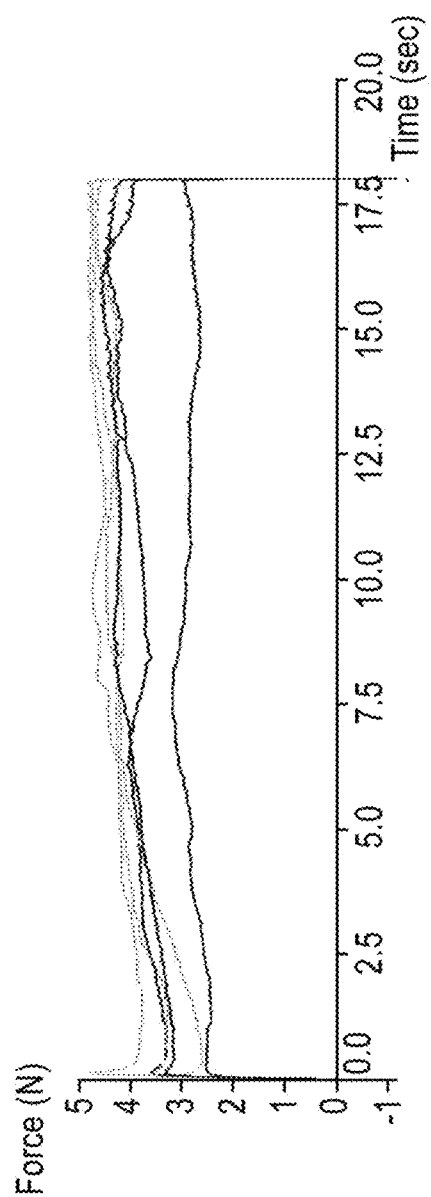
FIG. 38 is a graph showing texture analysis profiles for water 26 G needle (dark blue) and water 18 G (light blue), n=3.

At the start of the investigation empty syringes, syringes with 18 G needles and syringes with 26 G needles were analyzed (FIG. 37-38) to provide data on the resistance to movement inherent to equipment being used for the test (i.e., 5 mL syringe and needle). The empty syringe gave an average peak force of 3.043 N, with the 18 G needle averaging 4.146 N and the 26 G needle averaging 3.208 N. In each profile there was an initial maxima within the first second of the test which related to the force of stiction (the force required to set the plunger in motion). This could also be seen in the profiles for water through 18 G and 26 G needles FIG. 37

In order to minimise contribution of stiction from the equipment interfering with the test results, it was decided not to use these stiction maxima to characterise the data. Additionally, due to the nature of the ADF materials and the manipulated tablets, the time taken to reach a plateau force varied, or a smooth plateau was not achieved, meaning that the calculation of plateau force using the texture analyzer software was not practical.

As a result, it was decided that stiction, plateau and end constraint were not practical for characterising the syringeability profiles and comparing the gathered data. It was instead decided that the data should be characterised using two parameters: the peak force (N), and the area under the force time curve (Ns, a representation of the "work done" to move the plunger through 9 mm whilst expelling material from the needle). In cases where the peak force was achieved at the stiction maxima, the data was manually reprocessed to obtain the maxima achieved later in the run. It should be noted that this applied only one repeat of the empty syringe (where the peak force was adjusted from 2.558 N to 2.518 N), and one repeat of the manipulated filtered LD (where the peak force was adjusted from 4.744 N to 4.215 N). It was anticipated that using the average peak force and the average area under the curve for all repeats in each test set would provide a more complete and relevant set of data than stiction, plateau force and end constraint in this investigation.

Instead, the peak force and the area under the force time curve were calculated. In cases where the peak force was found to be in the "stiction" area, the data was reprocessed manually to obtain the peak force achieved during the main body of the test. It should be noted that this only applied to the empty syringe and the filtered LD.

Figure 39:
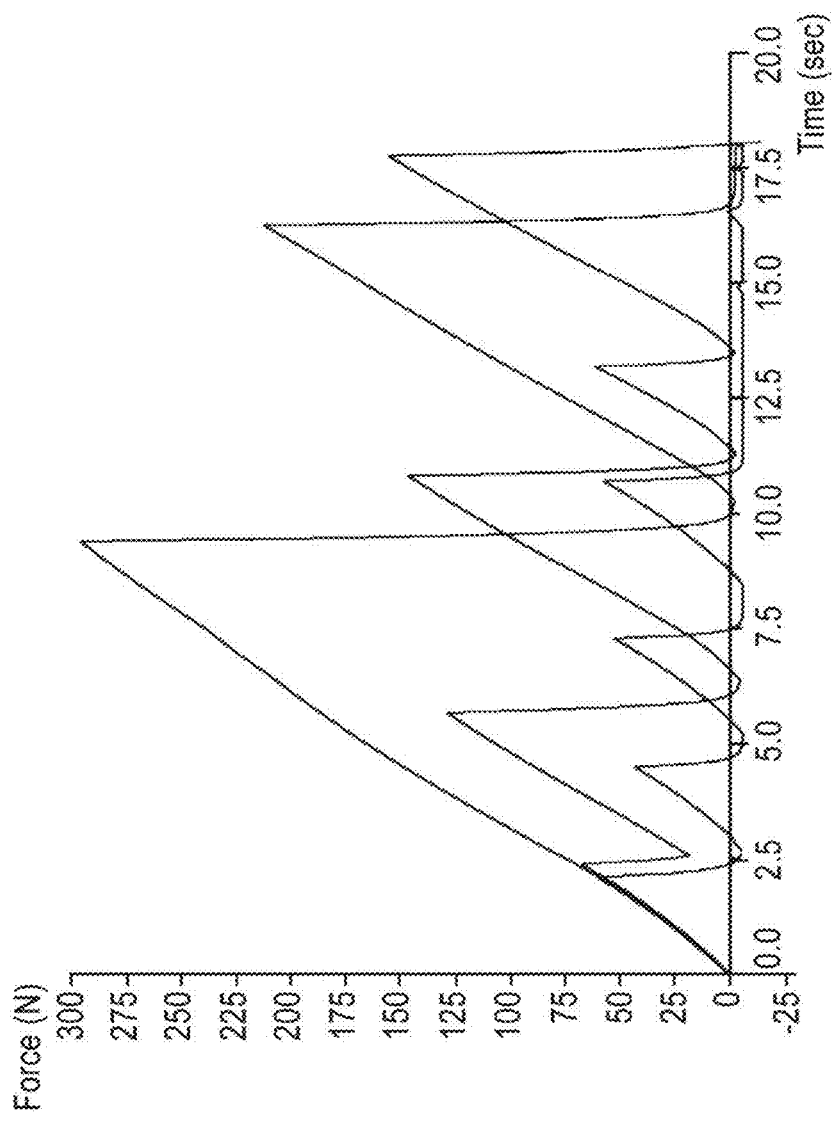
FIG. 39 is a graph showing texture analysis profiles for the unfiltered LD through a 26 G needle (n=3). Not that the multiple peaks and troughs are a result of particulates of the crushed tablet causing temporary blockages to the needle, n=3.
Figure 40:
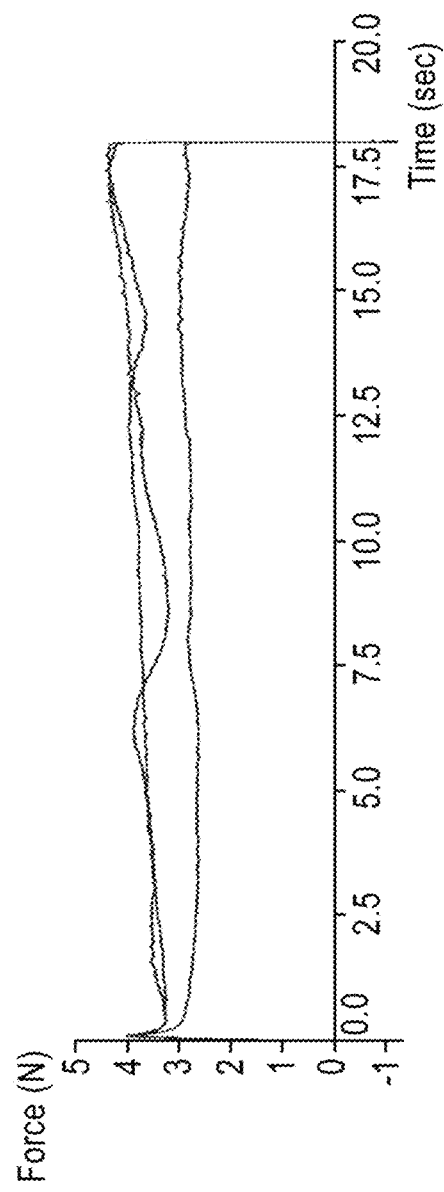
FIG. 40 is a graph showing texture analysis for the unfiltered manipulated LD using an 18 G needle, n=3.

For the unfiltered manipulated LD, the texture analyzer profiles showed a number of sharp peaks and troughs FIG. 39 This was thought to be a result of particles of crushed tablet causing intermittent blocking of the needle during the test. These required greater force to dislodge (the texture analyzer is programmed to adjust force so as to maintain a constant test speed, rather than to achieve a constant force). This effect was not seen when analysing an equivalent sample using an 18 G needle FIG. 40, due to the lager bore size of this needle. This effect is expected to be influenced by the degree of grinding that is applied by the operator. Additionally, it is not expected that an abuser would attempt to inject the manipulated LD without filtering the material first. The 18 G and 26 G data for these samples are shown separately for clarity.

Figure 41:
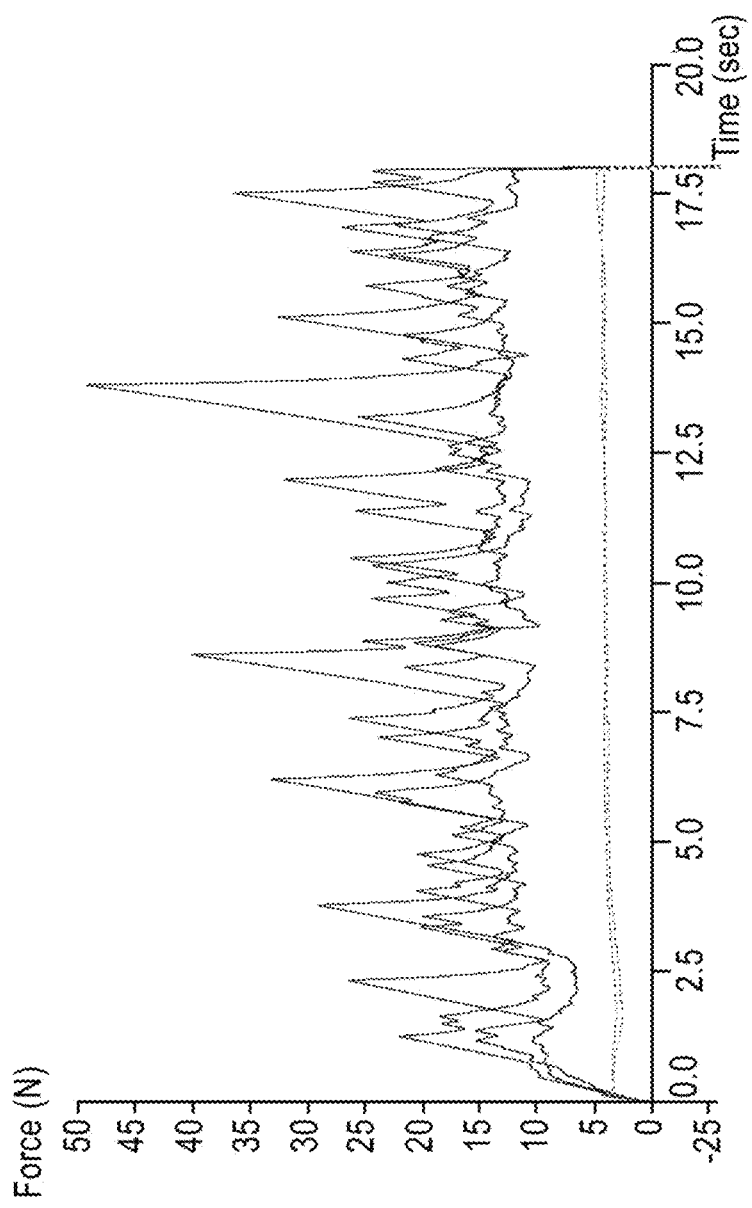
FIG. 41 is a graph showing texture analysis for manipulated ADAIR unfiltered through a 26 G (green) and 18 G (orange) needle, n=3.
Figure 42:
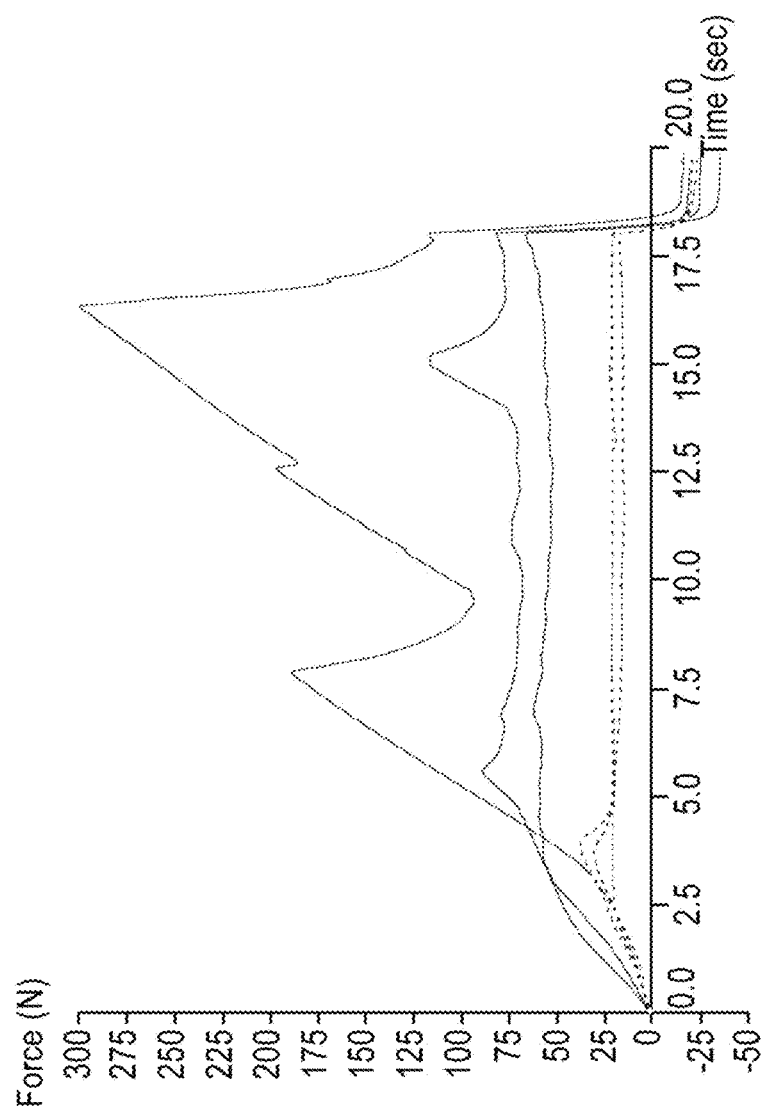
FIG. 42 is a graph showing texture analysis for manipulated placebo through an 18 G (pink) and 26 G needle (green), n=3.

The profiles obtained for the manipulated ADAIR and the manipulated placebo are shown in FIG. 41 and FIG. 42 respectively. In both of these samples the test using a 26 G needle produces an uneven profile with peaks associated with increased resistance to syringing, compared to the 18 G needle (wider bore) tests which produced a smoother profile, more typical of syringe testing.

Figure 43:
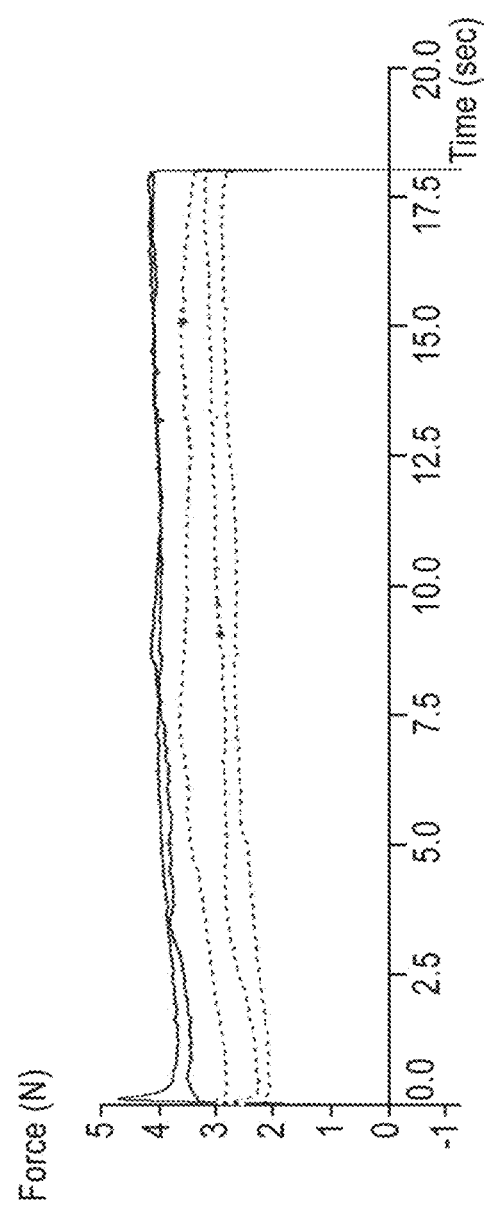
FIG. 43 is a graph showing texture analysis for manipulated filtered LD through an 18 G (green, n=3) and 26 G (red, n=2) needle.

During manipulation of a solid oral dosage form to prepare for injection, abusers will commonly filter the solution, rather than attempt to inject a solution containing powdered excipients. As a result, it was decided to filter a preparation of manipulated LD and analyze this FIG. 43. Note that a third repeat of the filtered LD through a 26 G needle could not be performed due to spillage of the sample during preparation for the test. An attempt was made to filter the manipulated ADAIR for a comparative analysis but sufficient material could not be obtained to carry out this test (n=1). The peak force (N) and area under the curve (Ns) for all samples, along with calculated average, standard deviation and coefficient of variation is shown is Table 91.

TABLE 91

Peak force and area under the curve for all samples analyzed using the texture analyzer.

| Sample set | Sample | Peak force (N) | Area under curve (Ns) |
|---|---|---|---|
| empty syringe | empty syringe 1 | 2.518 | 40.774 |
| | empty syringe 2 | 2.957 | 43.970 |
| | empty syringe 3 | 3.655 | 52.193 |
| | Average: | 3.043 | 45.646 |
| | S.D. | 0.573 | 5.891 |
| | Coef. of Variation | 18.831 | 12.906 |
| empty syringe 18 G | empty syringe 18 G needle 1 | 3.438 | 55.098 |
| | empty syringe 18 G needle 2 | 4.248 | 64.250 |
| | empty syringe 18 G needle 3 | 4.751 | 70.027 |
| | Average: | 4.146 | 63.125 |
| | S.D. | 0.662 | 7.528 |
| | Coef. of Variation | 15.977 | 11.925 |
| empty syringe 26 G | empty syringe 26 G needle 1 | 3.227 | 42.479 |
| | empty syringe 26 G needle 2 | 3.048 | 47.548 |
| | empty syringe 26 G needle 3 | 3.349 | 51.635 |
| | Average: | 3.208 | 47.221 |
| | S.D. | 0.151 | 4.587 |
| | Coef. of Variation | 4.714 | 9.714 |
| water 18 G | water 18 G 1 | 4.874 | 77.436 |
| | water 18 G 2 | 4.836 | 78.184 |
| | water 18 G 3 | 4.766 | 72.757 |
| | Average: | 4.825 | 76.126 |
| | S.D. | 0.054 | 2.942 |
| | Coef. of Variation | 1.127 | 3.864 |
| water 26 G | water 26 G 1 | 4.611 | 72.605 |
| | water 26 G 2 | 3.219 | 50.935 |
| | water 26 G 3 | 4.503 | 70.161 |
| | Average: | 4.111 | 64.567 |
| | S.D. | 0.774 | 11.869 |
| | Coef. of Variation | 18.833 | 18.382 |
| LD unfiltered 18 G | LD unfiltered 18 G 1 | 3.909 | 50.858 |
| | LD unfiltered 18 G 2 | 4.409 | 66.376 |
| | LD unfiltered 18 G 3 | 4.441 | 68.532 |
| | Average: | 4.253 | 61.922 |
| | S.D. | 0.298 | 9.642 |
| | Coef. of Variation | 7.017 | 15.571 |
| LD unfiltered 26 G | LD unfiltered 26 G 1 | 61.400 | 66.921 |
| | LD unfiltered 26 G 2 | 296.633 | 1457.148 |
| | LD unfiltered 26 G 3 | 156.687 | 334.931 |
| | Average: | 171.573 | 619.667 |
| | S.D. | 118.321 | 737.556 |
| | Coef. of Variation | 68.962 | 119.025 |
| ADAIR 18 G | ADAIR 18 G 1 | 4.937 | 70.267 |
| | ADAIR 18 G 2 | 3.784 | 63.791 |
| | ADAIR 18 G 3 | 4.524 | 73.589 |
| | Average: | 4.415 | 69.216 |
| | S.D. | 0.584 | 4.983 |
| | Coef. of Variation | 13.234 | 7.199 |

TABLE 91-continued

Peak force and area under the curve for all samples analyzed using the texture analyzer.

| Sample set | Sample | Peak force (N) | Area under curve (Ns) |
|---|---|---|---|
| ADAIR 26 G | ADAIR 26 G 1 | 49.546 | 265.710 |
| | ADAIR 26 G 2 | 40.375 | 308.208 |
| | ADAIR 26 G 3 | 36.644 | 298.530 |
| | Average: | 42.188 | 290.816 |
| | S.D. | 6.639 | 22.274 |
| | Coef. of Variation | 15.738 | 7.659 |
| LD filtered 18 G | LD filtered 18 G 1 | 3.692 | 61.637 |
| | LD filtered 18 G 2 | 2.954 | 47.169 |
| | LD filtered 18 G 3 | 3.253 | 52.503 |
| | Average: | 3.300 | 53.770 |
| | S.D. | 0.371 | 7.317 |
| | Coef. of Variation | 11.245 | 13.607 |
| LD filtered 26 G | LD filtered 26 G 1 | 4.215 | 71.760 |
| | LD filtered 26 G 2 | 4.167 | 70.514 |
| | LD filtered 26 G 3 | — | — |
| | Average: | 4.191 | 71.137 |
| | S.D. | 0.034 | 0.881 |
| | Coef. of Variation | 0.809 | 1.238 |
| Placebo 18G | Placebo 18 G 1 | 31.051 | 371.164 |
| | Placebo 18 G 2 | 38.233 | 320.998 |
| | Placebo 18 G 3 | 21.789 | 355.033 |
| | Average: | 30.358 | 349.065 |
| | S.D. | 8.244 | 25.610 |
| | Coef. of Variation | 27.155 | 7.337 |
| Placebo 26 G | Placebo 26 G 1 | 299.455 | 2408.156 |
| | Placebo 26 G 2 | 116.775 | 1225.739 |
| | Placebo 26 G 3 | 66.343 | 953.722 |
| | Average: | 160.858 | 1529.206 |
| | S.D. | 122.649 | 773.249 |
| | Coef. of Variation | 76.247 | 50.565 |

Figure 44:
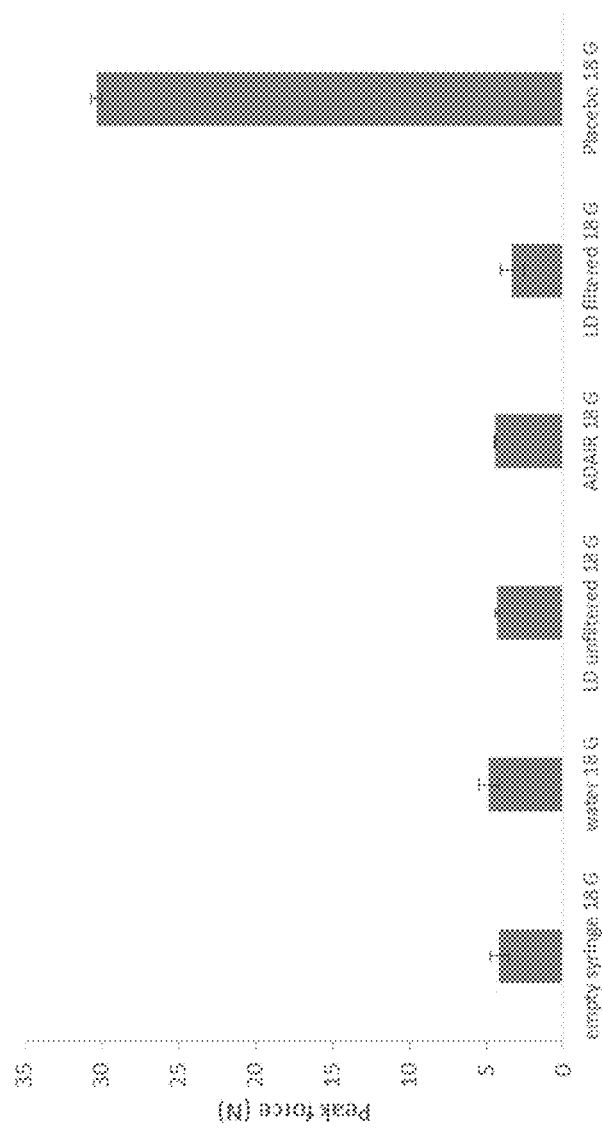
FIG. 44 is a bar chart showing the average peak force recorded for all manipulated samples measured on the texture analyzer using an 18 G needle. Error bars represent standard deviation (n=3).
Figure 45:
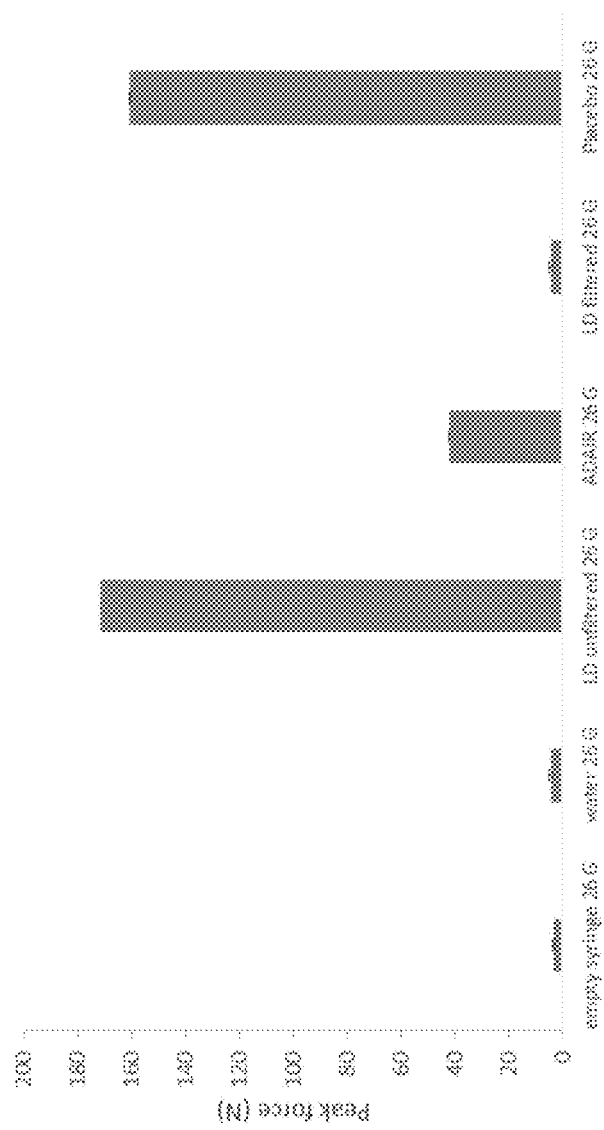
FIG. 45 is a bar chart showing the average peak force recorded for all manipulated samples measured on the texture analyzer using a 26 G needle. Error bars represent standard deviation (n=3, apart from LD filtered 26 G where n=2).
Figure 46:
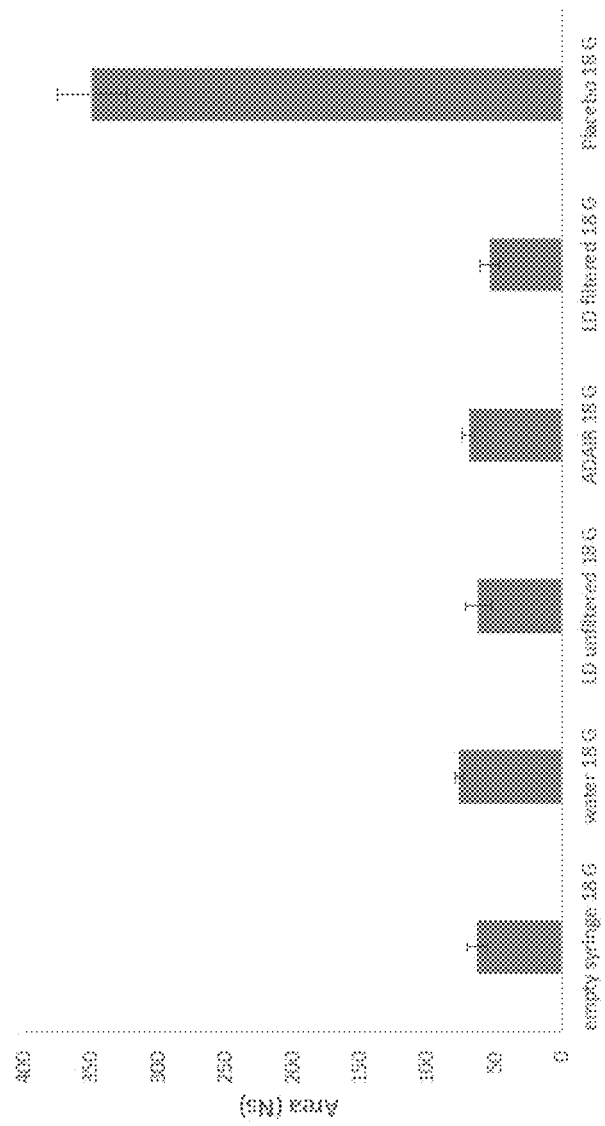
FIG. 46 is a bar chart showing the average area under the force vs time curve (in Ns) recorded for all manipulated samples measured on the texture analyzer using an 18 G needle. Error bars represent standard deviation (n=3).
Figure 47:
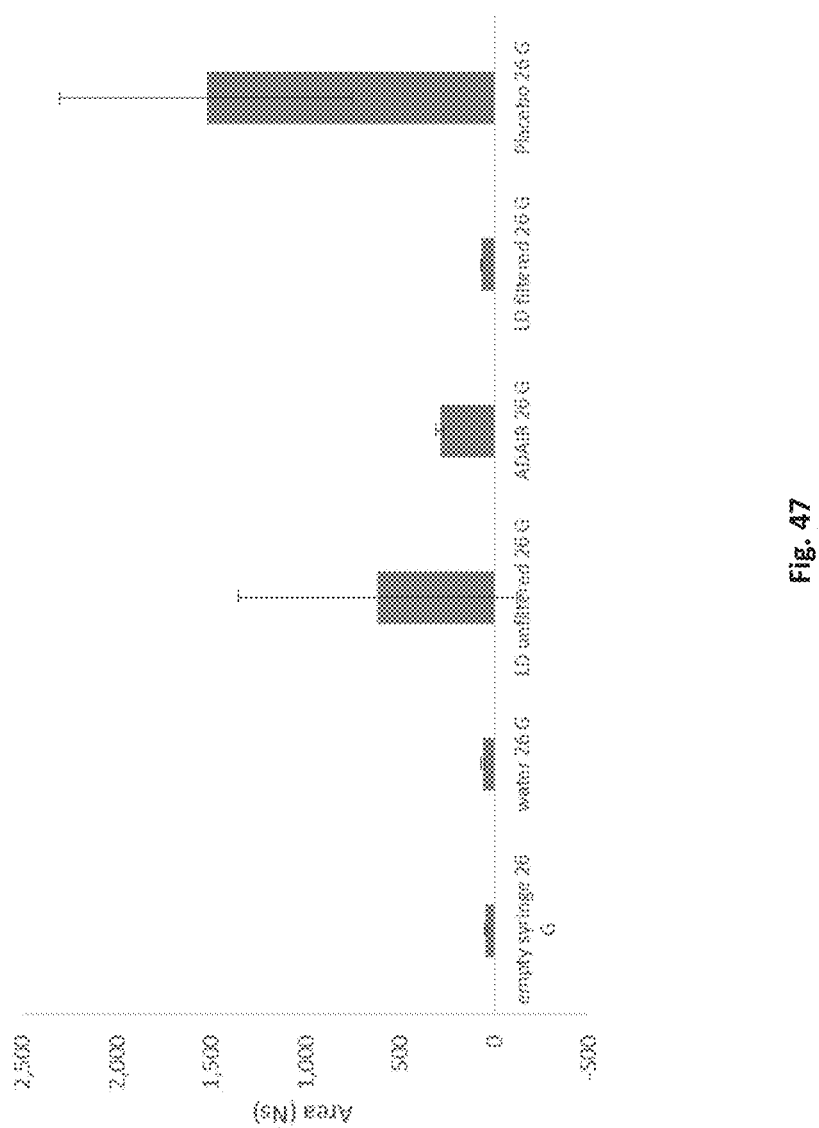
FIG. 47 is a bar chart showing the average area under the force vs time curve (in Ns) recorded for all manipulated samples measured on the texture analyzer using a 26 G needle. Error bars represent standard deviation (n=3, apart from LD filtered 26 G where n=2).

The graphs of average peak force for samples measured using 18 G and 26 G needles are shown in FIGS. 44 and 45, respectively. The graphs of average area under curve for samples measured using 18 G and 26 G needles are shown in FIG. 46 and FIG. 47, respectively.

Discussion of TA Data

Figure 48:
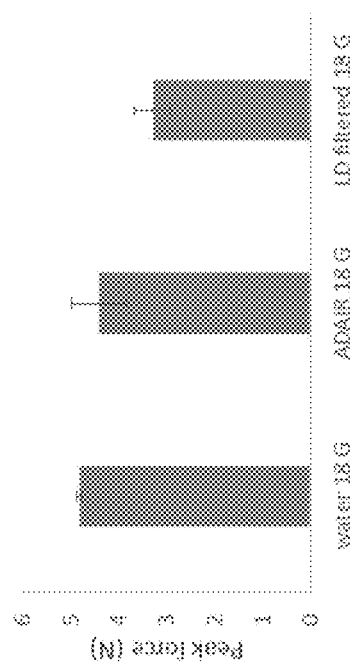
FIG. 48 is a bar chart showing the average peak force recorded for water, manipulated ADAIR and manipulated, filtered LD samples measured on the texture analyzer using an 18 G needle. Error bars represent standard deviation (n=3).
Figure 49:
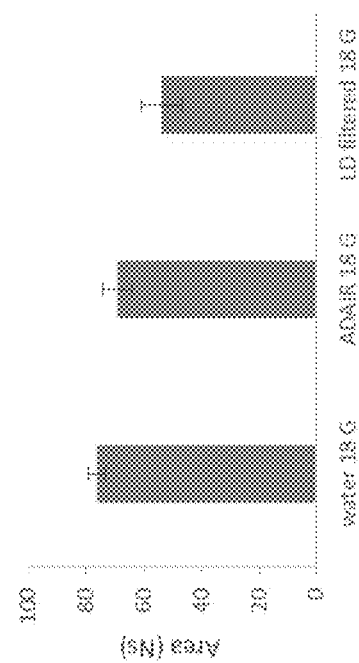
FIG. 49 is a bar chart showing the average peak area under the force vs time curve (in Ns), manipulated ADAIR and manipulated, filtered LD samples measured on the texture analyzer using an 18 G needle. Error bars represent standard deviation (n=3).

The data for the 18 G needles do not show a significant difference between the ADAIR formulation and water for either average peak force FIG. 48 or average area under curve FIG. 49 however this is a large bore size and unlikely to be used for intravenous abuse of dextroamphetamine sulfate.

Figure 50:
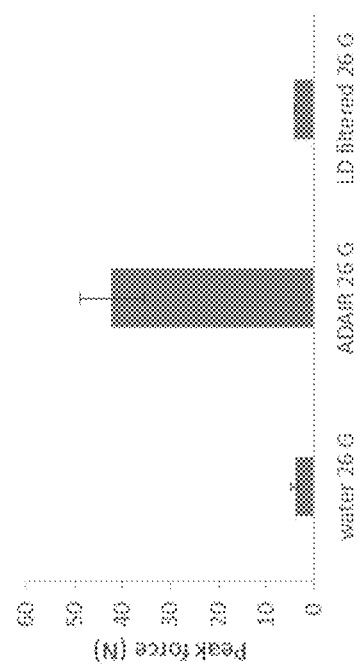
FIG. 50 is a bar chart showing the average peak force recorded for water, manipulated ADAIR and manipulated, filtered LD samples measured on the texture analyzer using a 26 G needle. Error bars represent standard deviation (n=3, apart from LD filtered 26 G where n=2).
Figure 51:
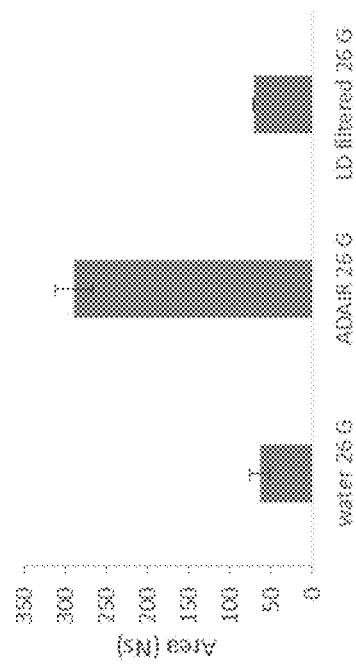
FIG. 51 is a bar chart showing the average area under the force vs time curve (in Ns) recorded for water, manipulated ADAIR and manipulated, filtered LD samples measured on the texture analyzer using a 26 G needle. Error bars represent standard deviation (n=3, apart from LD filtered 26 G where n=2).
Figure 52:
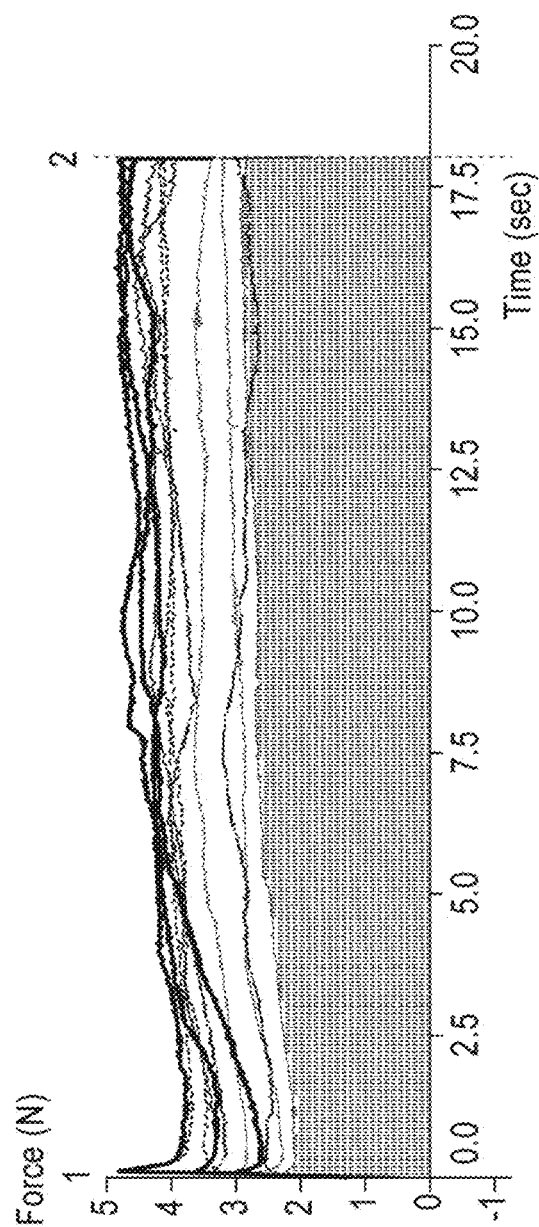
FIG. 52 is a graph showing texture analysis profiles for water 26 G (dark blue), water 18 G (light blue), filtered LD 18 G (orange) and filtered LD 26 G (red). Measurements are all in a similar order of magnitude. Red shading represents the area under the curve for one repeat of the LD 18 G.
Figure 54A:
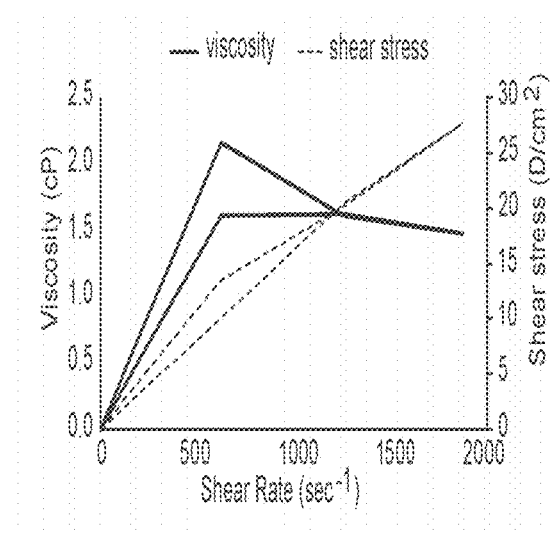
FIG. 54A-E are graphs showing viscosity and shear stress vs shear rate for the manipulated LD when unfiltered (FIG. 54A-B) and filtered (FIG. 54C-D) compared to a single repeat of water (FIG. 54E).
Figure 54B:
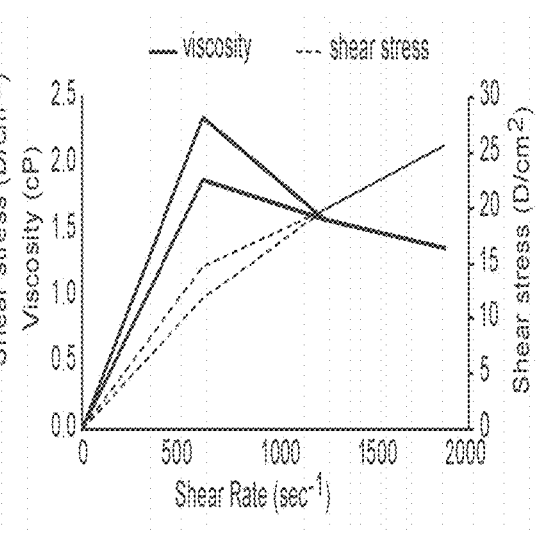
Figure 54C:
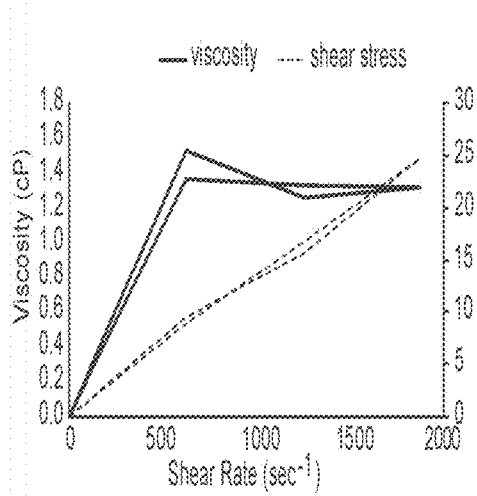
Figure 54D:
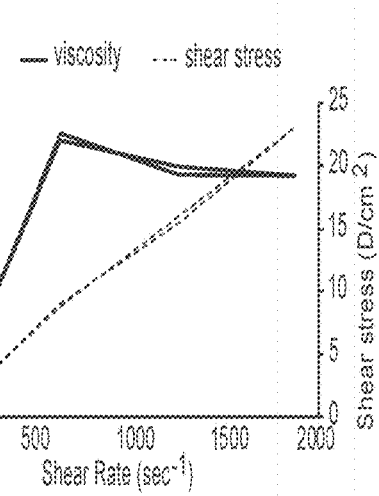
Figure 54E:
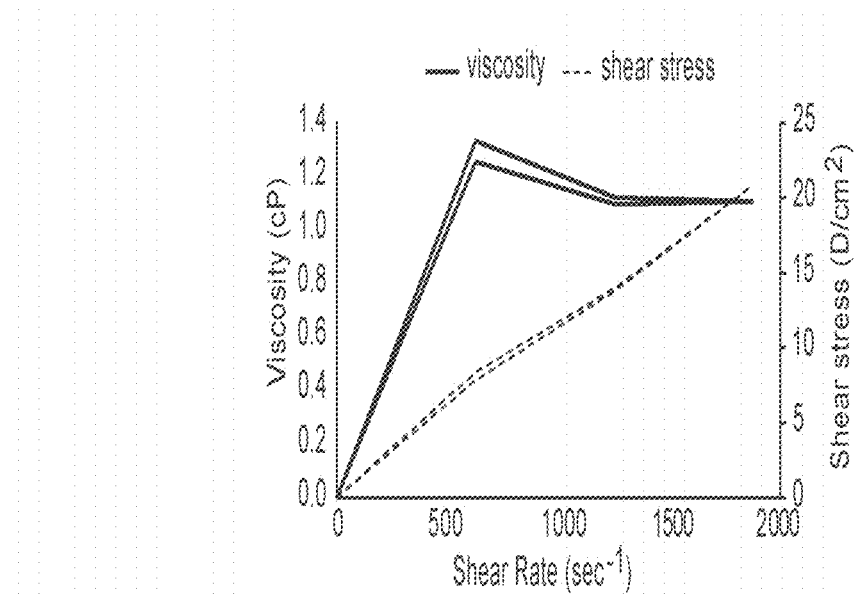
Figure 55A:
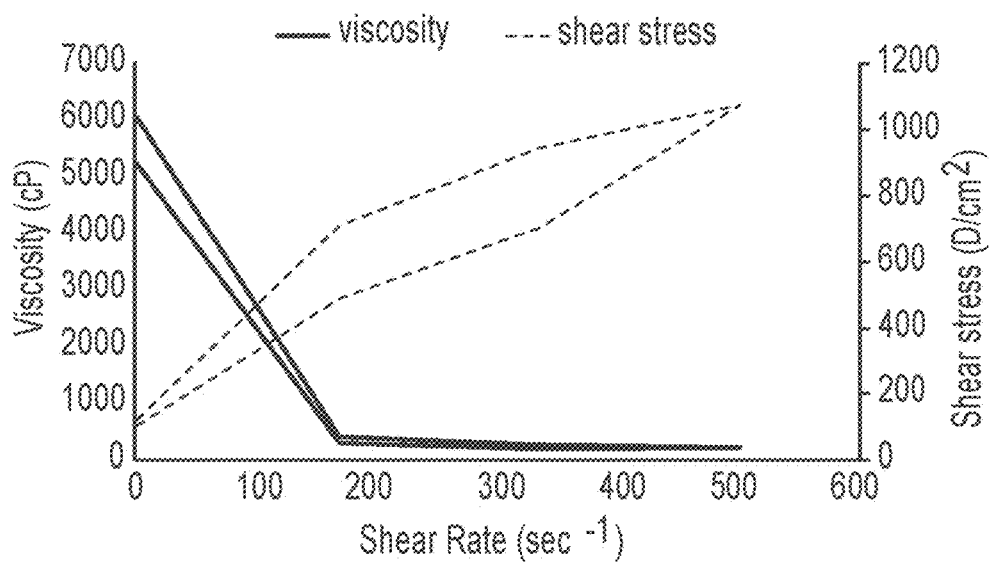
FIG. 55A-B are graphs showing viscosity and shear stress vs shear rate for two samples of manipulated ADAIR.
Figure 55B:
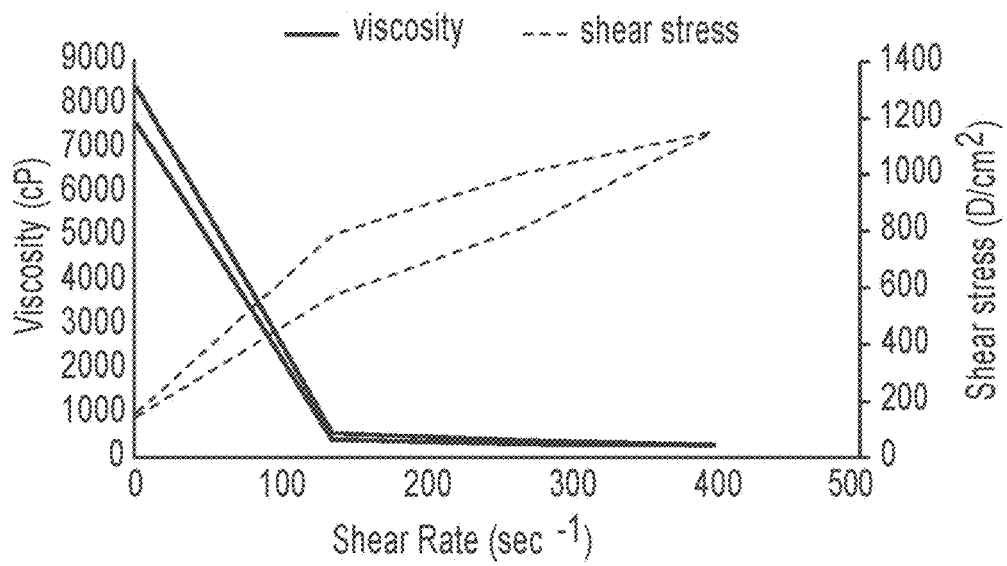

The data obtained using a 26 G needle show a more pronounced difference between the manipulated ADAIR versus both water and the filtered LD for average peak force (FIG. 50) and average area under the curve (FIG. 51). This suggests that using this more appropriate needle bore size, the ADAIR formulation provides a greater barrier to syringing than the filtered LD, under these conditions. Additionally, it was not possible to obtain enough filtrate from the manipulated ADAIR to carry out the test on a filtered sample. This inherent barrier to filtering provided by the ADAIR excipients is therefore expected to reduce appeal of injecting this material, to the majority of abusers. In the event however that an abuser attempts to inject the manipulated ADAIR without a filtration step, this material would be significantly more difficult to inject than the filtered manipulated LD (average peak force 42.188 N c.f. 4.191 N for the filtered LD, and average work done of 290.816 Ns c.f. 71.137 Ns for the filtered LD). Comparing the texture analyzer profiles for the samples it can be seen that the filtered manipulated LD shares a similar smooth force vs time profile to potable water (in a similar order of magnitude), whereas the manipulated LD required higher forces to depress the plunger than both water and the manipulated filtered LD for the duration of the tests. A rough profile with multiple peaks suggests that this material would not be associated with a smooth injection, which may also affect "likeability" to a potential abuser.

Rheology of Manipulated Samples

Sample rheology was examined by measuring the shear stress during an increasing and decreasing speed ramp. For the manipulated ADAIR and placebo, the small spindle (CP-52) was required. This is used for high viscosity samples. For water and the manipulated LD, a larger spindle (CP-40) was required. This spindle is used for low viscosity samples. The data acquired for each sample are shown in Tables 92 to 100.

Two separate samples of unfiltered manipulated LD were analyzed, along with two separate samples of filtered LD and a single water sample (FIG. 54). Whilst the unfiltered manipulated LD had a higher maximum measured viscosity than the water control (2.16 and 2.35 cP, c.f. 1.33 cP at 166.7 RPM) this was still in a similar order of magnitude to the water samples and both displayed similar profiles. The unfiltered LD showed a degree of hysteresis, which may have been a result of the presence of solid material in the sample shifting and aligning during the course of the test. The filtered LD shared a similar profile, but with less hysteresis and a viscosity more comparable to the water sample (1.53 and 1.45 cP at 83.33 RPM c.f. 1.33 cP at 166.7 RPM). This suggested that the manipulated LD had a similar rheology to water, with slight increase in viscosity when unfiltered. This supports the hypothesis that the higher forces required to syringe the manipulated LD are due to particulates of ground undissolved dosage form blocking the syringe, rather than high viscosity of the manipulated material.

TABLE 92

Rheology data for manipulated unfiltered LD, measured at 25° C., repeat 1.
manipulated unfiltered LD

| Viscosity (cP) | Speed (RPM) | Torque (%) | Shear Stress (D/cm$^2$) | Shear Rate (sec$^{-1}$) |
|---|---|---|---|---|
| 0.00 | 0.00 | −0.9 | 0.00 | 0.00 |
| 1.61 | 83.33 | 4.1 | 10.06 | 624.98 |
| 1.63 | 166.70 | 8.3 | 20.36 | 1250.25 |
| 1.48 | 250.00 | 11.3 | 27.71 | 1875.00 |
| 1.61 | 166.70 | 8.2 | 20.11 | 1250.25 |
| 2.16 | 83.33 | 5.5 | 13.49 | 624.98 |
| 0.00 | 0.00 | −1.4 | 0.00 | 0.00 |

TABLE 91

Rheology data for manipulated unfiltered LD, measured at 25° C., repeat 2.
manipulated unfiltered LD

| Viscosity (cP) | Speed (RPM) | Torque (%) | Shear Stress (D/cm$^2$) | Shear Rate (sec$^{-1}$) |
|---|---|---|---|---|
| 0.00 | 0.00 | −2.0 | 0.00 | 0.00 |
| 1.88 | 83.33 | 4.8 | 11.77 | 624.98 |
| 1.59 | 166.70 | 8.1 | 19.87 | 1250.25 |
| 1.37 | 250.00 | 10.5 | 25.75 | 1875.00 |
| 1.59 | 166.70 | 8.1 | 19.87 | 1250.25 |
| 2.35 | 83.33 | 6.0 | 14.71 | 624.98 |
| 0.00 | 0.00 | 0.0 | 0.00 | 0.00 |

TABLE 92

Rheology data for manipulated filtered LD, measured at 25° C., repeat 1.
Manipulated filtered LD

| Viscosity (cP) | Speed (RPM) | Torque (%) | Shear Stress (D/cm$^2$) | Shear Rate (sec$^{-1}$) |
|---|---|---|---|---|
| 0.00 | 0.00 | −0.4 | 0.00 | 0.00 |
| 1.53 | 83.33 | 3.9 | 9.56 | 624.98 |
| 1.26 | 166.70 | 6.4 | 15.70 | 1250.25 |
| 1.32 | 250.00 | 10.1 | 24.77 | 1875.00 |
| 1.33 | 166.70 | 6.8 | 16.68 | 1250.25 |
| 1.37 | 83.33 | 3.5 | 8.85 | 624.98 |
| 0.00 | 0.00 | −1.1 | 0.00 | 0.00 |

TABLE 93

Rheology data for manipulated filtered LD, measured at 25° C., repeat 2.
Manipulated filtered LD

| Viscosity (cP) | Speed (RPM) | Torque (%) | Shear Stress (D/cm$^2$) | Shear Rate (sec$^{-1}$) |
|---|---|---|---|---|
| 0.00 | 0.00 | −1.3 | 0.00 | 0.00 |
| 1.45 | 83.33 | 3.7 | 9.07 | 624.98 |
| 1.24 | 166.70 | 6.3 | 15.45 | 1250.25 |
| 1.23 | 250.00 | 9.4 | 23.05 | 1875.00 |
| 1.28 | 166.70 | 6.5 | 15.94 | 1250.25 |
| 1.41 | 83.33 | 3.6 | 8.83 | 624.98 |
| 0.00 | 0.00 | −0.2 | 0.00 | 0.00 |

TABLE 94

Rheology data for water, measured at 25° C., single repeat.
water

| Viscosity (cP) | Speed (RPM) | Torque (%) | Shear Stress (D/cm$^2$) | Shear Rate (sec$^{-1}$) |
|---|---|---|---|---|
| 0.00 | 0.00 | −0.4 | 0.00 | 0.00 |
| 1.26 | 83.33 | 3.2 | 7.85 | 624.98 |
| 1.10 | 166.70 | 5.6 | 13.73 | 1250.25 |
| 1.11 | 250.00 | 8.5 | 20.85 | 1875.00 |
| 1.12 | 166.70 | 5.7 | 13.98 | 1250.25 |
| 1.33 | 83.33 | 3.4 | 8.34 | 624.98 |
| 0.00 | 0.00 | −0.1 | 0.00 | 0.00 |

For the manipulated ADAIR and placebo samples, a different speed ramp was required for each sample, indicating a degree of variability in the rheological behaviour. This is not unexpected, due to the nature of the excipients and the variability involved in manipulating an ADF.

Two separate samples of manipulated ADAIR were analyzed (Tables 97, 98 and). Although the manipulated ADAIR showed shear-thinning behaviour (reduced resistance to flow under increased shear), the measured viscosity remained higher than even the unfiltered manipulated LD, with maximum viscosities of 6052.42 and 8334.48 cP at 1 RPM, c.f. maximum viscosities of 2.16 and 2.35 cP for the unfiltered manipulated LD. Additionally, there was hysteresis in both manipulated ADAIR viscosity measurements, with higher readings on the down ramp. This suggests that the manipulated ADAIR may display a time-dependent increase in viscosity. If this is the case, this could indicate that the longer the material is manipulated for (eg longer grinding time), the more viscous it would become. This could be investigated further by applying a constant shear rate for an extended time, rather than applying a speed ramp.

TABLE 95

Rheology data for manipulated ADAIR measured at 25° C., repeat 1.
Manipulated ADAIR

| Viscosity (cP) | Speed (RPM) | Torque (%) | Shear Stress (D/cm$^2$) | Shear Rate (sec$^{-1}$) |
|---|---|---|---|---|
| 5258.66 | 1.00 | 5.3 | 105.17 | 2.00 |
| 288.21 | 84.00 | 24.4 | 484.19 | 168.00 |
| 210.92 | 167.00 | 35.5 | 704.46 | 334.00 |
| 215.51 | 250.00 | 54.3 | 1077.53 | 500.00 |
| 283.40 | 167.00 | 47.7 | 946.56 | 334.00 |
| 421.69 | 84.00 | 35.7 | 708.43 | 168.00 |
| 6052.42 | 1.00 | 6.1 | 121.05 | 2.00 |

TABLE 96

Rheology data for manipulated ADAIR measured at 25° C., repeat 2.
Manipulated ADAIR

| Viscosity (cP) | Speed (RPM) | Torque (%) | Shear Stress (D/cm$^2$) | Shear Rate (sec$^{-1}$) |
|---|---|---|---|---|
| 7540.72 | 1.00 | 7.6 | 150.81 | 2.00 |
| 425.88 | 67.33 | 28.9 | 573.49 | 134.66 |
| 304.26 | 133.70 | 41.0 | 813.60 | 267.40 |
| 288.73 | 200.00 | 58.2 | 1154.92 | 400.00 |
| 375.51 | 133.70 | 50.6 | 1004.11 | 267.40 |
| 583.56 | 67.33 | 39.6 | 785.82 | 134.66 |
| 8334.48 | 1.00 | 8.4 | 166.69 | 2.00 |

Figure 56A:
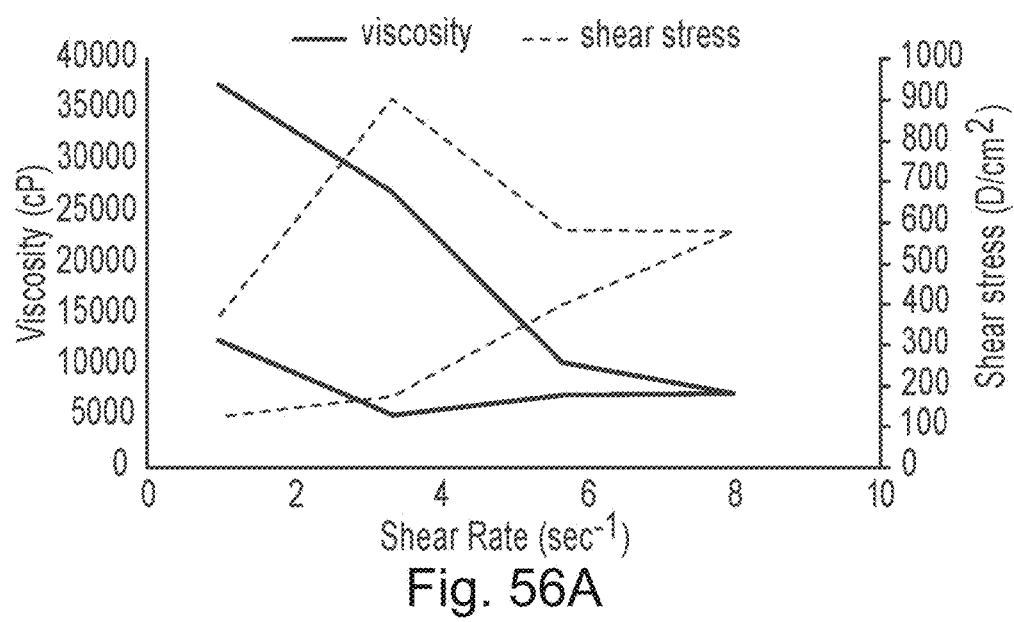
FIG. 56A-B are graphs showing viscosity and shear stress vs shear rate for two samples of manipulated placebo.
Figure 56B:
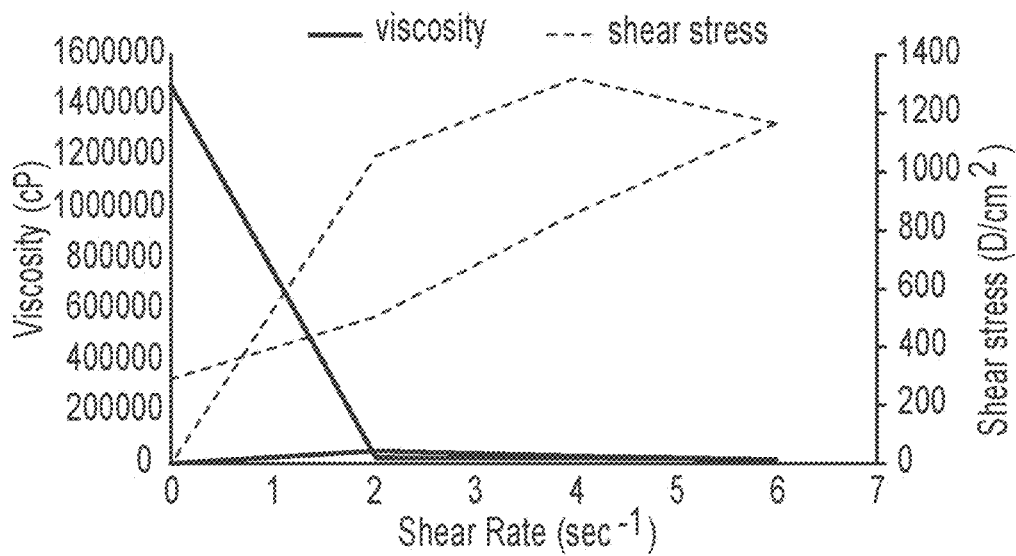
Figure 57:
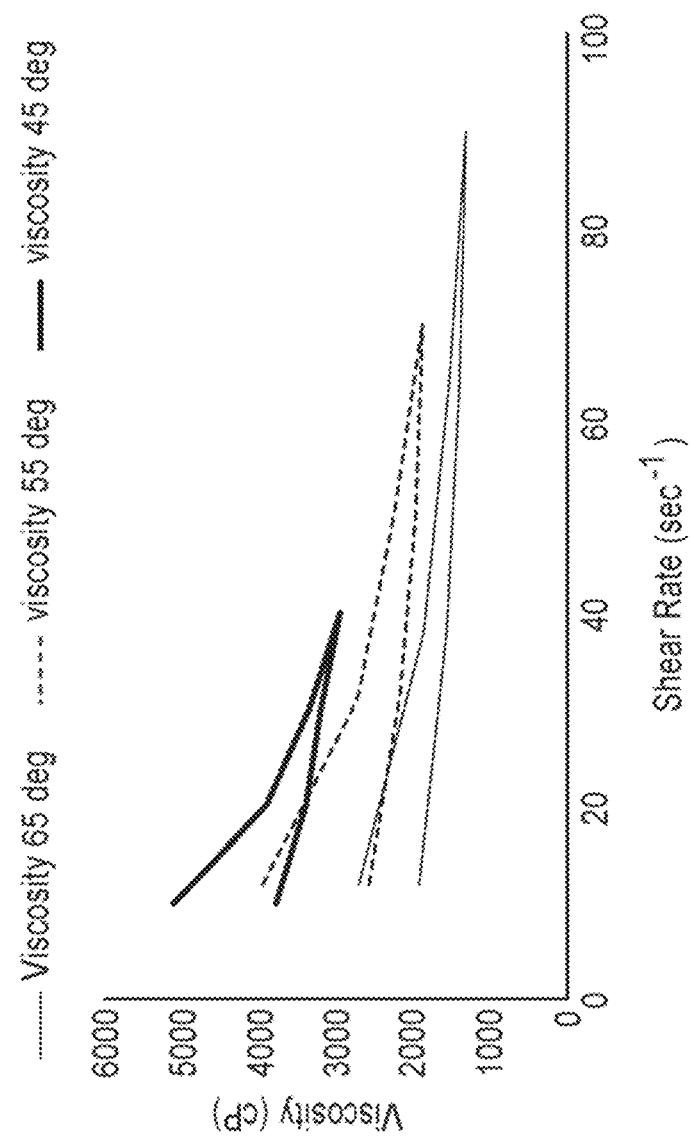
FIG. 57 are graphs showing viscosity vs shear rate for the placebo formulation at 65, 55 and 45° C.

The manipulated placebo samples also appeared to show shear thinning behaviour with a time-dependent increase in viscosity (FIG. 56A-B). In general, the viscosity of these samples was very high, with maximum measured viscosities of 12501.72 cP at 0.50 RPM and 1478378.00 cP at 0.01 RPM. This increased viscosity is expected to be due to Avicel PH101 particles dispersed in the hydrated matrix during the manipulation. It is also possible that the out-of-trend decrease in shear stress at the top end of the speed ramp on these samples was due to the plate/sample slipping during the test. This was further suggested when the placebo sample was examined at the end of the test and found to have moved in relation to the cone and plate, suggesting that movement of the spindle had relocated the sample, rather than the plate spinning on top of it. This may have been as a result of high cohesive forces in the sample.

TABLE 97

Rheology data for manipulated placebo, measured at 25° C., repeat 1.
Manipulated placebo

| Viscosity (cP) | Speed (RPM) | Torque (%) | Shear Stress (D/cm$^2$) | Shear Rate (sec$^{-1}$) |
|---|---|---|---|---|
| 37505.16 | 0.50 | 18.9 | 375.05 | 1.00 |
| 27092.41 | 1.67 | 45.6 | 904.89 | 3.34 |
| 10272.60 | 2.83 | 29.3 | 581.43 | 5.66 |
| 7218.26 | 4.00 | 29.1 | 577.46 | 8.00 |
| 7117.19 | 2.83 | 20.3 | 402.83 | 5.66 |
| 5228.36 | 1.67 | 8.8 | 174.63 | 3.34 |
| 12501.72 | 0.50 | 6.3 | 125.02 | 1.00 |

TABLE 100

Rheology data for manipulated placebo, measured at 25° C., repeat 2.
Manipulated placebo

| Viscosity (cP) | Speed (RPM) | Torque (%) | Shear Stress (D/cm$^2$) | Shear Rate (sec$^{-1}$) |
|---|---|---|---|---|
| 0.00 | 0.01 | -3.0 | 0.00 | 0.02 |
| 52262.42 | 1.01 | 53.2 | 1055.70 | 2.02 |
| 33089.87 | 2.00 | 66.7 | 1323.59 | 4.00 |
| 19414.05 | 3.00 | 58.7 | 1164.84 | 6.00 |
| 21431.52 | 2.00 | 43.2 | 857.26 | 4.00 |
| 24952.36 | 1.01 | 25.4 | 504.04 | 2.02 |
| 1478378.00 | 0.01 | 14.9 | 295.68 | 0.02 |

Filling Temperature Determination

Figure 58:
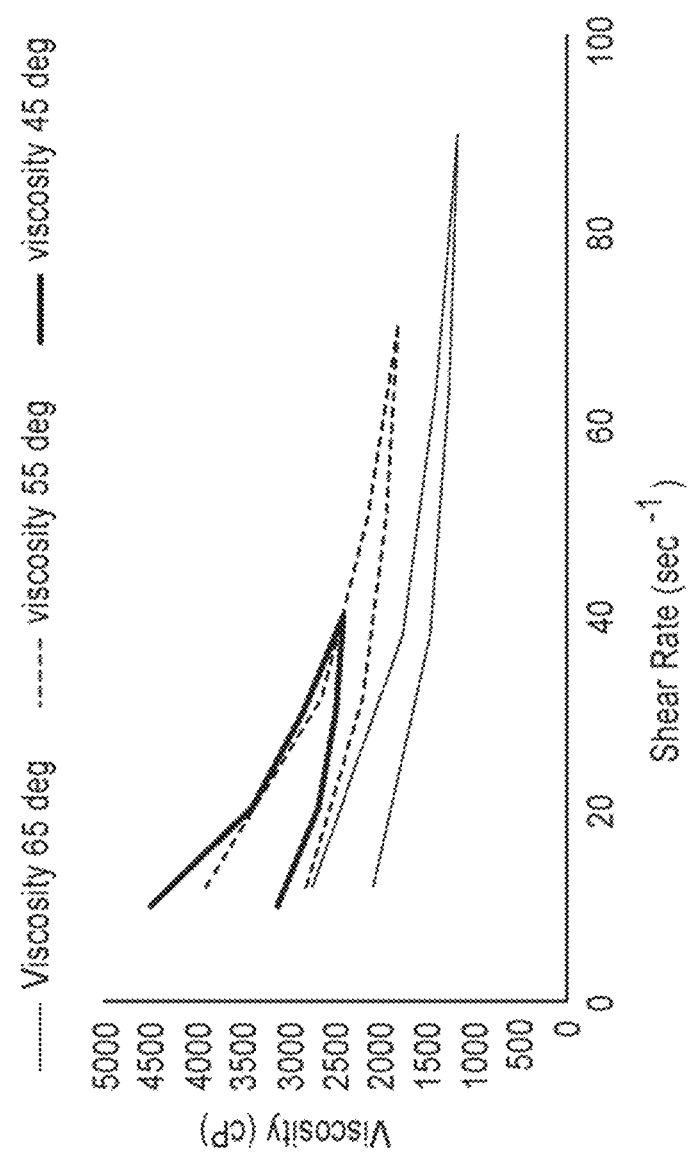
FIG. 58 are graphs showing viscosity vs shear rate for the ADAIR formulation at 65, 55 and 45° C.
Figure 59:
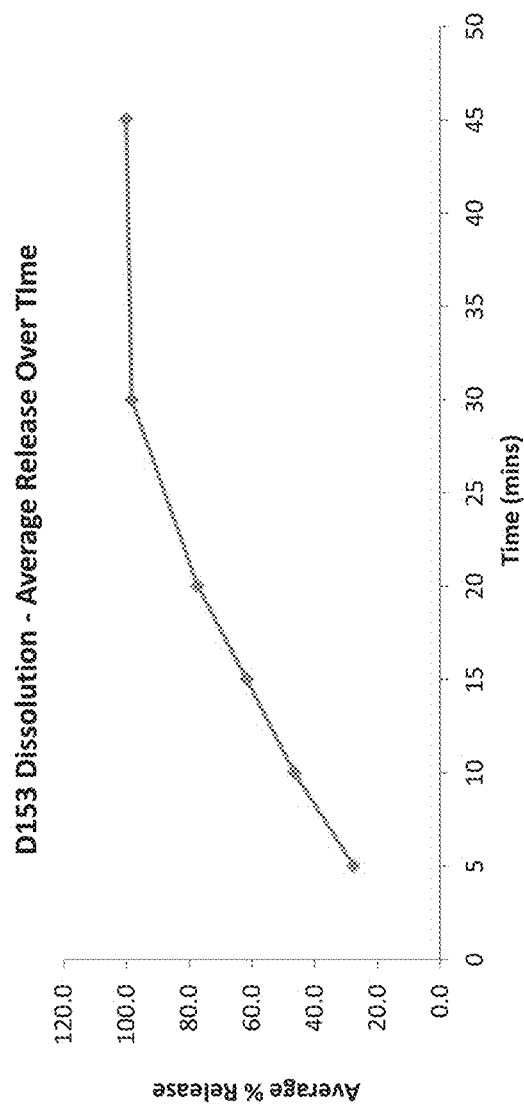
FIG. 59 is a graph showing the dissolution of 10 mg or LD in 0.01M HCL on apparatus 1.
Figure 60:
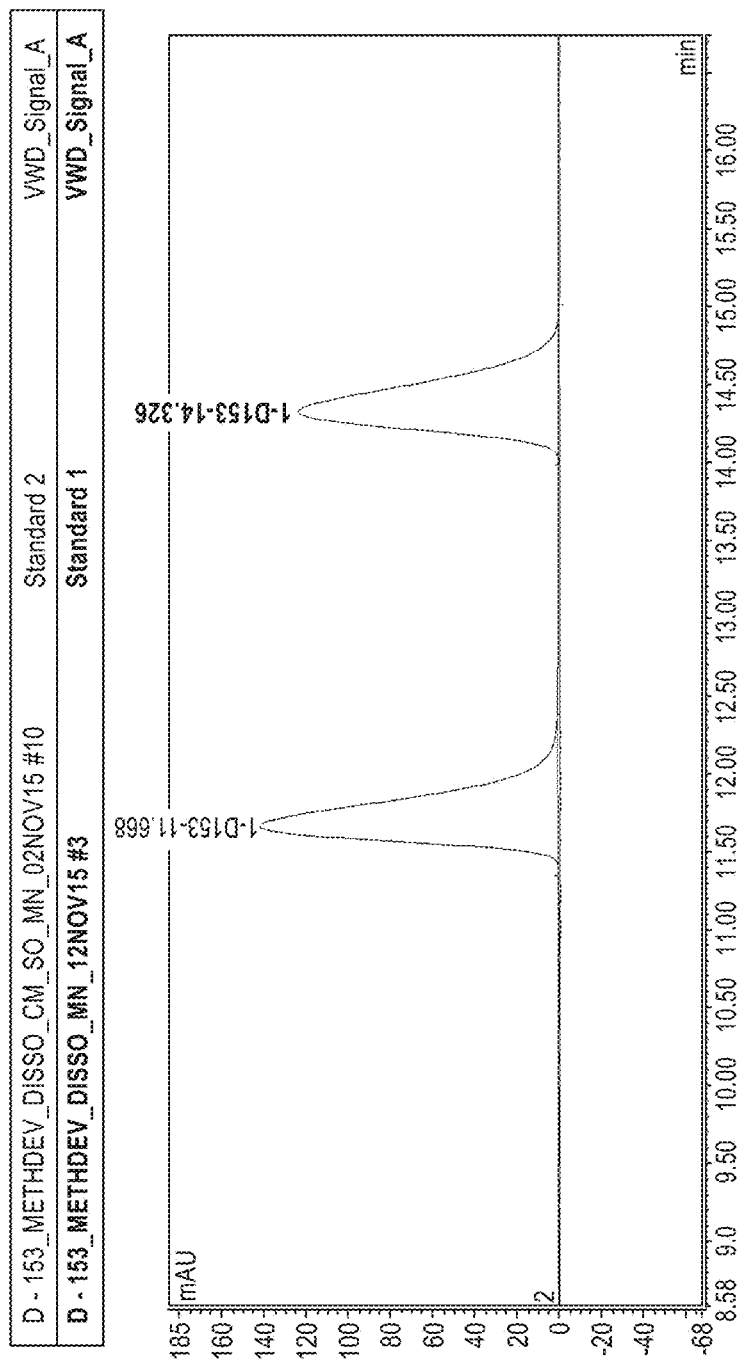
FIG. 60 is an image of a chromatogram showing the difference in retention time between the columns.
Figure 61:
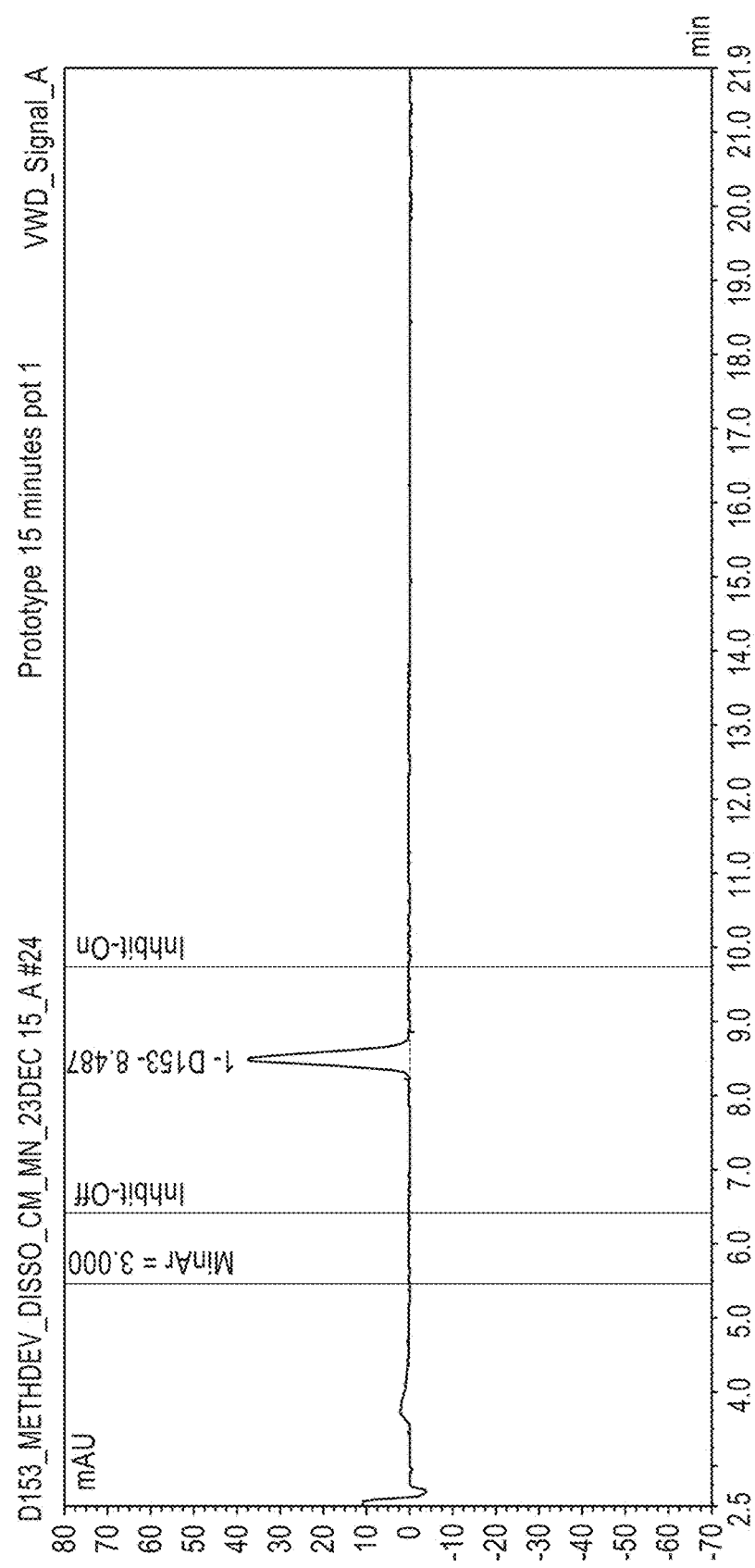
FIG. 61 is an image of a chromatogram showing 10 mg prototype 1 in 0.01M HCl on Apparatus 1—5 minutes.
Figure 62:
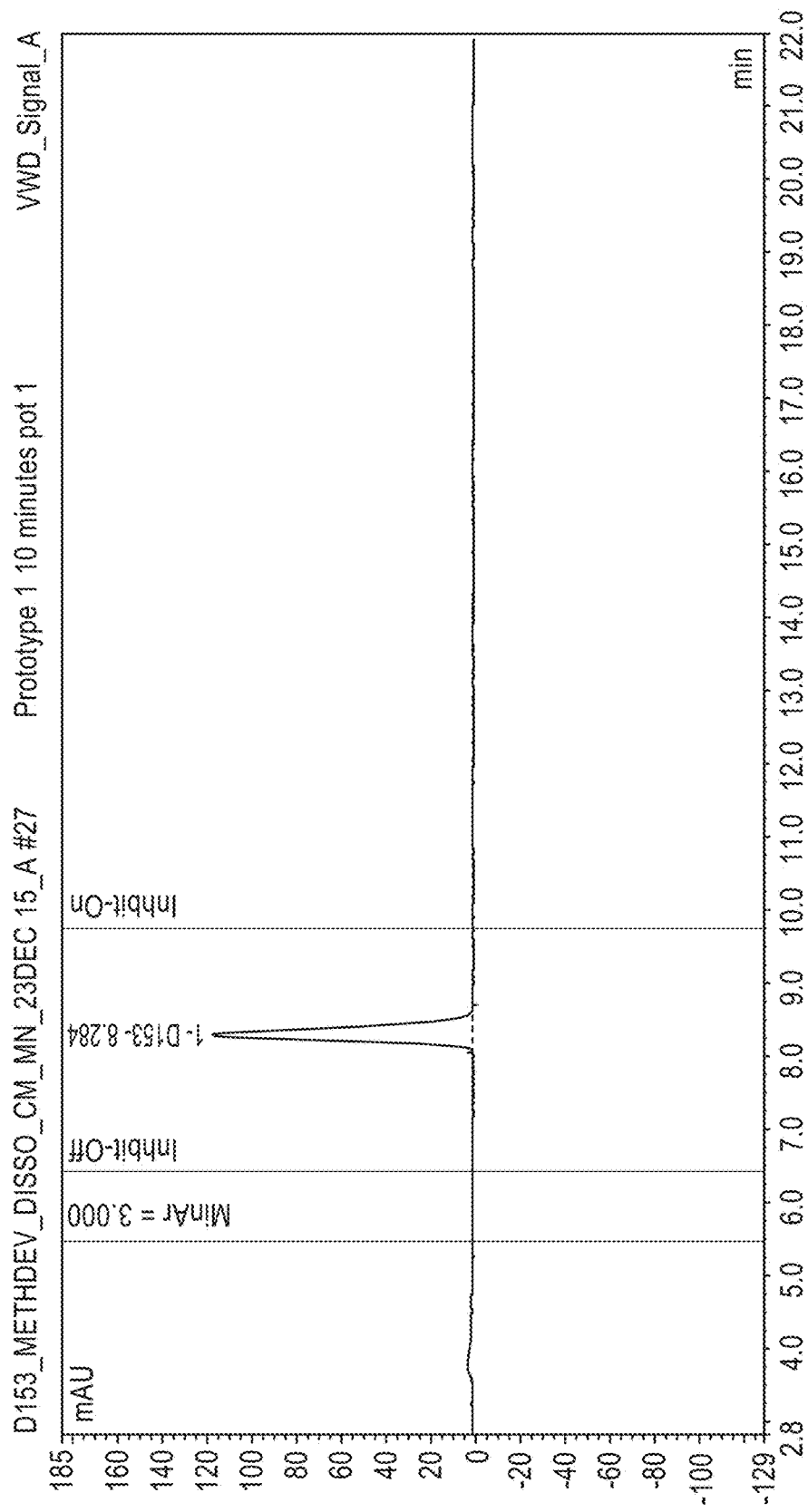
FIG. 62 is an image of a chromatogram showing 10 mg prototype 1 in 0.01M HCl on Apparatus 1—10 minutes.
Figure 63:
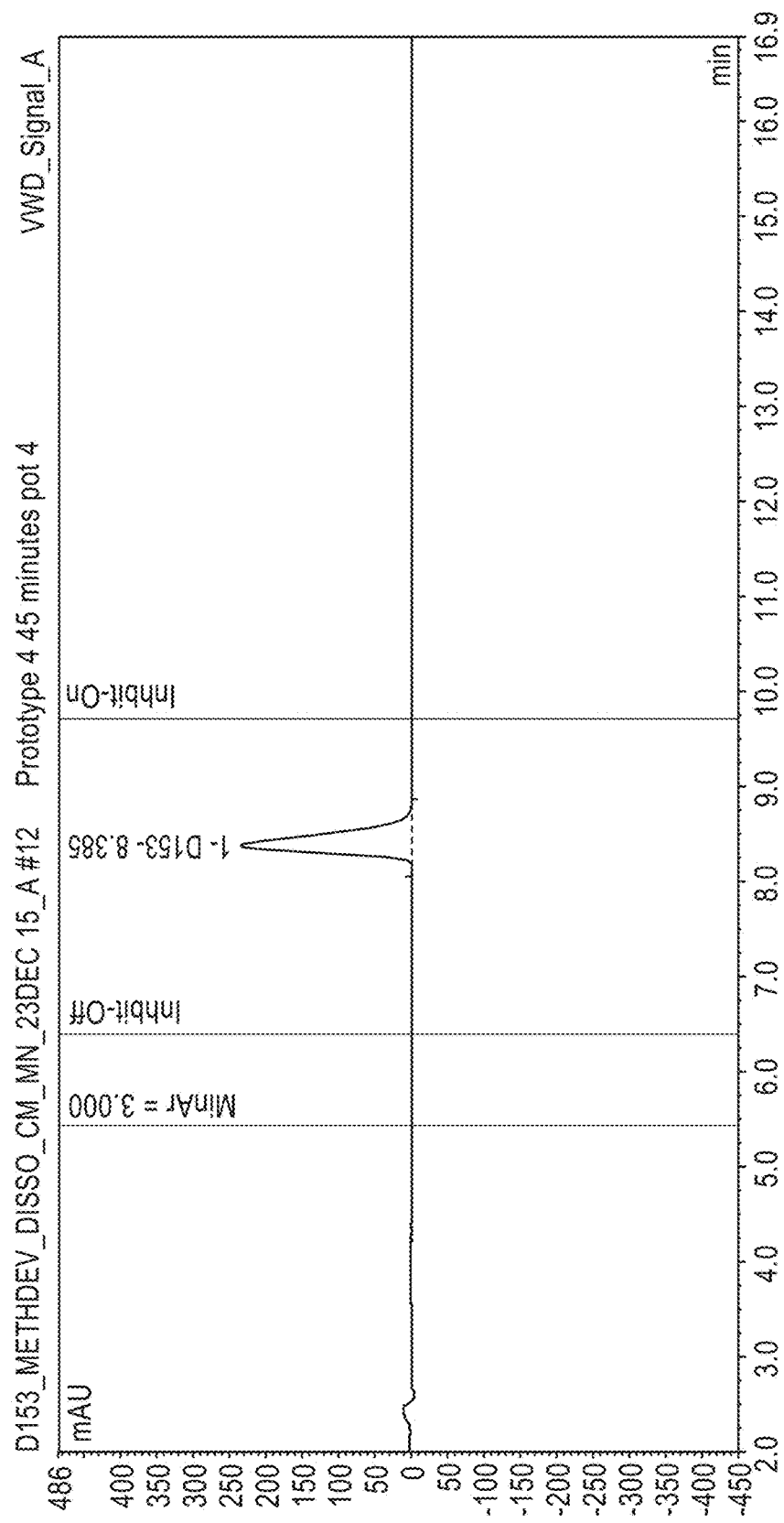
FIG. 63 is an image of a chromatogram showing 10 mg prototype 4 in 0.01M HCl on Apparatus 1—45 Minutes.
Figure 64:
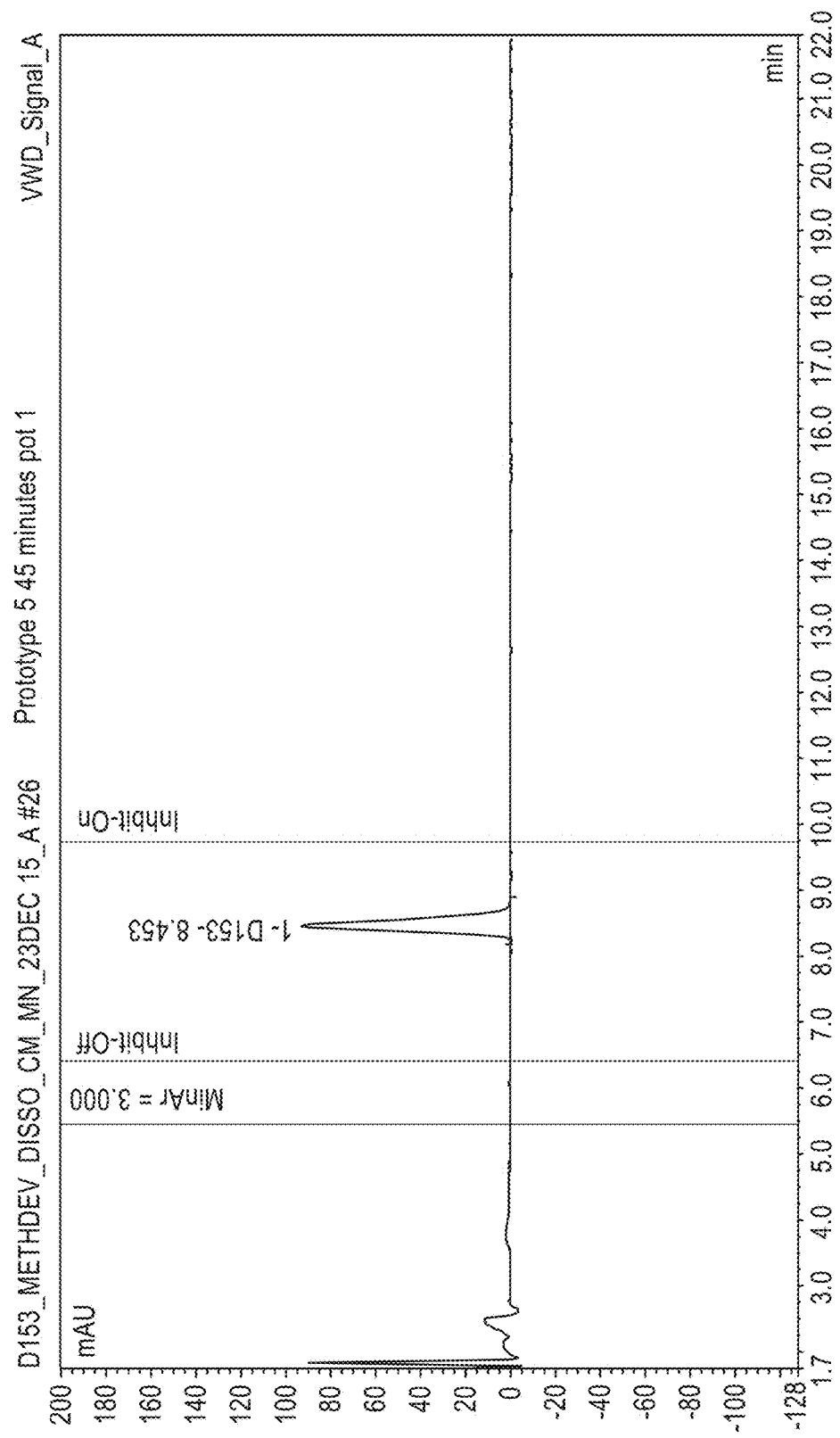
FIG. 64 is an image of a chromatogram showing 10 mg prototype 5 in 0.01M HCl on Apparatus 1—45 Minutes.
Figure 65:
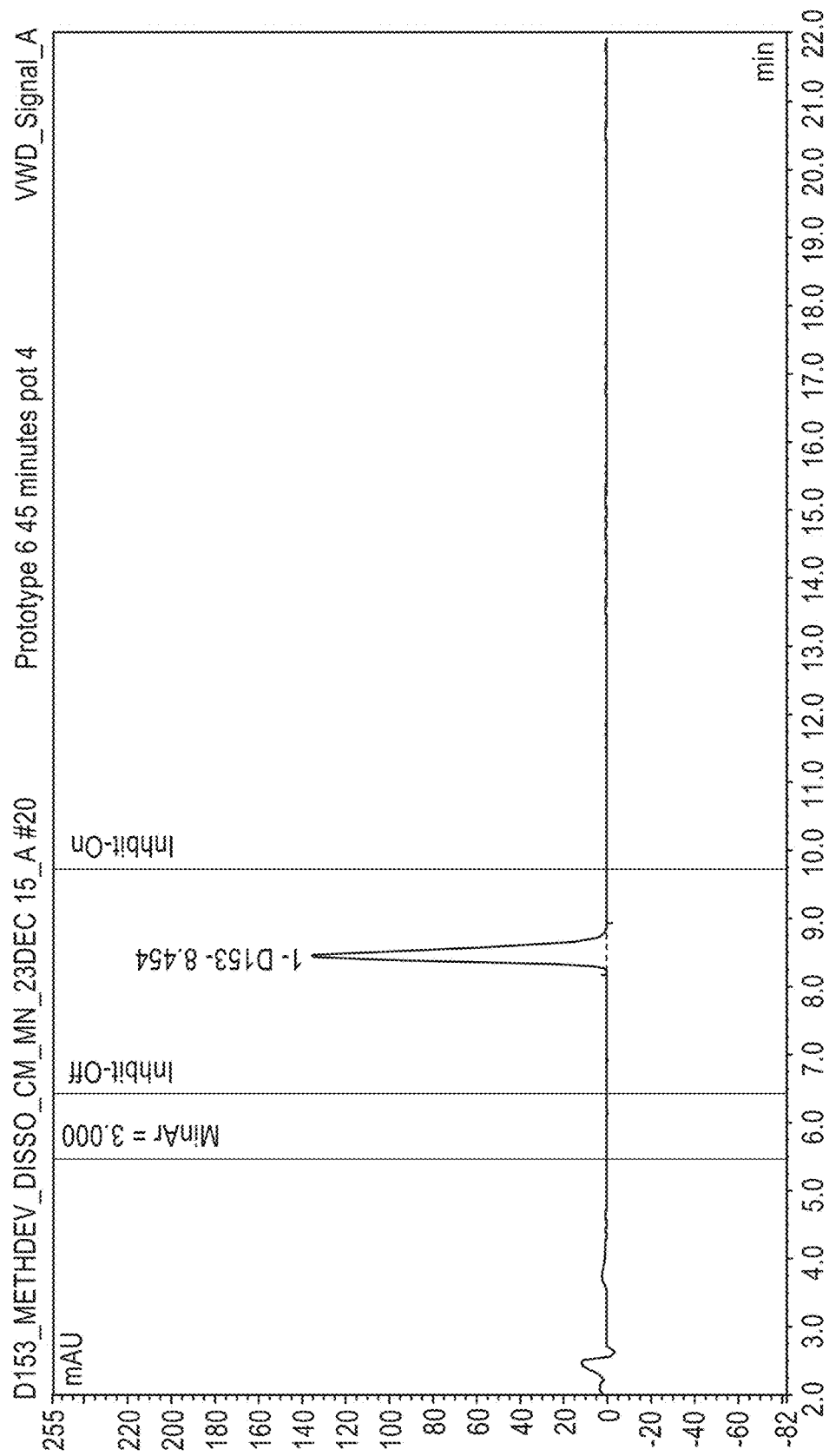
FIG. 65 is an image of a chromatogram showing 10 mg prototype 6 in 0.01M HCl on Apparatus 1—45 Minutes.
Figure 66:
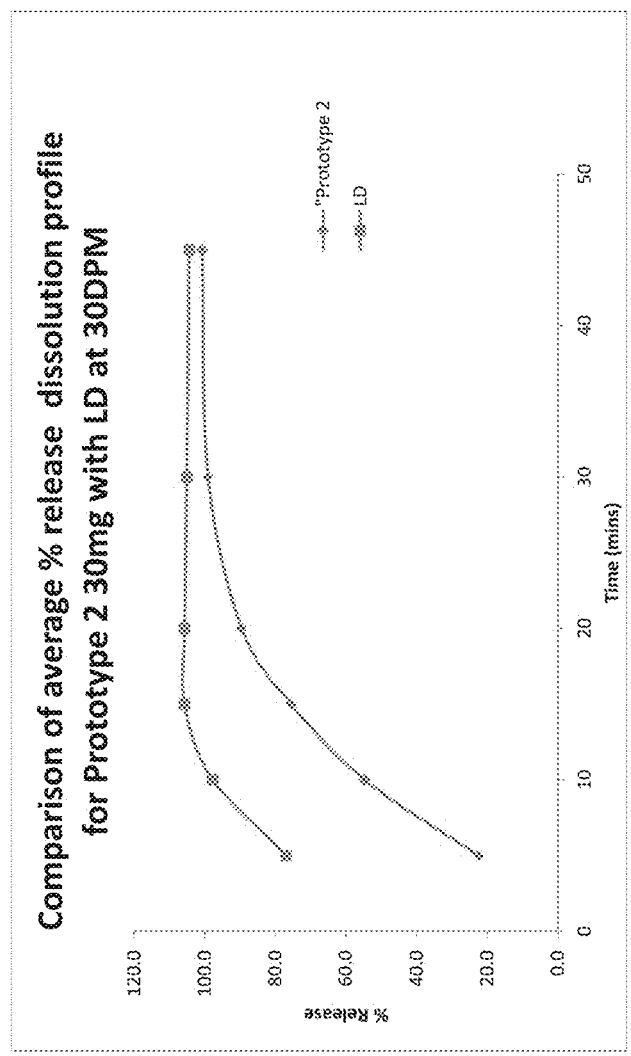
FIG. 66 is a graph showing the comparison of average % release dissolution profile for Protoype 2 30 mg with LD at 30 DPM.
Figure 67:
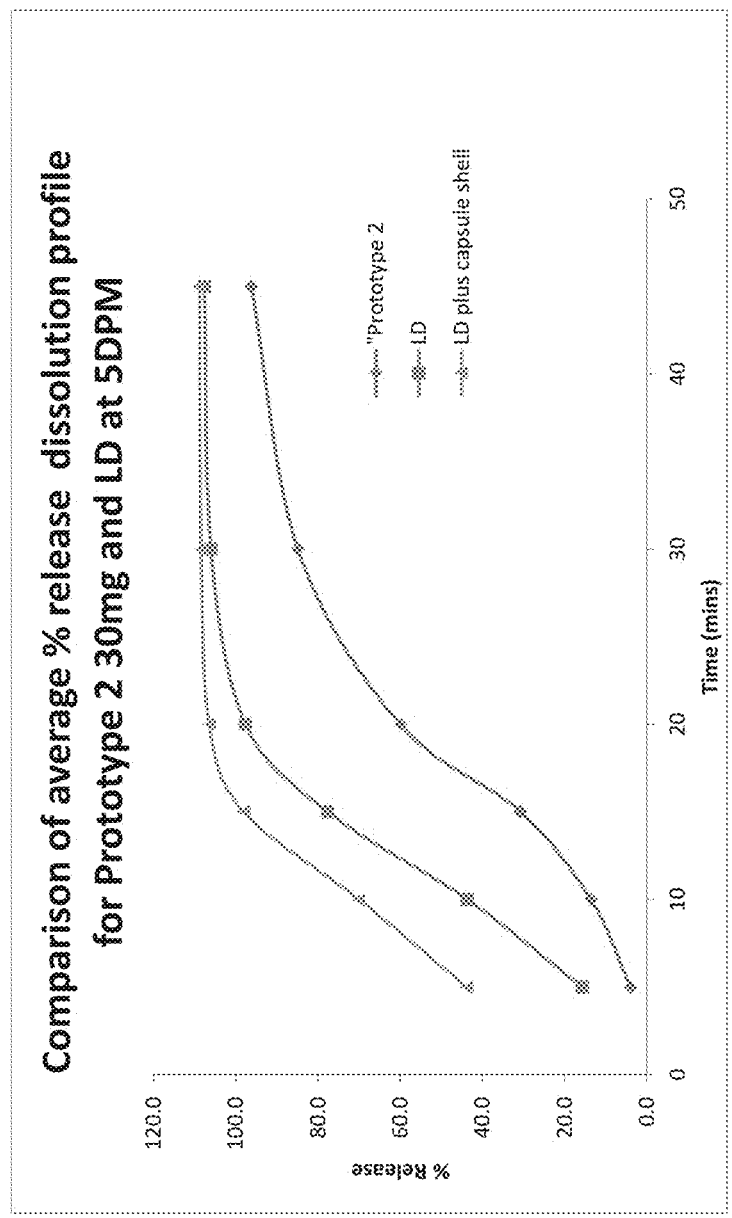
FIG. 67: is a graph showing the comparison of average % release dissolution profile for Prototype 2 30 mg and LD at 30 DPM 0.01M HCL using Apparatus 3 at 5 DPM.
Figure 68:
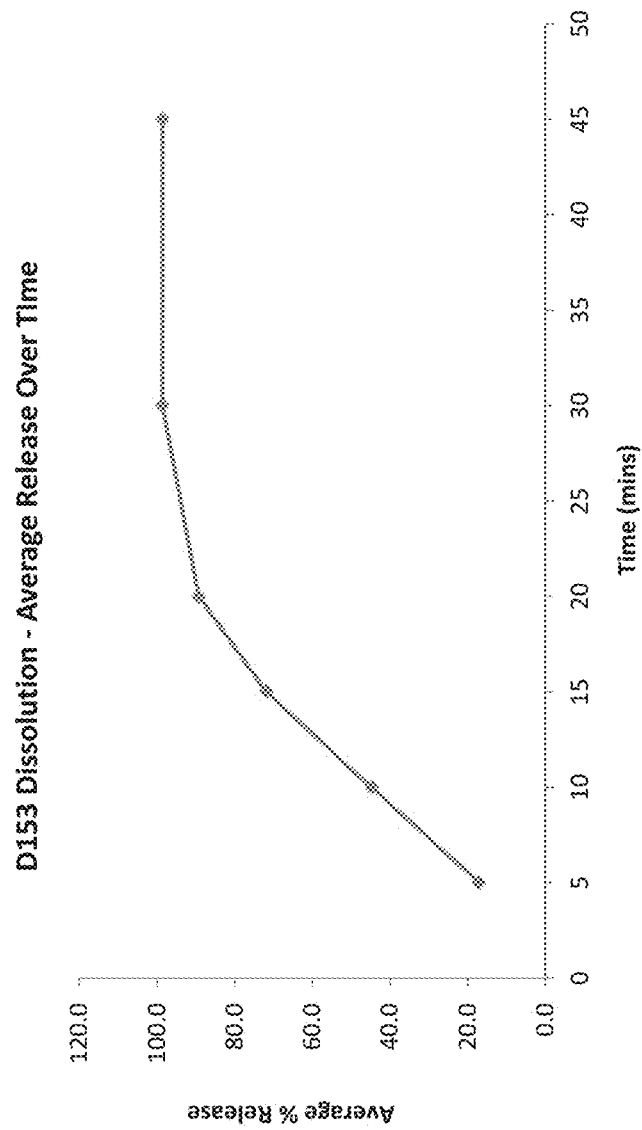
FIG. 68: is a graph showing the average dissolution of 10 mg LD in a size 00 shell n=6 in 0.01M HCL using Apparatus 3 at 5 DPM using the Gemini Column.
Figure 69:
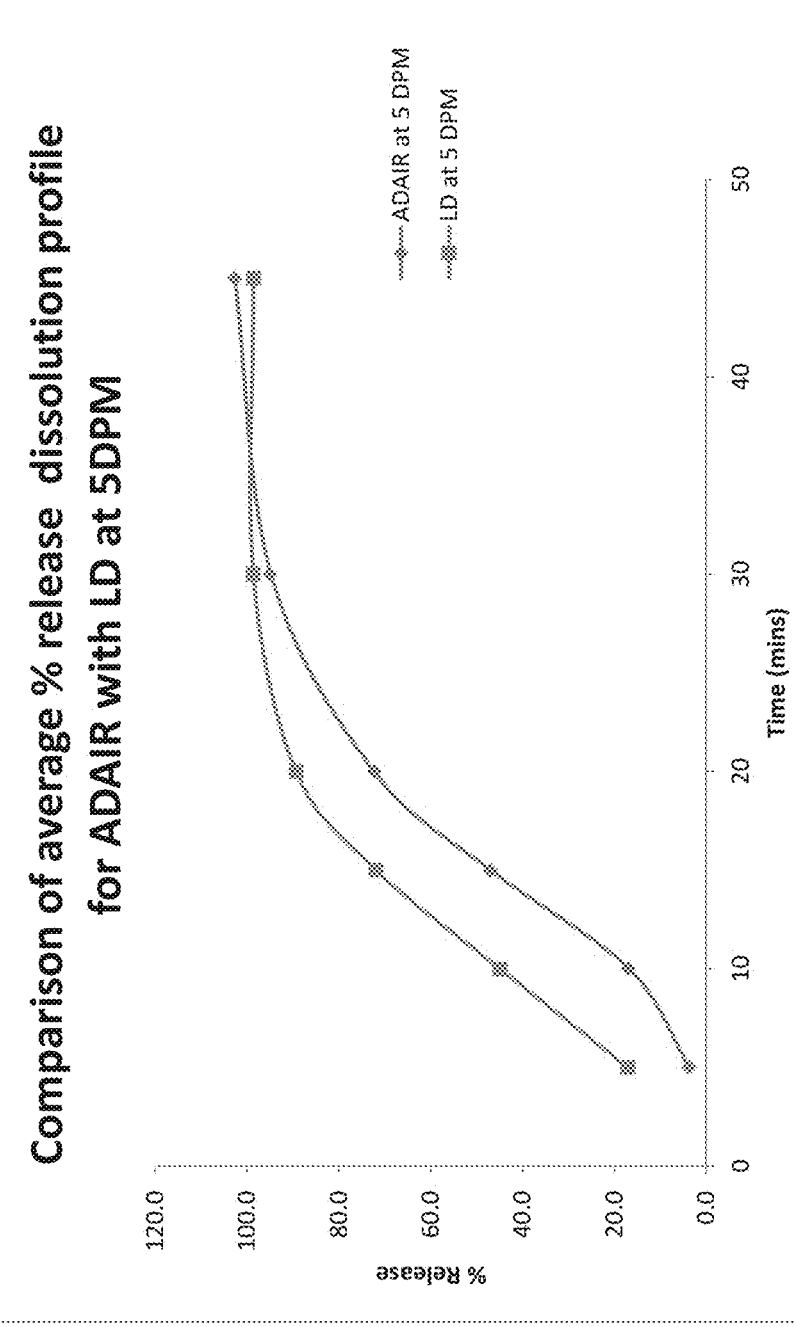
FIG. 69: is a graph showing the comparison of average % release of 10 mg ADAIR in 0.01M HCl Apparatus 3 at 5 DPM.
Figure 70:
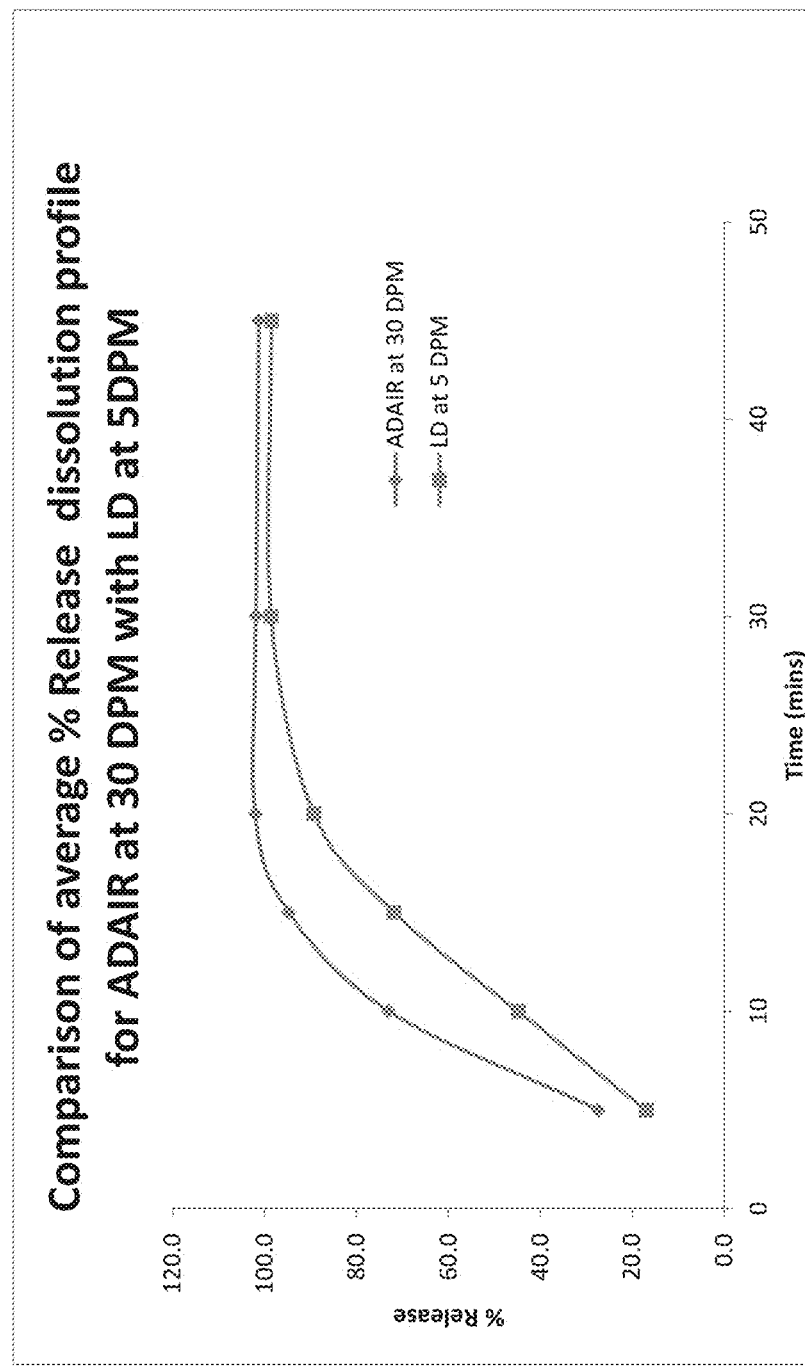
FIG. 70: is a graph showing the comparison of average % release of 10 mg ADAIR in 0.01M HCl Apparatus 3 at 30 DPM with LD at 5 DPM.
Figure 71:
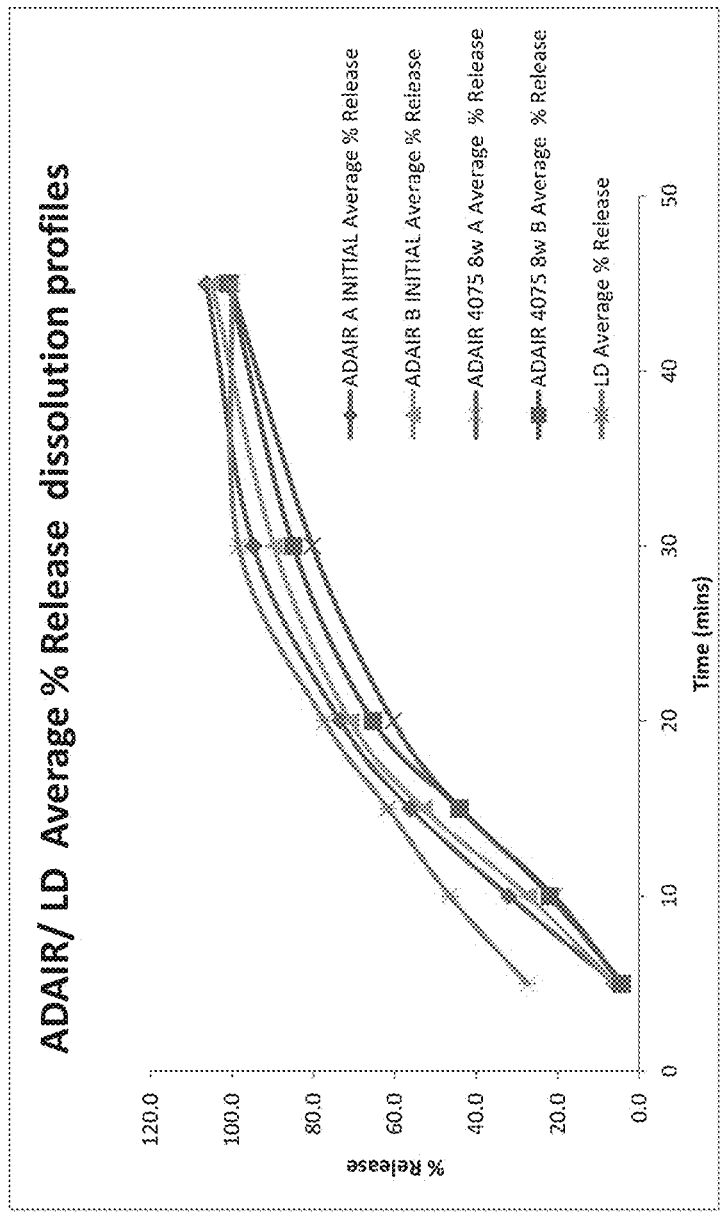
FIG. 71: is a graph showing the dissolution profile of 10 mg ADAIR in 0.01M HCl Apparatus 1 duplicate prep at Initial and at 40 C 75% RH compared to that of the LD.

In order to investigate the rheological behaviour of the ADAIR and placebo formulation bulk mixes and recommend a filling temperature, both bulk mixes were examined at various temperatures. The rheological data for the placebo at 65, 55 and 45° C. are shown in Table below. The rheological data for the ADAIR formulation at 65, 55 and 45° C. are shown in Tables below. The viscosity plot for the ADAIR formulation is shown in FIG. 58. An attempt was made to measure the placebo sample at 35° C. but the maximum torque level was exceeded immediately, suggesting that the material had become solid or close to solid.

These data indicate that both the placebo and ADAIR formulations have relatively high viscosity for liquid-filled hard capsule formulations, with a maximum measured viscosity of 5099.91 cP for the placebo formulation and 4504.59 cP for the ADAIR formulation (both measured at 5.00 RPM, 45° C.). Both formulations are also thermosoftening, with reduced viscosity upon increased temperature. The reduction in viscosity with increased rate of shear indicate that they are both shear thinning. As a result, it is recommended that the bulk mix remains under stirring during the filling process in order to optimise flow characteristics and process-ability. Additionally, both the placebo and ADAIR formulations show a hysteresis between the measurements obtained in the increasing speed ramp and those obtained on the decreasing speed ramp. Unlike the manipulated formulation, these show reduced viscosity on the downward speed ramp, c.f. the increasing ramp. This suggests a time dependent effect whereby viscosity is reduced when the time of stirring increases. This is known as thixotropy, and is a common behaviour in suspensions. These data indicate that although the formulation becomes more challenging to handle (less process-able) when manipulated with water, the bulk mixes can be processed well with the application of heat and stirring. Provided that there is no stability issue, a target filling temperature of 55±10° C. will be suitable for both the placebo and ADAIR formulations, with constant stirring of the filling machine hopper.

TABLE 82

Rheology data for placebo formulation, measured at 65° C.
Placebo 65° C.

| Viscosity (cP) | Speed (RPM) | Torque (%) | Shear Stress (D/cm$^2$) | Shear Rate (sec$^{-1}$) |
|---|---|---|---|---|
| 2695.48 | 6.00 | 16.3 | 323.46 | 12.00 |
| 1859.07 | 19.00 | 35.6 | 706.45 | 38.00 |
| 1516.21 | 32.00 | 48.9 | 970.37 | 64.00 |
| 1314.11 | 45.00 | 59.6 | 1182.70 | 90.00 |

TABLE 82-continued

Rheology data for placebo formulation, measured at 65° C.
Placebo 65° C.

| Viscosity (cP) | Speed (RPM) | Torque (%) | Shear Stress (D/cm$^2$) | Shear Rate (sec$^{-1}$) |
|---|---|---|---|---|
| 1404.58 | 32.00 | 45.3 | 898.93 | 64.00 |
| 1566.63 | 19.00 | 30.0 | 595.32 | 38.00 |
| 1918.25 | 6.00 | 11.6 | 230.19 | 12.00 |

TABLE 103

Rheology data for placebo formulation, measured at 55° C.
55° C.

| Viscosity (cP) | Speed (RPM) | Torque (%) | Shear Stress (D/cm$^2$) | Shear Rate (sec$^{-1}$) |
|---|---|---|---|---|
| 3952.26 | 6.00 | 23.9 | 474.27 | 12.00 |
| 2716.36 | 15.67 | 42.9 | 851.31 | 31.34 |
| 2244.50 | 25.33 | 57.3 | 1137.06 | 50.66 |
| 1876.68 | 35.00 | 66.2 | 1313.67 | 70.00 |
| 1974.22 | 25.33 | 50.4 | 1000.14 | 50.66 |
| 2171.82 | 15.67 | 34.3 | 680.65 | 31.34 |
| 2579.72 | 6.00 | 15.6 | 309.57 | 12.00 |

TABLE 104

Rheology data for placebo formulation, measured at 45° C.
45° C.

| Viscosity (cP) | Speed (RPM) | Torque (%) | Shear Stress (D/cm$^2$) | Shear Rate (sec$^{-1}$) |
|---|---|---|---|---|
| 5099.91 | 5.00 | 25.7 | 509.99 | 10.00 |
| 3939.03 | 10.00 | 39.7 | 787.81 | 20.00 |
| 3360.25 | 15.00 | 50.8 | 1008.08 | 30.00 |
| 2971.64 | 20.00 | 59.9 | 1188.66 | 40.00 |
| 3214.73 | 15.00 | 48.6 | 964.42 | 30.00 |
| 3413.17 | 10.00 | 34.4 | 682.63 | 20.00 |
| 3790.20 | 5.00 | 19.1 | 379.02 | 10.00 |

TABLE 9

Rheology data for ADAIR formulation, measured at 65° C.
ADAIR 65° C.

| Viscosity (cP) | Speed (RPM) | Torque (%) | Shear Stress (D/cm$^2$) | Shear Rate (sec$^{-1}$) |
|---|---|---|---|---|
| 2745.09 | 6.00 | 16.6 | 329.41 | 12.00 |
| 1780.74 | 19.00 | 34.1 | 676.68 | 38.00 |
| 1413.89 | 32.00 | 45.6 | 904.89 | 64.00 |
| 1186.23 | 45.00 | 53.8 | 1067.61 | 90.00 |
| 1280.56 | 32.00 | 41.3 | 819.56 | 64.00 |
| 1477.86 | 19.00 | 28.3 | 561.59 | 38.00 |
| 2083.62 | 6.00 | 12.6 | 250.03 | 12.00 |

TABLE 106

Rheology data for ADAIR formulation, measured at 55° C.
ADAIR 55° C.

| Viscosity (cP) | Speed (RPM) | Torque CYO | Shear Stress (D/cm$^2$) | Shear Rate (sec$^{-1}$) |
|---|---|---|---|---|
| 3902.65 | 6.00 | 23.6 | 468.32 | 12.00 |
| 2665.71 | 15.67 | 42.1 | 835.43 | 31.34 |
| 2150.48 | 25.33 | 54.9 | 1089.44 | 50.66 |
| 1822.81 | 35.00 | 64.3 | 1275.97 | 70.00 |
| 1946.80 | 25.33 | 49.7 | 986.25 | 50.66 |

TABLE 106-continued

Rheology data for ADAIR formulation, measured at 55° C.
ADAIR 55° C.

| Viscosity (cP) | Speed (RPM) | Torque CYO | Shear Stress (D/cm$^2$) | Shear Rate (sec$^{-1}$) |
|---|---|---|---|---|
| 2209.81 | 15.67 | 34.9 | 692.56 | 31.34 |
| 2827.77 | 6.00 | 17.1 | 339.33 | 12.00 |

TABLE 10

Rheology data for ADAIR formulation, measured at 45° C.
ADAIR 45° C.

| Viscosity (cP) | Speed (RPM) | Torque (%) | Shear Stress (D/cm$^2$) | Shear Rate (sec$^{-1}$) |
|---|---|---|---|---|
| 4504.59 | 5.00 | 22.7 | 450.46 | 10.00 |
| 3423.09 | 10.00 | 34.5 | 684.62 | 20.00 |
| 2857.54 | 15.00 | 43.2 | 857.26 | 30.00 |
| 2425.93 | 20.00 | 48.9 | 970.37 | 40.00 |
| 2506.96 | 15.00 | 37.9 | 752.09 | 30.00 |
| 2708.71 | 10.00 | 27.3 | 541.74 | 20.00 |
| 3135.35 | 5.00 | 15.8 | 313.54 | 10.00 |

A method to measure the force required to depress the plunger of a 5 mL syringe through 9 mm, expelling ~1 mL of material under test, has been established. This method had been used to measure the forces required to syringe manipulated ADAIR, manipulated placebo and manipulated LD. It has been shown that a significantly greater force is required to expel manipulated ADAIR through a 26 G needle than it does to expel manipulated filtered LD (average peak force 42.188 N c.f. 4.191 N for the filtered LD, and average work done of 290.816 Ns c.f. 71.137 Ns for the filtered LD). This indicates that it will be more challenging for an abuser to inject manipulated ADAIR than manipulated filtered LD, demonstrating abuse deterrent characteristics of the ADAIR formulation. A sufficient volume of filtrate could not be produced filtering the manipulated ADAIR to carry out the TAS test. This indicates that it would be challenging for an abuser to filter the manipulated ADAIR formulation, demonstrating abuse deterrent characteristics.
Examining the manipulated formulations using a rheometer found that the manipulated filtered and unfiltered LD had similar rheological behaviour to water. Presence of undissolved material in the unfiltered LD manifested as hysteresis between the viscosities measured during the increasing and decreasing speed ramp. This data was in agreement with the assumption that higher syringing forces measured for the unfiltered material through the 26 G needle in the TA assessments was due to blocking of the needle with larger undissolved particulates (a result of grinding the tablet), rather than high viscosity. The manipulated ADAIR formulation was found to have higher viscosity than even the unfiltered manipulated LD, with maximum viscosities of 6052.42 and 8334.48 cP at 1 RPM, c.f. maximum viscosities of 2.16 and 2.35 cP for the unfiltered manipulated LD. Both the manipulated ADAIR and manipulated placebo were found to be shear thinning (reduced viscosity with increased shear rate), but there was evidence to suggest that increased manipulation time could result in increased viscosity. Measuring viscosity for an extended time at a constant spindle speed could be used to investigate this further, if required.
A rheological evaluation of the placebo and ADAIR formulations at various fill temperatures has established a recommended fill temperature of 55±10° C., with constant stirring recommended to optimise flow characteristics. A thermal hold study has been carried out during a technical manufacture (report to follow), whereby the bulk mix was held and sampled at the filling temperature. For additional confidence in the suggested filling temperature limits, it is suggested that a thermal hold study be carried out at the highest limit of the fill temperature range, 65° C.

Example 5: Comparison of Prototype 2 and a Non-Abuse Deterrent Tablet: Dissolution Studies This example compares dissolution profiles of abuse-deterrent formulation Prototype 2, also known as abuse deterrence amphetamine immediate release (ADAIR) capsule 10 mg of Dextroamphetamine Sulfate, to the reference listed drug (LD) Dextroamphetamine sulfate 10 mg tablets.

1. INTRODUCTION

Method parameters for dissolution assessment of selected prototype formulations with that of the LD are described in this example. Prototype formulations that were used in the method development are listed in Table 106:

TABLE 108

Composition of prototypes 1, 2 (ADAIR), 4, 5 and 6

| | Batch Number | | | | |
|---|---|---|---|---|---|
| prototype No Component | 1003/57/01 1 % Fill | 1003/141/01 2 (ADAIR) % Fill | 1003/57/04 4 % Fill | 1003/57/05 5 % Fill | 1003/57/06 6 % Fill |
| Dextroamphetamine Sulfate | 5.5 | 5.5 | 5.5 | 5.5 | 5.5 |
| Poloxamer P124 | | 37.8 | | | |
| Gelucire 48/16 | | 28.4 | | 56.7 | |
| Kelcogel CGHA | | 28.4 | 37.8 | | |
| CMC 7H3SF | | | | | |
| Kolliphor EL | | | | | 56.7 |
| Luxura | 37.8 | | | | |
| Kolliphor RH40 | | | 56.2 | | |
| Xantural 75 | | | | | 37.8 |
| Kollisolv 124 | 56.7 | | | | |
| Capsule Shell and Size | Size 3 gelatin | Size 3 gelatin | Size 3 gelatin | Size 3 gelatin | Size 3 gelatin |
| Total | 100 | 100 | 100 | 100 | 100 |

2. ANALYTICAL METHODOLOGY

The analytical conditions given in the USP method for the analysis of Dextroamphetmaine Sulfate Tablets, USP39 (see Appendix A) were used as the starting point in the development of a suitable dissolution method for the analysis and comparison of the LD with Prototypes prototype 1, 2, 4, 5 and 6.

Following on from these initial development activities, a set of parameters for the dissolution method were established and these are given in Appendix F. The mobile phase and reagent preparation as stated in this draft method have been used during the development activities unless otherwise stated within the following sections.

3. METHOD DEVELOPMENT

3.1 Dissolution of 10 mg LD n=6 in 0.01M HCl Using Apparatus 1

Initial method development analysis was conducted using USP dissolution apparatus 1 and the LD-Barr's 10 mg IR tablet containing Dextroamphetamine sulfate.

| | |
|---|---|
| Dissolution Apparatus | USP apparatus I |
| Filter Type | 40 μm probe filter |
| Medium Type | 0.01M HCl |
| Medium Volume | 500 ml |
| Sample Times | 5, 10, 15, 20, 30 and 45 minutes. |
| Sample Volume | 1.5 ml (filter not replaced) straight to vial. |
| Vessel Temperature | 37° C. ± 0.5° C. |
| Speed | 100 rpm |

Observations during dissolution: At the end of the test a small amount of tablet residue remained.

HPLC Conditions as Follows for Dissolution Section 3.1

| | |
|---|---|
| Column | Agilent Zorbax Eclipse XDB-C18 5 um 4.6 × 250 mm, SN/USHR009398 (Development column) |
| Flow rate | 1.5 ml/min |
| Injection volume | 100 μl |
| Column temperature | 40° C. |
| Detection wavelength | 210 nm |
| Mobile phase | 100% Mobile phase |
| Run time | 20 min |

TABLE 107

10 mg LD in 0.01M HCl on Apparatus 1

| Time (min) | % Release | | | | | | | |
|---|---|---|---|---|---|---|---|---|
| | Pot 1 | Pot 2 | Pot 3 | Pot 4 | Pot 5 | Pot 6 | Mean | RSD |
| 5 | 27.10 | 27.63 | 29.51 | 30.76 | 24.71 | 25.33 | 27.5 | 8.5 |
| 10 | 44.05 | 45.44 | 52.32 | 52.16 | 42.32 | 42.48 | 46.5 | 9.9 |
| 15 | 58.80 | 60.36 | 66.95 | 71.93 | 55.81 | 56.21 | 61.7 | 10.4 |
| 20 | 72.99 | 81.80 | 81.01 | 90.40 | 69.47 | 68.12 | 77.3 | 11.1 |
| 30 | 98.56 | 103.49 | 98.68 | 100.83 | 96.74 | 92.27 | 98.4 | 3.9 |
| 45 | 100.55 | 103.48 | 98.37 | 100.52 | 102.39 | 95.56 | 100.1 | 2.8 |

3.2 HPLC Condition Method Development

Initial results for the dissolution test on Apparatus 1 in section 3.1 were conducted with a development column. The next step of the HPLC method development was to purchase new project specific columns and to check that the method conditions were still suitable and reproducible.

HPLC Conditions as Follows for Section 3.2

| | |
|---|---|
| Column | Agilent Zorbax Eclipse XDB-C18 5 um 4.6 × 250 mm, SN/USNH041812 (#632) |
| Flow rate | 1.5 ml/min |
| Injection volume | 100 μl |
| Column temperature | 40° C. |
| Detection wavelength | 210 nm |
| Mobile phase | 100% Mobile phase 1 |
| Run time | 20 min |

Chromatography evaluation of the new column showed that the new columns were suitable for use. The only difference between the development column and the new columns was the retention time of the main peak was now at approx. 14 mins compared to 11 mins.

3.3 Dissolution of Prototypes Prototype 1, 4, 5 and 6 in 0.01M HCl Using Apparatus 1

Initial method development analysis for the prototypes was conducted using USP dissolution apparatus 1 and prototypes 1, 4, 5 and 6.

Dissolution Conditions as Follows for Dissolution Section 3.1

| | |
|---|---|
| Dissolution Apparatus | USP apparatus I |
| Filter Type | 40 μm probe filter |
| Medium Type | 0.01M HCl |
| Medium Volume | 500 ml |
| Sample Times | 5, 10, 15, 20, 30 and 45 minutes. |
| Sample Volume | 1.5 ml (filter not replaced) straight to vial. |
| Vessel Temperature | 37° C. ± 0.5° C. |
| Speed | 100 rpm |

Description

Analysis on each prototype was performed in triplicate.

Prototype 1

At the end of the dissolution the capsule shell and the majority of the capsules slug appeared to have dissolved. Therefore all time points were selected to be analyzed. However due to problems with the guar gum blocking the column only the 5 and 10 min time points were able to be run on the HPLC.

Prototypes 4, 5 and 6

At the end of the dissolution only a small portion of the capsules had dissolved and so only the 45 min time point was analyzed.

HPLC Conditions as Follows for Dissolution 3.1

| | |
|---|---|
| Column | Agilent Zorbax Eclipse XDB-C18 5 um 4.6 × 250 mm, SN/USHR009398 (Development column) |
| Flow rate | 1.5 ml/min |
| Injection volume | 100 μl |
| Column temperature | 40° C. |
| Detection wavelength | 210 nm |
| Mobile phase | 100% Mobile phase |
| Run time | 20 min |

TABLE 109

10 mg prototype 1 in 0.01M HCl on Apparatus 1

| Sample Name | % Release | Mean % Release | % RSD |
|---|---|---|---|
| prototype 1 5 minutes pot 1 | 6.31 | 6.0 | 4.9 |
| prototype 1 5 minutes pot 2 | 5.79 | | |
| prototype 1 5 minutes pot 3 | 5.81 | | |
| prototype 1 10 minutes pot 1 | 20.19 | 21.5 | 13.9 |
| prototype 1 10 minutes pot 2 | 19.42 | | |
| prototype 1 10 minutes pot 3 | 24.93 | | |

TABLE 110

10 mg prototype 4 in 0.01M HCl on Apparatus 1

| Sample Name | % Release | Mean % Release | % RSD |
|---|---|---|---|
| prototype 4 45 minutes pot 4 | 43.99 | 48.8 | 9.9 |
| prototype 4 45 minutes pot 5 | 53.62 | | |
| prototype 4 45 minutes pot 6 | 48.85 | | |

TABLE 111

10 mg prototype 5 in 0.01M HCl on Apparatus 1

| Sample Name | % Release | Mean % Release | % RSD |
|---|---|---|---|
| prototype 5 45 minutes pot 1 | 15.69 | 14.0 | 13.1 |
| prototype 5 45 minutes pot 2 | 14.31 | | |
| prototype 5 45 minutes pot 3 | 12.05 | | |

10 mg prototype 6 in 0.01M HCl on Apparatus 1

| Sample Name | % Release | Mean % Release | % RSD |
|---|---|---|---|
| prototype 6 45 minutes pot 4 | 23.46 | 25.2 | 14.4 |
| prototype 6 45 minutes pot 5 | 22.75 | | |
| prototype 6 45 minutes pot 6 | 29.35 | | |

3.4 Dissolution of 10 mg LD and Prototype 2 30 mg in 0.01M HCl Using Apparatus 3 at 30 DPM Dissolution testing of the ADAIR was carried out using Apparatus 3 with reciprocating cylinder. An initial dip rate of 30 DPM (dips per minute) was selected again due to previous experience of its use.

Dissolution Conditions as Follows for Section 3.4:

| | |
|---|---|
| Dissolution Apparatus | USP apparatus III |
| Filter Type | 40/35 μm probe filter |
| Medium Type | 0.01M HCl |
| Medium Volume | 250 ml |
| Sample Times | 5, 10, 15, 20, 30 and 45 minutes. |
| Sample Volume | 2 ml (filter not replaced) |
| Vessel Temperature | 37° C. ± 0.5° C. |
| Dip Rate | 30 dips per minute |
| Mesh Screen Size | 840 micron |

Observations during dissolution: Tablets in all pots dissolved between 5-10 mins with a fine orange powder settled to bottom of the pot.

HPLC Conditions as Follows for Section 3.4

| | |
|---|---|
| Column | Agilent Zorbax Eclipse XDB-C18 5 um 4.6 × 250 mm, SN/USNH041816 (#661) |
| Flow rate | 2 ml/min |
| Injection volume | 100 μl |
| Column temperature | 50° C. |
| Detection wavelength | 210 nm |
| Mobile phase | 100% Mobile phase |
| Run time | 16 min |

TABLE 113

10 mg LD in a size 00 shell n = 6 in 0.01M HCl using Apparatus 3 at 30 DPM

| TIME (Mins) | POT 1 | POT 2 | POT 3 | POT 4 | POT 5 | POT 6 | Average | % RSD |
|---|---|---|---|---|---|---|---|---|
| 5 | 72.08 | 75.48 | 70.75 | 91.13 | 73.10 | 79.37 | 77.0 | 9.8 |
| 10 | 95.00 | 94.65 | 98.16 | 102.09 | 93.24 | 103.50 | 97.8 | 4.3 |
| 15 | 105.76 | 104.63 | 107.04 | 103.03 | 103.40 | 110.52 | 105.7 | 2.6 |
| 20 | 106.05 | 104.55 | 107.16 | 102.55 | 103.20 | 110.57 | 105.7 | 2.8 |
| 30 | 105.30 | 103.82 | 106.62 | 102.05 | 102.80 | 109.77 | 105.1 | 2.7 |
| 45 | 104.82 | 103.63 | 105.84 | 101.26 | 101.97 | 108.97 | 104.4 | 2.7 |

TABLE 114

30 mg Prototype 2 0.01M HCl using Apparatus 3 at 30 DPM Boof ref: 1050/109

| TIME (Mins) | POT 1 | POT 2 | POT 3 | POT 4 | POT 5 | POT 6 | Average | % RSD |
|---|---|---|---|---|---|---|---|---|
| 5 | 28.77 | 25.95 | 23.12 | 18.41 | 20.48 | 18.01 | 22.46 | 19.2 |
| 10 | 59.97 | 57.43 | 53.93 | 49.84 | 55.04 | 52.40 | 54.77 | 6.6 |
| 15 | 79.85 | 79.86 | 74.91 | 72.57 | 73.50 | 72.43 | 75.52 | 4.6 |
| 20 | 89.34 | 93.57 | 91.09 | 85.29 | 88.49 | 89.14 | 89.49 | 3.1 |
| 30 | 96.10 | 100.76 | 101.23 | 97.44 | 99.28 | 99.53 | 99.06 | 2.0 |
| 45 | 97.56 | 102.63 | 102.41 | 100.61 | 100.33 | 100.85 | 100.73 | 1.8 |

3.5 Dissolution of 10 mg LD and Prototype 2 30 mg n=6 in 0.01M HCl Using Apparatus 3 at 5 DPM Following on from section 3.4, the effect of dip rate on the dissolution rate and % recovery of the LD was further evaluated by a change in dip rate from 30 DPM to 5 DPM. Further to analysis of the LD at 5 DPM the LD was encased within a size 0 gelatin capsule shell in order to replicate the effect of the capsule shell on dissolution rate and % recovery results.

Dissolution Conditions as Follows for Section 3.5

| | |
|---|---|
| Dissolution Apparatus | USP apparatus III |
| Filter Type | 40/35 μm probe filter |
| Medium Type | 0.01M HCl |
| Medium Volume | 250 ml |
| Sample Times | 5, 10, 15, 20, 30 and 45 minutes. |
| Sample Volume | 2 ml (filter not replaced) |
| Vessel Temperature | 37° C. ± 0.5° C. |
| Dip Rate | 5 dips per minute |
| Mesh Screen Size | 840 micron |

Observations during dissolution: 5-15 minutes a fine dispersion was observed.
At 15 mins pots 1, 2, and 6 fully dissolved with a small residue remained for all other pots.
At 20 mins pots 3 and 4 fully dissolved.
A small residue remained for pot 5 at 30-45 mins.
HPLC Conditions as Follows for Section 3.

| | |
|---|---|
| Column | Agilent Zorbax Eclipse XDB-C18 5 um 4.6 × 250 mm, SN/USNH041816 (#661) |
| Flow rate | 2.0 ml/min |
| Injection volume | 100 μl |
| Column temperature | 50° C. |
| Detection wavelength | 210 nm |
| Mobile phase | 100% Mobile phase 1 |
| Run time | 15 min |

TABLE 115

10 mg LD n = 6 in 0.01M HCL using Apparatus 3 at 5 DPM

| TIME (Mins) | POT 1 | POT 2 | POT 3 | POT 4 | POT 5 | POT 6 | Average | % RSD |
|---|---|---|---|---|---|---|---|---|
| 5 | 46.83 | 43.22 | 42.60 | 44.77 | 33.82 | 51.57 | 43.8 | 13.4 |
| 10 | 72.42 | 71.19 | 69.82 | 69.21 | 57.96 | 80.11 | 70.1 | 10.2 |
| 15 | 102.00 | 103.47 | 96.36 | 92.35 | 90.72 | 103.47 | 98.1 | 5.8 |
| 20 | 107.28 | 107.61 | 105.04 | 104.30 | 105.88 | 109.17 | 106.5 | 1.7 |
| 30 | 109.00 | 109.28 | 104.99 | 109.35 | 109.54 | 108.85 | 108.5 | 1.6 |
| 45 | 109.14 | 109.52 | 105.08 | 110.77 | 109.71 | 109.02 | 108.9 | 1.8 |

TABLE 116

10 mg LD in a size 00 shell n = 6 in 0.01M HCL using Apparatus 3 at 5 DPM

| TIME (Mins) | POT 1 | POT 2 | POT 3 | POT 4 | POT 5 | POT 6 | Average | % RSD |
|---|---|---|---|---|---|---|---|---|
| 5 | 15.10 | 14.54 | 11.49 | 13.61 | 15.90 | 23.27 | 15.7 | 25.7 |
| 10 | 51.03 | 27.53 | 38.56 | 42.72 | 44.83 | 57.31 | 43.7 | 23.6 |
| 15 | 87.47 | 49.53 | 75.86 | 80.62 | 78.24 | 94.37 | 77.7 | 19.8 |
| 20 | 106.31 | 70.66 | 98.63 | 101.77 | 102.20 | 106.34 | 97.7 | 13.9 |
| 30 | 108.89 | 99.28 | 104.67 | 108.42 | 108.87 | 106.70 | 106.1 | 3.5 |
| 45 | 108.61 | 109.54 | 104.74 | 108.33 | 108.93 | 106.11 | 107.7 | 1.7 |

TABLE 117

Prototype 2 30 mg 0.01M HCL using Apparatus 3 at 5 DPM

| TIME (Mins) | POT 1 | POT 2 | POT 3 | POT 4 | POT 5 | POT 6 | Average | % RSD |
|---|---|---|---|---|---|---|---|---|
| 5 | 6.96 | 3.70 | 4.71 | 2.95 | 1.61 | 3.88 | 4.0 | 45.3 |
| 10 | 27.21 | 12.77 | 14.86 | 9.36 | 5.33 | 12.03 | 13.6 | 54.7 |
| 15 | 50.04 | 31.21 | 36.48 | 18.76 | 20.48 | 27.51 | 30.7 | 37.5 |
| 20 | 75.22 | 67.03 | 62.85 | 47.91 | 52.63 | 54.68 | 60.1 | 16.9 |
| 30 | 91.71 | 90.43 | 87.05 | 76.45 | 83.36 | 80.63 | 84.9 | 6.9 |
| 45 | 95.50 | 95.64 | 97.67 | 92.59 | 98.59 | 97.54 | 96.3 | 2.2 |

3.6 Dissolution of 10 mg Tablets in a Size 00 Shell n=6 in 0.01M HCL Using Apparatus 3 at 5 DPM Using the Gemini Column The experiment performed in section 3.9 was repeated using the new Gemini column.

Dissolution Conditions as Follows for Section 3.10

| | |
|---|---|
| Dissolution Apparatus | USP apparatus III |
| Filter Type | 40/35 μm probe filter |
| Medium Type | 0.01M HCl |
| Medium Volume | 250 ml |
| Sample Times | 5, 10, 15, 20, 30 and 45 minutes. |
| Sample Volume | 2 ml (filter not replaced) |
| Vessel Temperature | 37° C. ± 0.5° C. |
| Dip Rate | 5 dips per minute |
| Mesh Screen Size | 840 micron |

Observations during dissolution: Capsule shell breached at 2 mins. 5 mins capsule shell partially dissolved and tablet contents exposed. 10 mins shell fully dissolved tablets reduced in size. 15 mins tablets reduced in size further. 20 mins pots 4 and 5 fully dissolved. 30-45 mins pot 1, 2, 3, and 6 fully dissolved.

HPLC Conditions as Follows for Section 3.10

| | |
|---|---|
| Column | Phenomenex, Gemini C18 5 μm, 110A, 150 mm × 4.6 mm, SN: 557080-5 BN: 5520-87 (Development column) |
| Flow rate | 1.5 ml/min |
| Injection volume | 20 μl |
| Column temperature | 50° C. |
| Detection wavelength | 210 nm |
| Mobile phase | 100% Mobile phase |
| Run time | 10 min |

TABLE 118

10 mg LD in a size 00 shell n = 6 in 0.01M HCL using Apparatus 3 at 5 DPM using the Gemini Column

| Time (min) | Pot 1 | Pot 2 | Pot 3 | Pot 4 | Pot 5 | Pot 6 | Mean | RSD |
|---|---|---|---|---|---|---|---|---|
| 5 | 15.94 | 7.36 | 9.36 | 27.53 | 30.43 | 11.36 | 17 | 57.4 |
| 10 | 43.31 | 36.01 | 31.69 | 57.94 | 66.76 | 33.37 | 44.8 | 32.1 |
| 15 | 65.88 | 75.00 | 52.41 | 85.59 | 94.59 | 57.73 | 71.9 | 22.7 |
| 20 | 87.51 | 95.44 | 71.85 | 96.28 | 101.53 | 83.01 | 89.3 | 12.1 |
| 30 | 94.38 | 100.68 | 97.96 | 97.37 | 101.65 | 99.53 | 98.6 | 2.7 |
| 45 | 94.11 | 100.55 | 99.36 | 96.35 | 100.72 | 100.14 | 98.5 | 2.7 |

3.7 Comparison Dissolution Studies Between LD and ADAIR at 5 DPM

A comparison study between the LD and ADAIR was carried out at the 5 DPM.

TABLE 119

10 mg LD in 0.01M HCl using Apparatus 3 at 5 DPM

| TIME (Mins) | POT 1 | POT 2 | POT 3 | POT 4 | POT 5 | POT 6 | Average | % RSD |
|---|---|---|---|---|---|---|---|---|
| 5 | 15.94 | 7.36 | 9.36 | 27.53 | 30.43 | 11.36 | 17.0 | 57.4 |
| 10 | 43.31 | 36.01 | 31.69 | 57.94 | 66.76 | 33.37 | 44.8 | 32.1 |
| 15 | 65.88 | 75.00 | 52.41 | 85.59 | 94.59 | 57.73 | 71.9 | 22.7 |
| 20 | 87.51 | 95.44 | 71.85 | 96.28 | 101.53 | 83.01 | 89.3 | 12.1 |
| 30 | 94.38 | 100.68 | 97.96 | 97.37 | 101.65 | 99.53 | 98.6 | 2.7 |
| 45 | 94.11 | 100.55 | 99.36 | 96.35 | 100.72 | 100.14 | 98.5 | 2.7 |

TABLE 120

10 mg ADAIR (1003/141/01) in 0.01M HCl Apparatus 3 at 5 DPM

| TIME (Mins) | POT 1 | POT 2 | POT 3 | POT 4 | POT 5 | POT 6 | Average | % RSD |
|---|---|---|---|---|---|---|---|---|
| 5 | 3.61 | 3.44 | 3.88 | 3.98 | 2.63 | 4.04 | 3.6 | 14.7 |
| 10 | 13.95 | 20.41 | 20.14 | 13.56 | 8.62 | 24.23 | 16.8 | 34.1 |
| 15 | 49.45 | 59.67 | 50.79 | 40.31 | 38.83 | 42.73 | 47.0 | 16.8 |
| 20 | 76.31 | 82.97 | 73.18 | 63.35 | 70.13 | 67.84 | 72.3 | 9.5 |
| 30 | 101.39 | 102.58 | 94.24 | 87.26 | 94.84 | 88.41 | 94.8 | 6.7 |
| 45 | 110.13 | 105.82 | 102.41 | 98.25 | 102.52 | 96.63 | 102.6 | 4.8 |

TABLE 121

10 mg ADAIR (1003/141/01) in 0.01M HCl Apparatus 3 at 30 DPM

| TIME (Mins) | POT 1 | POT 2 | POT 3 | POT 4 | POT 5 | POT 6 | Average | % RSD |
|---|---|---|---|---|---|---|---|---|
| 5 | 30.54 | 32.32 | 8.90 | 33.47 | 29.34 | 29.33 | 27.3 | 33.6 |
| 10 | 75.13 | 76.33 | 64.44 | 71.62 | 79.22 | 71.27 | 73.0 | 7.1 |
| 15 | 92.78 | 95.89 | 96.81 | 90.52 | 99.38 | 92.97 | 94.7 | 3.4 |
| 20 | 98.68 | 101.63 | 107.96 | 97.42 | 107.70 | 99.12 | 102.1 | 4.6 |
| 30 | 98.51 | 101.32 | 107.98 | 97.88 | 106.92 | 98.72 | 101.9 | 4.4 |
| 45 | 97.67 | 100.57 | 107.60 | 97.22 | 106.29 | 98.35 | 101.3 | 4.5 |

3.8 Comparison Dissolution Studies Between LD and ADAIR

The studies carried out using Apparatus 1 in Section 3.3 did not include the ADAIR which was not one of the abuse deterrent prototype formulations analyzed at this time as the apparatus III method was most appropriate to show the comparison of the different formulations under test. Following the decision to progress the ADAIR formulation this was tested using the apparatus I method. The dissolution profiles for ADAIR at Initial conditions and after a period of 8 weeks being stored at 40° C. in 75% Relative humidity were obtained. At each condition the dissolution was carried out in duplicate to give a total of 12 dosage units tested. The results are given in Tables below and shown graphically in FIG. 13.

Dissolution of 10 mg ADAIR n=6 in 0.01M HCl Using Apparatus 1

Dissolution Conditions as Follows for Dissolution Section 3.1

| | |
|---|---|
| Dissolution Apparatus | USP apparatus I |
| Filter Type | 35 μm probe filter |
| Medium Type | 0.01M HCl |
| Medium Volume | 500 ml |
| Sample Times | 5, 10, 15, 20, 30 and 45 minutes. |
| Sample Volume | 1.5 ml (filter not replaced) straight to vial. |
| Vessel Temperature | 37° C. ± 0.5° C. |
| Speed | 100 rpm |

Observations during dissolution: At the end of the test a lumpy solid white residue remained.

HPLC Conditions as Follows for Dissolution Section 3.8

| | |
|---|---|
| Column | Agilent Zorbax Eclipse XDB-C18 5 um 4.6 × 250 mm, |
| Flow rate | 1.5 ml/min |
| Injection volume | 100 μl |
| Column temperature | 40° C. |
| Detection wavelength | 210 nm |
| Mobile phase | 100% Mobile phase |
| Run time | 20 min |

TABLE 122

Average % Release for ADAIR prep A at Initial conditions

| TIME (Mins) | POT 1 | POT 2 | POT 3 | POT 4 | POT 5 | POT 6 | Average | % RSD |
|---|---|---|---|---|---|---|---|---|
| 5 | 5.40 | 4.86 | 7.72 | 7.23 | 5.91 | 3.61 | 5.8 | 26.3 |
| 10 | 32.11 | 26.69 | 42.44 | 36.66 | 34.40 | 19.76 | 32.0 | 24.8 |
| 15 | 55.73 | 54.89 | 59.48 | 58.74 | 52.90 | 55.39 | 56.2 | 4.4 |
| 20 | 74.18 | 70.27 | 75.44 | 80.76 | 68.27 | 71.47 | 73.4 | 6.1 |
| 30 | 95.04 | 94.42 | 99.27 | 98.98 | 88.76 | 91.94 | 94.7 | 4.3 |
| 45 | 105.83 | 107.89 | 107.90 | 108.03 | 102.95 | 105.42 | 106.3 | 1.9 |

TABLE 123

Average % Release for ADAIR prep B at Initial conditions

| TIME (Mins) | POT 1 | POT 2 | POT 3 | POT 4 | POT 5 | POT 6 | Average | % RSD |
|---|---|---|---|---|---|---|---|---|
| 5 | 3.92 | 6.55 | 8.21 | 5.68 | 5.75 | 6.66 | 6.1 | 23.1 |
| 10 | 18.37 | 32.46 | 29.63 | 25.98 | 27.23 | 29.89 | 27.3 | 18.0 |
| 15 | 50.06 | 55.45 | 53.28 | 56.69 | 48.56 | 53.75 | 53.0 | 5.9 |
| 20 | 66.53 | 70.61 | 69.63 | 74.05 | 68.20 | 76.45 | 70.9 | 5.2 |
| 30 | 90.88 | 83.88 | 89.88 | 94.94 | 84.36 | 94.24 | 89.7 | 5.3 |
| 45 | 105.70 | 110.55 | 97.94 | 110.79 | 96.56 | 108.48 | 105.0 | 6.0 |

TABLE 124

Average % Release for ADAIR prep A at 40 C. 75% RH conditions

| TIME (Mins) | POT 1 | POT 2 | POT 3 | POT 4 | POT 5 | POT 6 | Average | % RSD |
|---|---|---|---|---|---|---|---|---|
| 5 | 2.71 | 4.51 | 4.85 | 3.20 | 4.63 | 5.73 | 4.3 | 26.2 |
| 10 | 11.95 | 24.04 | 21.95 | 20.93 | 26.36 | 20.44 | 20.9 | 23.5 |
| 15 | 40.17 | 41.83 | 46.02 | 45.29 | 47.61 | 42.94 | 44.0 | 6.4 |
| 20 | 58.35 | 56.55 | 59.43 | 59.89 | 64.10 | 64.27 | 60.4 | 5.2 |
| 30 | 79.74 | 81.55 | 77.67 | 79.70 | 80.94 | 82.05 | 80.3 | 2.0 |
| 45 | 98.76 | 100.49 | 99.92 | 99.08 | 100.47 | 103.33 | 100.3 | 1.6 |

TABLE 125

Average % Release for ADAIR prep B at 40 C. 75% RH conditions

| TIME (Mins) | POT 1 | POT 2 | POT 3 | POT 4 | POT 5 | POT 6 | Average | % RSD |
|---|---|---|---|---|---|---|---|---|
| 5 | 3.59 | 5.91 | 4.75 | 5.27 | 2.58 | 2.46 | 4.3 | 29.5 |
| 10 | 19.08 | 27.84 | 14.35 | 28.60 | 20.87 | 21.08 | 22.0 | 24.7 |
| 15 | 39.84 | 44.30 | 45.13 | 46.57 | 42.97 | 45.98 | 44.1 | 5.6 |
| 20 | 59.35 | 62.74 | 62.34 | 64.91 | 64.22 | 62.78 | 62.7 | 3.1 |
| 30 | 81.53 | 78.58 | 82.18 | 81.97 | 82.37 | 84.60 | 81.9 | 2.4 |
| 45 | 98.20 | 98.44 | 106.23 | 98.96 | 103.44 | 99.70 | 100.8 | 3.2 |

TABLE 126

Average % Release for LD

| TIME (Mins) | POT 1 | POT 2 | POT 3 | POT 4 | POT 5 | POT 6 | Average | % RSD |
|---|---|---|---|---|---|---|---|---|
| 5 | 27.10 | 27.63 | 29.51 | 30.76 | 24.71 | 25.33 | 27.5 | 8.5 |
| 10 | 44.05 | 45.44 | 52.32 | 52.16 | 42.32 | 42.48 | 46.5 | 9.9 |
| 15 | 58.80 | 60.36 | 66.95 | 71.93 | 55.81 | 56.21 | 61.7 | 10.4 |
| 20 | 72.99 | 81.80 | 81.01 | 90.40 | 69.47 | 68.12 | 77.3 | 11.1 |
| 30 | 98.56 | 103.49 | 98.68 | 100.83 | 96.74 | 92.27 | 98.4 | 3.9 |
| 45 | 100.55 | 103.48 | 98.37 | 100.52 | 102.39 | 95.56 | 100.1 | 2.8 |

4. CONCLUSION

From the results obtained during this study and previous abuse deterrent (AD) studies it can clearly be concluded that using Apparatus 3 proved more conducive to the analysis of a wider range of AD formulations than Apparatus 1 and therefore was used during the development phase of the project to determine the preferred formulation for progression. The method parameters set out in Appendix F were developed.

Following the selection of ADAIR as the formulation to be progressed with, this was tested using the Apparatus 1 in order to compare the profile to that of the LD. This data showed full release of the API from the ADAIR formulation at 45 minutes and at 30 minutes for the LD. A slight time-lag may be expected due to the required disintegration of the capsule shell for ADAIR to allow the formulation to be released.

The results obtained for the dissolution of ADAIR with Apparatus 1 were consistent the LD and equivalent dissolution profiles have been shown. The method is described in Appendix G.

APPENDIX A
PROTOCOL: Evaluation of Abuse Deterrent immediate release Formulations Of Dextroamphetamine Sulfate

1. INTRODUCTION

This protocol is designed to evaluate physical and chemical barriers to abuse including susceptibility to extraction, injection, and crushing (to deter snorting) under various conditions. The outcomes from this evaluation should enable the selection of a better-characterized lead prototype to be further developed into a final Abuse Deterrent Formulation-Immediate Release-dextroamphetamine.

2. OBJECTIVES

To evaluate the relative susceptibility to manipulation/abuse of novel prototypes of IR d-amph 10mg liquid fill capsules (which utilize the Abusolve™ technology) as compared to a related reference product (as appropriate).

It should be noted that there is no specific relevant regulatory guidance issued by the FDA for non-opiate drugs and therefore the tests included in this protocol are adopted from the FDA guidance for Opioids with the appropriate adaptations (ref: FDA Guidance: Abuse-Deterrent Opioids – Evaluation and Labelling, April 2015). Reference is also made to the March 2016 FDA guidance "General Principles for Evaluating the Abuse Deterrence of Generic Solid Oral Opioid Drug Products" from which appropriate elements and approaches were also adopted.

3. MATERIALS

All materials used should be recorded in the laboratory notebook and reported along with the results in the final report. Information recorded should include material name, supplier, source, batch number, expiry date and received raw material number, where appropriate.

4. EQUIPMENT

- Grade A, Laboratory Glassware.
- Coffee grinder.
- 5/6 place analytical balance.
- Ultrasonic and shaking water baths.
- Sieves (various sizes) and Sieve shaker.
- Fume hood.
- Mortars and pestles.
- Luer-lok syringe (no black or rubber septum syringes to be used).
- 18 to 29 gauge syringe needles.
- Various filters.

Analytical equipment must be qualified, calibrated and maintained in accordance with site procedures, prior to use. Details of the equipment used (including make and model) will be recorded in laboratory notebooks or worksheets as appropriate. Where needed additional equipment may be used and will be recorded appropriately.

5. RECORD KEEPING

All analytical work will be recorded in project specific laboratory notebooks. A report which will include full details of all results and subsequent evaluations against acceptance criteria will be transcription and calculation checked prior to issue. In addition, wherever possible and in all testing that include manipulation of the dosage form (such as syringeability), video recording and still images will be taken and attached to the report.

6. ANALYTICAL METHODS

Some evaluations are based on visual/physical assessments; others require analysis of the amount of drug substance. The Analytical methods used are based on compendial methods for Dextroamphetamine which have been verified for selectivity and may require limited further validation at a later stage of development. Where indicated, the method will be used (and modified as necessary) to determine either a % assay or a % release profile for Dextroamphetamine sulfate when applicable.

Dextroamphetamine sulfate extraction will be determined by the HPLC method detailed in SupplementI for the IR-ADF prototype products and using the current USP tablet method for the comparator, Barr's Dextroamphetamine sulfate 10mg.

7. EVALUATION PLAN

The physical/chemical deterrent methods in this protocol will be evaluated on the following prototype formulations:

| Component | mg/capsule | | |
| --- | --- | --- | --- |
| | Prototype 2 | Prototype 3 | Prototype 7 |
| Dextroamphetamine sulfate | 10 | 10 | 10 |
| Poloxamer 124 | 70 | - | - |
| Gelucire 48/16 | 52.5 | 122.5 | - |
| Kelcogel GCHA | 52.5 | 52.5 | - |
| Kolliphor EL | - | - | 122.5 |
| CMC 7H3SF | | | 52.5 |
| Capsule Shell and Size | Size 3 gelatin | Size 3 gelatin | Size 3 gelatin |
| Total fill weight (mg)* | 185 | 185 | 185 |

*Final fill weight to be confirmed experimentally*

Barr's 10mg Dextroamphetamine sulfate Tablets will also be evaluated as a comparator under the same test strategy.

A stepwise approach will be taken with all analyzes, initiating with "Phase I" analyzes of all three IR-ADF prototypes and the comparator, and gradually proceeding to more destructive mechanical and chemical manipulations, if applicable, in "Phase II" analyzes of those agreed-upon prototypes demonstrating appropriate AD characteristics (see section 8 for assessment criteria). The tests performed in both phases are summarized in the following table:

| Tested Characteristic | Test Type/Conditions | Phase |
|---|---|---|
| Physical Barriers to Crushing | Thermal pre-treatment requirement test | I |
| | Coffee Grinder Test | I |
| | Grinding with Flux | II |
| Extraction Barriers | Extraction in small and large volumes of Tier 1 solvents | I |
| | Extraction in small and large volumes of Tier 2 solvents | II |
| Syringeability Barriers | Ambient and hot syringeability test in water utilizing a 26-gauge needle | I |
| | Ambient and hot syringeability test in water utilizing 18 to 28-gauge needles | II |
| | Syringeability test of melted product | II |
| | Syringeability test using multi-pass filtering | II |

Physical and chemical abuse resistance testing

All testing will employ whole dose units. Physical testing will be conducted in duplicate, and all other testing in triplicate. Where physical testing produces poor replicates, a third test should be performed.

7.1 Tests of Physical Barriers to Abuse by Crushing, Cutting or Grinding

Each test in this section should include five (5) whole dose units. All prototypes as well as the comparator compound should be tested in Phase I studies. Record any observations such as the inability to grind the material or pass it through the sieve due to a waxy or other physical characteristic. Video/picture documentation should be included wherever possible.

A    Phase I Studies

1.    Establish requirement for thermal pre-treatment

Method: Obtain one whole dose unit. Remove the shell as quickly as possible with a scalpel then immediately after the shell is removed, grind with a coffee grinder for five (5) minutes. If product is milled to a size less than 1mm, no thermal pre-treatment will be used. Otherwise, thermal pre-treatment will be used in all consequent analyzes.

2. Milling with a coffee grinder.

Method: Where thermal pre-treatment is required, freeze the dosage units in a domestic freezer for 24 hrs. Remove the shells as quickly as possible with a scalpel then immediately after the shell is removed, grind with a coffee grinder for one minute. Determine the particle size distribution of the 5 capsule contents by pouring them onto the following sieve assembly: 1000, 500, 250, and 106 microns. Attempts can be made to further reduce any large particles by squeezing them with your fingers.

Mechanically shake the sieve assembly for 5 minutes and determine if anything passes through. Weigh any material that has passed through each sieve.

Determine API/Excipient segregation as required: Assay the material on each sieve. Calculate the approximate total capsule weight and %API recovery if sufficient material has passed through to facilitate an analysis.

B   Phase II Studies

Proceed with Phase II studies only for prototype formulations that met assessment criteria detailed in Section 8, or otherwise agreed-upon with Alcobra. No comparator product evaluation is required.

1. Grind with Flux (Flow Enhancers).

Method: Where thermal pre-treatment is required, freeze the dosage units in a domestic freezer for 24 hrs. Remove the shell with a scalpel as quickly as possible, transferring the contents to a mortar and pestle with as little loss as possible. Add 0.2 g of a flow enhancer then immediately grind for five minutes. Flow Enhancers to be used: Sodium Chloride and Talc. Repeat particle size determination and API/Excipient segregation as described above.

7.2   Tests of Barriers to Abuse Involving Chemical Extraction

For each test use whole dose units. All prototypes and the comparator product should undergo Phase I studies. Record any observations such as the inability to filter the material due to physical properties etc. Video/picture documentation will be included wherever possible.

Tier 1 solvents: Water, Acetic Acid (8%), 0.2% Sodium Bicarbonate, Ethanol (95%), carbonated soft drink (cola, acidic pH).

Tier 2 solvents: mineral (white) spirits, ethanol 40%, Isopropyl alcohol, methanol, acetone, 0.1N HCl, 0.1N NaOH.

A. Phase I Studies:

1) Extraction in small volumes of ambient Tier 1 solvents (Prepare each sample in triplicate).

Method: Crush with a mortar and pestle or otherwise reduce the particle size of the dose, then grind with 10 mL of Tier 1 solvent for 5 minutes or until homogeneous. Transfer the resulting suspension to a suitable scintillation vial, cover the lid in parafilm and shake in a water bath at ambient temperature, sampling at 5, 15, 60 and 180 minutes. Filter the sample through a 0.45 µm filter into a flask and dilute to an appropriate concentration with the standard assay method diluent. Quantify the API concentration by HPLC. Start with the comparator product first, then analyze the prototype formulations. Prototype formulations that show API concentrations greater or equal to the comparator product should not be taken further to the hot solvent extraction analysis (see Section 8).

An intermediate filtration step over Whatman filter paper (e.g. Grade 4) may be used where 0.45 µm filters become blocked. In this instance, open funnels and vessels should be covered in parafilm during filtration to minimise evaporation and an evaporation standard, prepared as method but filtered over Whatman should be prepared in addition to or from a portion of the assay standard.

2) Extraction in small volumes of hot Tier 1 solvents (Prepare each sample in triplicate).

Method: Crush with a mortar and pestle or otherwise reduce the particle size of the dose, then grind with 10 mL of pre-heated solvent for 5 minutes or until homogeneous. Transfer the resulting suspension to a suitable scintillation vial, cover the lid in parafilm and shake in a water bath at the temperature indicated in Appendix II: Table I, taking samples at 5, 15, 60 and 180 minutes. Filter the sample through a 0.45 µm filter into a flask and dilute to an appropriate concentration with the standard assay method diluent. Quantify the API concentration by HPLC, analysing the comparator product first, followed by the prototype formulations that advanced to this stage, starting with the 180 minute sample first. Where the 180 minute sample contains greater or equal concentrations of API than the comparator, no further testing is required.

As previously, an intermediate filtration step over Whatman filter paper (e.g. Grade 4) may be used where 0.45 µm filters become blocked.

3) Extraction in 100 mL of Tier 1 solvents at an ambient temperature (Prepare each sample in triplicate).

Method: Crush with a mortar and pestle or otherwise reduce the particle size of the dose, then grind with approximately 10 mL of Tier 1 solvent for 5 minutes or until homogeneous. Transfer the resulting suspension to a volumetric flask or other suitable vessel, add further solvent to a total volume of 100 mL, cover the lid in parafilm and place on a stirring plate at ambient temperature, stirring speed 50rpm, sampling at 5, 15, 60 and 180 minutes. Filter the sample through a 0.45 µm filter into a flask and dilute to an appropriate concentration with the standard assay method diluent. Quantify the API concentration by HPLC. Start with the comparator product first, then analyze the prototype formulations. Prototype formulations that show API concentrations greater or equal to the comparator product should not be taken further to the hot solvent extraction analysis (see Section 8).

As previously, an intermediate filtration step over Whatman filter paper (e.g. Grade 4) may be used where 0.45 µm filters become blocked.

4) Extraction in 100 mL of Tier 1 solvents at hot temperatures (Prepare each sample in triplicate).

Where the samples pass the test criteria at room temperature (section 3), repeat for tests with solvents pre-heated to the appropriate temperatures indicated in Supplement II: Table I.

B. Phase II Studies:

Repeat the procedures and instructions outlined above in Phase I for all Tier 2 solvents utilizing the comparator compound and prototypes meeting criteria or as otherwise agreed with Alcobra.

7.3 Test of Syringeability Barriers

For each test use whole dose units of both the comparator product and formulation prototypes. Record any observations such as the inability to draw the material due to physical properties etc. Video/picture documentation will be included wherever possible.

%. A table of needle gauges is included in Supplement III: Table I.

A. Phase I Studies:

1) Syringeability after preparation in ambient and hot water (Prepare each sample in triplicate)

Method: Crush with a mortar and pestle or otherwise reduce the particle size of the dose, then grind with 10 mL of water at ambient temperature for up to 30 minutes or until the solution is homogenous. Test whether the mix becomes sufficiently fluid to be drawn up into a Luer-lok syringe via a 26-gauge needle. Draw back the syringe plunger to the 5 mL mark, maintaining a maximum pressure for 30 seconds or until the syringe has equilibrated pressure. If approximately 1 mL or greater has been drawn into the syringe and is fluid enough to be expelled through the needle (for injection) then dispense the syringe contents into a suitably sized volumetric flask and dilute with Assay diluent to an appropriate concentration. Quantify the amount of API available for injection by HPLC.

If the samples pass the test criteria at room temperature as specified in Section 8 (<5% yield), repeat for water heated to 90-95 °C.

B. Phase II Studies:

Only prototype formulations that met criteria in Phase I Studies should be analyzed in Phase II studies, or unless otherwise agreed upon with Alcobra 1) Syringeability in different gauge needles after preparation with water (Prepare each sample in triplicate)

Method: Crush with a mortar and pestle or otherwise reduce the particle size of the dose, then grind with 10 mL of solvent at ambient temperature for 5 minutes or until the solution is homogenous. Test whether the mix becomes sufficiently fluid to be drawn up into a Luer-lok syringe via an 18-gauge needle. Draw back the syringe plunger to the 5 mL mark, maintaining a maximum pressure for 30 seconds or until the syringe has equilibrated pressure. If approximately 1 mL or greater has been drawn into the syringe and is fluid enough to be expelled through the needle (for injection) then dispense the syringe contents into a suitably sized volumetric flask and dilute with Assay diluent to an appropriate concentration. Quantify the amount of API available for injection by HPLC.

Repeat the above, attempting to draw the fluid via a 0.22 μm filter, a wad of cotton wool and a cigarette filter tip. A fresh sample should be prepared for each filter used.

Repeat the above experiment using a narrower gauge needle for any samples that were syringeable with the 18-gauge needle and progress via the 20 and 23 gauge needles as long as the recovered quantity of API is greater than 5%.

If the samples pass the test criteria at room temperature, repeat with solvent heated to 90-95 °C.

2) Application of heat – melting temperature (Prepare each sample in duplicate)

Method: Place the crushed contents of a dosage unit on a watch glass and heat using a hot plate, preferably with temperature readout, until melted. Determine the temperature of melting and test whether the mix becomes sufficiently fluid to be drawn up into a Luer-lok syringe via an 18, 20, 26 and 28-gauge needle. If the mix cannot be drawn into the syringe there is no requirement to progress to a narrower needle gauge. Pre-weigh the syringe and then draw the syringe plunger back, maintain maximum pressure for 30 seconds or until the syringe has equilibrated pressure to the 5 mL mark. By weighing, measure the percentage entering into the syringe.

3) Syringeability after preparation in water and multi-pass filtering (Prepare each sample in triplicate)

Method: Crush with a mortar and pestle or otherwise reduce the particle size of the dose, then grind with 10 mL of water at ambient temperature for up to 30 minutes or until the solution is homogenous. Test whether the mix becomes sufficiently fluid to be drawn up into a Luer-lok syringe via an 18-gauge needle (or as otherwise agreed upon with Alcobra, based on previous studies). Place a cigarette filter in the mortar and allow it to absorb the liquid. Place the needle in the cigarette filter, draw back the syringe plunger to the 5 mL mark, maintaining a maximum pressure for 30 seconds or until the syringe has equilibrated pressure. If approximately 1 mL or greater has been drawn into the syringe and is fluid enough to be expelled through the needle (for injection) then remove from the cigarette filter and dispense the syringe contents into a suitably sized vessel. Repeat the filtering process twice more or until the fluid is translucent. Where this produces a translucent solution, dispense into a suitably sized volumetric flask and dilute with Assay diluent to an appropriate concentration. Quantify the amount of API available for injection (by HPLC). If a translucent solution is not achieved after three filtration steps, stop and do not analyze the solution.

8. TARGET ASSESSMENT CRITERIA

| Test | Description | Target Criteria |
|---|---|---|
| Physical Manipulation | % API recovery from the 500 µm sieve (coffee grinder and with Flux) | <10% |
| Chemical Extraction | API quantity extracted (timepoint, solvent, volume, temperature) | For Information, <Comparator |
| Syringeability | API quantity (weight and volume) syringeable (solvent,, temperature, needle gauge, filter) | <5% |

Supplement I

METHOD CONDITIONS

Weights and volumes are given for guidance only and may be modified provided the final working concentration and the ratios of components remain the same.

Note: Additional filtration steps, dilutions and guard columns may be required to prevent damage to HPLC systems and to produce results within the validated range of the method.

1     Reagents

| | |
|---|---|
| Trifluoroacetic acid | HPLC Grade ($\geq$99.0%) or equivalent |
| Water | HPLC Grade or equivalent |
| Acetonitrile | HPLC Grade or equivalent |
| Ammonium Hydroxide | Analytical Reagent Grade or equivalent |

2     Safety

| | |
|---|---|
| Dextroamphetamine sulfate | Refer to COSHH A010 |
| Acetonitrile | Refer to COSHH R008 |
| Trifluoroacetic acid | Refer to COSHH R041 |
| Ammonia | Refer to COSHH R070 |

3     Chromatographic Conditions

| | |
|---|---|
| Column | Phenomenex Prodigy C18, 150 x 3.0mm, (5µm) |
| Guard Column | C18 guard column as required |
| Flow rate | 0.7 mL/min |

| | |
|---|---|
| Injection volume | 20 μL |
| Column temperature | 40 °C |
| Detection Wavelength | 257 nm |
| Mobile phase A | TFA: Water: Acetonitrile 90/0.5/10 v/v/v (pH2.2) |
| Mobile phase B | 100% Acetonitrile |

| Gradient | Time (min) | %A | %B |
|---|---|---|---|
| | 0 | 100 | 0 |
| | 15 | 65 | 35 |
| | 20 | 0 | 100 |
| | 22 | 0 | 100 |
| | 23 | 100 | 0 |
| | 30 | 100 | 0 |

| | |
|---|---|
| Run time | 30 min |

Expected Rt (Dextroamphetamine sulfate) - Approximately 6 -7 min

4    Preparation of Mobile Phase A/ Diluent

- Dissolve 5 mL of Trifluoroacetic Acid in 900 mL of water.
- Adjust to a pH of 2.2 (±0.1) with Ammonium Hydroxide.
- Add 100 mL of Acetonitrile and mix.
- Allow to equilibrate to room temperature before use.

5    Preparation of Mobile Phase B

Transfer 1000 mL of HPLC grade Acetonitrile into an appropriate container.

6    Preparation of Reference Standards (Prepare in Duplicate)

- Accurately weigh approximately 25 mg of Dextroamphetamine sulfate reference standard into a 100 mL volumetric flask.
- Add approximately 80 mL of diluent and sonicate until the drug substance is fully dissolved.
- Dilute to volume with diluent and mix well. This is the Dextroamphetamine sulfate standard solution (0.25 µg/mL).

7    Preparation of Sample Solutions (Prepare in Duplicate)

10 mg dose

- Place 5 capsules in a 200 ml volumetric flask.
- Add approximately 160 mL of diluent and shake for 2 hours at 37°C.
- Allow to cool and dilute to volume with diluent.
- Filter and aliquot using 0.45 µm Nylon or GHP filter and analyze using the conditions specified in Section 3.

8    PROCEDURE

Allow mobile phase to flow through the system until equilibrated and a consistent baseline is achieved.

8.1    System Precision

Calculate the % relative standard deviation (%RSD) of the Dextroamphetamine sulfate peak area for six injections of Dextroamphetamine sulfate Standard 1. The %RSD must not be more than 2.0%.

Calculate the % relative standard deviation (%RSD) of the Dextroamphetamine sulfate peak area for each of the bracketing standards throughout the run. The %RSD must not be more than 2.0%.

System Verification

Verify the response factors of the Dextroamphetamine sulfate peak area for two injections of Standard 2 relative to the last two injections of Standard 1. Standard 2 must verify as 98.0 – 102.0% of Standard 1.

No peaks should be detected in either of the diluent blanks which may interfere with the Dextroamphetamine sulfate and have an area which is greater than 0.5% of that observed for Standard 1.

9  Typical Sequence

| | | |
|---|---|---|
| Blank | (x2) | Confirm absence of interference |
| Std 1 | (x6) | Calculate system precision, standard verification |
| Std 2 | (x2) | Standard verification/Bracketing standard, |
| Sample 1 | (x1) | Single sample solution, single injection |
| Sample 2 | (x1) | Single sample solution, single injection |
| Sample 3 | (x1) | Single sample solution, single injection |
| Sample 4 | (x1) | Single sample solution, single injection |
| Std 2 | (x1) | Bracket up to 4 sample injection with single standard set | etc.

10  Calculations $$Assay\ (\%\ LC) = \frac{R\ sample}{R\ standard} \times \frac{W\ std}{Standard\ DF} \times \frac{SampleDf}{Nx\ Dose} \times Pstd \times 1000$$

Where:

| | |
|---|---|
| R sample | Area response of the Dextroamphetamine sulfate in the sample chromatogram (mAU*s) |
| R standard | Mean area response of the Dextroamphetamine sulfate bracketing standards (mAU*s) |

| | |
|---|---|
| W std | Bracketing standard weight (mg) |
| P std | Purity of the standard (%) |
| Sample DF | Volume of sample flask (mL) |
| Standard DF | Volume of standard flask (mL) |
| N | The number of capsules used in the sample preparation |

Supplement II

*Table I: Solvent boiling points and extraction temperatures. (Refer to Risk Assessment RA058)*

| Solvent | Boiling Point (°C) | Proposed Extraction Temperature (°C) | COSHH Reference * | COSHH Category * |
|---|---|---|---|---|
| Acetone | 56 | 50 | R218 | III |
| Methanol | 64.7 | 50 | R035 | III |
| Mineral (White) Spirit | 65** | 50 | R172 | III |
| 95% Ethanol | 78 | 60 | R095 | I |
| IPA | 82 | 60 | R092 | III |
| Water / Carbonated soft drink | 100 | 90 | R143 | I |
| 0.1N HCl | 100 | 90 | R031 | III |
| 0.1N NaOH | 100 | 90 | R061 | II |
| 0.2% Sodium Bicarbonate | 100 | 90 | R147 | I |
| 8% Acetic Acid | 118 | 90 | R032 | I |

*As SOP-EHS-0563*
**conservative estimate due to low flash point*

Supplement III

*Table I: Needle Gauges and Internal diameters*

| Needle Gauge | Internal Diameter* |
|---|---|
| 18 | 0.84 |
| 20 | 0.60 |
| 23 | 0.34 |
| 26 | 0.26 |
| 28 | 0.18 |

*\* As Sigma UK Needle Gauge chart. Precise IDs may vary by manufacturer.*

APPENDIX B

Protocol Addendum For The Evaluation Of Abuse Deterrent Immediate Release Formulations Of Dextroamphetamine Sulfate

1. INTRODUCTION

This protocol addendum is intended to capture several tests in addition to those identified in the original protocol  The outcomes from this evaluation and those in the original protocol together should enable the selection of a better-characterized lead prototype to be further developed into a final ADF-IR-d-amph.

2. OBJECTIVES

To evaluate the relative susceptibility to manipulation/abuse of novel prototypes of IR d-amph 10mg liquid fill capsules (which utilize the Abusolve™ technology) as compared to a related reference product (as appropriate).

It should be noted that there is no specific relevant regulatory guidance issued by the FDA for non-opiate drugs and therefore the tests included in this protocol addendum are adopted from the FDA guidance for Opioids with the appropriate adaptations (ref: FDA Guidance: Abuse-Deterrent Opioids – Evaluation and Labelling, April 2015).  Reference is also made to the March 2016 FDA guidance "General Principles for Evaluating the Abuse Deterrence of Generic Solid Oral Opioid Drug Products" from which appropriate elements and approaches were also adopted.

3. MATERIALS

All materials used should be recorded in the laboratory notebook and reported along with the results in the final report.  Information recorded should include material name, supplier, source, batch number, expiry date and received raw material number, where appropriate.

4. EQUIPMENT

- Grade A, Laboratory Glassware.
- 5/6 place analytical balance.
- Ultrasonic and shaking water baths.
- Sieves (various sizes) and Sieve shaker.

- Fume hood.
- Mortars and pestles.
- Luer-lok syringe (no black or rubber septum syringes to be used).
- 18 to 26 gauge syringe needles.
- Various filters.

Analytical equipment must be qualified, calibrated and maintained in accordance with site procedures, prior to use. Details of the equipment used (including make and model) will be recorded in laboratory notebooks or worksheets as appropriate. Where needed additional equipment may be used and will be recorded appropriately.

5. RECORD KEEPING

All analytical work will be recorded in project specific laboratory notebooks. A report which will include full details of all results and subsequent evaluations against any acceptance criteria will be transcription and calculation checked prior to issue. In addition, wherever possible and in all testing that include manipulation of the dosage form (such as syringeability), video recording and still images will be taken and attached to the report.

6. ANALYTICAL METHODS

Some evaluations are based on visual/physical assessments; others require analysis of the amount of drug substance. The analytical methods used are based on compendial methods for Dextroamphetamine which have been verified for selectivity and may require limited further validation at a later stage of development. Where indicated, the method will be used (and modified as necessary) to determine either a % assay or a % release profile for Dextroamphetamine sulfate when applicable.

Dextroamphetamine sulfate extraction will be determined by the HPLC method detailed in Supplement I for the IR-ADF prototype products.

7. EVALUATION PLAN

The physical/chemical deterrent methods in this protocol will be evaluated on the following prototype formulations:

| Component | mg/capsule |
|---|---|
| | Prototype 2 |
| Dextroamphetamine sulfate | 10 |
| Poloxamer 124 | 70 |
| Gelucire 48/16 | 52.5 |
| Kelcogel GCHA | 52.5 |
| Kolliphor EL | - |
| CMC 7H3SF | |
| Capsule Shell and Size | Size 3 gelatin |
| Total fill weight (mg)* | 185 |

*Final fill weight to be confirmed experimentally*

Barr's 10mg Dextroamphetamine sulphate Tablets will also be evaluated as a comparator under the same test strategy (where applicable).

Physical and chemical abuse resistance testing

All testing will employ whole dose units of Prototype 2. Physical testing will be conducted in duplicate, and all other testing in triplicate. Where physical testing produces poor replicates, a third test should be performed.

7.1  Test of Syringeability

For prototype 2 formulation and comparator only

Syringeability in different gauge needles after preparation with ambient and heated water (Prepare each sample in triplicate)

Method: Crush with a mortar and pestle or otherwise reduce the particle size of the dose, then grind with 5 mL of water at ambient temperature for up to 30 minutes or until the solution is homogenous. Test whether the mix becomes sufficiently fluid to be drawn up into a Luer-lok syringe via a 26-gauge needle. Draw back the syringe plunger to the 5 mL mark, maintaining a maximum pressure for 30 seconds or until the syringe has equilibrated pressure. If approximately 1 mL or greater has been drawn into the syringe and is fluid enough to be expelled through the needle (for injection) then dispense the syringe contents into a suitably sized volumetric flask and dilute with Assay diluent to an appropriate concentration. Quantify the amount of API available for injection by HPLC.

Repeat section 7.1 using water heated to 90-95 °C.

Repeat the above experiment for ambient and heated water using narrower gauge needles (18, 20 and 23 gauge).

7.2 Test Abuse Involving Chemical Extraction

For prototype 2 formulation and comparatoronly

1) Extraction in small volumes of ambient 0.2% Sodium Bicarbonate solution (Prepare each sample in triplicate).

Method: Crush with a mortar and pestle or otherwise reduce the particle size of the dose, then grind with 5 mL of 0.2% Sodium Bicarbonate solution solvent for 5 minutes or until homogeneous. Transfer the resulting suspension to a suitable scintillation vial, cover the lid in parafilm and shake in a water bath at ambient temperature, sampling at 60 minutes. Filter the sample through a 0.45 μm filter into a flask and dilute to an appropriate concentration with the standard assay method diluent. Quantify the API concentration by HPLC, analysing An intermediate filtration step over Whatman filter paper (e.g. Grade 4) may be used where 0.45 μm filters become blocked. In this instance, open funnels and vessels should be covered in parafilm during filtration to minimise evaporation and an evaporation standard, prepared as method but filtered over Whatman should be prepared in addition to or from a portion of the assay standard.

Repeat the experiment using 2ml of ambient 0.2% Sodium Bicarbonate solution

2) Extraction in small volumes of hot 0.2% Sodium Bicarbonate solution (Prepare each sample in triplicate).

Method: Crush with a mortar and pestle or otherwise reduce the particle size of the dose, then grind with 5 mL of pre-heated 0.2% Sodium Bicarbonate solution for 5 minutes or until homogeneous. Transfer the resulting suspension to a suitable scintillation vial, cover the lid in parafilm and shake in a water bath at the temperature indicated in Supplement II: Table I, taking samples at 60 minutes. Filter the sample through a 0.45 μm filter into a flask and dilute to an appropriate concentration with the standard assay method diluent. Quantify the API concentration by HPLC, As previously, an intermediate filtration step over Whatman filter paper (e.g. Grade 4) may be used where 0.45 μm filters become blocked.

Repeat the experiment using 2ml of heated 0.2% Sodium Bicarbonate solution

7.3 Ethanol extraction test

For prototype 2 formulation only

Method: Crush with a mortar and pestle or otherwise reduce the particle size of the dose, then grind with 10 mL of 95% Ethanol solution for 5 minutes or until homogeneous. Filter the sample through a 0.45μm nylon filter into a round bottom flask. Evaporate the Ethanol off by adding the round bottom flask containing the solution to a beaker full of water on a hot plate.

Observe, document and photograph the resultant mixture.

If the resultant mixture exhibits a powder-like consistency then subject it to the insufflation assessment.

APPENDIX C

Protocol Addendum for the Evaluation of Abuse Deterrent immediate release Formulations of Dextroamphetamine Sulfate

1. INTRODUCTION

Alcobra has engaged Encap Drug Delivery (Encap) to provide development services for a novel abuse deterrent formulation (ADF) of dextroamphetamine sulfate (d-amph), targeting a comparable dissolution profile to Barr's 10mg Dextroamphetamine approved Immediate Release (IR) tablet product. Based on preliminary development efforts and initial evaluations, 3 prototype formulations have been identified as the most promising leads to be further evaluated more extensively for abuse deterrence properties. This protocol addendum is intended to capture several tests in addition to those identified in the original protocol The outcomes from this evaluation and those in the original protocol together should enable the selection of a better-characterized lead prototype to be further developed into a final ADF-IR-d-amph.

2. OBJECTIVES

To evaluate the relative susceptibility to manipulation/abuse of novel prototypes of IR d-amph 10mg liquid fill capsules (which utilize the Abusolve™ technology) as compared to a related reference product (as appropriate).

It should be noted that there is no specific relevant regulatory guidance issued by the FDA for non-opiate drugs and therefore the tests included in this protocol addendum are adopted from the FDA guidance for Opioids with the appropriate adaptations (ref: FDA Guidance: Abuse-Deterrent Opioids – Evaluation and Labelling, April 2015). Reference is also made to the March 2016 FDA guidance "General Principles for Evaluating the Abuse Deterrence of Generic Solid Oral Opioid Drug Products" from which appropriate elements and approaches were also adopted.

3. MATERIALS

All materials used should be recorded in the laboratory notebook and reported along with the results in the final report. Information recorded should include material name, supplier, source, batch number, expiry date and received raw material number, where appropriate.

4. EQUIPMENT

- Grade A, Laboratory Glassware.
- 5/6 place analytical balance.
- Ultrasonic and shaking water baths.
- Sieves (various sizes) and Sieve shaker.
- Fume hood.
- Mortars and pestles.
- Luer-lok syringe (no black or rubber septum syringes to be used).
- 18 to 26 gauge syringe needles.
- Various filters.
- Domestic grater.
- Microwave
- Oven Analytical equipment must be qualified, calibrated and maintained in accordance with site procedures, prior to use. Details of the equipment used (including make and model) will be recorded in laboratory notebooks or worksheets as appropriate. Where needed additional equipment may be used and will be recorded appropriately.

5. RECORD KEEPING

All analytical work will be recorded in project specific laboratory notebooks. A report which will include full details of all results and subsequent evaluations against any acceptance criteria will be transcription and calculation checked prior to issue. In addition, wherever possible and in all testing that include manipulation of the dosage form (such as syringeability), video recording and still images will be taken and attached to the report.

6. ANALYTICAL METHODS

Some evaluations are based on visual/physical assessments; others require analysis of the amount of drug substance. The analytical methods used are based on compendial methods for Dextroamphetamine which have been verified for selectivity and may require limited further validation at a later stage of development. Where indicated, the method will be used (and modified as necessary) to determine either a % assay or a % release profile for Dextroamphetamine sulfate when applicable.

Dextroamphetamine sulfate extraction will be determined by the HPLC method detailed in Supplement I for the IR-ADF prototype products.

7. EVALUATION PLAN

The physical/chemical deterrent methods in this protocol will be evaluated on the following prototype formulations:

| Component | mg/capsule |
| --- | --- |
|  | Prototype 2 |
| Dextroamphetamine sulfate | 10 |
| Poloxamer 124 | 70 |
| Gelucire 48/16 | 52.5 |
| Kelcogel GCHA | 52.5 |
| Capsule Shell and Size | Size 3 gelatin |
| Total fill weight (mg)* | 185 |

*Final fill weight to be confirmed experimentally*

Barr's 10mg Dextroamphetamine sulphate Tablets will also be evaluated as a comparator under the same test strategy (where applicable).

Physical and chemical abuse resistance testing

All testing will employ whole dose units of Prototype 2. Physical testing will be conducted in duplicate, and all other testing in triplicate. Where physical testing produces poor replicates, a third test should be performed.

7.1 Tests of Physical Barriers to Abuse by Crushing, Cutting or Grinding

Each test in this section should include five (5) whole dose units. Prototype 2 as well as the comparator compound should be tested. Record any observations such as the inability to grind the material or pass it through the sieve due to a waxy or other physical characteristic. Video/picture documentation should be included wherever possible.

1) Effects of heating pre treatment

Method: Pre-treat the dosage units in an oven set at 105°C for 24 hrs. Remove the shells as quickly as possible with a scalpel then immediately after the shell is removed, grind with a coffee grinder for one minute. Observse capsules after one minute grinding and if it appears that the particle size can be further reduced continue grinding in the coffee grinder for up to 5 minutes in total and note exact time in the laboratory notebook.

Determine the particle size distribution of the 5 capsule contents by pouring them onto the following sieve assembly: 1000, 500, 250, and 106 microns. Attempts can be made to further reduce any large particles by squeezing them with your fingers.

Mechanically shake the sieve assembly for 5 minutes and determine if anything passes through. Weigh any material that has passed through each sieve.

Determine API/Excipient segregation as required: Assay the material on each sieve. Calculate the approximate total capsule weight and %API recovery if sufficient material has passed through to facilitate an analysis.

Repeat above experiment pre-treating the dosage units in a microwave at full power (700-800W) for 4 minutes (if time capsules are in the microwave requires to be longer or shorter than 4 minutes this will be documented in the laboratory note book).

2) Effects of using different household tools

Method: Freeze the dosage units in a domestic freezer for 24 hrs. Remove the shells as quickly as possible with a scalpel then immediately after the shell is removed, grate the capsule contents with a small domestic grater. Determine the particle size distribution of the 5 capsule contents by pouring them onto the following sieve assembly: 1000, 500, 250, and 106 microns. Attempts can be made to further reduce any large particles by squeezing them with your fingers.

Mechanically shake the sieve assembly for 5 minutes and determine if anything passes through. Weigh any material that has passed through each sieve.

Determine API/Excipient segregation as required: Assay the material on each sieve. Calculate the approximate total capsule weight and %API recovery if sufficient material has passed through to facilitate an analysis.

Repeat the above experiment using a scalpel blade to finely cut the capsule contents.

3) Milling with a coffee grinder (Extended grinding time)

Method: Freeze the dosage units in a domestic freezer for 24 hrs. Remove the shells as quickly as possible with a scalpel then immediately after the shell is removed, grind with a coffee grinder for five minutes. Determine the particle size distribution of the 5 capsule contents by pouring them onto the following sieve assembly: 1000, 500, 250, and 106 microns. Attempts can be made to further reduce any large particles by squeezing them with your fingers.

Mechanically shake the sieve assembly for 5 minutes and determine if anything passes through. Weigh any material that has passed through each sieve.

Determine API/Excipient segregation as required: Assay the material on each sieve. Calculate the approximate total capsule weight and %API recovery if sufficient material has passed through to facilitate an analysis.

4) Effects of cooling with dry ice

Method: Freeze the dosage units using dry ice for 10 minutes. Carefully remove the shells as quickly as possible with a scalpel then immediately after the shell is removed, grind with a coffee grinder for one minutes incorporating sufficient pellets of dry ice to keep the contents cold. Determine the particle size distribution of the 5 capsule contents by pouring them onto the following sieve assembly: 1000, 500, 250, and 106 microns. Attempts can be made to further reduce any large particles by squeezing them with your fingers.

Mechanically shake the sieve assembly for 5 minutes and determine if anything passes through. Weigh any material that has passed through each sieve.

Determine API/Excipient segregation as required: Assay the material on each sieve. Calculate the approximate total capsule weight and %API recovery if sufficient material has passed through to facilitate an analysis.

5) Effects of cooling grinder

Method: Place the section of the grinder the capsules are placed in a freezer for an hour. Freeze the dosage units in a domestic freezer for 24 hrs. Carefully remove the shells as quickly as possible with a scalpel then immediately after the shell is removed, grind with a coffee grinder for one minutes. Determine the particle size distribution of the 5 capsule contents by pouring them onto the following sieve assembly: 1000, 500, 250, and 106 microns. Attempts can be made to further reduce any large particles by squeezing them with your fingers.

Mechanically shake the sieve assembly for 5 minutes and determine if anything passes through. Weigh any material that has passed through each sieve.

Determine API/Excipient segregation as required: Assay the material on each sieve. Calculate the approximate total capsule weight and %API recovery if sufficient material has passed through to facilitate an analysis.

7.2 Test of Syringeability

For prototype 2 formulation and comparator only

1) Syringeability in different gauge needles after preparation with water (Prepare each sample in triplicate)

Method: Crush with a mortar and pestle or otherwise reduce the particle size of a dose unit, then grind with 10 mL of water at ambient temperature for 5 minutes or until the solution is homogenous. Test whether the mix becomes sufficiently fluid to be drawn up into a Luer-lok syringe via an 18-gauge needle. Draw back the syringe plunger to the 10 mL mark, maintaining a maximum pressure until all solution which is syringeable has been drawn in to the syringe. If a quantifiable amount has been drawn into the syringe and is fluid enough to be expelled through the needle (for injection) then dispense the syringe contents into a suitably sized volumetric flask and dilute with Assay diluent to an appropriate concentration. Quantify the amount of API available for injection by HPLC.

Repeat the above, attempting to draw the fluid via a cigarette filter tip. A fresh sample should be prepared for each filter used.

Repeat the above experiment using a narrower gauge needle for any samples that were syringeable with the 18-gauge needle and progress via the 20, 23 and 26 gauge needles as long as the recovered quantity of API is greater than 5%.

Repeat syringeability with water heated to 90-95 °C.

2) Syringeability in water using multiple capsules

Method: Crush with a mortar and pestle or otherwise reduce the particle size of 3 dose units, then grind with 10 mL of water at ambient temperature for 5 minutes or until the solution is homogenous. Test whether the mix becomes sufficiently fluid to be drawn up into a Luer-lok syringe via an 18-gauge needle. Draw back the syringe plunger to the 10 mL mark, maintaining a maximum pressure until all solution which is syringeable has been drawn in to the syringe. If a quantifiable amount has been drawn into the syringe and is fluid enough to be expelled through the needle (for injection) then dispense the syringe contents into a suitably sized volumetric flask and dilute with Assay diluent to an appropriate concentration. Quantify the amount of API available for injection by HPLC.

Repeat the experiment with water heated to 90-95 °C.

3) Syringeability in water after extensive grinding of dosage units

Method: Crush with a mortar and pestle or otherwise reduce the particle size of 1 dose unit, then grind with 10 mL of water at ambient temperature for 30 minutes, photographing the mixture after every 5 minutes of grinding. Test whether the mix becomes sufficiently fluid to be drawn up into a Luer-lok syringe via an 26-gauge needle. Draw back the syringe plunger to the 10 mL mark, maintaining a maximum pressure until all solution which is syringeable has been drawn in to the syringe. If a quantifiable amount has been drawn into the syringe and is fluid enough to be expelled through the needle (for injection) then dispense the syringe contents into a suitably sized volumetric flask and dilute with Assay diluent to an appropriate concentration. Quantify the amount of API available for injection by HPLC.

7.3 Test Abuse Involving Chemical Extraction

For prototype 2 formulation and comparator only

1) Extraction in small volumes of ambient, ethanol 40% and ethanol 95% (Prepare each sample in triplicate).

Method: Crush with a mortar and pestle or otherwise reduce the particle size of the dose, then grind with 5 mL of 40% Ethanol for 5 minutes or until homogeneous. Transfer the resulting suspension to a suitable scintillation vial, cover the lid in parafilm and shake in a water bath at ambient temperature, sampling at 60 minutes. Filter the sample through a 0.45 μm filter into a flask and dilute to an appropriate concentration with the standard assay method diluent. Quantify the API concentration by HPLC, analysing An intermediate filtration step over Whatman filter paper (e.g. Grade 4) may be used where 0.45 μm filters become blocked. In this instance, open funnels and vessels should be covered in parafilm during filtration to minimise evaporation and an evaporation standard, prepared as method but filtered over Whatman should be prepared in addition to or from a portion of the assay standard.

Repeat the above experiment with 95% Ethanol.

7.4 Turpentine and/or 0.2% sodium bicarbonate extraction test

For prototype 2 formulation and the comparator only

Method: Crush with a mortar and pestle or otherwise reduce the particle size of the dose, then grind with 10 mL of turpentine solution for 5 minutes or until homogeneous. Filter the sample through a 0.45μm nylon filter into a round bottom flask. Evaporate the turpentine off by adding the round bottom flask containing the solution to a beaker full of water on a hot plate.

Observe, document and photograph the resultant mixture.

If the resultant mixture exhibits a powder-like consistency then subject it to the insufflation assessment.

Repeat the experiment extracting dosage units in 0.2% sodium bicarbonate solution.

APPENDIX D

Protocol Addendum for the Evaluation of Smokeability of an Abuse Deterrent Immediate Release Formulations of Dextroamphetamine Sulfate

1. INTRODUCTION

This protocol is designed to evaluate prototype 2 physical barriers to abuse by smoking. The outcomes from this evaluation should enable the selection of a better-characterized lead prototype to be further developed into a final ADF-IR-d-amph.

2. OBJECTIVES

To evaluate the relative susceptibility to manipulation/abuse by smoking of novel prototypes of IR d-amph 10mg liquid fill capsules as compared to a related reference product (as appropriate).

It should be noted that there is no specific relevant regulatory guidance issued by the FDA for non-opiate drugs and therefore the tests included in this protocol are adopted from the FDA guidance for Opioids with the appropriate adaptations (ref: FDA Guidance: Abuse-Deterrent Opioids – Evaluation and Labelling, April 2015). Reference is also made to the March 2016 FDA guidance "General Principles for Evaluating the Abuse Deterrence of Generic Solid Oral Opioid Drug Products" from which appropriate elements and approaches were also adopted.

3. MATERIALS

All materials used should be recorded in the laboratory notebook and reported along with the results in the final report. Information recorded should include material name, supplier, source, batch number, expiry date and received raw material number, where appropriate.

4. EQUIPMENT

- Grade A, Laboratory Glassware.
- 5/6 place analytical balance.
- Fume hood.
- Various filters.
- Sand bath
- Heating Mantle
- Calibrated thermometer

- Cooling device

Analytical equipment must be qualified, calibrated and maintained in accordance with site procedures, prior to use. Details of the equipment used (including make and model) will be recorded in laboratory notebooks or worksheets as appropriate. Where needed additional equipment may be used and will be recorded appropriately.

5. RECORD KEEPING

All analytical work will be recorded in project specific laboratory notebooks. A report which will include full details of all results and subsequent evaluations against acceptance criteria will be transcription and calculation checked prior to issue. In addition, wherever possible and in all testing that include manipulation of the dosage form, video recording and still images will be taken and attached to the report.

6. ANALYTICAL METHODS

Some evaluations are based on visual/physical assessments; others require analysis of the amount of drug substance. The analytical methods used are based on compendial methods for Dextroamphetamine which have been verified for selectivity and may require limited further validation at a later stage of development. Where indicated, the method will be used (and modified as necessary) to determine a % assay for Dextroamphetamine sulfate when applicable.

Dextroamphetamine sulfate extraction will be determined by the HPLC method detailed in Supplement I for the IR-ADF prototype and using the current USP tablet method for the comparator, Barr's Dextroamphetamine sulfate 10mg.

7. EVALUATION PLAN

The physical/chemical deterrent methods in this protocol will be evaluated on the following prototype formulation:

| Component | mg/capsule |
| --- | --- |

|  | Prototype 2 |
|---|---|
| Dextroamphetamine sulfate | 10 |
| Poloxamer 124 | 70 |
| Gelucire 48/16 | 52.5 |
| Kelcogel GCHA | 52.5 |
| Capsule Shell and Size | Size 3 gelatin |
| Total fill weight (mg)* | 185 |

*Final fill weight to be confirmed experimentally*

Barr's 10mg Dextroamphetamine Sulfate tablets will also be evaluated as a comparator under the same test strategy.

Physical abuse resistance testing

All testing will employ three (3) whole dose units. Testing will be conducted in duplicate. Where testing produces poor replicates, a third test should be performed.

7.1 Test of Smokability Barriers (To determine if dextroamphetamine tablet and capsules formulations can be abused by smoking)

The process of "smoking" a drug involves application of a heat source that is sufficient to vapourise by sublimation a portion of the drug in a localised manner such that the resulting vapour can be inhaled. There is no recognised method of testing this route of abuse therefore, in order to assess the feasibility of it in the laboratory, the following experiment has been designed to capture any potentially volatilised API in an enclosed vessel.

The contents of the collection vessel and the original heated vessel can be assayed to quantify amounts of API present and also to determine if the API has decomposed (degraded). A temperature of 233°C has been selected since this is the ignition temperature of paper.

For the test, use three whole dose units of both the comparator product and formulation prototype 2. Record any observations noted throughout each test. Video/picture documentation will be included wherever possible.

Smokability barriers (prepare in duplicate):

Prototype 2:-

Open three full dose units of prototype 2 with a scalpel and add to a 50 ml round bottom flask. Place the flask in a sand bath connected to the apparatus shown in Fig. 1.

Comparator:-

Add three full dose units of the comparator to a 50 ml round bottom flask. Place the flask in a sand bath connected to the apparatus shown in Fig. 1.

For both Prototype 2 and the comparator:-

Heat the sand bath to 233°C and hold for 15minutes. Observe the dosage units over those 15 minutes and photograph or video when possible.

Prototype 2:-

Add 30ml of diluent to the original flask containing the capsules and mix thoroughly. Sonicate if required to aid dissolution of the sample. Filter an aliquot of this solution through a 0.45 μm nylon filter, discarding the first 2ml to waste then pipette 1ml of the resultant filtrate into a 10ml volumetric flask and dilute to volume with diluent.

Inspect the 25ml round bottom collection flask for evidence of any sublimed API which has vapourised and and condensed. If any residue is apparent then add an appropriate amount of assay diluent to the flask (eg 2-5ml) and mix thoroughly.

Comparator:-

Add 30ml of diluent to the original flask containing the comparator tablets and mix thoroughly. Sonicate if required to aid dissolution of the sample. Filter an aliquot of this solution through a 0.45

µm nylon filter, discarding the first 2ml to waste then pipette 2ml of the resultant filtrate into a 10ml volumetric flask and dilute to volume with diluent.

Inspect the 25ml round bottom collection flask for evidence of any sublimed API which has vapourised and and condensed. If any residue is apparent then add an appropriate amount of assay diluent to the flask (eg 2-5ml) and mix thoroughly.

Assay each solution by HPLC analysis in order to quantify the dextroamphetamine present.

ENCAP ANALYTICAL METHOD

2.3. Dissolution Conditions

2.3.1 Dissolution Apparatus

| | |
|---|---|
| Dissolution Apparatus | USP apparatus III |
| Filter Type | 40/35 μm probe filter |
| Medium Type | 0.01M HCl |
| Medium Volume | 250 ml |
| Sample Times | 5, 10, 15, 20, 30 and 45 minutes |
| Sample Volume | 2 ml (filter not replaced) |
| Vessel Temperature | 37°C ± 0.5°C |
| Dip Rate | 30 dips per minute |
| Mesh Screen Size | 840 micron |

2.3.2 HPLC Conditions

| | | |
|---|---|---|
| Column | - | Gemini C18 5μm 110A 150 mm x 4.6 mm |
| Flow Rate | - | 1.5ml/min |
| Injection volume | - | 20 μl |
| Column temperature | - | 50°C |
| Detection wavelength | - | 210 nm |
| Mobile phase | - | 100% mobile phase as section 2.4.2 |
| Run Time | - | 10min |
| Expected Rt | - | 4.6min |

2.4 Preparation of Reagents

Weights and volumes are given for guidance only and may be modified provided the final working concentration and the ratios of components remains the same.

2.4.1 Dissolution Medium: 0.01M HCl 0.1M HCl prepared by dissolving 8.5ml of Hydrochloric acid in 800ml UHQ water, mixed well then made to volume in a 1000ml Volumetric flask.

To prepare 1 litre of 0.01M HCl, 100ml of 0.1M HCl dissolved in 900ml of UHQ Water and mixed well.

2.4.2 Preparation of Mobile Phase

To prepare 1 litre of mobile phase:
- Dissolve 1.1g of Sodium-1-heptanesulfonate in 575ml of UHQ water.
- Add 25ml of dilute glacial acetic acid (14ml acetic acid into 100ml UHQ water).
- Add 400ml of Methanol.
- Measure the pH of this solution. A pH of 3.3 ± 0.1 is acceptable. If required, adjust the pH accordingly using dropwise addition of glacial acetic acid.

2.5    Preparation of Standard Solution (Prepare in Duplicate)
Note: Weights and volumes are included for guidance only and may be modified provided the final working concentration remains the same.
Accurately weigh 8 mg of Dextroamphetamine Sulfate into a 200 ml volumetric flask. Add 150 ml of dissolution media and sonicate for 10 minutes to dissolve. Once cooled, dilute to volume with dissolution media. This is the working standard solution for Dextroamphetamine Sulfate.
   Reference standard solutions are stable for 4 days at ambient or refrigerated conditions in clear glassware.

2.6    Dissolution Procedure
Weigh each capsule before analysis for information only.
Decant 250 ml of dissolution medium into each vessel and equilibrate to 37°C ± 0.5°C.
Place one capsule in the sample inner tube prior to attaching to the sample holder and lowering into the vessel.
Remove 2 ml at each time point: 5, 10, 15, 20, 30 and 45 minutes with a cannula attached with a 40/35 μm probe filter.
Transfer filtered sampled solution into a HPLC vial for analysis.

2.7    HPLC Procedure
Allow mobile phase to flow through the system until equilibrated and a consistent baseline is achieved.

2.7.1   System Precision
Calculate the relative standard deviation (RSD) of the mean Dextroamphetamine Sulfate peak area for six injections of standard 1. The RSD is not more than 2%.

2.7.1   Standard Verification
Verify the mean peak response factors of two injection of standard 2 relative to the response factor of the last two injection of Standard 1. Standard 2 must verify as 98 – 102% of standard 1.

2.7.3   Repeatability throughout the run
Calculate the relative standard deviation (%RSD) of the peak area for all of the bracketing standards throughout the run. The RSD is not more than 2%.

2.7.4   Specificity
There must be no interference greater than or equal to 1.0% of the mean reference standard peak area in the blank injections at the retention time of the peak.

2.7.5   Typical Injection Sequence
| | | |
|---|---|---|
| Blank | (x2) | Confirm absence of interference |
| Standard 1 | (x6) | Calculate system precision |
| Standard 2 | (x1) | Calculate standard verification |

| | | |
|---|---|---|
| Sample 1a | (x1) | Single sample solution, single injection |
| Sample 1b | (x1) | Single sample solution, single injection |
| Sample 1c | (x1) | Single sample solution, single injection |
| Sample 1d | (x1) | Single sample solution, single injection |
| Sample 1e | (x1) | Single sample solution, single injection |
| Sample 1f | (x1) | Single sample solution, single injection |
| Standard 2 | (x1) | Bracket six samples between each standard |
| Sample 2a | (x1) | Single sample solution, single injection |
| Sample 2b | (x1) | Single sample solution, single injection |
| Sample 2c | (x1) | Single sample solution, single injection |
| Sample 2d | (x1) | Single sample solution, single injection |
| Sample 2e | (x1) | Single sample solution, single injection |
| Sample 2f | (x1) | Single sample solution, single injection |
| Standard 2 | (x1) | Bracket six samples between each standard |
| Sample 3a | (x1) | Single sample solution, single injection |
| etc. | | |

2.8 Calculations

Determine the % release for each product relative to the reference standard material using the equation.

% Release $$(\%\text{Release}) = \frac{A_{sam}}{A_{std}} \times \frac{W_{std}}{\text{Dose}} \times \frac{\text{Vol}_{smp}}{\text{Vol}_{std}} \times P_{std} \times 100$$

Where:

| | |
|---|---|
| Asam | Area response for Dextroaphetamine Sulfate in the sample chromatogram |
| Astd | Mean area response of bracketing standard injections |
| Wstd | Bracketing standard weight (mg) |
| Pstd | Purity of the standard (decimal form or mg/mg) |
| Vol smp | Volume of dissolution medium at the time point (ml) |
| Vol std | Dilution factor of reference standard (ml) |
| Dose | Theoretical content of Dextroaphetamine Sulfate in a single capsule (mg) |

Correct for volume of media removed at each dissolution time-point. Report the % Release to 1 decimal place for individual pots.

3. REVISION HISTORY
3.1    New June 2016

Encap Analytical Method EAM0297 vs. 01

APPENDIX E

1. PURPOSE

This method will be used in the Dissolution testing and analysis of Dextroamphetamine Sulfate in 10 mg capsules. This is an HPLC method using a reverse phase C18 column and UV detection at 210nm.

2. METHOD CONDITIONS 2.1. Reagents

| | |
|---|---|
| Sodium-1-HeptaneSulfonate | - Analytical Grade or equivalent |
| Water | - HPLC grade or equivalent |
| Acetic Acid Glacial | - HPLC grade or equivalent |
| Methanol | - HPLC grade or equivalent |
| Hydrochloric Acid | - Analytical Grade or equivalent |
| Dextroamphetamine Sulfate | - USP Reference Standard |

2.2. Safety

| | |
|---|---|
| Sodium-1-HeptaneSulfonate | - Refer to COSHH assessment R027 |
| Water | - Refer to COSHH assessment R143 |
| Acetic Acid Glacial | - Refer to COSHH assessment R032 |
| Methanol | - Refer to COSHH assessment R035 |
| Hydrochloric Acid | - Refer to COSHH assessment R031 |
| Dextroamphetamine Sulfate | - Refer to COSHH assessment A010 |

2.3. Method Conditions 2.3.1 Dissolution Apparatus

| | |
|---|---|
| Dissolution apparatus | - USP apparatus I |
| Filter type | - 35µm probe filter |
| Medium type | - 0.01M HCl |
| Medium volume | - 500ml |
| Sample times | - 5, 10, 15, 20, 30 and 45 minutes. |
| Sample volume | - 1.5 ml (filter not replaced) |
| Vessel temperature | - 37°C ± 0.5°C |
| Speed | - 100rpm |

2.3.2 HPLC Conditions

| | |
|---|---|
| Column | - Zorbax Eclipse XDB-C18 5μm 250 mm x 4.6 mm |
| Flow rate | - 1.5ml/min |
| Injection volume | - 100 μl |
| Column temperature | - 40°C |
| Detection wavelength | - 210nm |
| Mobile phase | - 100% Mobile phase |
| Run time | - 20min |
| Expected Rt | - 12min |

2.4 Preparation of Reagents

Weights and volumes are given for guidance only and may be modified provided the final working concentration and the ratios of components remains the same.

2.4.1 Dissolution Medium: 0.01M HCl

To prepare 10 litre of 0.01M HCl, add 8.5ml of Hydrochloric acid in 9000ml of UHQ water, mix well then make to volume using UHQ water.

2.4.2 Preparation of Mobile Phase

To prepare 1 litre of mobile phase:
- Dissolve 1.1g of Sodium-1-heptanesulfonate in 575ml of UHQ Water.
- Add 25ml of dilute glacial acetic acid (14ml acetic acid into 100ml UHQ Water)
- Add 400ml of Methanol.
- Measure the pH of this solution. A pH of 3.3 ± 0.1 is acceptable. If required, adjust the pH accordingly using dropwise addition of glacial acetic acid.

2.5 Preparation of Standard Solution (Prepare in Duplicate)

Note: weights and volumes are included for guidance only and may be modified provided the final working concentration remains the same.

- Accurately weigh 6mg of Dextroamphetamine Sulfate into a 10ml volumetric flask
- Add 7ml of dissolution media and sonicate for 10 minutes to dissolve
- Once cooled, dilute to volume with dissolution media. This is the working standard solution for Dextroamphetamine Sulfate (600μg/ml)
- Transfer 2ml of the stock solution into a 20ml volumetric flask and make to volume with dissolution media. This is the 60μg/ml standard solution.

Reference standard solutions are stable for 4 days at ambient or refrigerated conditions in clear glassware.

2.6 Dissolution Procedure

Weigh each capsule before analysis.

Ensure the sampling system is clean and dry and contains no residual moisture prior to use. Fit 35μm probe tip filters to each cannula.

Decant 500 ml of dissolution medium into each vessel and equilibrate to 37°C ± 0.5°C.

Place one capsule in the basket and lower into the vessel to start the dissolution testing. Set the paddle speed to 100rpm.

Remove 1.5ml at each time point: 5, 10, 15, 20, 30 and 45 minutes. All samples should be dispensed straight into labelled HPLC vials for analysis.

2.7 HPLC Procedure

Allow mobile phase to flow through the system until equilibrated and a consistent baseline is achieved.

2.7.1 System Precision

Calculate the relative standard deviation (RSD) of the mean Dextroamphetamine Sulfate peak area for six injections of standard 1. The RSD is not more than 2%

2.7.2 Standard Verification

Verify the mean peak response factors of two injection of standard 2 relative to the response factor of the last two injection of Standard 1. Standard 2 must verify as 98 – 102% of standard 1.

2.7.3 Repeatability throughout the run

Calculate the relative standard deviation (%RSD) of the peak area for all of the bracketing standards throughout the run. The RSD is not more than 2%

2.7.4 Specificity

There must be no interference greater than or equal to 1.0% of the mean reference standard peak area in the blank injections at the retention time of the peak.

2.7.5 Typical Injection Sequence

| | | |
|---|---|---|
| Blank | (x2) | Confirm absence of interference |
| Standard 1 | (x6) | Calculate system precision |
| Standard 2 | (x2) | Calculate standard verification |
| Sample 1a | (x1) | Single sample solution, single injection |
| Sample 1b | (x1) | Single sample solution, single injection |
| Sample 1c | (x1) | Single sample solution, single injection |
| Sample 1d | (x1) | Single sample solution, single injection |
| Sample 1e | (x1) | Single sample solution, single injection |
| Sample 1f | (x1) | Single sample solution, single injection |
| Standard 2 | (x1) | Bracket six samples between each standard |
| etc. | | |

2.8 Calculations

Determine the % release for each product relative to the reference standard material using the equation.

% Release

$$(\% \text{Release}) = \frac{A_{sam}}{A_{std}} \times \frac{W_{std}}{Dose} \times \frac{Vol_{smp}}{Vol_{std}} \times P_{std} \times 100$$

Where:

| | |
|---|---|
| $A_{sam}$ | Area response for Dextroamphetamine Sulfate in the sample chromatogram |
| $A_{std}$ | Mean area response of bracketing standard injections |
| $W_{std}$ | Bracketing standard weight (mg) |
| $P_{std}$ | Purity of the standard (decimal form or mg/mg) |
| Vol smp | Volume of dissolution medium at time point (ml) |
| Vol std | Dilution factor of reference standard (ml) |
| Dose | Theoretical content of Dextroamphetamine Sulfate in a single capsule (mg) |

Correct for volume of media removed at each dissolution time-point. Report the % Release to 1 decimal place for individual pots.

We claim:

1. An abuse-deterrent formulation, comprising medicament, poloxamer, water-soluble anionic polysaccharide, and PEG ester;
wherein the medicament is

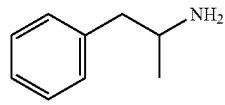

or a pharmaceutically acceptable salt thereof.

2. The abuse-deterrent formulation of claim 1, wherein the poloxamer is poloxamer 124.

3. The abuse-deterrent formulation of claim 1, wherein the water-soluble anionic polysaccharide is gellan gum.

4. The abuse-deterrent formulation of claim 1, wherein the PEG ester is polyoxyl stearate.

5. The abuse-deterrent formulation of claim 1, wherein the ratio of poloxamer:water-soluble anionic polysaccharide:PEG ester is about 40:30:30.

6. The abuse-deterrent formulation of claim 1, comprising 33-43 wt % of poloxamer; 24-32 wt % of water-soluble anionic polysaccharide; and 24-32 wt % of PEG ester.

7. The abuse-deterrent formulation of claim 1, wherein the poloxamer is poloxamer 124, the water-soluble anionic polysaccharide is gellan gum, and the PEG ester is polyoxyl stearate.

8. The abuse-deterrent formulation of claim 7, wherein the ratio of poloxamer 124:gellan gum:polyoxyl stearate is about 40:30:30.

9. The abuse-deterrent formulation of claim 1, wherein the poloxamer is Kollisolv P124, the water-soluble anionic polysaccharide is Kelcogel CGHA, and the PEG ester is Gelucire 48/16.

10. The abuse-deterrent formulation of claim 1, wherein the medicament is the S enantiomer, or a pharmaceutically acceptable salt thereof.

11. The abuse-deterrent formulation of claim 1, wherein the medicament is dextroamphetamine, or a pharmaceutically acceptable salt thereof.

12. The abuse-deterrent formulation of claim 1, wherein the medicament is a sulfate salt.

13. The abuse-deterrent formulation of claim 1, further comprising a capsule.

14. The abuse-deterrent formulation of claim 1, comprising about 10 mg to about 50 mg of medicament.

15. An abuse-deterrent formulation, comprising medicament, poloxamer 124, gellan gum, and polyoxyl stearate;
wherein the ratio of poloxamer 124:gellan gum:polyoxyl stearate is about 40:30:30;
the medicament is

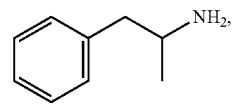

or a pharmaceutically acceptable salt thereof; and
wherein at least 80% of the medicament is released in solution within 45 minutes.

16. The abuse-deterrent formulation of claim 15, wherein the medicament is the S enantiomer, or a pharmaceutically acceptable salt thereof.

17. The abuse-deterrent formulation of claim 15, wherein the medicament is dextroamphetamine, or a pharmaceutically acceptable salt thereof.

18. The abuse-deterrent formulation of claim 15, wherein the medicament is a sulfate salt.

19. The abuse-deterrent formulation of claim 15, comprising about 10 mg to about 50 mg of medicament.

20. The abuse-deterrent formulation of claim 15, wherein the poloxamer 124 is Kollisolv P124, the gellan gum is Kelcogel CGHA, and the polyoxyl stearate is Gelucire 48/16.

* * * * *

UNITED STATES PATENT AND TRADEMARK OFFICE
CERTIFICATE OF CORRECTION

PATENT NO.          : 9,931,303 B1
APPLICATION NO.     : 15/591677
DATED               : April 3, 2018
INVENTOR(S)         : Yaron Daniely et al.

Page 1 of 1

It is certified that error appears in the above-identified patent and that said Letters Patent is hereby corrected as shown below:

On the Title Page

Under item ( * ), delete "This patent is subject to a terminal disclaimer."

Signed and Sealed this
Fourteenth Day of August, 2018

Andrei Iancu
*Director of the United States Patent and Trademark Office*